United States Patent
Shen et al.

(10) Patent No.: US 10,995,145 B2
(45) Date of Patent: May 4, 2021

(54) ANTIBODIES WHICH BIND HUMAN GLUCAGON RECEPTOR

(71) Applicant: NGM BIOPHARMACEUTICALS, INC., South San Francisco, CA (US)

(72) Inventors: Wenyan Shen, Redwood City, CA (US); Yan Wang, Foster City, CA (US); Hugo Matern, San Mateo, CA (US); Zhonghao Liu, Redwood City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/881,493

(22) Filed: Jan. 26, 2018

(65) Prior Publication Data

US 2018/0273629 A1    Sep. 27, 2018

Related U.S. Application Data

(60) Provisional application No. 62/451,603, filed on Jan. 27, 2017.

(51) Int. Cl.
- *C07K 16/28* (2006.01)
- *A61K 39/395* (2006.01)
- *A61K 39/00* (2006.01)
- *A61K 45/06* (2006.01)

(52) U.S. Cl.
CPC ...... *C07K 16/2869* (2013.01); *A61K 39/3955* (2013.01); *A61K 45/06* (2013.01); *A61K 2039/505* (2013.01); *C07K 2317/21* (2013.01); *C07K 2317/24* (2013.01); *C07K 2317/31* (2013.01); *C07K 2317/34* (2013.01); *C07K 2317/56* (2013.01); *C07K 2317/565* (2013.01); *C07K 2317/76* (2013.01); *C07K 2317/92* (2013.01)

(58) Field of Classification Search
CPC .... C07K 16/00; C07K 16/28; C07K 16/2869; C07K 2317/21; C07K 2317/24; C07K 2317/31; C07K 2317/56; C07K 2317/565; C07K 2317/76; C07K 2317/92; A61K 39/395; A61K 39/3955; A61K 45/06; A61K 2039/505

See application file for complete search history.

(56) References Cited

U.S. PATENT DOCUMENTS

| | | |
|---|---|---|
| 5,317,092 A | 5/1994 | Markussen |
| 5,770,445 A | 6/1998 | Kindsvogel et al. |
| 5,776,725 A | 7/1998 | Kindsvogel et al. |
| 5,919,635 A | 7/1999 | Kindsvogel et al. |
| 7,947,809 B2 | 5/2011 | Yan et al. |
| 7,968,686 B2 | 6/2011 | Korytko et al. |
| 8,158,759 B2 | 4/2012 | Yan et al. |
| 8,545,847 B2 | 10/2013 | Okamoto et al. |
| 8,771,696 B2 | 7/2014 | Harp et al. |
| 9,102,732 B2 | 8/2015 | Lee et al. |
| 9,127,068 B2 | 9/2015 | Okamoto et al. |
| 9,248,189 B2 | 2/2016 | Forgie et al. |
| 9,358,287 B2 | 6/2016 | Harp et al. |
| 9,587,029 B2 | 3/2017 | Okamoto et al. |
| 2008/0213288 A1 | 9/2008 | Michelsen et al. |
| 2009/0041784 A1 | 2/2009 | Yan et al. |
| 2009/0252727 A1 | 10/2009 | Korytko et al. |
| 2011/0212092 A1 | 9/2011 | Korytko et al. |
| 2012/0128679 A1 | 5/2012 | Okamoto et al. |
| 2013/0149315 A1 | 6/2013 | Lee et al. |
| 2013/0344538 A1 | 12/2013 | Okamoto et al. |
| 2014/0255419 A1 | 9/2014 | Harp et al. |
| 2014/0335091 A1 | 11/2014 | Forgie et al. |
| 2015/0337045 A1 | 11/2015 | Okamoto et al. |
| 2016/0257757 A1 | 9/2016 | Harp et al. |
| 2016/0311912 A1 | 10/2016 | Forgie et al. |
| 2017/0129960 A1 | 5/2017 | Okamoto et al. |
| 2020/0048356 A1 | 2/2020 | Liu |

FOREIGN PATENT DOCUMENTS

| | | |
|---|---|---|
| WO | WO 1994/005789 A1 | 3/1994 |
| WO | WO 2006/005469 A2 | 7/2005 |
| WO | WO 2008/036341 A2 | 3/2008 |
| WO | WO 2009/120530 A1 | 10/2009 |
| WO | WO 2011/030935 A1 | 3/2011 |
| WO | WO 2012/071372 A2 | 5/2012 |
| WO | WO 2013/059531 A1 | 4/2013 |
| WO | WO 2014/181229 A2 | 11/2014 |
| WO | WO 2015/154795 | 10/2015 |
| WO | WO 2015/189698 A2 | 12/2015 |
| WO | WO 2016/044337 | 3/2016 |
| WO | WO 2016/161154 A1 | 6/2016 |
| WO | WO 2017/040986 A1 | 3/2017 |
| WO | WO 2017/062693 A1 | 4/2017 |
| WO | WO 2017/120261 | 7/2017 |
| WO | WO 2018/075792 | 4/2018 |

(Continued)

OTHER PUBLICATIONS

Edwards, BM et al. (2003) J. Mol. Biol. 334:103-118. (doi:10.1016/j.jmb.2003.09.054 J.).*
Lloyd, C et al. (2009) Protein Engineering, Design & Selection. 22(3):159-168. (doi:10.1093/protein/gzn058).*
Buggy et al., "Glucagon glucagon-like peptide I receptor chimeras reveal domains that determine specificity of glucagon binding," *J. Biol. Chem.*, 270(13):7474-7478 (1995).
Cerf, "Beta cell dysfunction and insulin resistance," *Front. Endocrinol.*, 4:Article 37 (2013).
Damond et al., "Blockade of glucagon signaling prevents or reverses diabetes onset only if residual β-cells persist," *eLife*, 5:e13828 (2016).
Gelling et al., "Lower blood glucose, hyperglucagonemia, and pancreatic alpha cell hyperplasia in glucagon receptor knockout mice," *Proc. Natl. Acad. Sci. USA*, 100(3):1438-1443 (2003).

(Continued)

*Primary Examiner* — Robert S Landsman
(74) *Attorney, Agent, or Firm* — Fish & Richardson P.C.

(57) ABSTRACT

The present disclosure provides binding proteins, such as antibodies, that bind glucagon receptors, including a human glucagon receptor, and methods of their use.

29 Claims, 8 Drawing Sheets

Specification includes a Sequence Listing.

(56) References Cited

FOREIGN PATENT DOCUMENTS

| WO | WO 2018/140729 | 8/2018 |
|---|---|---|
| WO | WO 2020/023847 | 1/2020 |

OTHER PUBLICATIONS

Gu et al., "Long-term inhibition of the glucagon receptor with a monoclonal antibody in mice causes sustained improvement in glycemic control, with reversible alpha-cell hyperplasia and hyperglucagonemia," *J. Pharmacol. Exp. Ther.*, 331(3):871-881 (2009).

Koth et al., "Molecular basis for negative regulation of the glucagon receptor," *Proc. Natl. Acad. Sci. USA*, 109(36):14393-14398 (2012).

Longuet et al., "Liver-specific disruption of the murine glucagon receptor produces α-cell hyperplasia: evidence for a circulating α-cell growth factor," *Diabetes*, 62:1196-1205 (2013).

Mukund et al., "Inhibitory mechanism of an allosteric antibody targeting the glucagon receptor," *J. Biol. Chem.*, 288(50):36168-36178 (2013).

Okamoto et al., "Glucagon Receptor Blockade With a Human Antibody Normalizes Blood Glucose in Diabetic Mice and Monkeys," *Endocrinology*, 156(8):2781-2794 (2015).

Scheen et al., "Investigational glucagon receptor antagonists in Phase I and II clinical trials for diabetes," *Expert. Opin. Investig. Drugs*, 26(12):1373-1389 (2017).

Sloop et al., "Hepatic and glucagon-like peptide-1-mediated reversal of diabetes by glucagon receptor antisense oligonucleotide inhibitors," *J. Clin. Invest.*, 113(11):1571-1581 (2004).

Yan et al., "Fully Human Monoclonal Antibodies Antagonizing the Glucagon Receptor Improve Glucose Homeostasis in Mice and Monkeys," *J. Pharmacol. Exp. Ther.*, 329(1):102-111 (2009).

Yang et al., "Conformational states of the full-length glucagon receptor," *Nat. Commun.*, 6:7859 (2015).

Kostic et al., "A first-in-human pharmacodynamic and pharmacokinetic study of a fully human anti-glucagon receprot monoclonal antibody in normal healthy volunteers," Diabetes Obes. Metabl., 2017, 1-9.

GenBank Accession No. 005585314.1, "PREDICTED: glucagon receptor isoform X3 [Macaca fascicularis]" Jan. 25, 2016, 2 pages.

International Search Report and Written Opinion of the International Searching Authority in International Appl. No. PCT/US2018/015452, dated Apr. 15, 2018, 8 pages.

Leighton et al.,"A Practical Review of C-Peptide Testing in Diabetes," Jun. 2017, Diabetes Therapy, 8:475-487.

Malin et al., "β-Cell Dysfunction is Associated with Metabolic Syndrome Severity in Adults," Mar. 2014, Metabolic Syndrome and Related Disorders, 12:79-85.

Arellano et al., "Regulatory T Cell-based Therapies for Autoimmunity," Discov Med., 2016, 22(119):73-80.

Daifotis et al., "Anti-CD3 clinical trials in type 1 diabetes mellitus," Clinical Immunology, 2013, 149:268-278.

Deweerdt, "Cell Savers," Nature, May 2012, 485:54-55.

Dimeglio et al., "Type 1 Diabetes," The Lancet, 2018, 391(10138):2449-2462.

Kazda et al., "Evaluation of Efficacy and Safety of the Glucagon Receptor Antagonist LY2409021 in Patients With Type 2 Diabetes: 12- and 24-Week Phase 2 Studies," Diabetes Care, Jul. 2016, 39:1241-1249.

Kopan et al., "Approaches in Immunotherapy, Regenerative Medicine, and Bioengineering for Type 1 Diabetes," Frontiers in Immunology, Jun. 2018, 9(1354).

Kuhn et al., "Therapeutic anti-CD3 monoclonal antibodies: from bench to bedside," Immunotherapy, 2016, 8(8), 889-906.

PCT International Search Report and Written Opinion in International Appln. No. PCTUS2019/043609, dated Oct. 8, 2019, 16 pages.

Pearson et al., "Clinical Trials, Triumphs, and Tribulations of Glucagon Receptor Antagonists," Diabetes Care, 2016, 39:1075-1077.

Penaranda et al., "Anti-CD3 Therapy Promotes Tolerance by Selectively Depleting Pathogenic Cells while Preserving Regulatory T Cells," J Immunol, 2011, 187:2015-2022.

Pettus et al., "Effect of a glucagon receptor antibody (REMD-477) in type 1 diabetes: A randomized controlled trial," Diabetes, Obesity and Metabolism, 2018, 20(5):1302-1305.

Tooley et al., "New and future immunomodulatory therapy in type 1 diabetes," Trends Mol Med., Mar. 2012, 18(3):173-181.

Waldron-Lynch et al., "Immunomodulatory therapy to preserve pancreatic β-cell function in type 1 diabetes," Nature Reviews Drug Discovery, Jun. 2011, 10(6):439-452.

Wang et al., "Glucagon receptor antibody completely suppresses type 1 diabetes phenotype without insulin by disrupting a novel diabetogenic pathway," Proceedings of National Academy of Sciences PNAS, 2015, 112(8):2503-2508.

Fine et al., "Glucocorticoids Reprogram β-Cell Signaling to Preserve Insulin Secretion," Diabetes, Feb. 2018, 67(2):278-290.

Gelling et al., "Pancreatic Beta-Cell Overexpression of the Glucagon Receptor Gene Results in Enhanced Beta-Cell Function and Mass," Am J Physiol Endocrinol Metab., Sep. 2009, 297(3):E695-707.

Koizmni et al., "Sub-chronic Stimulation of Glucocorticoid Receptor Impairs and Mineralocorticoid Receptor Protects Cytosolic Ca2+ Responses to Glucose in Pancreatic Beta-Cells," J Endocrinol, May 2008, 197(2):221-9.

PCT International Preliminary Report on Patentability in International Appl. No. PCT/US2018/015452, dated Jul. 30, 2019, 6 pages.

U.S. Appl. No. 16/522,778, filed Jul. 26, 2019, Liu.

\* cited by examiner

VH Domain

| Name | | | | | | |
|---|---|---|---|---|---|---|
| Kabat | 1 | 10 | 22 | 31-----35 | 40 | 50---a-----60---65 |
| AbM | 1 | 10 | 22 | 26-----35 | 40 | 50---a-----58 65 |
| Chothia | 1 | 10 | 22 | 26-----32 | 40 | a-55 65 |
| Contact | 1 | 10 | 22 | 30-----35 | 40 | 47-----a-----58 65 |
| IMGT | 1 | 10 | 23 | 27-----38 | 41 | 56-----65 74 |
| AHon | 1 | 10 | 23 | 27 42 | | 57 76 |
| 6B5 | QVQLQQSGTELVRPGTSVKISCKAS | GFTFTNHWLG | WVKQRPGHGLEWIG | DIYPGGYINYNEKFKG |
| 3H5 | QVQLQQSGAELVKPGASVRLSCKAS | GNTFTNYWMH | WVKQRPGQGLEWIG | MIHPNSGSTHYNEKFKN |
| 5B11 | QVQLQQSGAELVKPGASVKLSCKAS | GNTFTSHWMH | WVKQRPGQGLEWIG | MSHPNSGSSNYSGKFKS |
| 1C1 | EVQLQQSGPELVKPGATVKMSCKAS | GYTFTRNVIH | WVKQKPGQGLEWIG | YINPYNDGAKYNAKFKG |
| 1C3 | EVQLQQSGPELVKPGASVKMSCKAS | GYTFTSSVMH | WVKQKPGQALEWIG | YINPYNDGTKYNENFKG |
| 1H2 | QVQLQQPGAELVKPGASVKMSCKVS | GYTFTSYWIT | WVKQRPGQGLEWIG | DIHPGGGDTNYNKKFKS |
| 4F8 | QVQLQQSGAELVRPGTSVTMSCKAS | GYTFSNYWIG | WVKQRPGHGLEWIG | DIYPGFYDNYNDKFKG |
| 13G9 | QVQLQQSGAELVKPGTSVKISCKAS | GYTFTNYWLG | WVKQRPGHGLEWIG | DIYPGGDYNNYNGKFKG |
| 14F4 | QVQLQQSGAELVRPGTSVNMSCKAT | GYTFTNYWIG | WVKQRPGHGLEWIG | DIFPGGFYSNYNEKFKG |
| 14E9 | QVQLQQSGAELVRPGTSVKMSCKAA | GYTFTNYWIG | WVKQRPGHGLEWIG | DISPGNYYTNYNAKFKD |

FIG. 1A-1

|        |    |     |        |                              |    |     |                |                 |     |                |
|--------|----|-----|--------|------------------------------|----|-----|----------------|-----------------|-----|----------------|
| Kabat  | 70 |     | 80 abc |                              | 90 |     | 95--100----102 |                 |     |                |
| AbM    | 70 |     | 80 abc |                              | 90 |     | 95--100----102 |                 |     |                |
| Chothia| 70 |     | 80 abc |                              | 90 |     | 96--100----101 |                 |     |                |
| Contact| 70 |     | 80 abc |                              | 90 |     | ---100----101  |                 |     |                |
| IMGT   |    | 75  |        | 89                           |    | 93- |------117       |                 |     |                |
| AHon   |    |     |        |                              |    |     | 105----------- |                 |     |                |
|        |    |     |        |                              |    |     | 106 109    138 |                 |     |                |
| 6B5    |    |     |        | KATLTADTSSSTAYMQLSSLITSEDSAVYFCAR | HTNY-----GSDY | WGQGTTLTVSS | (SEQ ID NO:25)  |
| 3H5    |    |     |        | KATLTVDKSSNTAYMQLSSLITSEDSAVYYCGA | TADY------VMDY | WGQGTSVTVSS | (SEQ ID NO:51)  |
| 5B11   |    |     |        | KATLTVDRSSTAYMQLNSLITSEDSAVYYCAR  | TDYDY-----DGDY | WGQGTTLTVSS | (SEQ ID NO:71)  |
| 1C1    |    |     |        | KATVTSDKSSSTAYMELSSLITSEDSAVYYCAR | WGNYEDF--AMDY  | WGQGTSVTVSS | (SEQ ID NO:97)  |
| 1C3    |    |     |        | KATLTSDRSSTTAYMELSSLITSEDSAVYYCVT | GAGYDRGPMAMDY  | WGQGTSVTVSS | (SEQ ID NO:122) |
| 1H2    |    |     |        | KATLTVDTSSSTAYMQLSSLITSEDSAVYHCTS | DDNYV----GFTY  | WGQGTLVTVSA | (SEQ ID NO:144) |
| 4F8    |    |     |        | KATLTTDTSSSTAYMQLSSLITSEDSAIYYCTR | SGGLPGA--GFTY  | WGQGTLVTVSA | (SEQ ID NO:164) |
| 13G9   |    |     |        | KATLTADTSSSTAYIQLSSLITSEDSAVYFCVR | SD-------DGYS  | WGQGTTLTVSS | (SEQ ID NO:188) |
| 14F4   |    |     |        | KATLTTDTSSSTGYMQLSSLITSEDSAIYYCAR | IWDR-----GFDY  | WGQGTTLTVSS | (SEQ ID NO:203) |
| 14E9   |    |     |        | KVSLTADTSSSTAYMQLSSLITSEDSAIYYCAR | YD-------EFAY  | WGQGTLVTVSA | (SEQ ID NO:218) |

FIG. 1A-2

| VL Domain | | | | | | | |
|---|---|---|---|---|---|---|---|
| Kabat | 1 | 10 | 20 | 24-27abcde----34 | 40 | 50-----56 | |
| AbM | 1 | 10 | 20 | 24----30abcde---34 | 40 | 50-----56 | |
| Chothia | 1 | 10 | 20 | 26--30abcde-32 | 40 | 50-- | |
| Contact | 1 | 10 | 20 | 30abcde-----36 | 40 | 46-------55 | |
| IMGT | 1 | | 23 | 27------38 41 | | 56-65 69 | |
| | | | | | | | |
| AHon | 1 | | 23 | 42 | | 58 72 | |
| 6B5 | DVLMTQIPLSLPVSLGDQASISC | | | RSSQSIVDSYGN-TFLE | WYLQKPGQSPKLLIY | KVSNRLS | |
| 3H5 | DIVLTQTPLSLPVNIGDQASISC | | | KSTKSLLNSDGF-TYLD | WYLQKPGQSPQLLIN | LVSNRFS | |
| 5B11 | DVVLTQTPLSLPVNIGDQASISC | | | KSSKSLLNSDGL-TYLD | WYLQKPGQSPQLLIY | LVSNRFS | |
| 1C1 | NIVLTQSPPSLAVSLGQRATISC | | | RASESVDIYGN--SYMH | WYQQKPGQPPKLLIY | LASNLES | |
| 1C3 | NIVLTQSPASLAVSLGQRATISC | | | RASESVDSYGD--SFVH | WYQQKPGQPPKLLIY | FASNLES | |
| 1H2 | DVLMTQTPLSLPVSLGDQASISC | | | RSSQTIHSDGN-TYLE | WYLQKPGQSPILLIY | KVSNRFS | |
| 4F8 | DVLMTQTPLSLPVSLGDQASISC | | | RSSQHIVYSDGN-TYLE | WYLQKPGQSPKLLIY | KVSNRFS | |
| 13G9 | DVLMTQSPLSLPVSLGDQASISC | | | RSSQSIVDSYGN-TYLE | WYQQKPGQSPTLLIY | KVSNRFA | |
| 14F4 | DVLMTQTPLSLPVSLGDQASISC | | | RSSQSIVDSYGN-TYLE | WYLQKPGQSPKLLIY | KVSNRFS | |
| 14E9 | DVLMTQTPLSLSVSLGDQASISC | | | RSSQSIVHSDGN-TYLE | WYLQKPGQSPKLLIY | KVSNRFS | |

FIG. 1B-1

| | | | | | |
|---|---|---|---|---|---|
| Kabat | 60 | 70 | 80 | 89------97 | |
| AbM | 60 | 70 | 80 | 89------97 | |
| Chothia | 60 | 70 | 80 | 91------96 | |
| Contact | 60 | 70 | 80 | 89------96 | |
| IMGT | 70 | 89 | | 105------117 | |
| AHon | 73 | 91 | | 107 138 | |
| 6B5 | GVPDRFSGTGAGTDFTLKISRVEAEDLGIYYC | | | FQGSHVPWT | FGGGTKLEIK (SEQ ID NO:26) |
| 3H5 | GVPDRFSGSGSGTEFILKISRVEAEDLGVYYC | | | FQSNFLPLT | FGAGTKLELK (SEQ ID NO:52) |
| 5B11 | GVPDRFSGSGSGTDFTLKISRVEADDLGVYYC | | | FQSNFLPLT | FGAGTKLEIK (SEQ ID NO:72) |
| 1C1 | GVPARFSGSGSRTEFSLTIDPVEAGDAATYYC | | | QQNNEDPFT | FGGGTKLEIK (SEQ ID NO:98) |
| 1C3 | GVPARFSGSGSGSRTDFTLTIDPVEADDTATYYC | | | QQNNEVPFT | FGSGTKLELK (SEQ ID NO:123) |
| 1H2 | GVPDRFSGSGSGTDFTLKISRVEAEDLGVYYC | | | FQGSHVPWT | FGGGTKLEIK (SEQ ID NO:145) |
| 4F8 | GVPDRFSGSGSGTDFTLEISRVEAEDLGVYYC | | | FQGSHVPWT | FGGGTKLEIK (SEQ ID NO:165) |
| 13G9 | GVPDRFSGSGSGTDFTLKISRVEAEDLGVYYC | | | FQGSHIPWT | FGGGTKVEIK (SEQ ID NO:189) |
| 14F4 | GVPDRFSGSGSGTDFTLKISRVEAERDRGLYYC | | | FQGSHVPYT | FGGGTKLEIK (SEQ ID NO:204) |
| 14E9 | GVPDRFSGSGSGTDFTLKISRVEAEDLGVYYC | | | FQGSHVPWT | FGGGTKLEIK (SEQ ID NO:219) |

FIG. 1B-2

SEQUENCE LISTING

<160> NUMBER OF SEQ ID NOS: 238

<210> SEQ ID NO 1
<211> LENGTH: 10
<212> TYPE: PRT
<213> ORGANISM: Artificial Sequence
<220> FEATURE:
<223> OTHER INFORMATION: CDR Sequence

<400> SEQUENCE: 1

Gly Phe Thr Phe Thr Asn His Trp Leu Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR Sequence

<400> SEQUENCE: 2

Asp Ile Tyr Pro Gly Gly Tyr Tyr Ile Asn Tyr Asn Glu Lys Phe Lys
1               5                   10                  15

Gly

<210> SEQ ID NO 3
<211> LENGTH: 8

```
<212> TYPE: PRT
<213> ORGANISM: Artificial Sequence
<220> FEATURE:
<223> OTHER INFORMATION: CDR Sequence

<400> SEQUENCE: 3

His Thr Asn Tyr Gly Ser Asp Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: CDR Sequence

<400> SEQUENCE: 4

Arg Ser Ser Gln Ser Ile Val Asp Ser Tyr Gly Asn Thr Phe Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR Sequence

<400> SEQUENCE: 5

Lys Val Ser Asn Arg Leu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR Sequence

<400> SEQUENCE: 6

Phe Gln Gly Ser His Val Pro Trp Thr
1               5

<210> SEQ ID NO 7
<211> LENGTH: 8
<212> TYPE: PRT
<213> ORGANISM: Artificial Sequence
<220> FEATURE:
<223> OTHER INFORMATION: CDR Sequence

<400> SEQUENCE: 7

Gly Phe Thr Phe Thr Asn His Trp
1               5

<210> SEQ ID NO 8
<211> LENGTH: 8
<212> TYPE: PRT
<213> ORGANISM: Artificial Sequence
<220> FEATURE:
<223> OTHER INFORMATION: CDR Sequence

<400> SEQUENCE: 8

Ile Tyr Pro Gly Gly Tyr Tyr Ile
1               5

<210> SEQ ID NO 9
<211> LENGTH: 10
<212> TYPE: PRT
```

```
<213> ORGANISM: Artificial Sequence
<220> FEATURE:
<223> OTHER INFORMATION: CDR Sequence

<400> SEQUENCE: 9

Ala Arg His Thr Asn Tyr Gly Ser Asp Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: CDR Sequence

<400> SEQUENCE: 10

Gln Ser Ile Val Asp Ser Tyr Gly Asn Thr Phe
1               5                   10

<210> SEQ ID NO 11
<211> LENGTH: 3
<212> TYPE: PRT
<213> ORGANISM: Artificial Sequence
<220> FEATURE:
<223> OTHER INFORMATION: CDR Sequence

<400> SEQUENCE: 11

Lys Val Ser
1

<210> SEQ ID NO 12
<211> LENGTH: 5
<212> TYPE: PRT
<213> ORGANISM: Artificial Sequence
<220> FEATURE:
<223> OTHER INFORMATION: CDR Sequence

<400> SEQUENCE: 12

Asn His Trp Leu Gly
1               5

<210> SEQ ID NO 13
<211> LENGTH: 7
<212> TYPE: PRT
<213> ORGANISM: Artificial Sequence
<220> FEATURE:
<223> OTHER INFORMATION: CDR Sequence

<400> SEQUENCE: 13

Gly Phe Thr Phe Thr Asn His
1               5

<210> SEQ ID NO 14
<211> LENGTH: 4
<212> TYPE: PRT
<213> ORGANISM: Artificial Sequence
<220> FEATURE:
<223> OTHER INFORMATION: CDR Sequence

<400> SEQUENCE: 14

Pro Gly Gly Tyr
1

<210> SEQ ID NO 15
<211> LENGTH: 6
<212> TYPE: PRT
<213> ORGANISM: Artificial Sequence
```

```
<220> FEATURE:
<223> OTHER INFORMATION: CDR Sequence

<400> SEQUENCE: 15

Thr Asn Tyr Gly Ser Asp
1               5

<210> SEQ ID NO 16
<211> LENGTH: 12
<212> TYPE: PRT
<213> ORGANISM: Artificial Sequence
<220> FEATURE:
<223> OTHER INFORMATION: CDR Sequence

<400> SEQUENCE: 16

Ser Gln Ser Ile Val Asp Ser Tyr Gly Asn Thr Phe
1               5                   10

<210> SEQ ID NO 17
<211> LENGTH: 6
<212> TYPE: PRT
<213> ORGANISM: Artificial Sequence
<220> FEATURE:
<223> OTHER INFORMATION: CDR Sequence

<400> SEQUENCE: 17

Gly Ser His Val Pro Trp
1               5

<210> SEQ ID NO 18
<211> LENGTH: 6
<212> TYPE: PRT
<213> ORGANISM: Artificial Sequence
<220> FEATURE:
<223> OTHER INFORMATION: CDR Sequence

<400> SEQUENCE: 18

Thr Asn His Trp Leu Gly
1               5

<210> SEQ ID NO 19
<211> LENGTH: 13
<212> TYPE: PRT
<213> ORGANISM: Artificial Sequence
<220> FEATURE:
<223> OTHER INFORMATION: CDR Sequence

<400> SEQUENCE: 19

Trp Ile Gly Asp Ile Tyr Pro Gly Gly Tyr Tyr Ile Asn
1               5                   10

<210> SEQ ID NO 20
<211> LENGTH: 9
<212> TYPE: PRT
<213> ORGANISM: Artificial Sequence
<220> FEATURE:
<223> OTHER INFORMATION: CDR Sequence

<400> SEQUENCE: 20

Ala Arg His Thr Asn Tyr Gly Ser Asp
1               5

<210> SEQ ID NO 21
<211> LENGTH: 12
<212> TYPE: PRT
<213> ORGANISM: Artificial Sequence
<220> FEATURE:
```

```
<223> OTHER INFORMATION: CDR Sequence

<400> SEQUENCE: 21

Val Asp Ser Tyr Gly Asn Thr Phe Leu Glu Trp Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: CDR Sequence

<400> SEQUENCE: 22

Leu Leu Ile Tyr Lys Val Ser Asn Arg Leu
1               5                   10

<210> SEQ ID NO 23
<211> LENGTH: 8
<212> TYPE: PRT
<213> ORGANISM: Artificial Sequence
<220> FEATURE:
<223> OTHER INFORMATION: CDR Sequence

<400> SEQUENCE: 23

Phe Gln Gly Ser His Val Pro Trp
1               5

<210> SEQ ID NO 24
<211> LENGTH: 10
<212> TYPE: PRT
<213> ORGANISM: Artificial Sequence
<220> FEATURE:
<223> OTHER INFORMATION: CDR Sequence

<400> SEQUENCE: 24

Asp Ile Tyr Pro Gly Gly Tyr Tyr Ile Asn
1               5                   10

<210> SEQ ID NO 25
<211> LENGTH: 117
<212> TYPE: PRT
<213> ORGANISM: Artificial Sequence
<220> FEATURE:
<223> OTHER INFORMATION: 6B5 Heavy chain variable region

<400> SEQUENCE: 25

Gln Val Gln Leu Gln Gln Ser Gly Thr Glu Leu Val Arg Pro Gly Thr
1               5                   10                  15

Ser Val Lys Ile Ser Cys Lys Ala Ser Gly Phe Thr Phe Thr Asn His
                20                  25                  30

Trp Leu Gly Trp Val Lys Gln Arg Pro Gly His Gly Leu Glu Trp Ile
            35                  40                  45

Gly Asp Ile Tyr Pro Gly Gly Tyr Tyr Ile Asn Tyr Asn Glu Lys Phe
        50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg His Thr Asn Tyr Gly Ser Asp Tyr Trp Gly Gln Gly Thr Thr
            100                 105                 110

Leu Thr Val Ser Ser
            115
```

<210> SEQ ID NO 26
<211> LENGTH: 112
<212> TYPE: PRT
<213> ORGANISM: Artificial Sequence
<220> FEATURE:
<223> OTHER INFORMATION: 6B5 Light chain variable region

<400> SEQUENCE: 26

```
Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val Asp Ser
            20                  25                  30

Tyr Gly Asn Thr Phe Leu Glu Trp Tyr Leu Gln Lys Pro Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Thr Gly Ala Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 27
<211> LENGTH: 10
<212> TYPE: PRT
<213> ORGANISM: Artificial Sequence
<220> FEATURE:
<223> OTHER INFORMATION: CDR Sequence

<400> SEQUENCE: 27

```
Gly Asn Thr Phe Thr Asn Tyr Trp Met His
1               5                   10
```

<210> SEQ ID NO 28
<211> LENGTH: 17
<212> TYPE: PRT
<213> ORGANISM: Artificial Sequence
<220> FEATURE:
<223> OTHER INFORMATION: CDR Sequence

<400> SEQUENCE: 28

```
Met Ile His Pro Asn Ser Gly Ser Thr His Tyr Asn Glu Lys Phe Lys
1               5                   10                  15

Asn
```

<210> SEQ ID NO 29
<211> LENGTH: 8
<212> TYPE: PRT
<213> ORGANISM: Artificial Sequence
<220> FEATURE:
<223> OTHER INFORMATION: CDR Sequence

<400> SEQUENCE: 29

```
Thr Ala Asp Tyr Val Met Asp Tyr
1               5
```

<210> SEQ ID NO 30
<211> LENGTH: 16
<212> TYPE: PRT
<213> ORGANISM: Artificial Sequence
<220> FEATURE:

```
<223> OTHER INFORMATION: CDR Sequence

<400> SEQUENCE: 30

Lys Ser Thr Lys Ser Leu Leu Asn Ser Asp Gly Phe Thr Tyr Leu Asp
1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: CDR Sequence

<400> SEQUENCE: 31

Leu Val Ser Asn Arg Phe Ser
1               5

<210> SEQ ID NO 32
<211> LENGTH: 9
<212> TYPE: PRT
<213> ORGANISM: Artificial Sequence
<220> FEATURE:
<223> OTHER INFORMATION: CDR Sequence

<400> SEQUENCE: 32

Phe Gln Ser Asn Phe Leu Pro Leu Thr
1               5

<210> SEQ ID NO 33
<211> LENGTH: 8
<212> TYPE: PRT
<213> ORGANISM: Artificial Sequence
<220> FEATURE:
<223> OTHER INFORMATION: CDR Sequence

<400> SEQUENCE: 33

Gly Asn Thr Phe Thr Asn Tyr Trp
1               5

<210> SEQ ID NO 34
<211> LENGTH: 8
<212> TYPE: PRT
<213> ORGANISM: Artificial Sequence
<220> FEATURE:
<223> OTHER INFORMATION: CDR Sequence

<400> SEQUENCE: 34

Ile His Pro Asn Ser Gly Ser Thr
1               5

<210> SEQ ID NO 35
<211> LENGTH: 10
<212> TYPE: PRT
<213> ORGANISM: Artificial Sequence
<220> FEATURE:
<223> OTHER INFORMATION: CDR Sequence

<400> SEQUENCE: 35

Gly Ala Thr Ala Asp Tyr Val Met Asp Tyr
1               5                   10

<210> SEQ ID NO 36
<211> LENGTH: 11
<212> TYPE: PRT
<213> ORGANISM: Artificial Sequence
<220> FEATURE:
<223> OTHER INFORMATION: CDR Sequence
```

<400> SEQUENCE: 36

Lys Ser Leu Leu Asn Ser Asp Gly Phe Thr Tyr
1               5                   10

<210> SEQ ID NO 37
<211> LENGTH: 3
<212> TYPE: PRT
<213> ORGANISM: Artificial Sequence
<220> FEATURE:
<223> OTHER INFORMATION: CDR Sequence

<400> SEQUENCE: 37

Leu Val Ser
1

<210> SEQ ID NO 38
<211> LENGTH: 5
<212> TYPE: PRT
<213> ORGANISM: Artificial Sequence
<220> FEATURE:
<223> OTHER INFORMATION: CDR Sequence

<400> SEQUENCE: 38

Asn Tyr Trp Met His
1               5

<210> SEQ ID NO 39
<211> LENGTH: 7
<212> TYPE: PRT
<213> ORGANISM: Artificial Sequence
<220> FEATURE:
<223> OTHER INFORMATION: CDR Sequence

<400> SEQUENCE: 39

Gly Asn Thr Phe Thr Asn Tyr
1               5

<210> SEQ ID NO 40
<211> LENGTH: 4
<212> TYPE: PRT
<213> ORGANISM: Artificial Sequence
<220> FEATURE:
<223> OTHER INFORMATION: CDR Sequence

<400> SEQUENCE: 40

Pro Asn Ser Gly
1

<210> SEQ ID NO 41
<211> LENGTH: 6
<212> TYPE: PRT
<213> ORGANISM: Artificial Sequence
<220> FEATURE:
<223> OTHER INFORMATION: CDR Sequence

<400> SEQUENCE: 41

Ala Asp Tyr Val Met Asp
1               5

<210> SEQ ID NO 42
<211> LENGTH: 11
<212> TYPE: PRT
<213> ORGANISM: Artificial Sequence
<220> FEATURE:
<223> OTHER INFORMATION: CDR Sequence

```
<400> SEQUENCE: 42

Thr Lys Ser Leu Asn Ser Asp Gly Phe Thr Tyr
1               5                   10

<210> SEQ ID NO 43
<211> LENGTH: 6
<212> TYPE: PRT
<213> ORGANISM: Artificial Sequence
<220> FEATURE:
<223> OTHER INFORMATION: CDR Sequence

<400> SEQUENCE: 43

Ser Asn Phe Leu Pro Leu
1               5

<210> SEQ ID NO 44
<211> LENGTH: 6
<212> TYPE: PRT
<213> ORGANISM: Artificial Sequence
<220> FEATURE:
<223> OTHER INFORMATION: CDR Sequence

<400> SEQUENCE: 44

Thr Asn Tyr Trp Met His
1               5

<210> SEQ ID NO 45
<211> LENGTH: 13
<212> TYPE: PRT
<213> ORGANISM: Artificial Sequence
<220> FEATURE:
<223> OTHER INFORMATION: CDR Sequence

<400> SEQUENCE: 45

Trp Ile Gly Met Ile His Pro Asn Ser Gly Ser Thr His
1               5                   10

<210> SEQ ID NO 46
<211> LENGTH: 9
<212> TYPE: PRT
<213> ORGANISM: Artificial Sequence
<220> FEATURE:
<223> OTHER INFORMATION: CDR Sequence

<400> SEQUENCE: 46

Gly Ala Thr Ala Asp Tyr Val Met Asp
1               5

<210> SEQ ID NO 47
<211> LENGTH: 12
<212> TYPE: PRT
<213> ORGANISM: Artificial Sequence
<220> FEATURE:
<223> OTHER INFORMATION: CDR Sequence

<400> SEQUENCE: 47

Leu Asn Ser Asp Gly Phe Thr Tyr Leu Asp Trp Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: CDR Sequence

<400> SEQUENCE: 48
```

```
Leu Leu Ile Asn Leu Val Ser Asn Arg Phe
1               5                   10

<210> SEQ ID NO 49
<211> LENGTH: 8
<212> TYPE: PRT
<213> ORGANISM: Artificial Sequence
<220> FEATURE:
<223> OTHER INFORMATION: CDR Sequence

<400> SEQUENCE: 49

Phe Gln Ser Asn Phe Leu Pro Leu
1               5

<210> SEQ ID NO 50
<211> LENGTH: 10
<212> TYPE: PRT
<213> ORGANISM: Artificial Sequence
<220> FEATURE:
<223> OTHER INFORMATION: CDR Sequence

<400> SEQUENCE: 50

Met Ile His Pro Asn Ser Gly Ser Thr His
1               5                   10

<210> SEQ ID NO 51
<211> LENGTH: 117
<212> TYPE: PRT
<213> ORGANISM: Artificial Sequence
<220> FEATURE:
<223> OTHER INFORMATION: 3H5 Heavy chain variable region

<400> SEQUENCE: 51

Gln Val Gln Leu Gln Gln Ser Gly Ala Glu Leu Val Lys Pro Gly Ala
1               5                   10                  15

Ser Val Arg Leu Ser Cys Lys Ala Ser Gly Asn Thr Phe Thr Asn Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr His Tyr Asn Glu Lys Phe
    50                  55                  60

Lys Asn Lys Ala Thr Leu Thr Val Asp Lys Ser Ser Asn Thr Ala Tyr
65                  70                  75                  80

Met Gln Leu Ser Gly Leu Thr Ser Glu Asp Ser Ala Val Tyr Tyr Cys
                85                  90                  95

Gly Ala Thr Ala Asp Tyr Val Met Asp Tyr Trp Gly Gln Gly Thr Ser
                100                 105                 110

Val Thr Val Ser Ser
        115

<210> SEQ ID NO 52
<211> LENGTH: 112
<212> TYPE: PRT
<213> ORGANISM: Artificial Sequence
<220> FEATURE:
<223> OTHER INFORMATION: 3H5 Light chain variable region

<400> SEQUENCE: 52

Asp Ile Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
            20                  25                  30
```

```
Asp Gly Phe Thr Tyr Leu Asp Trp Tyr Leu Gln Lys Pro Gly Gln Ser
        35                  40                  45

Pro Gln Leu Leu Ile Asn Leu Val Ser Asn Arg Phe Ser Gly Val Pro
    50                  55                  60

Asp Arg Phe Ser Gly Ser Gly Ser Gly Thr Glu Phe Ile Leu Lys Ile
65                  70                  75                  80

Ser Arg Val Glu Ala Glu Asp Leu Gly Val Tyr Tyr Cys Phe Gln Ser
                85                  90                  95

Asn Phe Leu Pro Leu Thr Phe Gly Ala Gly Thr Lys Leu Glu Leu Lys
            100                 105                 110

<210> SEQ ID NO 53
<211> LENGTH: 10
<212> TYPE: PRT
<213> ORGANISM: Artificial Sequence
<220> FEATURE:
<223> OTHER INFORMATION: CDR Sequence

<400> SEQUENCE: 53

Gly Asn Thr Phe Thr Ser His Trp Met His
1               5                   10

<210> SEQ ID NO 54
<211> LENGTH: 17
<212> TYPE: PRT
<213> ORGANISM: Artificial Sequence
<220> FEATURE:
<223> OTHER INFORMATION: CDR Sequence

<400> SEQUENCE: 54

Met Ser His Pro Asn Ser Gly Ser Ser Asn Tyr Ser Gly Lys Phe Lys
1               5                   10                  15

Ser

<210> SEQ ID NO 55
<211> LENGTH: 9
<212> TYPE: PRT
<213> ORGANISM: Artificial Sequence
<220> FEATURE:
<223> OTHER INFORMATION: CDR Sequence

<400> SEQUENCE: 55

Thr Asp Tyr Asp Tyr Asp Gly Asp Tyr
1               5

<210> SEQ ID NO 56
<211> LENGTH: 16
<212> TYPE: PRT
<213> ORGANISM: Artificial Sequence
<220> FEATURE:
<223> OTHER INFORMATION: CDR Sequence

<400> SEQUENCE: 56

Lys Ser Ser Lys Ser Leu Leu Asn Ser Asp Gly Leu Thr Tyr Leu Asp
1               5                   10                  15

<210> SEQ ID NO 57
<211> LENGTH: 8
<212> TYPE: PRT
<213> ORGANISM: Artificial Sequence
<220> FEATURE:
<223> OTHER INFORMATION: CDR Sequence

<400> SEQUENCE: 57
```

Gly Asn Thr Phe Thr Ser His Trp
1               5

<210> SEQ ID NO 58
<211> LENGTH: 9
<212> TYPE: PRT
<213> ORGANISM: Artificial Sequence
<220> FEATURE:
<223> OTHER INFORMATION: CDR Sequence

<400> SEQUENCE: 58

Ser His Pro Asn Ser Gly Ser Ser Asn
1               5

<210> SEQ ID NO 59
<211> LENGTH: 11
<212> TYPE: PRT
<213> ORGANISM: Artificial Sequence
<220> FEATURE:
<223> OTHER INFORMATION: CDR Sequence

<400> SEQUENCE: 59

Ala Arg Thr Asp Tyr Asp Tyr Asp Gly Asp Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: CDR Sequence

<400> SEQUENCE: 60

Lys Ser Leu Leu Asn Ser Asp Gly Leu Thr Tyr
1               5                   10

<210> SEQ ID NO 61
<211> LENGTH: 5
<212> TYPE: PRT
<213> ORGANISM: Artificial Sequence
<220> FEATURE:
<223> OTHER INFORMATION: CDR Sequence

<400> SEQUENCE: 61

Ser His Trp Met His
1               5

<210> SEQ ID NO 62
<211> LENGTH: 7
<212> TYPE: PRT
<213> ORGANISM: Artificial Sequence
<220> FEATURE:
<223> OTHER INFORMATION: CDR Sequence

<400> SEQUENCE: 62

Gly Asn Thr Phe Thr Ser His
1               5

<210> SEQ ID NO 63
<211> LENGTH: 7
<212> TYPE: PRT
<213> ORGANISM: Artificial Sequence
<220> FEATURE:
<223> OTHER INFORMATION: CDR Sequence

<400> SEQUENCE: 63

Asp Tyr Asp Tyr Asp Gly Asp
1               5

<210> SEQ ID NO 64
<211> LENGTH: 12
<212> TYPE: PRT
<213> ORGANISM: Artificial Sequence
<220> FEATURE:
<223> OTHER INFORMATION: CDR Sequence

<400> SEQUENCE: 64

Ser Lys Ser Leu Leu Asn Ser Asp Gly Leu Thr Tyr
1               5                   10

<210> SEQ ID NO 65
<211> LENGTH: 6
<212> TYPE: PRT
<213> ORGANISM: Artificial Sequence
<220> FEATURE:
<223> OTHER INFORMATION: CDR Sequence

<400> SEQUENCE: 65

Thr Ser His Trp Met His
1               5

<210> SEQ ID NO 66
<211> LENGTH: 13
<212> TYPE: PRT
<213> ORGANISM: Artificial Sequence
<220> FEATURE:
<223> OTHER INFORMATION: CDR Sequence

<400> SEQUENCE: 66

Trp Ile Gly Met Ser His Pro Asn Ser Gly Ser Ser Asn
1               5                   10

<210> SEQ ID NO 67
<211> LENGTH: 10
<212> TYPE: PRT
<213> ORGANISM: Artificial Sequence
<220> FEATURE:
<223> OTHER INFORMATION: CDR Sequence

<400> SEQUENCE: 67

Ala Arg Thr Asp Tyr Asp Tyr Asp Gly Asp
1               5                   10

<210> SEQ ID NO 68
<211> LENGTH: 12
<212> TYPE: PRT
<213> ORGANISM: Artificial Sequence
<220> FEATURE:
<223> OTHER INFORMATION: CDR Sequence

<400> SEQUENCE: 68

Leu Asn Ser Asp Gly Leu Thr Tyr Leu Asp Trp Tyr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: CDR Sequence

<400> SEQUENCE: 69

Leu Leu Ile Tyr Leu Val Ser Asn Arg Phe

```
1               5                    10
```

<210> SEQ ID NO 70
<211> LENGTH: 10
<212> TYPE: PRT
<213> ORGANISM: Artificial Sequence
<220> FEATURE:
<223> OTHER INFORMATION: CDR Sequence

<400> SEQUENCE: 70

Met Ser His Pro Asn Ser Gly Ser Ser Asn
1               5                   10

<210> SEQ ID NO 71
<211> LENGTH: 118
<212> TYPE: PRT
<213> ORGANISM: Artificial Sequence
<220> FEATURE:
<223> OTHER INFORMATION: 5B11 Heavy Chain variable region

<400> SEQUENCE: 71

Gln Val Gln Leu Gln Gln Ser Gly Ala Glu Leu Val Lys Pro Gly Ala
1               5                   10                  15

Ser Val Lys Leu Ser Cys Lys Ala Ser Gly Asn Thr Phe Thr Ser His
            20                  25                  30

Trp Met His Trp Val Lys Gln Arg Pro Gly Gln Gly Leu Glu Trp Ile
        35                  40                  45

Gly Met Ser His Pro Asn Ser Gly Ser Ser Asn Tyr Ser Gly Lys Phe
    50                  55                  60

Lys Ser Lys Ala Thr Leu Thr Val Asp Arg Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Thr Asp Tyr Asp Tyr Asp Gly Asp Tyr Trp Gly Gln Gly Thr
            100                 105                 110

Thr Leu Thr Val Ser Ser
        115

<210> SEQ ID NO 72
<211> LENGTH: 112
<212> TYPE: PRT
<213> ORGANISM: Artificial Sequence
<220> FEATURE:
<223> OTHER INFORMATION: 5B11 Light Chain variable region

<400> SEQUENCE: 72

Asp Val Val Leu Thr Gln Thr Pro Leu Ser Leu Pro Val Asn Ile Gly
1               5                   10                  15

Asp Gln Ala Ser Ile Ser Cys Lys Ser Ser Lys Ser Leu Leu Asn Ser
            20                  25                  30

Asp Gly Leu Thr Tyr Leu Asp Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Tyr Cys Phe Gln Ser
                85                  90                  95

Asn Phe Leu Pro Leu Thr Phe Gly Ala Gly Thr Lys Leu Glu Leu Lys
            100                 105                 110

<210> SEQ ID NO 73
<211> LENGTH: 10
<212> TYPE: PRT
<213> ORGANISM: Artificial Sequence
<220> FEATURE:
<223> OTHER INFORMATION: CDR Sequence

<400> SEQUENCE: 73

Gly Tyr Thr Phe Thr Arg Asn Val Ile His
1               5                   10

<210> SEQ ID NO 74
<211> LENGTH: 17
<212> TYPE: PRT
<213> ORGANISM: Artificial Sequence
<220> FEATURE:
<223> OTHER INFORMATION: CDR Sequence

<400> SEQUENCE: 74

Tyr Ile Asn Pro Tyr Asn Asp Gly Ala Lys Tyr Asn Ala Lys Phe Lys
1               5                   10                  15

Gly

<210> SEQ ID NO 75
<211> LENGTH: 11
<212> TYPE: PRT
<213> ORGANISM: Artificial Sequence
<220> FEATURE:
<223> OTHER INFORMATION: CDR Sequence

<400> SEQUENCE: 75

Trp Gly Asn Tyr Glu Asp Phe Ala Met Asp Tyr
1               5                   10

<210> SEQ ID NO 76
<211> LENGTH: 15
<212> TYPE: PRT
<213> ORGANISM: Artificial Sequence
<220> FEATURE:
<223> OTHER INFORMATION: CDR Sequence

<400> SEQUENCE: 76

Arg Ala Ser Glu Ser Val Asp Ile Tyr Gly Asn Ser Tyr Met His
1               5                   10                  15

<210> SEQ ID NO 77
<211> LENGTH: 7
<212> TYPE: PRT
<213> ORGANISM: Artificial Sequence
<220> FEATURE:
<223> OTHER INFORMATION: CDR Sequence

<400> SEQUENCE: 77

Leu Ala Ser Asn Leu Glu Ser
1               5

<210> SEQ ID NO 78
<211> LENGTH: 9
<212> TYPE: PRT
<213> ORGANISM: Artificial Sequence
<220> FEATURE:
<223> OTHER INFORMATION: CDR Sequence

<400> SEQUENCE: 78

Gln Gln Asn Asn Glu Asp Pro Phe Thr

```
<210> SEQ ID NO 79
<211> LENGTH: 8
<212> TYPE: PRT
<213> ORGANISM: Artificial Sequence
<220> FEATURE:
<223> OTHER INFORMATION: CDR Sequence

<400> SEQUENCE: 79

Gly Tyr Thr Phe Thr Arg Asn Val
1               5

<210> SEQ ID NO 80
<211> LENGTH: 8
<212> TYPE: PRT
<213> ORGANISM: Artificial Sequence
<220> FEATURE:
<223> OTHER INFORMATION: CDR Sequence

<400> SEQUENCE: 80

Ile Asn Pro Tyr Asn Asp Gly Ala
1               5

<210> SEQ ID NO 81
<211> LENGTH: 13
<212> TYPE: PRT
<213> ORGANISM: Artificial Sequence
<220> FEATURE:
<223> OTHER INFORMATION: CDR Sequence

<400> SEQUENCE: 81

Ala Arg Trp Gly Asn Tyr Glu Asp Phe Ala Met Asp Tyr
1               5                   10

<210> SEQ ID NO 82
<211> LENGTH: 10
<212> TYPE: PRT
<213> ORGANISM: Artificial Sequence
<220> FEATURE:
<223> OTHER INFORMATION: CDR Sequence

<400> SEQUENCE: 82

Glu Ser Val Asp Ile Tyr Gly Asn Ser Tyr
1               5                   10

<210> SEQ ID NO 83
<211> LENGTH: 3
<212> TYPE: PRT
<213> ORGANISM: Artificial Sequence
<220> FEATURE:
<223> OTHER INFORMATION: CDR Sequence

<400> SEQUENCE: 83

Leu Ala Ser
1

<210> SEQ ID NO 84
<211> LENGTH: 5
<212> TYPE: PRT
<213> ORGANISM: Artificial Sequence
<220> FEATURE:
<223> OTHER INFORMATION: CDR Sequence

<400> SEQUENCE: 84

Arg Asn Val Ile His
1               5
```

<210> SEQ ID NO 85
<211> LENGTH: 7
<212> TYPE: PRT
<213> ORGANISM: Artificial Sequence
<220> FEATURE:
<223> OTHER INFORMATION: CDR Sequence

<400> SEQUENCE: 85

Gly Tyr Thr Phe Thr Arg Asn
1               5

<210> SEQ ID NO 86
<211> LENGTH: 4
<212> TYPE: PRT
<213> ORGANISM: Artificial Sequence
<220> FEATURE:
<223> OTHER INFORMATION: CDR Sequence

<400> SEQUENCE: 86

Pro Tyr Asn Asp
1

<210> SEQ ID NO 87
<211> LENGTH: 9
<212> TYPE: PRT
<213> ORGANISM: Artificial Sequence
<220> FEATURE:
<223> OTHER INFORMATION: CDR Sequence

<400> SEQUENCE: 87

Gly Asn Tyr Glu Asp Phe Ala Met Asp
1               5

<210> SEQ ID NO 88
<211> LENGTH: 11
<212> TYPE: PRT
<213> ORGANISM: Artificial Sequence
<220> FEATURE:
<223> OTHER INFORMATION: CDR Sequence

<400> SEQUENCE: 88

Ser Glu Ser Val Asp Ile Tyr Gly Asn Ser Tyr
1               5                   10

<210> SEQ ID NO 89
<211> LENGTH: 6
<212> TYPE: PRT
<213> ORGANISM: Artificial Sequence
<220> FEATURE:
<223> OTHER INFORMATION: CDR Sequence

<400> SEQUENCE: 89

Asn Asn Glu Asp Pro Phe
1               5

<210> SEQ ID NO 90
<211> LENGTH: 6
<212> TYPE: PRT
<213> ORGANISM: Artificial Sequence
<220> FEATURE:
<223> OTHER INFORMATION: CDR Sequence

<400> SEQUENCE: 90

Thr Arg Asn Val Ile His
1               5

<210> SEQ ID NO 91
<211> LENGTH: 13
<212> TYPE: PRT
<213> ORGANISM: Artificial Sequence
<220> FEATURE:
<223> OTHER INFORMATION: CDR Sequence

<400> SEQUENCE: 91

Trp Ile Gly Tyr Ile Asn Pro Tyr Asn Asp Gly Ala Lys
1               5                   10

<210> SEQ ID NO 92
<211> LENGTH: 12
<212> TYPE: PRT
<213> ORGANISM: Artificial Sequence
<220> FEATURE:
<223> OTHER INFORMATION: CDR Sequence

<400> SEQUENCE: 92

Ala Arg Trp Gly Asn Tyr Glu Asp Phe Ala Met Asp
1               5                   10

<210> SEQ ID NO 93
<211> LENGTH: 11
<212> TYPE: PRT
<213> ORGANISM: Artificial Sequence
<220> FEATURE:
<223> OTHER INFORMATION: CDR Sequence

<400> SEQUENCE: 93

Asp Ile Tyr Gly Asn Ser Tyr Met His Trp Tyr
1               5                   10

<210> SEQ ID NO 94
<211> LENGTH: 10
<212> TYPE: PRT
<213> ORGANISM: Artificial Sequence
<220> FEATURE:
<223> OTHER INFORMATION: CDR Sequence

<400> SEQUENCE: 94

Leu Leu Ile Tyr Leu Ala Ser Asn Leu Glu
1               5                   10

<210> SEQ ID NO 95
<211> LENGTH: 8
<212> TYPE: PRT
<213> ORGANISM: Artificial Sequence
<220> FEATURE:
<223> OTHER INFORMATION: CDR Sequence

<400> SEQUENCE: 95

Gln Gln Asn Asn Glu Asp Pro Phe
1               5

<210> SEQ ID NO 96
<211> LENGTH: 10
<212> TYPE: PRT
<213> ORGANISM: Artificial Sequence
<220> FEATURE:
<223> OTHER INFORMATION: CDR Sequence

<400> SEQUENCE: 96

Tyr Ile Asn Pro Tyr Asn Asp Gly Ala Lys
1               5                   10

```
<210> SEQ ID NO 97
<211> LENGTH: 120
<212> TYPE: PRT
<213> ORGANISM: Artificial Sequence
<220> FEATURE:
<223> OTHER INFORMATION: 1C1 Heavy chain variable region

<400> SEQUENCE: 97
```

Glu Val Gln Leu Gln Gln Ser Gly Pro Glu Leu Val Lys Pro Gly Ala
1               5                   10                  15

Thr Val Lys Met Ser Cys Lys Ala Ser Gly Tyr Thr Phe Thr Arg Asn
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Ala Lys Tyr Asn Ala Lys Phe
    50                  55                  60

Lys Gly Lys Ala Thr Val Thr Ser Asp Lys Ser Ser Thr Ala Tyr
65                  70                  75                  80

Met Glu Leu Ser Ser Leu Thr Ser Glu Asp Ser Ala Val Tyr Tyr Cys
            85                  90                  95

Ala Arg Trp Gly Asn Tyr Glu Asp Phe Ala Met Asp Tyr Trp Gly Gln
        100                 105                 110

Gly Thr Ser Val Thr Val Ser Ser
    115                 120

```
<210> SEQ ID NO 98
<211> LENGTH: 111
<212> TYPE: PRT
<213> ORGANISM: Artificial Sequence
<220> FEATURE:
<223> OTHER INFORMATION: 1C1 Light chain variable region

<400> SEQUENCE: 98
```

Asn Ile Val Leu Thr Gln Ser Pro Pro Ser Leu Ala Val Ser Leu Gly
1               5                   10                  15

Gln Arg Ala Thr Ile Ser Cys Arg Ala Ser Glu Ser Val Asp Ile Tyr
            20                  25                  30

Gly Asn Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Glu Phe Ser Leu Thr Ile Asp
65                  70                  75                  80

Pro Val Glu Ala Gly Asp Ala Ala Thr Tyr Tyr Cys Gln Gln Asn Asn
            85                  90                  95

Glu Asp Pro Phe Thr Phe Gly Gly Gly Thr Lys Leu Glu Ile Lys
        100                 105                 110

```
<210> SEQ ID NO 99
<211> LENGTH: 10
<212> TYPE: PRT
<213> ORGANISM: Artificial Sequence
<220> FEATURE:
<223> OTHER INFORMATION: CDR Sequence

<400> SEQUENCE: 99
```

Gly Tyr Thr Phe Thr Ser Ser Val Met His
1               5                   10

```
<210> SEQ ID NO 100
```

<211> LENGTH: 17
<212> TYPE: PRT
<213> ORGANISM: Artificial Sequence
<220> FEATURE:
<223> OTHER INFORMATION: CDR Sequence

<400> SEQUENCE: 100

Tyr Ile Asn Pro Tyr Asn Asp Gly Thr Lys Tyr Asn Glu Asn Phe Lys
1               5                   10                  15
Gly

<210> SEQ ID NO 101
<211> LENGTH: 13
<212> TYPE: PRT
<213> ORGANISM: Artificial Sequence
<220> FEATURE:
<223> OTHER INFORMATION: CDR Sequence

<400> SEQUENCE: 101

Gly Ala Gly Tyr Asp Arg Gly Pro Met Ala Met Asp Tyr
1               5                   10

<210> SEQ ID NO 102
<211> LENGTH: 15
<212> TYPE: PRT
<213> ORGANISM: Artificial Sequence
<220> FEATURE:
<223> OTHER INFORMATION: CDR Sequence

<400> SEQUENCE: 102

Arg Ala Ser Glu Ser Val Asp Ser Tyr Gly Asp Ser Phe Val His
1               5                   10                  15

<210> SEQ ID NO 103
<211> LENGTH: 7
<212> TYPE: PRT
<213> ORGANISM: Artificial Sequence
<220> FEATURE:
<223> OTHER INFORMATION: CDR Sequence

<400> SEQUENCE: 103

Phe Ala Ser Asn Leu Glu Ser
1               5

<210> SEQ ID NO 104
<211> LENGTH: 9
<212> TYPE: PRT
<213> ORGANISM: Artificial Sequence
<220> FEATURE:
<223> OTHER INFORMATION: CDR Sequence

<400> SEQUENCE: 104

Gln Gln Asn Asn Glu Val Pro Phe Thr
1               5

<210> SEQ ID NO 105
<211> LENGTH: 8
<212> TYPE: PRT
<213> ORGANISM: Artificial Sequence
<220> FEATURE:
<223> OTHER INFORMATION: CDR Sequence

<400> SEQUENCE: 105

Gly Tyr Thr Phe Thr Ser Ser Val
1               5

```
<210> SEQ ID NO 106
<211> LENGTH: 8
<212> TYPE: PRT
<213> ORGANISM: Artificial Sequence
<220> FEATURE:
<223> OTHER INFORMATION: CDR Sequence

<400> SEQUENCE: 106

Ile Asn Pro Tyr Asn Asp Gly Thr
1               5

<210> SEQ ID NO 107
<211> LENGTH: 15
<212> TYPE: PRT
<213> ORGANISM: Artificial Sequence
<220> FEATURE:
<223> OTHER INFORMATION: CDR Sequence

<400> SEQUENCE: 107

Ala Arg Gly Ala Gly Tyr Asp Arg Gly Pro Met Ala Met Asp Tyr
1               5                   10                  15

<210> SEQ ID NO 108
<211> LENGTH: 10
<212> TYPE: PRT
<213> ORGANISM: Artificial Sequence
<220> FEATURE:
<223> OTHER INFORMATION: CDR Sequence

<400> SEQUENCE: 108

Glu Ser Val Asp Ser Tyr Gly Asp Ser Phe
1               5                   10

<210> SEQ ID NO 109
<211> LENGTH: 3
<212> TYPE: PRT
<213> ORGANISM: Artificial Sequence
<220> FEATURE:
<223> OTHER INFORMATION: CDR Sequence

<400> SEQUENCE: 109

Phe Ala Ser
1

<210> SEQ ID NO 110
<211> LENGTH: 5
<212> TYPE: PRT
<213> ORGANISM: Artificial Sequence
<220> FEATURE:
<223> OTHER INFORMATION: CDR Sequence

<400> SEQUENCE: 110

Ser Ser Val Met His
1               5

<210> SEQ ID NO 111
<211> LENGTH: 7
<212> TYPE: PRT
<213> ORGANISM: Artificial Sequence
<220> FEATURE:
<223> OTHER INFORMATION: CDR Sequence

<400> SEQUENCE: 111

Gly Tyr Thr Phe Thr Ser Ser
1               5

<210> SEQ ID NO 112
```

```
<211> LENGTH: 11
<212> TYPE: PRT
<213> ORGANISM: Artificial Sequence
<220> FEATURE:
<223> OTHER INFORMATION: CDR Sequence

<400> SEQUENCE: 112

Ala Gly Tyr Asp Arg Gly Pro Met Ala Met Asp
1               5                   10

<210> SEQ ID NO 113
<211> LENGTH: 11
<212> TYPE: PRT
<213> ORGANISM: Artificial Sequence
<220> FEATURE:
<223> OTHER INFORMATION: CDR Sequence

<400> SEQUENCE: 113

Ser Glu Ser Val Asp Ser Tyr Gly Asp Ser Phe
1               5                   10

<210> SEQ ID NO 114
<211> LENGTH: 6
<212> TYPE: PRT
<213> ORGANISM: Artificial Sequence
<220> FEATURE:
<223> OTHER INFORMATION: CDR Sequence

<400> SEQUENCE: 114

Asn Asn Glu Val Pro Phe
1               5

<210> SEQ ID NO 115
<211> LENGTH: 6
<212> TYPE: PRT
<213> ORGANISM: Artificial Sequence
<220> FEATURE:
<223> OTHER INFORMATION: CDR Sequence

<400> SEQUENCE: 115

Thr Ser Ser Val Met His
1               5

<210> SEQ ID NO 116
<211> LENGTH: 13
<212> TYPE: PRT
<213> ORGANISM: Artificial Sequence
<220> FEATURE:
<223> OTHER INFORMATION: CDR Sequence

<400> SEQUENCE: 116

Trp Ile Gly Tyr Ile Asn Pro Tyr Asn Asp Gly Thr Lys
1               5                   10

<210> SEQ ID NO 117
<211> LENGTH: 14
<212> TYPE: PRT
<213> ORGANISM: Artificial Sequence
<220> FEATURE:
<223> OTHER INFORMATION: CDR Sequence

<400> SEQUENCE: 117

Ala Arg Gly Ala Gly Tyr Asp Arg Gly Pro Met Ala Met Asp
1               5                   10

<210> SEQ ID NO 118
<211> LENGTH: 11
```

```
<212> TYPE: PRT
<213> ORGANISM: Artificial Sequence
<220> FEATURE:
<223> OTHER INFORMATION: CDR Sequence

<400> SEQUENCE: 118

Asp Ser Tyr Gly Asp Ser Phe Val His Trp Tyr
1               5                   10

<210> SEQ ID NO 119
<211> LENGTH: 10
<212> TYPE: PRT
<213> ORGANISM: Artificial Sequence
<220> FEATURE:
<223> OTHER INFORMATION: CDR Sequence

<400> SEQUENCE: 119

Leu Leu Ile Tyr Phe Ala Ser Asn Leu Glu
1               5                   10

<210> SEQ ID NO 120
<211> LENGTH: 8
<212> TYPE: PRT
<213> ORGANISM: Artificial Sequence
<220> FEATURE:
<223> OTHER INFORMATION: CDR Sequence

<400> SEQUENCE: 120

Gln Gln Asn Asn Glu Val Pro Phe
1               5

<210> SEQ ID NO 121
<211> LENGTH: 10
<212> TYPE: PRT
<213> ORGANISM: Artificial Sequence
<220> FEATURE:
<223> OTHER INFORMATION: CDR Sequence

<400> SEQUENCE: 121

Tyr Ile Asn Pro Tyr Asn Asp Gly Thr Lys
1               5                   10

<210> SEQ ID NO 122
<211> LENGTH: 122
<212> TYPE: PRT
<213> ORGANISM: Artificial Sequence
<220> FEATURE:
<223> OTHER INFORMATION: 1C3 Heavy chain variable region

<400> SEQUENCE: 122

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Ser
            20                  25                  30

Val Met His Trp Val Lys Gln Lys Pro Gly Gln Ala Leu Glu Trp Ile
        35                  40                  45

Gly Tyr Ile Asn Pro Tyr Asn Asp Gly Thr Lys Tyr Asn Glu Asn Phe
    50                  55                  60

Lys Gly Lys Ala Thr Leu Thr Ser Asp Arg Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Val Thr Gly Ala Gly Tyr Asp Arg Gly Pro Met Ala Met Asp Tyr Trp
            100                 105                 110
```

```
Gly Gln Gly Thr Ser Val Thr Val Ser Ser
        115                 120

<210> SEQ ID NO 123
<211> LENGTH: 111
<212> TYPE: PRT
<213> ORGANISM: Artificial Sequence
<220> FEATURE:
<223> OTHER INFORMATION: 1C3 Light chain variable region

<400> SEQUENCE: 123

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asp Ser Phe Val His Trp Tyr Gln Gln Lys Pro Gly Gln Pro Pro
        35                  40                  45

Lys Leu Leu Ile Tyr Phe Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Thr Ala Thr Tyr Tyr Cys Gln Gln Asn Asn
                85                  90                  95

Glu Val Pro Phe Thr Phe Gly Ser Gly Thr Lys Leu Glu Leu Lys
            100                 105                 110

<210> SEQ ID NO 124
<211> LENGTH: 10
<212> TYPE: PRT
<213> ORGANISM: Artificial Sequence
<220> FEATURE:
<223> OTHER INFORMATION: CDR Sequence

<400> SEQUENCE: 124

Gly Tyr Thr Phe Thr Ser Tyr Trp Ile Thr
1               5                   10

<210> SEQ ID NO 125
<211> LENGTH: 17
<212> TYPE: PRT
<213> ORGANISM: Artificial Sequence
<220> FEATURE:
<223> OTHER INFORMATION: CDR Sequence

<400> SEQUENCE: 125

Asp Ile His Pro Gly Gly Gly Asp Thr Asn Tyr Asn Lys Lys Phe Lys
1               5                   10                  15

Ser

<210> SEQ ID NO 126
<211> LENGTH: 9
<212> TYPE: PRT
<213> ORGANISM: Artificial Sequence
<220> FEATURE:
<223> OTHER INFORMATION: CDR Sequence

<400> SEQUENCE: 126

Asp Asp Asn Tyr Val Gly Phe Thr Tyr
1               5

<210> SEQ ID NO 127
<211> LENGTH: 16
```

<212> TYPE: PRT
<213> ORGANISM: Artificial Sequence
<220> FEATURE:
<223> OTHER INFORMATION: CDR Sequence

<400> SEQUENCE: 127

Arg Ser Ser Gln Thr Ile Ile His Ser Asp Gly Asn Thr Tyr Leu Glu
1               5                   10                  15

<210> SEQ ID NO 128
<211> LENGTH: 7
<212> TYPE: PRT
<213> ORGANISM: Artificial Sequence
<220> FEATURE:
<223> OTHER INFORMATION: CDR Sequence

<400> SEQUENCE: 128

Lys Val Ser Asn Arg Phe Ser
1               5

<210> SEQ ID NO 129
<211> LENGTH: 8
<212> TYPE: PRT
<213> ORGANISM: Artificial Sequence
<220> FEATURE:
<223> OTHER INFORMATION: CDR Sequence

<400> SEQUENCE: 129

Gly Tyr Thr Phe Thr Ser Tyr Trp
1               5

<210> SEQ ID NO 130
<211> LENGTH: 8
<212> TYPE: PRT
<213> ORGANISM: Artificial Sequence
<220> FEATURE:
<223> OTHER INFORMATION: CDR Sequence

<400> SEQUENCE: 130

Ile His Pro Gly Gly Gly Asp Thr
1               5

<210> SEQ ID NO 131
<211> LENGTH: 11
<212> TYPE: PRT
<213> ORGANISM: Artificial Sequence
<220> FEATURE:
<223> OTHER INFORMATION: CDR Sequence

<400> SEQUENCE: 131

Ala Arg Asp Asp Asn Tyr Val Gly Phe Thr Tyr
1               5                   10

<210> SEQ ID NO 132
<211> LENGTH: 11
<212> TYPE: PRT
<213> ORGANISM: Artificial Sequence
<220> FEATURE:
<223> OTHER INFORMATION: CDR Sequence

<400> SEQUENCE: 132

Gln Thr Ile Ile His Ser Asp Gly Asn Thr Tyr
1               5                   10

<210> SEQ ID NO 133
<211> LENGTH: 5
<212> TYPE: PRT

```
<213> ORGANISM: Artificial Sequence
<220> FEATURE:
<223> OTHER INFORMATION: CDR Sequence

<400> SEQUENCE: 133

Ser Tyr Trp Ile Thr
1               5

<210> SEQ ID NO 134
<211> LENGTH: 7
<212> TYPE: PRT
<213> ORGANISM: Artificial Sequence
<220> FEATURE:
<223> OTHER INFORMATION: CDR Sequence

<400> SEQUENCE: 134

Gly Tyr Thr Phe Thr Ser Tyr
1               5

<210> SEQ ID NO 135
<211> LENGTH: 4
<212> TYPE: PRT
<213> ORGANISM: Artificial Sequence
<220> FEATURE:
<223> OTHER INFORMATION: CDR Sequence

<400> SEQUENCE: 135

Pro Gly Gly Gly
1

<210> SEQ ID NO 136
<211> LENGTH: 7
<212> TYPE: PRT
<213> ORGANISM: Artificial Sequence
<220> FEATURE:
<223> OTHER INFORMATION: CDR Sequence

<400> SEQUENCE: 136

Asp Asn Tyr Val Gly Phe Thr
1               5

<210> SEQ ID NO 137
<211> LENGTH: 12
<212> TYPE: PRT
<213> ORGANISM: Artificial Sequence
<220> FEATURE:
<223> OTHER INFORMATION: CDR Sequence

<400> SEQUENCE: 137

Ser Gln Thr Ile Ile His Ser Asp Gly Asn Thr Tyr
1               5                   10

<210> SEQ ID NO 138
<211> LENGTH: 6
<212> TYPE: PRT
<213> ORGANISM: Artificial Sequence
<220> FEATURE:
<223> OTHER INFORMATION: CDR Sequence

<400> SEQUENCE: 138

Thr Ser Tyr Trp Ile Thr
1               5

<210> SEQ ID NO 139
<211> LENGTH: 13
<212> TYPE: PRT
<213> ORGANISM: Artificial Sequence
```

-continued

<220> FEATURE:
<223> OTHER INFORMATION: CDR Sequence

<400> SEQUENCE: 139

Trp Ile Gly Asp Ile His Pro Gly Gly Gly Asp Thr Asn
1               5                   10

<210> SEQ ID NO 140
<211> LENGTH: 10
<212> TYPE: PRT
<213> ORGANISM: Artificial Sequence
<220> FEATURE:
<223> OTHER INFORMATION: CDR Sequence

<400> SEQUENCE: 140

Ala Arg Asp Asp Asn Tyr Val Gly Phe Thr
1               5                   10

<210> SEQ ID NO 141
<211> LENGTH: 12
<212> TYPE: PRT
<213> ORGANISM: Artificial Sequence
<220> FEATURE:
<223> OTHER INFORMATION: CDR Sequence

<400> SEQUENCE: 141

Ile His Ser Asp Gly Asn Thr Tyr Leu Glu Trp Tyr
1               5                   10

<210> SEQ ID NO 142
<211> LENGTH: 10
<212> TYPE: PRT
<213> ORGANISM: Artificial Sequence
<220> FEATURE:
<223> OTHER INFORMATION: CDR Sequence

<400> SEQUENCE: 142

Leu Leu Ile Tyr Lys Val Ser Asn Arg Phe
1               5                   10

<210> SEQ ID NO 143
<211> LENGTH: 10
<212> TYPE: PRT
<213> ORGANISM: Artificial Sequence
<220> FEATURE:
<223> OTHER INFORMATION: CDR Sequence

<400> SEQUENCE: 143

Asp Ile His Pro Gly Gly Gly Asp Thr Asn
1               5                   10

<210> SEQ ID NO 144
<211> LENGTH: 118
<212> TYPE: PRT
<213> ORGANISM: Artificial Sequence
<220> FEATURE:
<223> OTHER INFORMATION: 1H2 Heavy chain variable region

<400> SEQUENCE: 144

Gln Val Gln Leu Gln Gln Pro Gly Ala Glu Leu Val Lys Pro Gly Ala
1               5                   10                  15

Ser Val Lys Met Ser Cys Lys Val Ser Gly Tyr Thr Phe Thr Ser Tyr
                20                  25                  30

Trp Ile Thr Trp Val Lys Gln Arg Pro Gly Gln Gly Leu Glu Trp Ile
            35                  40                  45

Gly Asp Ile His Pro Gly Gly Gly Asp Thr Asn Tyr Asn Lys Lys Phe
    50                  55                  60

Lys Ser Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr His Cys
                85                  90                  95

Thr Ser Asp Asp Asn Tyr Val Gly Phe Thr Tyr Trp Gly Gln Gly Thr
                100                 105                 110

Leu Val Thr Val Ser Ala
        115

<210> SEQ ID NO 145
<211> LENGTH: 112
<212> TYPE: PRT
<213> ORGANISM: Artificial Sequence
<220> FEATURE:
<223> OTHER INFORMATION: 1H2 Light chain variable region

<400> SEQUENCE: 145

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Ile His Ser
            20                  25                  30

Asp Gly Asn Thr Tyr Leu Glu Trp Tyr Leu Gln Lys Pro Gly Gln Ser
        35                  40                  45

Pro Ile Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
                100                 105                 110

<210> SEQ ID NO 146
<211> LENGTH: 10
<212> TYPE: PRT
<213> ORGANISM: Artificial Sequence
<220> FEATURE:
<223> OTHER INFORMATION: CDR Sequence

<400> SEQUENCE: 146

Gly Tyr Thr Phe Ser Asn Tyr Trp Ile Gly
1               5                   10

<210> SEQ ID NO 147
<211> LENGTH: 17
<212> TYPE: PRT
<213> ORGANISM: Artificial Sequence
<220> FEATURE:
<223> OTHER INFORMATION: CDR Sequence

<400> SEQUENCE: 147

Asp Ile Tyr Pro Gly Gly Phe Tyr Asp Asn Tyr Asn Asp Lys Phe Lys
1               5                   10                  15

Gly

<210> SEQ ID NO 148
<211> LENGTH: 11
<212> TYPE: PRT
<213> ORGANISM: Artificial Sequence

```
<220> FEATURE:
<223> OTHER INFORMATION: CDR Sequence

<400> SEQUENCE: 148

Ser Gly Gly Leu Pro Gly Ala Gly Phe Thr Tyr
1               5                   10

<210> SEQ ID NO 149
<211> LENGTH: 16
<212> TYPE: PRT
<213> ORGANISM: Artificial Sequence
<220> FEATURE:
<223> OTHER INFORMATION: CDR Sequence

<400> SEQUENCE: 149

Arg Ser Ser Gln His Ile Val Tyr Ser Asp Gly Asn Thr Tyr Leu Glu
1               5                   10                  15

<210> SEQ ID NO 150
<211> LENGTH: 8
<212> TYPE: PRT
<213> ORGANISM: Artificial Sequence
<220> FEATURE:
<223> OTHER INFORMATION: CDR Sequence

<400> SEQUENCE: 150

Gly Tyr Thr Phe Ser Asn Tyr Trp
1               5

<210> SEQ ID NO 151
<211> LENGTH: 9
<212> TYPE: PRT
<213> ORGANISM: Artificial Sequence
<220> FEATURE:
<223> OTHER INFORMATION: CDR Sequence

<400> SEQUENCE: 151

Ile Tyr Pro Gly Gly Phe Tyr Asp Asn
1               5

<210> SEQ ID NO 152
<211> LENGTH: 13
<212> TYPE: PRT
<213> ORGANISM: Artificial Sequence
<220> FEATURE:
<223> OTHER INFORMATION: CDR Sequence

<400> SEQUENCE: 152

Ala Arg Ser Gly Gly Leu Pro Gly Ala Gly Phe Thr Tyr
1               5                   10

<210> SEQ ID NO 153
<211> LENGTH: 11
<212> TYPE: PRT
<213> ORGANISM: Artificial Sequence
<220> FEATURE:
<223> OTHER INFORMATION: CDR Sequence

<400> SEQUENCE: 153

Gln His Ile Val Tyr Ser Asp Gly Asn Thr Tyr
1               5                   10

<210> SEQ ID NO 154
<211> LENGTH: 5
<212> TYPE: PRT
<213> ORGANISM: Artificial Sequence
<220> FEATURE:
```

<223> OTHER INFORMATION: CDR Sequence

<400> SEQUENCE: 154

Asn Tyr Trp Ile Gly
1               5

<210> SEQ ID NO 155
<211> LENGTH: 7
<212> TYPE: PRT
<213> ORGANISM: Artificial Sequence
<220> FEATURE:
<223> OTHER INFORMATION: CDR Sequence

<400> SEQUENCE: 155

Gly Tyr Thr Phe Ser Asn Tyr
1               5

<210> SEQ ID NO 156
<211> LENGTH: 4
<212> TYPE: PRT
<213> ORGANISM: Artificial Sequence
<220> FEATURE:
<223> OTHER INFORMATION: CDR Sequence

<400> SEQUENCE: 156

Pro Gly Gly Phe
1

<210> SEQ ID NO 157
<211> LENGTH: 9
<212> TYPE: PRT
<213> ORGANISM: Artificial Sequence
<220> FEATURE:
<223> OTHER INFORMATION: CDR Sequence

<400> SEQUENCE: 157

Gly Gly Leu Pro Gly Ala Gly Phe Thr
1               5

<210> SEQ ID NO 158
<211> LENGTH: 12
<212> TYPE: PRT
<213> ORGANISM: Artificial Sequence
<220> FEATURE:
<223> OTHER INFORMATION: CDR Sequence

<400> SEQUENCE: 158

Ser Gln His Ile Val Tyr Ser Asp Gly Asn Thr Tyr
1               5                   10

<210> SEQ ID NO 159
<211> LENGTH: 6
<212> TYPE: PRT
<213> ORGANISM: Artificial Sequence
<220> FEATURE:
<223> OTHER INFORMATION: CDR Sequence

<400> SEQUENCE: 159

Ser Asn Tyr Trp Ile Gly
1               5

<210> SEQ ID NO 160
<211> LENGTH: 13
<212> TYPE: PRT
<213> ORGANISM: Artificial Sequence
<220> FEATURE:
<223> OTHER INFORMATION: CDR Sequence

<400> SEQUENCE: 160

Trp Ile Gly Asp Ile Tyr Pro Gly Gly Phe Tyr Asp Asn
1               5                   10

<210> SEQ ID NO 161
<211> LENGTH: 12
<212> TYPE: PRT
<213> ORGANISM: Artificial Sequence
<220> FEATURE:
<223> OTHER INFORMATION: CDR Sequence

<400> SEQUENCE: 161

Ala Arg Ser Gly Gly Leu Pro Gly Ala Gly Phe Thr
1               5                   10

<210> SEQ ID NO 162
<211> LENGTH: 12
<212> TYPE: PRT
<213> ORGANISM: Artificial Sequence
<220> FEATURE:
<223> OTHER INFORMATION: CDR Sequence

<400> SEQUENCE: 162

Val Tyr Ser Asp Gly Asn Thr Tyr Leu Glu Trp Tyr
1               5                   10

<210> SEQ ID NO 163
<211> LENGTH: 10
<212> TYPE: PRT
<213> ORGANISM: Artificial Sequence
<220> FEATURE:
<223> OTHER INFORMATION: CDR Sequence

<400> SEQUENCE: 163

Asp Ile Tyr Pro Gly Gly Phe Tyr Asp Asn
1               5                   10

<210> SEQ ID NO 164
<211> LENGTH: 120
<212> TYPE: PRT
<213> ORGANISM: Artificial Sequence
<220> FEATURE:
<223> OTHER INFORMATION: 4F8 Heavy chain variable region

<400> SEQUENCE: 164

Gln Val Gln Leu Gln Gln Ser Gly Ala Glu Leu Val Arg Pro Gly Thr
1               5                   10                  15

Ser Val Thr Met Ser Cys Lys Ala Ala Gly Tyr Thr Phe Ser Asn Tyr
            20                  25                  30

Trp Ile Gly Trp Val Lys Gln Arg Pro Gly His Gly Leu Glu Trp Ile
        35                  40                  45

Gly Asp Ile Tyr Pro Gly Gly Phe Tyr Asp Asn Tyr Asn Asp Lys Phe
    50                  55                  60

Lys Gly Lys Ala Thr Leu Thr Thr Asp Thr Ser Ser Thr Ala Tyr
65                  70                  75                  80

Met Gln Leu Ser Ser Leu Thr Ser Glu Asp Ser Ala Ile Tyr Tyr Cys
                85                  90                  95

Thr Arg Ser Gly Gly Leu Pro Gly Ala Gly Phe Thr Tyr Trp Gly Gln
            100                 105                 110

Gly Thr Leu Val Thr Val Ser Ala
        115                 120

<210> SEQ ID NO 165
<211> LENGTH: 112
<212> TYPE: PRT
<213> ORGANISM: Artificial Sequence
<220> FEATURE:
<223> OTHER INFORMATION: 4F8 Light chain variable region

<400> SEQUENCE: 165

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln His Ile Val Tyr Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Glu Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 166
<211> LENGTH: 10
<212> TYPE: PRT
<213> ORGANISM: Artificial Sequence
<220> FEATURE:
<223> OTHER INFORMATION: CDR Sequence

<400> SEQUENCE: 166

```
Gly Tyr Thr Phe Thr Asn Tyr Trp Leu Gly
1               5                   10
```

<210> SEQ ID NO 167
<211> LENGTH: 17
<212> TYPE: PRT
<213> ORGANISM: Artificial Sequence
<220> FEATURE:
<223> OTHER INFORMATION: CDR Sequence

<400> SEQUENCE: 167

```
Asp Ile Tyr Pro Gly Gly Asp Tyr Asn Asn Tyr Asn Gly Lys Phe Lys
1               5                   10                  15

Gly
```

<210> SEQ ID NO 168
<211> LENGTH: 6
<212> TYPE: PRT
<213> ORGANISM: Artificial Sequence
<220> FEATURE:
<223> OTHER INFORMATION: CDR Sequence

<400> SEQUENCE: 168

```
Ser Asp Asp Gly Tyr Ser
1               5
```

<210> SEQ ID NO 169
<211> LENGTH: 16
<212> TYPE: PRT
<213> ORGANISM: Artificial Sequence
<220> FEATURE:
<223> OTHER INFORMATION: CDR Sequence

<400> SEQUENCE: 169

Arg Ser Ser Gln Ser Ile Val Asp Ser Tyr Gly Asn Thr Tyr Leu Glu
1               5                   10                  15

<210> SEQ ID NO 170
<211> LENGTH: 7
<212> TYPE: PRT
<213> ORGANISM: Artificial Sequence
<220> FEATURE:
<223> OTHER INFORMATION: CDR Sequence

<400> SEQUENCE: 170

Lys Val Ser Asn Arg Phe Ala
1               5

<210> SEQ ID NO 171
<211> LENGTH: 9
<212> TYPE: PRT
<213> ORGANISM: Artificial Sequence
<220> FEATURE:
<223> OTHER INFORMATION: CDR Sequence

<400> SEQUENCE: 171

Phe Gln Gly Ser His Ile Pro Trp Thr
1               5

<210> SEQ ID NO 172
<211> LENGTH: 8
<212> TYPE: PRT
<213> ORGANISM: Artificial Sequence
<220> FEATURE:
<223> OTHER INFORMATION: CDR Sequence

<400> SEQUENCE: 172

Gly Tyr Thr Phe Thr Asn Tyr Trp
1               5

<210> SEQ ID NO 173
<211> LENGTH: 8
<212> TYPE: PRT
<213> ORGANISM: Artificial Sequence
<220> FEATURE:
<223> OTHER INFORMATION: CDR Sequence

<400> SEQUENCE: 173

Ile Tyr Pro Gly Gly Asp Tyr Asn
1               5

<210> SEQ ID NO 174
<211> LENGTH: 8
<212> TYPE: PRT
<213> ORGANISM: Artificial Sequence
<220> FEATURE:
<223> OTHER INFORMATION: CDR Sequence

<400> SEQUENCE: 174

Ala Arg Ser Asp Asp Gly Tyr Ser
1               5

<210> SEQ ID NO 175
<211> LENGTH: 11
<212> TYPE: PRT
<213> ORGANISM: Artificial Sequence
<220> FEATURE:
<223> OTHER INFORMATION: CDR Sequence

```
<400> SEQUENCE: 175

Gln Ser Ile Val Asp Ser Tyr Gly Asn Thr Tyr
1               5                   10

<210> SEQ ID NO 176
<211> LENGTH: 5
<212> TYPE: PRT
<213> ORGANISM: Artificial Sequence
<220> FEATURE:
<223> OTHER INFORMATION: CDR Sequence

<400> SEQUENCE: 176

Asn Tyr Trp Leu Gly
1               5

<210> SEQ ID NO 177
<211> LENGTH: 7
<212> TYPE: PRT
<213> ORGANISM: Artificial Sequence
<220> FEATURE:
<223> OTHER INFORMATION: CDR Sequence

<400> SEQUENCE: 177

Gly Tyr Thr Phe Thr Asn Tyr
1               5

<210> SEQ ID NO 178
<211> LENGTH: 4
<212> TYPE: PRT
<213> ORGANISM: Artificial Sequence
<220> FEATURE:
<223> OTHER INFORMATION: CDR Sequence

<400> SEQUENCE: 178

Pro Gly Gly Asp
1

<210> SEQ ID NO 179
<211> LENGTH: 4
<212> TYPE: PRT
<213> ORGANISM: Artificial Sequence
<220> FEATURE:
<223> OTHER INFORMATION: CDR Sequence

<400> SEQUENCE: 179

Asp Asp Gly Tyr
1

<210> SEQ ID NO 180
<211> LENGTH: 12
<212> TYPE: PRT
<213> ORGANISM: Artificial Sequence
<220> FEATURE:
<223> OTHER INFORMATION: CDR Sequence

<400> SEQUENCE: 180

Ser Gln Ser Ile Val Asp Ser Tyr Gly Asn Thr Tyr
1               5                   10

<210> SEQ ID NO 181
<211> LENGTH: 6
<212> TYPE: PRT
<213> ORGANISM: Artificial Sequence
<220> FEATURE:
<223> OTHER INFORMATION: CDR Sequence

<400> SEQUENCE: 181
```

```
Gly Ser His Ile Pro Trp
1               5

<210> SEQ ID NO 182
<211> LENGTH: 6
<212> TYPE: PRT
<213> ORGANISM: Artificial Sequence
<220> FEATURE:
<223> OTHER INFORMATION: CDR Sequence

<400> SEQUENCE: 182

Thr Asn Tyr Trp Leu Gly
1               5

<210> SEQ ID NO 183
<211> LENGTH: 13
<212> TYPE: PRT
<213> ORGANISM: Artificial Sequence
<220> FEATURE:
<223> OTHER INFORMATION: CDR Sequence

<400> SEQUENCE: 183

Trp Ile Gly Asp Ile Tyr Pro Gly Gly Asp Tyr Asn Asn
1               5                   10

<210> SEQ ID NO 184
<211> LENGTH: 7
<212> TYPE: PRT
<213> ORGANISM: Artificial Sequence
<220> FEATURE:
<223> OTHER INFORMATION: CDR Sequence

<400> SEQUENCE: 184

Ala Arg Ser Asp Asp Gly Tyr
1               5

<210> SEQ ID NO 185
<211> LENGTH: 12
<212> TYPE: PRT
<213> ORGANISM: Artificial Sequence
<220> FEATURE:
<223> OTHER INFORMATION: CDR Sequence

<400> SEQUENCE: 185

Val Asp Ser Tyr Gly Asn Thr Tyr Leu Glu Trp Tyr
1               5                   10

<210> SEQ ID NO 186
<211> LENGTH: 8
<212> TYPE: PRT
<213> ORGANISM: Artificial Sequence
<220> FEATURE:
<223> OTHER INFORMATION: CDR Sequence

<400> SEQUENCE: 186

Phe Gln Gly Ser His Ile Pro Trp
1               5

<210> SEQ ID NO 187
<211> LENGTH: 10
<212> TYPE: PRT
<213> ORGANISM: Artificial Sequence
<220> FEATURE:
<223> OTHER INFORMATION: CDR Sequence

<400> SEQUENCE: 187
```

```
Asp Ile Tyr Pro Gly Gly Asp Tyr Asn Asn
1               5                  10
```

```
<210> SEQ ID NO 188
<211> LENGTH: 115
<212> TYPE: PRT
<213> ORGANISM: Artificial Sequence
<220> FEATURE:
<223> OTHER INFORMATION: 13G9 Heavy chain variable region

<400> SEQUENCE: 188

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Asp Tyr Asn Asn Tyr Asn Gly Lys Phe
    50                  55                  60

Lys Gly Lys Ala Thr Leu Thr Ala Asp Thr Ser Ser Ser Thr Ala Tyr
65                  70                  75                  80

Ile Gln Leu Ser Ser Leu Thr Ser Glu Asp Ser Ala Val Tyr Phe Cys
                85                  90                  95

Val Arg Ser Asp Asp Gly Tyr Ser Trp Gly Gln Gly Thr Thr Leu Thr
            100                 105                 110

Val Ser Ser
        115
```

```
<210> SEQ ID NO 189
<211> LENGTH: 112
<212> TYPE: PRT
<213> ORGANISM: Artificial Sequence
<220> FEATURE:
<223> OTHER INFORMATION: 13G9 Light chain variable region

<400> SEQUENCE: 189

Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Val Asp Ser
            20                  25                  30

Tyr Gly Asn Thr Tyr Leu Glu Trp Tyr Gln Gln Lys Pro Gly Gln Ser
        35                  40                  45

Pro Thr Leu Leu Ile Tyr Lys Val Ser Asn Arg Phe Ala Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Trp Thr Phe Gly Gly Gly Thr Lys Val Glu Ile Lys
            100                 105                 110
```

```
<210> SEQ ID NO 190
<211> LENGTH: 10
<212> TYPE: PRT
<213> ORGANISM: Artificial Sequence
<220> FEATURE:
<223> OTHER INFORMATION: CDR Sequence

<400> SEQUENCE: 190

Gly Tyr Thr Phe Thr Asn Tyr Trp Ile Gly
```

-continued

```
1               5                   10
```

<210> SEQ ID NO 191
<211> LENGTH: 17
<212> TYPE: PRT
<213> ORGANISM: Artificial Sequence
<220> FEATURE:
<223> OTHER INFORMATION: CDR Sequence

<400> SEQUENCE: 191

```
Asp Ile Phe Pro Gly Gly Phe Tyr Ser Asn Tyr Asn Glu Lys Phe Lys
1               5                   10                  15
Gly
```

<210> SEQ ID NO 192
<211> LENGTH: 8
<212> TYPE: PRT
<213> ORGANISM: Artificial Sequence
<220> FEATURE:
<223> OTHER INFORMATION: CDR Sequence

<400> SEQUENCE: 192

```
Ile Trp Asp Arg Gly Phe Asp Tyr
1               5
```

<210> SEQ ID NO 193
<211> LENGTH: 9
<212> TYPE: PRT
<213> ORGANISM: Artificial Sequence
<220> FEATURE:
<223> OTHER INFORMATION: CDR Sequence

<400> SEQUENCE: 193

```
Phe Gln Gly Ser His Val Pro Tyr Thr
1               5
```

<210> SEQ ID NO 194
<211> LENGTH: 8
<212> TYPE: PRT
<213> ORGANISM: Artificial Sequence
<220> FEATURE:
<223> OTHER INFORMATION: CDR Sequence

<400> SEQUENCE: 194

```
Ile Phe Pro Gly Gly Phe Tyr Ser
1               5
```

<210> SEQ ID NO 195
<211> LENGTH: 10
<212> TYPE: PRT
<213> ORGANISM: Artificial Sequence
<220> FEATURE:
<223> OTHER INFORMATION: CDR Sequence

<400> SEQUENCE: 195

```
Ala Arg Ile Trp Asp Arg Gly Phe Asp Tyr
1               5                   10
```

<210> SEQ ID NO 196
<211> LENGTH: 6
<212> TYPE: PRT
<213> ORGANISM: Artificial Sequence
<220> FEATURE:
<223> OTHER INFORMATION: CDR Sequence

<400> SEQUENCE: 196

```
Trp Asp Arg Gly Phe Asp
1               5

<210> SEQ ID NO 197
<211> LENGTH: 6
<212> TYPE: PRT
<213> ORGANISM: Artificial Sequence
<220> FEATURE:
<223> OTHER INFORMATION: CDR Sequence

<400> SEQUENCE: 197

Gly Ser His Val Pro Tyr
1               5

<210> SEQ ID NO 198
<211> LENGTH: 6
<212> TYPE: PRT
<213> ORGANISM: Artificial Sequence
<220> FEATURE:
<223> OTHER INFORMATION: CDR Sequence

<400> SEQUENCE: 198

Thr Asn Tyr Trp Ile Gly
1               5

<210> SEQ ID NO 199
<211> LENGTH: 13
<212> TYPE: PRT
<213> ORGANISM: Artificial Sequence
<220> FEATURE:
<223> OTHER INFORMATION: CDR Sequence

<400> SEQUENCE: 199

Trp Ile Gly Asp Ile Phe Pro Gly Gly Phe Tyr Ser Asn
1               5                   10

<210> SEQ ID NO 200
<211> LENGTH: 9
<212> TYPE: PRT
<213> ORGANISM: Artificial Sequence
<220> FEATURE:
<223> OTHER INFORMATION: CDR Sequence

<400> SEQUENCE: 200

Ala Arg Ile Trp Asp Arg Gly Phe Asp
1               5

<210> SEQ ID NO 201
<211> LENGTH: 8
<212> TYPE: PRT
<213> ORGANISM: Artificial Sequence
<220> FEATURE:
<223> OTHER INFORMATION: CDR Sequence

<400> SEQUENCE: 201

Phe Gln Gly Ser His Val Pro Tyr
1               5

<210> SEQ ID NO 202
<211> LENGTH: 10
<212> TYPE: PRT
<213> ORGANISM: Artificial Sequence
<220> FEATURE:
<223> OTHER INFORMATION: CDR Sequence

<400> SEQUENCE: 202

Asp Ile Phe Pro Gly Gly Phe Tyr Ser Asn
```

<210> SEQ ID NO 203
<211> LENGTH: 117
<212> TYPE: PRT
<213> ORGANISM: Artificial Sequence
<220> FEATURE:
<223> OTHER INFORMATION: 14F4 Heavy chain variable region

<400> SEQUENCE: 203

```
Gln Val Gln Leu Gln Gln Ser Gly Ala Glu Leu Val Arg Pro Gly Thr
1               5                   10                  15

Ser Val Asn Met Ser Cys Lys Ala Thr Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile Phe Pro Gly Gly Phe Tyr Ser Asn Tyr Asn Glu Lys Phe
    50                  55                  60

Lys Gly Lys Ala Thr Leu Thr Thr Asp Thr Ser Ser Thr Gly Tyr
65                  70                  75                  80

Met Gln Leu Ser Ser Leu Thr Ser Glu Asp Ser Ala Ile Tyr Tyr Cys
                85                  90                  95

Ala Arg Ile Trp Asp Arg Gly Phe Asp Tyr Trp Gly Gln Gly Thr Thr
            100                 105                 110

Leu Thr Val Ser Ser
        115
```

<210> SEQ ID NO 204
<211> LENGTH: 112
<212> TYPE: PRT
<213> ORGANISM: Artificial Sequence
<220> FEATURE:
<223> OTHER INFORMATION: 14F4 Light chain variable region

<400> SEQUENCE: 204

```
Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Ile Val Asp Ser
            20                  25                  30

Tyr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Arg Gly Leu Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 205
<211> LENGTH: 17
<212> TYPE: PRT
<213> ORGANISM: Artificial Sequence
<220> FEATURE:
<223> OTHER INFORMATION: CDR Sequence

<400> SEQUENCE: 205

```
Asp Ile Ser Pro Gly Asn Tyr Tyr Thr Asn Tyr Asn Ala Lys Phe Lys
1               5                   10                  15
```

Asp

<210> SEQ ID NO 206
<211> LENGTH: 6
<212> TYPE: PRT
<213> ORGANISM: Artificial Sequence
<220> FEATURE:
<223> OTHER INFORMATION: CDR Sequence

<400> SEQUENCE: 206

Tyr Asp Glu Phe Ala Tyr
1               5

<210> SEQ ID NO 207
<211> LENGTH: 16
<212> TYPE: PRT
<213> ORGANISM: Artificial Sequence
<220> FEATURE:
<223> OTHER INFORMATION: CDR Sequence

<400> SEQUENCE: 207

Arg Ser Ser Gln Ser Ile Val His Ser Asp Gly Asn Thr Tyr Leu Glu
1               5                   10                  15

<210> SEQ ID NO 208
<211> LENGTH: 8
<212> TYPE: PRT
<213> ORGANISM: Artificial Sequence
<220> FEATURE:
<223> OTHER INFORMATION: CDR Sequence

<400> SEQUENCE: 208

Ile Ser Pro Gly Asn Tyr Tyr Thr
1               5

<210> SEQ ID NO 209
<211> LENGTH: 8
<212> TYPE: PRT
<213> ORGANISM: Artificial Sequence
<220> FEATURE:
<223> OTHER INFORMATION: CDR Sequence

<400> SEQUENCE: 209

Ala Arg Tyr Asp Glu Phe Ala Tyr
1               5

<210> SEQ ID NO 210
<211> LENGTH: 11
<212> TYPE: PRT
<213> ORGANISM: Artificial Sequence
<220> FEATURE:
<223> OTHER INFORMATION: CDR Sequence

<400> SEQUENCE: 210

Gln Ser Ile Val His Ser Asp Gly Asn Thr Tyr
1               5                   10

<210> SEQ ID NO 211
<211> LENGTH: 4
<212> TYPE: PRT
<213> ORGANISM: Artificial Sequence
<220> FEATURE:
<223> OTHER INFORMATION: CDR Sequence

<400> SEQUENCE: 211

Pro Gly Asn Tyr

<210> SEQ ID NO 212
<211> LENGTH: 4
<212> TYPE: PRT
<213> ORGANISM: Artificial Sequence
<220> FEATURE:
<223> OTHER INFORMATION: CDR Sequence

<400> SEQUENCE: 212

Asp Glu Phe Ala
1

<210> SEQ ID NO 213
<211> LENGTH: 12
<212> TYPE: PRT
<213> ORGANISM: Artificial Sequence
<220> FEATURE:
<223> OTHER INFORMATION: CDR Sequence

<400> SEQUENCE: 213

Ser Gln Ser Ile Val His Ser Asp Gly Asn Thr Tyr
1               5                   10

<210> SEQ ID NO 214
<211> LENGTH: 13
<212> TYPE: PRT
<213> ORGANISM: Artificial Sequence
<220> FEATURE:
<223> OTHER INFORMATION: CDR Sequence

<400> SEQUENCE: 214

Trp Ile Gly Asp Ile Ser Pro Gly Asn Tyr Tyr Thr Asn
1               5                   10

<210> SEQ ID NO 215
<211> LENGTH: 7
<212> TYPE: PRT
<213> ORGANISM: Artificial Sequence
<220> FEATURE:
<223> OTHER INFORMATION: CDR Sequence

<400> SEQUENCE: 215

Ala Arg Tyr Asp Glu Phe Ala
1               5

<210> SEQ ID NO 216
<211> LENGTH: 12
<212> TYPE: PRT
<213> ORGANISM: Artificial Sequence
<220> FEATURE:
<223> OTHER INFORMATION: CDR Sequence

<400> SEQUENCE: 216

Val His Ser Asp Gly Asn Thr Tyr Leu Glu Trp Tyr
1               5                   10

<210> SEQ ID NO 217
<211> LENGTH: 10
<212> TYPE: PRT
<213> ORGANISM: Artificial Sequence
<220> FEATURE:
<223> OTHER INFORMATION: CDR Sequence

<400> SEQUENCE: 217

Asp Ile Ser Pro Gly Asn Tyr Tyr Thr Asn
1               5                   10

```
<210> SEQ ID NO 218
<211> LENGTH: 115
<212> TYPE: PRT
<213> ORGANISM: Artificial Sequence
<220> FEATURE:
<223> OTHER INFORMATION: 14E9 Heavy chain variable region

<400> SEQUENCE: 218

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile Ser Pro Gly Asn Tyr Tyr Thr Asn Tyr Asn Ala Lys Phe
    50                  55                  60

Lys Asp Lys Val Ser Leu Thr Ala Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Tyr Asp Glu Phe Ala Tyr Trp Gly Gln Gly Thr Leu Val Thr
            100                 105                 110

Val Ser Ala
        115

<210> SEQ ID NO 219
<211> LENGTH: 112
<212> TYPE: PRT
<213> ORGANISM: Artificial Sequence
<220> FEATURE:
<223> OTHER INFORMATION: 14E9 Light chain variable region

<400> SEQUENCE: 219

Asp Val Leu Met Thr Gln Thr Pro Leu Ser Leu Ser Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 220
<211> LENGTH: 117
<212> TYPE: PRT
<213> ORGANISM: Artificial Sequence
<220> FEATURE:
<223> OTHER INFORMATION: Hz6B5 Heavy chain variable region

<400> SEQUENCE: 220

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Phe Thr Phe Thr Asn His
             20                  25                  30

Trp Leu Gly Trp Val Arg Gln Ala Pro Gly Gln Gly Leu Glu Trp Ile
         35                  40                  45

Gly Asp Ile Tyr Pro Gly Gly Tyr Tyr Ile Asn Tyr Asn Glu Lys Phe
     50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Thr Asn Tyr Gly Ser Asp Tyr Trp Gly Gln Gly Thr Thr
            100                 105                 110

Val Thr Val Ser Ser
        115

<210> SEQ ID NO 221
<211> LENGTH: 112
<212> TYPE: PRT
<213> ORGANISM: Artificial Sequence
<220> FEATURE:
<223> OTHER INFORMATION: Hz6B5 Light chain variable region

<400> SEQUENCE: 221

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Ile Val Asp Ser
             20                  25                  30

Tyr Gly Asn Thr Phe Leu Glu Trp Tyr Gln Gln Arg Pro Gly Gln Ser
         35                  40                  45

Pro Arg Leu Leu Ile Tyr Lys Val Ser Asn Arg Leu Ser Gly Val Pro
     50                  55                  60

Asp Arg Phe Ser Gly Ser Gly Ser Gly Thr Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Trp Thr Phe Gly Gln Gly Thr Lys Leu Glu Ile Lys
            100                 105                 110

<210> SEQ ID NO 222
<211> LENGTH: 477
<212> TYPE: PRT
<213> ORGANISM: Homo sapiens
<220> FEATURE:
<223> OTHER INFORMATION: Human CGCR with predicted signal sequence

<400> SEQUENCE: 222

Met Pro Pro Cys Gln Pro Gln Arg Pro Leu Leu Leu Leu Leu Leu Leu
 1               5                  10                  15

Leu Ala Cys Gln Pro Gln Val Pro Ser Ala Gln Val Met Asp Phe Leu
             20                  25                  30

Phe Glu Lys Trp Lys Leu Tyr Gly Asp Gln Cys His His Asn Leu Ser
         35                  40                  45

Leu Leu Pro Pro Pro Thr Glu Leu Val Cys Asn Arg Thr Phe Asp Lys
     50                  55                  60

Tyr Ser Cys Trp Pro Asp Thr Pro Ala Asn Thr Thr Ala Asn Ile Ser
 65                  70                  75                  80

Cys Pro Trp Tyr Leu Pro Trp His His Lys Val Gln His Arg Phe Val
                 85                  90                  95
```

Phe Lys Arg Cys Gly Pro Asp Gly Gln Trp Val Arg Pro Arg Gly
                100                 105                 110

Gln Pro Trp Arg Asp Ala Ser Gln Cys Gln Met Asp Gly Glu Ile
            115                 120                 125

Glu Val Gln Lys Glu Val Ala Lys Met Tyr Ser Ser Phe Gln Val Met
130                 135                 140

Tyr Thr Val Gly Tyr Ser Leu Ser Leu Gly Ala Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
            195                 200                 205

Asp Leu Ser Val Ser Thr Trp Leu Ser Asp Gly Ala Val Ala Gly Cys
210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
            275                 280                 285

Phe Glu Asn Val Gln Cys Trp Thr Ser Asn Asp Asn Met Gly Phe Trp
290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
            355                 360                 365

Thr Asp Glu His Ala Gln Gly Thr Leu Arg Ser Ala Lys Leu Phe Phe
370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Glu Arg Asn Thr Ser Asn
            420                 425                 430

His Arg Ala Ser Ser Ser Pro Gly His Gly Pro Pro Ser Lys Glu Leu
            435                 440                 445

Gln Phe Gly Arg Gly Gly Ser Gln Asp Ser Ser Ala Glu Thr Pro
            450                 455                 460

Leu Ala Gly Gly Leu Pro Arg Leu Ala Glu Ser Pro Phe
465                 470                 475

<210> SEQ ID NO 223
<211> LENGTH: 452
<212> TYPE: PRT
<213> ORGANISM: Homo sapiens
<220> FEATURE:

<223> OTHER INFORMATION: Human CGCR without predicted signal sequence

<400> SEQUENCE: 223

```
Ala Gln Val Met Asp Phe Leu Phe Glu Lys Trp Lys Leu Tyr Gly Asp
1               5                   10                  15
Gln Cys His His Asn Leu Ser Leu Leu Pro Pro Pro Thr Glu Leu Val
                20                  25                  30
Cys Asn Arg Thr Phe Asp Lys Tyr Ser Cys Trp Pro Asp Thr Pro Ala
            35                  40                  45
Asn Thr Thr Ala Asn Ile Ser Cys Pro Trp Tyr Leu Pro Trp His His
        50                  55                  60
Lys Val Gln His Arg Phe Val Phe Lys Arg Cys Gly Pro Asp Gly Gln
65                  70                  75                  80
Trp Val Arg Gly Pro Arg Gly Gln Pro Trp Arg Asp Ala Ser Gln Cys
                85                  90                  95
Gln Met Asp Gly Glu Glu Ile Glu Val Gln Lys Glu Val Ala Lys Met
            100                 105                 110
Tyr Ser Ser Phe Gln Val Met Tyr Thr Val Gly Tyr Ser Leu Ser Leu
        115                 120                 125
Gly Ala Leu Leu Leu Ala Leu Ala Ile Leu Gly Gly Leu Ser Lys Leu
130                 135                 140
His Cys Thr Arg Asn Ala Ile His Ala Asn Leu Phe Ala Ser Phe Val
145                 150                 155                 160
Leu Lys Ala Ser Ser Val Leu Val Ile Asp Gly Leu Leu Arg Thr Arg
                165                 170                 175
Tyr Ser Gln Lys Ile Gly Asp Asp Leu Ser Val Ser Thr Trp Leu Ser
            180                 185                 190
Asp Gly Ala Val Ala Gly Cys Arg Val Ala Ala Val Phe Met Gln Tyr
        195                 200                 205
Gly Ile Val Ala Asn Tyr Cys Trp Leu Leu Val Glu Gly Leu Tyr Leu
    210                 215                 220
His Asn Leu Leu Gly Leu Ala Thr Leu Pro Glu Arg Ser Phe Phe Ser
225                 230                 235                 240
Leu Tyr Leu Gly Ile Gly Trp Gly Ala Pro Met Leu Phe Val Val Pro
                245                 250                 255
Trp Ala Val Val Lys Cys Leu Phe Glu Asn Val Gln Cys Trp Thr Ser
            260                 265                 270
Asn Asp Asn Met Gly Phe Trp Trp Ile Leu Arg Phe Pro Val Phe Leu
        275                 280                 285
Ala Ile Leu Ile Asn Phe Phe Ile Phe Val Arg Ile Val Gln Leu Leu
    290                 295                 300
Val Ala Lys Leu Arg Ala Arg Gln Met His His Thr Asp Tyr Lys Phe
305                 310                 315                 320
Arg Leu Ala Lys Ser Thr Leu Thr Leu Ile Pro Leu Leu Gly Val His
                325                 330                 335
Glu Val Val Phe Ala Phe Val Thr Asp Glu His Ala Gln Gly Thr Leu
            340                 345                 350
Arg Ser Ala Lys Leu Phe Phe Asp Leu Phe Leu Ser Ser Phe Gln Gly
        355                 360                 365
Leu Leu Val Ala Val Leu Tyr Cys Phe Leu Asn Lys Glu Val Gln Ser
    370                 375                 380
Glu Leu Arg Arg Arg Trp His Arg Trp Arg Leu Gly Lys Val Leu Trp
385                 390                 395                 400
```

-continued

```
Glu Glu Arg Asn Thr Ser Asn His Arg Ala Ser Ser Pro Gly His
                405                 410                 415

Gly Pro Pro Ser Lys Glu Leu Gln Phe Gly Arg Gly Gly Ser Gln
            420                 425                 430

Asp Ser Ser Ala Glu Thr Pro Leu Ala Gly Gly Leu Pro Arg Leu Ala
        435                 440                 445

Glu Ser Pro Phe
    450

<210> SEQ ID NO 224
<211> LENGTH: 111
<212> TYPE: PRT
<213> ORGANISM: Homo sapiens
<220> FEATURE:
<223> OTHER INFORMATION: Human CGCR extracellular domain (amino acids
      26-136)

<400> SEQUENCE: 224

Ala Gln Val Met Asp Phe Leu Phe Glu Lys Trp Lys Leu Tyr Gly Asp
1               5                   10                  15

Gln Cys His His Asn Leu Ser Leu Leu Pro Pro Pro Thr Glu Leu Val
            20                  25                  30

Cys Asn Arg Thr Phe Asp Lys Tyr Ser Cys Trp Pro Asp Thr Pro Ala
        35                  40                  45

Asn Thr Thr Ala Asn Ile Ser Cys Pro Trp Tyr Leu Pro Trp His His
    50                  55                  60

Lys Val Gln His Arg Phe Val Phe Lys Arg Cys Gly Pro Asp Gly Gln
65                  70                  75                  80

Trp Val Arg Gly Pro Arg Gly Gln Pro Trp Arg Asp Ala Ser Gln Cys
                85                  90                  95

Gln Met Asp Gly Glu Glu Ile Glu Val Gln Lys Glu Val Ala Lys
            100                 105                 110

<210> SEQ ID NO 225
<211> LENGTH: 96
<212> TYPE: PRT
<213> ORGANISM: Homo sapiens
<220> FEATURE:
<223> OTHER INFORMATION: Human CGCR extracellular domain (amino acids
      28-123)

<400> SEQUENCE: 225

Val Met Asp Phe Leu Phe Glu Lys Trp Lys Leu Tyr Gly Asp Gln Cys
1               5                   10                  15

His His Asn Leu Ser Leu Leu Pro Pro Pro Thr Glu Leu Val Cys Asn
            20                  25                  30

Arg Thr Phe Asp Lys Tyr Ser Cys Trp Pro Asp Thr Pro Ala Asn Thr
        35                  40                  45

Thr Ala Asn Ile Ser Cys Pro Trp Tyr Leu Pro Trp His His Lys Val
    50                  55                  60

Gln His Arg Phe Val Phe Lys Arg Cys Gly Pro Asp Gly Gln Trp Val
65                  70                  75                  80

Arg Gly Pro Arg Gly Gln Pro Trp Arg Asp Ala Ser Gln Cys Gln Met
                85                  90                  95

<210> SEQ ID NO 226
<211> LENGTH: 40
<212> TYPE: PRT
<213> ORGANISM: Homo sapiens
<220> FEATURE:
```

-continued

<223> OTHER INFORMATION: Human CGCR extracellular domain (amino acids 80-119)

<400> SEQUENCE: 226

Ser Cys Pro Trp Tyr Leu Pro Trp His His Lys Val Gln His Arg Phe
1               5                   10                  15

Val Phe Lys Arg Cys Gly Pro Asp Gly Gln Trp Val Arg Gly Pro Arg
            20                  25                  30

Gly Gln Pro Trp Arg Asp Ala Ser
        35                  40

<210> SEQ ID NO 227
<211> LENGTH: 448
<212> TYPE: PRT
<213> ORGANISM: Macaca fascicularis
<220> FEATURE:
<223> OTHER INFORMATION: GCGR - cynomolgus monkey

<400> SEQUENCE: 227

Met Pro Pro Cys Gln Pro Arg Arg Pro Leu Leu Leu Leu Leu Leu Leu
1               5                   10                  15

Leu Ala Cys Gln Pro Gln Ala Pro Ser Ala Gln Val Met Asp Phe Leu
            20                  25                  30

Phe Glu Lys Trp Lys Leu Tyr Gly Asp Gln Cys His His Asn Leu Ser
        35                  40                  45

Leu Leu Pro Pro Pro Thr Glu Leu Val Cys Asn Arg Thr Phe Asp Lys
    50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Leu
        115                 120                 125

Glu Val Gln Lys Glu Val Ala Lys Met Tyr Ser Ser Phe Gln Val Met
130                 135                 140

Tyr Thr Val Gly Tyr Ser Leu Ser Leu Gly Ala Leu Leu Leu Ala Leu
145                 150                 155                 160

Ala Val Leu Gly Gly Ile Ser Lys Leu His Cys Thr Arg Asn Ala Ile
                165                 170                 175

His Ala Asn Leu Phe Val Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Ile Trp Leu Ser Asp Gly Ala Val Ala Gly Cys
    210                 215                 220

Arg Val Ala Ala Val Phe Met Gln Tyr Gly Val Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Ile Ile Pro Trp Val Val Val Arg Cys Leu
        275                 280                 285

Phe Glu Asn Ile Gln Cys Trp Thr Ser Asn Asp Asn Met Gly Phe Trp

-continued

```
                290                 295                 300

Trp Ile Leu Arg Phe Pro Val Phe Leu Ala Ile Leu Ile Asn Phe Phe
305                 310                 315                 320

Ile Phe Ile Arg Ile Val His Leu Leu Val Ala Lys Leu Arg Ala Arg
                325                 330                 335

Glu Met His His Thr Asp Tyr Lys Phe Arg Ser Phe Gln Gly Leu Leu
                340                 345                 350

Val Ala Val Leu Tyr Cys Phe Leu Asn Lys Glu Val Gln Ser Glu Leu
                355                 360                 365

Arg Arg His Trp His Arg Trp Arg Leu Gly Lys Val Leu Gln Glu Glu
            370                 375                 380

Arg Gly Thr Ser Asn His Lys Ala Pro Ser Ala Pro Gly Gln Gly Leu
385                 390                 395                 400

Pro Gly Lys Lys Leu Gln Ser Gly Arg Asp Gly Gly Ser Gln Asp Ser
                405                 410                 415

Ser Ala Glu Ile Pro Leu Ala Gly Gly Leu Pro Arg Leu Ala Glu Ser
                420                 425                 430

Pro Phe Ser Thr Leu Leu Gly Pro Gln Leu Gly Leu Asp Ser Gly Thr
            435                 440                 445

<210> SEQ ID NO 228
<211> LENGTH: 485
<212> TYPE: PRT
<213> ORGANISM: Mus musculus
<220> FEATURE:
<223> OTHER INFORMATION: GCGR - mouse

<400> SEQUENCE: 228

Met Pro Leu Thr Gln Leu His Cys Pro His Leu Leu Leu Leu Leu Leu
1               5                   10                  15

Val Leu Ser Cys Leu Pro Glu Ala Pro Ser Ala Gln Val Met Asp Phe
                20                  25                  30

Leu Phe Glu Lys Trp Lys Leu Tyr Ser Asp Gln Cys His His Asn Leu
            35                  40                  45

Ser Leu Leu Pro Pro Pro Thr Glu Leu Val Cys Asn Arg Thr Phe Asp
        50                  55                  60

Asn Tyr Ser Cys Trp Pro Asp Thr Pro Pro Asn Thr Thr Ala Asn Ile
65                  70                  75                  80

Ser Cys Pro Trp Tyr Leu Pro Trp Cys His Lys Val Gln His Arg Leu
                85                  90                  95

Val Phe Lys Arg Cys Gly Pro Asp Gly Gln Trp Val Arg Gly Pro Arg
                100                 105                 110

Gly Gln Pro Trp Arg Asn Ala Ser Gln Cys Gln Leu Asp Asp Glu Glu
            115                 120                 125

Ile Glu Val Gln Lys Gly Val Ala Lys Met Tyr Ser Ser Gln Gln Val
        130                 135                 140

Met Tyr Thr Val Gly Tyr Ser Leu Ser Leu Gly Ala Leu Leu Leu Ala
145                 150                 155                 160

Leu Val Ile Leu Leu Gly Leu Arg Lys Leu His Cys Thr Arg Asn Tyr
                165                 170                 175

Ile His Gly Asn Leu Phe Ala Ser Phe Val Leu Lys Ala Gly Ser Val
                180                 185                 190

Leu Val Ile Asp Trp Leu Leu Lys Thr Arg Tyr Ser Gln Lys Ile Gly
            195                 200                 205

Asp Asp Leu Ser Val Ser Val Trp Leu Ser Asp Gly Ala Met Ala Gly
```

```
            210                 215                 220
Cys Arg Val Ala Thr Val Ile Met Gln Tyr Gly Ile Pro Asn Tyr
225                 230                 235                 240

Cys Trp Leu Leu Val Glu Gly Val Tyr Leu Tyr Ser Leu Leu Ser Leu
                245                 250                 255

Ala Thr Phe Ser Glu Arg Ser Phe Phe Ser Leu Tyr Leu Gly Ile Gly
                260                 265                 270

Trp Gly Ala Pro Leu Leu Phe Val Ile Pro Trp Val Val Lys Cys
                275                 280                 285

Leu Phe Glu Asn Val Gln Cys Trp Thr Ser Asn Asp Asn Met Gly Phe
290                 295                 300

Trp Trp Ile Leu Arg Ile Pro Val Phe Leu Ala Leu Leu Ile Asn Phe
305                 310                 315                 320

Phe Ile Phe Val His Ile Ile Gln Leu Leu Val Ala Lys Leu Arg Ala
                325                 330                 335

His Gln Met His Tyr Ala Asp Tyr Lys Phe Arg Leu Ala Arg Ser Thr
                340                 345                 350

Leu Thr Leu Ile Pro Leu Leu Gly Val His Glu Val Val Phe Ala Phe
                355                 360                 365

Val Thr Asp Glu His Ala Gln Gly Thr Leu Arg Ser Thr Lys Leu Phe
                370                 375                 380

Phe Asp Leu Phe Leu Ser Ser Phe Gln Gly Leu Leu Val Ala Val Leu
385                 390                 395                 400

Tyr Cys Phe Leu Asn Lys Glu Val Gln Ala Glu Leu Met Arg Arg Trp
                405                 410                 415

Arg Gln Trp Gln Glu Gly Lys Ala Leu Gln Glu Arg Leu Ala Ser
                420                 425                 430

Ser His Gly Ser His Met Ala Pro Ala Gly Pro Cys His Gly Asp Pro
                435                 440                 445

Cys Glu Lys Leu Gln Leu Met Ser Ala Gly Ser Ser Ser Gly Thr Gly
                450                 455                 460

Cys Val Pro Ser Met Glu Thr Ser Leu Ala Ser Ser Leu Pro Arg Leu
465                 470                 475                 480

Ala Asp Ser Pro Thr
                485

<210> SEQ ID NO 229
<211> LENGTH: 485
<212> TYPE: PRT
<213> ORGANISM: Rattus norvegicus
<220> FEATURE:
<223> OTHER INFORMATION: GCGR - rat

<400> SEQUENCE: 229

Met Leu Leu Thr Gln Leu His Cys Pro Tyr Leu Leu Leu Leu Val
1               5                   10                  15

Val Leu Ser Cys Leu Pro Lys Ala Pro Ser Ala Gln Val Met Asp Phe
                20                  25                  30

Leu Phe Glu Lys Trp Lys Leu Tyr Ser Asp Gln Cys His His Asn Leu
            35                  40                  45

Ser Leu Leu Pro Pro Pro Thr Glu Leu Val Cys Asn Arg Thr Phe Asp
            50                  55                  60

Lys Tyr Ser Cys Trp Pro Asp Thr Pro Pro Asn Thr Thr Ala Asn Ile
65                  70                  75                  80

Ser Cys Pro Trp Tyr Leu Pro Trp Tyr His Lys Val Gln His Arg Leu
```

```
                  85                  90                  95
Val Phe Lys Arg Cys Gly Pro Asp Gly Gln Trp Val Arg Gly Pro Arg
                100                 105                 110

Gly Gln Ser Trp Arg Asp Ala Ser Gln Cys Gln Met Asp Asp Asp Glu
                115                 120                 125

Ile Glu Val Gln Lys Gly Val Ala Lys Met Tyr Ser Ser Tyr Gln Val
            130                 135                 140

Met Tyr Thr Val Gly Tyr Ser Leu Ser Leu Gly Ala Leu Leu Leu Ala
145                 150                 155                 160

Leu Val Ile Leu Leu Gly Leu Arg Lys Leu His Cys Thr Arg Asn Tyr
                165                 170                 175

Ile His Gly Asn Leu Phe Ala Ser Phe Val Leu Lys Ala Gly Ser Val
                180                 185                 190

Leu Val Ile Asp Trp Leu Leu Lys Thr Arg Tyr Ser Gln Lys Ile Gly
                195                 200                 205

Asp Asp Leu Ser Val Ser Val Trp Leu Ser Asp Gly Ala Val Ala Gly
                210                 215                 220

Cys Arg Val Ala Thr Val Ile Met Gln Tyr Gly Ile Ile Ala Asn Tyr
225                 230                 235                 240

Cys Trp Leu Leu Val Glu Gly Val Tyr Leu Tyr Ser Leu Leu Ser Ile
                245                 250                 255

Thr Thr Phe Ser Glu Lys Ser Phe Phe Ser Leu Tyr Leu Cys Ile Gly
                260                 265                 270

Trp Gly Ser Pro Leu Leu Phe Val Ile Pro Trp Val Val Lys Cys
                275                 280                 285

Leu Phe Glu Asn Val Gln Cys Trp Thr Ser Asn Asp Asn Met Gly Phe
                290                 295                 300

Trp Trp Ile Leu Arg Ile Pro Val Leu Leu Ala Ile Leu Ile Asn Phe
305                 310                 315                 320

Phe Ile Phe Val Arg Ile Ile His Leu Leu Val Ala Lys Leu Arg Ala
                325                 330                 335

His Gln Met His Tyr Ala Asp Tyr Lys Phe Arg Leu Ala Arg Ser Thr
                340                 345                 350

Leu Thr Leu Ile Pro Leu Leu Gly Val His Glu Val Val Phe Ala Phe
                355                 360                 365

Val Thr Asp Glu His Ala Gln Gly Thr Leu Arg Ser Thr Lys Leu Phe
                370                 375                 380

Phe Asp Leu Phe Phe Ser Ser Phe Gln Gly Leu Leu Val Ala Val Leu
385                 390                 395                 400

Tyr Cys Phe Leu Asn Lys Glu Val Gln Ala Glu Leu Leu Arg Arg Trp
                405                 410                 415

Arg Arg Trp Gln Glu Gly Lys Ala Leu Gln Glu Arg Met Ala Ser
                420                 425                 430

Ser His Gly Ser His Met Ala Pro Ala Gly Thr Cys His Gly Asp Pro
                435                 440                 445

Cys Glu Lys Leu Gln Leu Met Ser Ala Gly Ser Ser Ser Gly Thr Gly
                450                 455                 460

Cys Glu Pro Ser Ala Lys Thr Ser Leu Ala Ser Ser Leu Pro Arg Leu
465                 470                 475                 480

Ala Asp Ser Pro Thr
                485

<210> SEQ ID NO 230
```

```
<211> LENGTH: 330
<212> TYPE: PRT
<213> ORGANISM: Homo sapiens
<220> FEATURE:
<223> OTHER INFORMATION: Human IgG1

<400> SEQUENCE: 230

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 231
<211> LENGTH: 330
<212> TYPE: PRT
<213> ORGANISM: Homo sapiens
<220> FEATURE:
<223> OTHER INFORMATION: Human IgG1 E233A/L235A
```

-continued

<400> SEQUENCE: 231

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Ala Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 232
<211> LENGTH: 330
<212> TYPE: PRT
<213> ORGANISM: Homo sapiens
<220> FEATURE:
<223> OTHER INFORMATION: Human IgG1 L234A/L235A

<400> SEQUENCE: 232

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 233
<211> LENGTH: 469
<212> TYPE: PRT
<213> ORGANISM: Artificial Sequence
<220> FEATURE:
<223> OTHER INFORMATION: Hz6B5 Heavy Chain with signal sequence

<400> SEQUENCE: 233

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Phe Thr Phe Thr Asn His Trp Leu Gly Trp Val Arg Gln Ala Pro Gly
```

```
            50                  55                  60
Gln Gly Leu Glu Trp Ile Gly Asp Ile Tyr Pro Gly Gly Tyr Tyr Ile
 65                  70                  75                  80

Asn Tyr Asn Glu Lys Phe Lys Gly Arg Val Thr Ile Thr Ala Asp Glu
                     85                  90                  95

Ser Thr Ser Thr Ala Tyr Met Glu Leu Ser Ser Leu Arg Ser Glu Asp
                100                 105                 110

Thr Ala Val Tyr Tyr Cys Ala Arg His Thr Asn Tyr Gly Ser Asp Tyr
                115                 120                 125

Trp Gly Gln Gly Thr Thr Val Thr Val Ser Ser Ala Ser Thr Lys Gly
                130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
                210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Ala Leu
                245                 250                 255

Ala Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
                290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Glu Glu Met Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
                450                 455                 460

Leu Ser Pro Gly Lys
465
```

<210> SEQ ID NO 234
<211> LENGTH: 447
<212> TYPE: PRT
<213> ORGANISM: Artificial Sequence
<220> FEATURE:
<223> OTHER INFORMATION: Hz6B5 Heavy Chain without signal sequence

<400> SEQUENCE: 234

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asn His
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Tyr Tyr Ile Asn Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Thr Asn Tyr Gly Ser Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Ala Leu Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

-continued

Val Lys Gly Phe Tyr Pro Ser Asp Ile Ala Val Glu Trp Glu Ser Asn
    370                      375                380

Gly Gln Pro Glu Asn Asn Tyr Lys Thr Thr Pro Pro Val Leu Asp Ser
385                  390                      395                      400

Asp Gly Ser Phe Phe Leu Tyr Ser Lys Leu Thr Val Asp Lys Ser Arg
                405                      410                415

Trp Gln Gln Gly Asn Val Phe Ser Cys Ser Val Met His Glu Ala Leu
        420                    425                430

His Asn His Tyr Thr Gln Lys Ser Leu Ser Leu Ser Pro Gly Lys
                435                      440                445

<210> SEQ ID NO 235
<211> LENGTH: 241
<212> TYPE: PRT
<213> ORGANISM: Artificial Sequence
<220> FEATURE:
<223> OTHER INFORMATION: Hz6B5 Light chain with signal sequence

<400> SEQUENCE: 235

Met Asp Met Arg Val Pro Ala Gln Leu Leu Gly Leu Leu Leu Leu Trp
1                  5                      10                  15

Leu Arg Gly Ala Arg Cys Asp Val Val Met Thr Gln Ser Pro Leu Ser
                20                      25                  30

Leu Pro Val Thr Leu Gly Gln Pro Ala Ser Ile Ser Cys Arg Ser Ser
                  35                    40                45

Gln Ser Ile Val Asp Ser Tyr Gly Asn Thr Phe Leu Glu Trp Tyr Gln
    50                      55                    60

Gln Arg Pro Gly Gln Ser Pro Arg Leu Leu Ile Tyr Lys Val Ser Asn
65                  70                      75                    80

Arg Leu Ser Gly Val Pro Asp Arg Phe Ser Gly Ser Gly Ser Gly Thr
                  85                    90                    95

Asp Phe Thr Leu Lys Ile Ser Arg Val Glu Ala Glu Asp Val Gly Val
                100                      105                110

Tyr Tyr Cys Phe Gln Gly Ser His Val Pro Trp Thr Phe Gly Gln Gly
        115                    120                125

Thr Lys Leu Glu Ile Lys Arg Thr Val Ala Ala Pro Ser Val Phe Ile
130                  135                      140

Phe Pro Pro Ser Asp Glu Gln Leu Lys Ser Gly Thr Ala Ser Val Val
145                  150                      155                160

Cys Leu Leu Asn Asn Phe Tyr Pro Arg Glu Ala Lys Val Gln Trp Lys
                165                      170                175

Val Asp Asn Ala Leu Gln Ser Gly Asn Ser Gln Glu Ser Val Thr Glu
        180                    185                190

Gln Asp Ser Lys Asp Ser Thr Tyr Ser Leu Ser Ser Thr Leu Thr Leu
                195                      200                205

Ser Lys Ala Asp Tyr Glu Lys His Lys Val Tyr Ala Cys Glu Val Thr
        210                    215                220

His Gln Gly Leu Ser Ser Pro Val Thr Lys Ser Phe Asn Arg Gly Glu
225                  230                      235                240

Cys

<210> SEQ ID NO 236
<211> LENGTH: 219
<212> TYPE: PRT
<213> ORGANISM: Artificial Sequence
<220> FEATURE:

<223> OTHER INFORMATION: Hz6B5 Light chain without signal sequence

<400> SEQUENCE: 236

```
Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Ile Val Asp Ser
            20                  25                  30
Tyr Gly Asn Thr Phe Leu Glu Trp Tyr Gln Gln Arg Pro Gly Gln Ser
        35                  40                  45
Pro Arg Leu Leu Ile Tyr Lys Val Ser Asn Arg Leu Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Trp Thr Phe Gly Gln Gly Thr Lys Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

<210> SEQ ID NO 237
<211> LENGTH: 17
<212> TYPE: PRT
<213> ORGANISM: Artificial Sequence
<220> FEATURE:
<223> OTHER INFORMATION: Heavy chain CDR2 consensus sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 237

```
Asp Ile Xaa Pro Gly Gly Xaa Tyr Xaa Asn Tyr Asn Xaa Lys His Lys
1               5                   10                  15
```

Xaa

```
<210> SEQ ID NO 238
<211> LENGTH: 16
<212> TYPE: PRT
<213> ORGANISM: Artificial Sequence
<220> FEATURE:
<223> OTHER INFORMATION: Light chain CDR1 consensus sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 238

Arg Ser Ser Gln Xaa Ile Val Xaa Ser Xaa Gly Asn Thr Tyr Leu Glu
1               5                  10                  15
```

ANTIBODIES WHICH BIND HUMAN GLUCAGON RECEPTOR

CROSS-REFERENCE TO RELATED APPLICATIONS

This application claims the priority benefit of U.S. Provisional Application No. 62/451,603, filed Jan. 27, 2017, which is hereby incorporated by reference herein in its entirety.

FIELD

The present disclosure generally relates to proteins, such as antibodies, that bind to glucagon receptor (GCGR), including human GCGR, as well as methods of using the binding proteins for the treatment and/or prevention of diseases.

BACKGROUND

Glucagon is a 29-amino acid peptide hormone secreted by pancreatic alpha cells. Glucagon secretion generally increases in response to falling blood glucose levels, for example, during fasting. Glucagon can raise the concentration of blood glucose by stimulating hepatic glycogenolysis and gluconeogenesis. In contrast, insulin is produced by pancreatic beta cells. The stimulus for insulin secretion is high blood glucose. Although there is always a low level of insulin secreted by the pancreas, the amount secreted into the blood increases as blood glucose rises. Similarly, as blood glucose falls, the amount of insulin secreted by the pancreatic beta cells goes down. Acting together, glucagon and insulin help maintain normal blood glucose levels.

Glucagon binds to and activates the glucagon receptor (GCGR). GCGR is a member of the class B type of G-protein coupled receptors (GPCRs). GPCRs are characterized by a N-terminal extracellular domain, a core seven alpha-helix transmembrane region, and a cytoplasmic C-terminal region. Typically, GPCRs are associated with one or more intracellular signaling pathways via effector proteins. The effector proteins are heterotrimeric guanine-nucleotide binding proteins (G proteins), such as Gα (Gαs, Gαi, and Gαo), Gβ, and Gγ.

Through G protein coupling, GCGR stimulation can result in activation of adenylyl cyclase and cAMP-dependent intracellular signaling pathways as well as phosphoinositol-mediated signaling. Subsequent increases in the expression of gluconeogenic enzymes, including phosphoenolpyruvate carboxykinase, fructose-1,6-bisphosphatase, and glucose-6-phosphatase, promote gluconeogenesis. In addition, GCGR signaling can result in activation of glycogen phosphorylase and inhibition of glycogen synthase, and thereby promote glycogenolysis.

In a healthy individual pancreatic beta cells function to store and release insulin. Typically, beta cells respond quickly to spikes in blood glucose concentrations by secreting some of their stored insulin while simultaneously producing more. Problems arise when blood glucose levels are not regulated efficiently.

Diseases, disorders, or conditions associated with unregulated blood glucose levels include, hyperglycemia and the health issues resulting from hyperglycemia, including Type 1 and Type 2 diabetes. Diseases, disorders, or conditions associated with beta cell dysfunction include hyperglycemia and metabolic diseases, such as Type 1 and Type 2 diabetes. A subject's ability to produce and secrete insulin into the blood and to regulate blood glucose can be severely impaired when the subject has a disease associated with beta cell dysfunction. New methods and therapeutic agents for treating diseases, disorders, or conditions associated with unregulated blood glucose levels, hyperglycemia, and/or beta cell dysfunction are needed.

SUMMARY

The present disclosure provides proteins that bind to glucagon receptors (GCGRs), including binding proteins such as antibodies, and methods of their use. Such binding proteins ("GCGR-binding proteins") (e.g., antibodies) may bind to a GCGR polypeptide, a GCGR fragment, and/or a GCGR epitope. The GCGR-binding proteins may be antagonists (e.g., inhibit binding of glucagon to GCGR, inhibit glucagon-induced signaling of GCGR, or inhibit a glucagon/GCGR complex). The present disclosure also provides methods for treating or preventing beta cell defective diseases, disorders, or conditions, or symptoms thereof, using effective amounts of GCGR-binding proteins described herein (e.g., antibodies). In some embodiments, beta cell defective diseases, disorders, or conditions include unregulated blood glucose, hyperglycemia, metabolic diseases (e.g., Type 1 and Type 2 diabetes), and/or any disease in which there is a loss of beta cell function.

The present disclosure also provides binding proteins, including antibodies or fragments thereof, that (i) bind to human GCGR, (ii) inhibit glucagon signaling, (iii) inhibit GCGR signaling, and/or (iv) compete with glucagon for interaction with GCGR (e.g., antibodies comprising CDR, heavy chain variable region, and/or light chain variable region sequences shown in Tables 1-10).

In some embodiments, the GCGR-binding proteins are antibodies or humanized antibodies that bind to a GCGR polypeptide, a GCGR fragment, or a GCGR epitope. In some embodiments, an anti-GCGR antibody comprises at least one heavy chain CDR and/or at least one light chain CDR of a monoclonal antibody designated as 6B5, 3H5, 5B11, 1C1, 1C3, 1H2, 4F8, 13G9, 14F4, or 14E9 described herein, (e.g., Tables 1-10) or a humanized variant thereof. In certain embodiments, an anti-GCGR antibody further comprises at least one framework region of a human immunoglobulin amino acid sequence or a variant thereof.

In some embodiments, a GCGR-binding protein (e.g., an antibody) comprises six CDRs or less than six CDRs of an antibody defined in Tables 1-10. In some embodiments, a GCGR-binding protein (e.g., an antibody) comprises one, two, three, four, five, or six CDRs selected from heavy chain CDR1, CDR2, CDR3 and/or light chain CDR1, CD2, CDR3 of an antibody defined in Tables 1-10. In some embodiments, a GCGR-binding protein (e.g., an antibody) comprises one, two, three, four, five, or six CDRs of a monoclonal antibody designated as 6B5, 3H5, 5B11, 1C1, 1C3, 1H2, 4F8, 13G9, 14F4, or 14E9 described herein or a humanized variant thereof. In some embodiments, a GCGR-binding protein (e.g., an antibody) further comprises a scaffold region or framework region(s) of a human immunoglobulin amino acid sequence or a variant thereof.

In some embodiments, a GCGR-binding protein is an antibody. In some embodiments, the antibody is a humanized antibody, a monoclonal antibody, a recombinant antibody, an antigen-binding fragment, or any combination thereof. In some embodiments, the antibody is a monoclonal antibody. In some embodiments, the antibody is a humanized antibody. In some embodiments, the antibody is a humanized monoclonal antibody that binds to a GCGR polypeptide (e.g., a cell-surface expressed or a soluble GCGR), a GCGR fragment, or a GCGR epitope. In some embodiments, the antibody is a human antibody. In some embodiments, the antibody is a chimeric antibody. In some embodiments, the antibody is a bispecific or multispecific antibody. In some embodiments, the antibody is an antibody fragment comprising at least one antigen-binding site. In some embodiments, the antibody is an IgG antibody. In some embodiments, the antibody is an IgG1 antibody, an IgG2 antibody, or an IgG4 antibody.

The present disclosure also provides binding proteins, including antibodies or fragments thereof, that (i) bind to an epitope of human GCGR and cynomolgus ("cyno") monkey GCGR recognized by an antibody comprising a heavy chain variable region comprising SEQ ID NO:25 and a light chain variable region comprising SEQ ID NO:26; or (ii) compete for binding to human GCGR with an antibody comprising a heavy chain variable region comprising SEQ ID NO:25 and a light chain variable region comprising SEQ ID NO:26. In some embodiments, binding proteins, including antibodies or fragments thereof, are provided herein that bind to a region, including an epitope, of human GCGR or cyno GCGR. In some embodiments, GCGR-binding proteins (e.g., antibodies) can inhibit glucagon signaling, inhibit GCGR signaling, or inhibit a glucagon/GCGR complex in a cell that expresses human GCGR. Additionally, in some embodiments, the GCGR-binding protein is an antibody and that antibody is a monoclonal antibody, a humanized antibody, human antibody, and/or chimeric antibody.

In some embodiments, a GCGR-binding protein is an antibody that specifically binds human GCGR, wherein the antibody comprises: (a) a heavy chain CDR1 comprising GFTFTNHWLG (SEQ ID NO:1), a heavy chain CDR2 comprising DIYPGGYYINYNEKFKG (SEQ ID NO:2), and a heavy chain CDR3 comprising HTNYGSDY (SEQ ID NO:3); and/or (b) a light chain CDR1 comprising RSSQSIVDSYGNTFLE (SEQ ID NO:4), a light chain CDR2 comprising KVSNRLS (SEQ ID NO:5), and a light chain CDR3 comprising FQGSHVPWT (SEQ ID NO:6). In some embodiments, a GCGR-binding protein is an antibody that specifically binds human GCGR, wherein the antibody comprises (a) a heavy chain variable region having at least 90% sequence identity to SEQ ID NO:25 and a light chain variable region having at least 90% sequence identity to SEQ ID NO:26; or (b) a heavy chain variable region having at least 90% sequence identity to SEQ ID NO:220 and a light chain variable region having at least 90% sequence identity to SEQ ID NO:221. In some embodiments, a GCGR-binding protein is an antibody that specifically binds human GCGR, wherein the antibody comprises: (a) a heavy chain variable region having at least 95% sequence identity to SEQ ID NO:25 and a light chain variable region having at least 95% sequence identity to SEQ ID NO:26; or (b) a heavy chain variable region having at least 95% sequence identity to SEQ ID NO:220 and a light chain variable region having at least 95% sequence identity to SEQ ID NO:221. In some embodiments, a GCGR-binding protein is an antibody that specifically binds human GCGR, wherein the antibody comprises a heavy chain variable region comprising SEQ ID NO:25 and a light chain variable region comprising SEQ ID NO:26. In some embodiments, a GCGR-binding protein is an antibody that specifically binds human GCGR, wherein the antibody comprises a heavy chain variable region comprising SEQ ID NO:220 and a light chain variable region comprising SEQ ID NO:221.

In another aspect, the disclosure provides GCGR-binding proteins (e.g., antibodies) (i) that competitively block (e.g., in a dose-dependent manner) an anti-GCGR antibody described herein (e.g., antibody 6B5 with CDR sequences defined in Table 1) from binding to a GCGR polypeptide (e.g., a cell-surface expressed or a soluble GCGR), a GCGR fragment, or a GCGR epitope, and/or (ii) that bind to a GCGR epitope that is bound by an anti-GCGR antibody described herein (e.g., antibody 6B5). In some embodiments, a GCGR-binding protein (e.g., an antibody) competitively blocks monoclonal antibody 6B5 described herein or a humanized variant thereof from binding to a GCGR polypeptide (e.g., a cell-surface expressed or a soluble GCGR), a GCGR fragment, or a GCGR epitope. In some embodiments, a GCGR-binding protein (e.g., an antibody) binds to a GCGR epitope that is bound (e.g., recognized) by monoclonal antibody 6B5 described herein or a humanized variant thereof.

In some embodiments, a GCGR-binding protein competes for specific binding to GCGR with at least one of the anti-GCGR antibodies described herein. In some embodiments, a GCGR-binding protein (e.g., an antibody) competes for binding to GCGR with a reference antibody, wherein the reference antibody comprises a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, a GCGR-binding protein (e.g., an antibody) competes for binding to GCGR with a reference antibody, wherein the reference antibody comprises a heavy chain CDR1 comprising SEQ ID NO:27, a heavy chain CDR2 comprising SEQ ID NO:28, a heavy chain CDR3 comprising SEQ ID NO:29, a light chain CDR1 comprising SEQ ID NO:30, a light chain CDR2 comprising SEQ ID NO:31, and a light chain CDR3 comprising SEQ ID NO:32. In some embodiments, a GCGR-binding protein (e.g., an antibody) competes for binding to GCGR with a reference antibody, wherein the reference antibody comprises a heavy chain CDR1 comprising SEQ ID NO:53, a heavy chain CDR2 comprising SEQ ID NO:54, a heavy chain CDR3 comprising SEQ ID NO:55, a light chain CDR1 comprising SEQ ID NO:56, a light chain CDR2 comprising SEQ ID NO:31, and a light chain CDR3 comprising SEQ ID NO:32. In some embodiments, a GCGR-binding protein (e.g., an antibody) competes for binding to GCGR with a reference antibody, wherein the reference antibody comprises a heavy chain CDR1 comprising SEQ ID NO:73, a heavy chain CDR2 comprising SEQ ID NO:74, a heavy chain CDR3 comprising SEQ ID NO:75, a light chain CDR1 comprising SEQ ID NO:76, a light chain CDR2 comprising SEQ ID NO:77, and a light chain CDR3 comprising SEQ ID NO:78. In some embodiments, a GCGR-binding protein (e.g., an antibody) competes for binding to GCGR with a reference antibody, wherein the reference antibody comprises a heavy chain CDR1 comprising SEQ ID NO:99, a heavy chain CDR2 comprising SEQ ID NO:100, a heavy chain CDR3 comprising SEQ ID NO:101, a light chain CDR1 comprising SEQ ID NO:102, a light chain CDR2 comprising SEQ ID NO:103, and a light chain CDR3 comprising SEQ ID NO:104. In some embodiments, a GCGR-binding protein (e.g., an antibody) competes for binding to GCGR with a reference antibody, wherein the reference antibody comprises a heavy chain CDR1 comprising SEQ ID NO:124, a heavy chain CDR2 comprising SEQ ID NO:125, a heavy chain CDR3 comprising SEQ ID NO:126, a light chain CDR1 comprising SEQ ID NO:127, a light chain CDR2 comprising SEQ ID NO:128, and a light chain CDR3 comprising SEQ ID NO:6. In some embodiments, a GCGR-binding protein (e.g., an antibody) competes for binding to GCGR with a reference antibody, wherein the reference antibody comprises a heavy chain CDR1 comprising SEQ ID NO:146, a heavy chain CDR2 comprising SEQ ID NO:147, a heavy chain CDR3 comprising SEQ ID NO:148, a light chain CDR1 comprising SEQ ID NO:149, a light chain CDR2 comprising SEQ ID NO:128, and a light chain CDR3 comprising SEQ ID NO:6. In some embodiments, a GCGR-binding protein (e.g., an antibody) competes for binding to GCGR with a reference antibody, wherein the reference antibody comprises a heavy chain CDR1 comprising SEQ ID NO:166, a heavy chain CDR2 comprising SEQ ID NO:167, a heavy chain CDR3 comprising SEQ ID NO:168, a light chain CDR1 comprising SEQ ID NO:169, a light chain CDR2 comprising SEQ ID NO:170, and a light chain CDR3 comprising SEQ ID NO:171. In some embodiments, a GCGR-binding protein (e.g., an antibody) competes for binding to GCGR with a reference antibody, wherein the reference antibody comprises a heavy chain CDR1 comprising SEQ ID NO:190, a heavy chain CDR2 comprising SEQ ID NO:191, a heavy chain CDR3 comprising SEQ ID NO:192, a light chain CDR1 comprising SEQ ID NO:169, a light chain CDR2 comprising SEQ ID NO:128, and a light chain CDR3 comprising SEQ ID NO:193. In some embodiments, a GCGR-binding protein (e.g., an antibody) competes for binding to GCGR with a reference antibody, wherein the reference antibody comprises a heavy chain CDR1 comprising SEQ ID NO:190, a heavy chain CDR2 comprising SEQ ID NO:205, a heavy chain CDR3 comprising SEQ ID NO:206, a light chain CDR1 comprising SEQ ID NO:207, a light chain CDR2 comprising SEQ ID NO:128, and a light chain CDR3 comprising SEQ ID NO:6.

In some embodiments, the antibody that competes for binding to GCGR comprises heavy chain variable region comprising SEQ ID NO:25 and a light chain variable region comprising SEQ ID NO:26. In some embodiments, the antibody that competes for binding to GCGR comprises heavy chain variable region comprising SEQ ID NO:220 and a light chain variable region comprising SEQ ID NO:221. In some embodiments, the antibody that competes for binding to GCGR comprises (a) heavy chain variable region comprising SEQ ID NO:51 and a light chain variable region comprising SEQ ID NO:52; (b) heavy chain variable region comprising SEQ ID NO:71 and a light chain variable region comprising SEQ ID NO:72; (c) heavy chain variable region comprising SEQ ID NO:97 and a light chain variable region comprising SEQ ID NO:98; (d) heavy chain variable region comprising SEQ ID NO:122 and a light chain variable region comprising SEQ ID NO:123; (e) heavy chain variable region comprising SEQ ID NO:144 and a light chain variable region comprising SEQ ID NO:145; (f) heavy chain variable region comprising SEQ ID NO:164 and a light chain variable region comprising SEQ ID NO:165; (g) heavy chain variable region comprising SEQ ID NO:188 and a light chain variable region comprising SEQ ID NO:189; (h) heavy chain variable region comprising SEQ ID NO:203 and a light chain variable region comprising SEQ ID NO:204; or (i) heavy chain variable region comprising SEQ ID NO:218 and a light chain variable region comprising SEQ ID NO:219.

In some embodiments, a GCGR-binding protein binds the same epitope on GCGR as at least one of the antibodies described herein. In some embodiments, a GCGR-binding protein binds an epitope on GCGR that overlaps with the epitope on GCGR bound by at least one of the antibodies described herein. In some embodiments, a GCGR-binding protein binds the same epitope as an antibody comprising the heavy chain CDR1, CDR2, and CDR3 and the light chain CDR1, CDR2, and CDR3 of an antibody selected from the group consisting of: 6B5, 3H5, 5B11, 1C1, 1C3, 1H2, 4F8, 13G9, 14F4, and 14E9. In some embodiments, a GCGR-binding protein binds an epitope that overlap with the epitope bound by an antibody comprising the heavy chain CDR1, CDR2, and CDR3 and the light chain CDR1, CDR2, and CDR3 of an antibody selected from the group consisting of: 6B5, 3H5, 5B11, 1C1, 1C3, 1H2, 4F8, 13G9, 14F4, and 14E9. In some embodiments, a GCGR-binding protein binds the same epitope as an antibody comprising the heavy chain variable region and the light chain variable region from an antibody selected from the group consisting of: Hz6B5, 6B5, 3H5, 5B11, 1C1, 1C3, 1H2, 4F8, 13G9, 14F4, and 14E9. In some embodiments, a GCGR-binding protein binds an epitope that overlaps with the epitope bound by an antibody comprising the heavy chain variable region and the light chain variable region from an antibody selected from the group consisting of: Hz6B5, 6B5, 3H5, 5B11, 1C1, 1C3, 1H2, 4F8, 13G9, 14F4, and 14E9.

In some embodiments, a GCGR-binding protein is a humanized antibody comprising a heavy chain having the amino acid sequence of SEQ ID NO:234 and a light chain having the amino acid sequence of SEQ ID NO:236.

In some embodiments, a GCGR-binding protein (e.g., an antibody) described herein is combined with, conjugated to, or recombinantly linked to a diagnostic agent, detectable agent, or therapeutic agent. In some embodiments, the GCGR-binding protein is an antibody that is conjugated to a detectable marker. In some embodiments, the detectable agent is selected from the group consisting of a radioisotope, a metal chelator, an enzyme, a fluorescent compound, a bioluminescent compound, or a chemiluminescent compound. In some embodiments, the therapeutic agent is selected from the group consisting of: biguanides and sulfonylureas (e.g., metformin tolbutamide, chlorpropamide, acetohexamide, tolazamide, glibenclamide, glyburide, and glipizide), thiazolidinediones (e.g., rosiglitazone and pioglitazone), GLP-1 analogs, PPAR gamma agonists, dipeptidyl peptidase-4 (DPP-4) inhibitors (e.g., JANUVIA and ONGLYZA), bromocriptine, bile acid sequestrants (e.g., colesevelam), insulin (e.g., bolus and basal analogs), alpha glucosidase inhibitors (e.g., acarbose, roglibose), SGLT-2 inhibitors, and appetite suppression or weight loss drugs (e.g., XENICAL).

In some embodiments, a GCGR-binding protein (e.g., an antibody) described herein inhibits GCGR signaling in cells expressing GCGR. In some embodiments, a GCGR-binding protein inhibits glucagon-induced GCGR signaling. In some embodiments, a GCGR-binding protein inhibits GCGR activity in a cell. In some embodiments, a GCGR-binding protein inhibits cAMP activity.

In some embodiments, a GCGR-binding protein (e.g., an antibody) described herein (i) reduces blood glucose levels; (ii) increases the level of C-peptide; and/or (iii) increases the level of insulin. In some embodiments, the level of C-peptide is measured in a blood sample, a serum sample, a plasma sample, or a pancreatic sample. In some embodiments, the level of insulin is measured in a blood sample, a serum sample, a plasma sample, or a pancreatic sample.

In another aspect, the disclosure provides a cell comprising or producing a GCGR-binding protein described herein. In some embodiments, a cell comprises an antibody described herein (e.g., as defined by CDR sequences in Tables 1-10). In some embodiments, a cell comprises the antibody designated 6B5 or the humanized version designated Hz6B5. In some embodiments, a cell produces an antibody described herein (e.g., as defined by CDR sequences in Tables 1-10). In some embodiments, a cell produces the antibody designated 6B5 or the humanized version designated Hz6B5.

In another aspect, the disclosure provides compositions comprising a GCGR-binding protein described herein. In some embodiments, the disclosure provides pharmaceutical compositions comprising a GCGR-binding protein described herein and a pharmaceutically acceptable carrier.

In some embodiments of each of the aforementioned aspects, as well as other aspects and/or embodiments described elsewhere herein, the GCGR-binding protein is isolated. In some embodiments, the GCGR-binding protein is substantially pure.

In another aspect, the disclosure provides polynucleotide molecules comprising a polynucleotide that encodes a GCGR-binding protein (e.g., an antibody) described herein. In some embodiments, nucleic acid molecules encode an immunoglobulin heavy chain, an immunoglobulin light chain, a heavy chain variable region, a light chain variable region, heavy chain CDRs, and/or light chain CDRs of GCGR-binding proteins (e.g., antibodies) that bind to GCGR, a GCGR fragment, or a GCGR epitope. In some embodiments, a nucleic acid molecule encodes a heavy chain variable region and/or a light chain variable region of a monoclonal antibody designated as 6B5, 3H5, 5B11, 1C1, 1C3, 1H2, 4F8, 13G9, 14F4, or 14E9 as described herein (see, e.g., Tables 1-10), or a humanized variant thereof. In some embodiments, a nucleic acid molecule further encodes a scaffold region or a framework region of a human immunoglobulin amino acid sequence or a variant thereof. In some embodiments, a polynucleotide molecule comprises a polynucleotide that encodes a polypeptide of SEQ ID NO:233, SEQ ID NO:234, SEQ ID NO:235, or SEQ ID NO:236. In some embodiments, a polynucleotide molecule comprises a polynucleotide that encodes a polypeptide comprising SEQ ID NO:233 and SEQ ID NO:235. In some embodiments, a polynucleotide molecule comprises a polynucleotide that encodes a polypeptide comprising SEQ ID NO:234 and SEQ ID NO:236. In some embodiments, the polynucleotide is isolated. In some embodiments, the polynucleotide is substantially pure.

Also provided herein are vectors that comprise the nucleic acid molecules encoding a GCGR-binding protein (e.g., an antibody), as well as cells that comprise the vector and/or the polynucleotides. In some embodiments, the disclosure provides methods of producing a GCGR-binding protein (e.g., antibody) by culturing host cells provided herein under conditions that promote the production of the GCGR-binding protein.

In another aspect, the present disclosure provides methods of using the GCGR-binding proteins (e.g., antibodies) described herein. In some embodiments, a method of inhibiting GCGR signaling in a cell comprises contacting the cell with a GCGR-binding protein (e.g., an antibody) described herein. In some embodiments, the cell expresses human GCGR. In some embodiments, the GCGR signaling is induced by glucagon.

In some embodiments, a method of reducing or lowering blood glucose levels in a subject comprises administering to the subject a therapeutically effective amount of a GCGR-binding protein (e.g., an antibody) described herein. In some embodiments, a method of increasing the level of C-peptide in the blood of a subject comprises administering to the subject a therapeutically effective amount of a GCGR-binding protein (e.g., an antibody) described herein. In some embodiments, a method of increasing the level of insulin in the blood of a subject comprises administering to the subject a therapeutically effective amount of a GCGR-binding protein (e.g., an antibody) described herein. In some embodiments, a method of reducing or lowering blood glucose levels and increasing the level of C-peptide in the blood of a subject, comprises administering to the subject a therapeutically effective amount of a GCGR-binding protein (e.g., an antibody) described herein. In some embodiments, the level of C-peptide is measured in a blood sample, a serum sample, a plasma sample, or a pancreatic sample. In some embodiments, the level of insulin is measured in a blood sample, a serum sample, a plasma sample, or a pancreatic sample.

In some embodiments, a method of treating Type 1 diabetes in a subject comprises administering to the subject a therapeutically effective amount of a GCGR-binding protein (e.g., an antibody) described herein. In some embodiments, the Type 1 diabetes is latent autoimmune diabetes of adults (LADA). In some embodiments, a method of treating Type 2 diabetes in a subject comprises administering to the subject a therapeutically effective amount of a GCGR-binding protein (e.g., an antibody) described herein. In some embodiments, a method of treating hyperglycemia in a subject comprises administering to the subject a therapeutically effective amount of a GCGR-binding protein (e.g., an antibody) described herein.

In some embodiments, a method of treating or preventing a disease, disorder or condition associated with beta cell dysfunction in a subject comprises administering to the subject a therapeutically effective amount of a GCGR-binding protein (e.g., an antibody) described herein. In some embodiments, a method of treating or preventing a beta cell defective disease, disorder or condition, or a symptom thereof, in a subject comprises administering to the subject a therapeutically effective amount of a GCGR-binding protein (e.g., an antibody) described herein. In some embodiments, the disease, disorder or condition is hyperglycemia. In some embodiments, the disease, disorder or condition is Type 1 diabetes. In some embodiments, the disease, disorder or condition is Type 2 diabetes. In some embodiments of the methods described herein, the treatment (i) reduces blood glucose levels, (ii) increases C-peptide level in the blood, (iii) increases C-peptide levels in the pancreas, (iv) reduces blood glucose levels and increases C-peptide in the blood, and/or (v) reduces blood glucose levels and increases C-peptide in the pancreas. In some embodiments, a method of improving beta cell function in a subject comprises administering to the subject a therapeutically effective amount of a GCGR-binding protein (e.g., an antibody) described herein. In some embodiments, the improvement in beta cell function is indicated by a decrease in blood glucose, an increase in C-peptide, and/or an increase in insulin.

In some embodiments of the methods described herein, the subject receives a daily dosage of insulin. In some embodiments of the methods described herein, the subject does not receive a daily dosage of insulin. In some embodiments of the methods described herein, the subject has Type 1 diabetes or a symptom thereof. In some embodiments of the methods described herein, the subject has Type 2 diabetes, or a symptom thereof. In some embodiments of the methods described herein, the subject has hyperglycemia. In some embodiments of the methods described herein, the subject has insulin resistance. In some embodiments of the methods described herein, the subject has insulin-dependent diabetes. In some embodiments of the methods described herein, the subject has non-insulin dependent diabetes.

In some embodiments of the methods described herein, the subject has a beta cell defective disease, disorder, or condition, or a symptom thereof. In some embodiments of the methods described herein, the beta cell defective disease, disorder, or condition is Type 1 diabetes. In some embodiments of the methods described herein, the beta cell defective disease, disorder, or condition is Type 2 diabetes. In some embodiments of the methods described herein, the beta cell defective disease, disorder, or condition is a metabolic disease. In some embodiments of the methods described herein, one or more symptoms are prevented or treated.

In some embodiments of the methods described herein, the subject has an increase in serum glucagon, serum insulin, and/or C-peptide following the administration of a GCGR-binding protein described herein. In some embodiments of the methods described herein, the subject has a decrease in blood glucose (e.g., whole blood, serum, or plasma glucose) following the administration of a GCGR-binding protein described herein. In some embodiments of the methods described herein, the subject has a decrease in blood glucose and an increase in C-peptide (e.g., serum C-peptide, pancreatic C-peptide, or both).

In some embodiments of the methods described herein, a method comprises administering at least one additional therapeutic agent to the subject. In some embodiments, the additional therapeutic agent is a diabetes or hyperglycemia drug. In some embodiments, the diabetes or hyperglycemia drug is a biguanide, a sulfonylurea, a meglitinide derivative, an alpha-glucosidase inhibitor, a thiazolidinedione (TZDs), a glucagon-like peptide-1 (GLP-1) agonist, a dipeptidyl peptidase 4 (DPP-4) inhibitor, a selective sodium-glucose transporter-2 (SGLT-2) inhibitor, an insulin or insulin mimetic, an amylinomimetic, a bile acid sequestrant, and/or a dopamine agonist. In some embodiments, the additional therapeutic agent is an obesity drug, an appetite suppressant, or a weight loss drug. In some embodiments, the subject receives a daily dosage of insulin. In some embodiments, the daily dosage of insulin is decreased following administration of a GCGR-binding protein (e.g., an antibody).

In some embodiments of the methods described herein, an effective amount of a GCGR-binding protein (e.g., an antibody) is from about 1 mg/kg to about 100 mg/kg. In some embodiments, the effective amount is an amount that is about 2-fold to about 10-fold more than the amount needed to decrease the level of blood glucose (e.g., whole blood, serum or plasma glucose) in the subject. In some embodiments, the amount is about 2-fold, about 3-fold, about 4-fold, about 5-fold, about 6-fold, about 7-fold, about 8-fold, about 9-fold or about 10-fold more than the amount needed to decrease the level of blood glucose in the subject.

In some embodiments of the methods described herein, an effective amount of a GCGR-binding protein is administered in four or more doses, such as 4, 5, 6, 7, 8, 9, 10 or more doses, or any interval thereof. In some embodiments, the effective amount is delivered weekly for four or more weeks, such as about 5 weeks, about 6 weeks, about 8 weeks, about 10 weeks, about 12 weeks, about 4 months, about 5 months, about 6 months, about 1 year, about 2 years or longer, or any interval thereof. In some embodiments, the effective amount is delivered about once every two weeks, about once every three weeks, or about once every four weeks.

In some embodiments of the methods described herein, wherein a subject has previously received a dose of a GCGR-binding protein, the amount of binding protein administered is from about 2-fold to about 10-fold higher than the prior dose of antibody. In some embodiments, the prior dose was an individual dose.

When aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed invention.

BRIEF DESCRIPTION OF THE FIGURES

FIGS. 1A-1 and 1A-2 show sequence alignments of heavy chain variable regions of anti-GCGR antibodies designated 6B5, 3H5, 5B11, 1C1, 1C3, 1H2, 4F8, 13G9, 14F4, and 14E9. Boundaries of CDRs are indicated by Kabat, AbM, Chothia, Contact, and IMGT numbering.

FIGS. 1B-1 and 1B-2 show sequence alignments of light chain variable regions of anti-GCGR antibodies designated 6B5, 3H5, 5B11, 1C1, 1C3, 1H2, 4F8, 13G9, 14F4, and 14E9. Boundaries of CDRs are indicated by Kabat, AbM, Chothia, Contact, and IMGT numbering.

FIG. 2 depicts a set of representative results from an alanine scanning experiment showing the binding of anti-GCGR antibody 6B5 to 3 GCGR extracellular domain variants comprising single amino acid substitutions.

DETAILED DESCRIPTION

Figure 2:
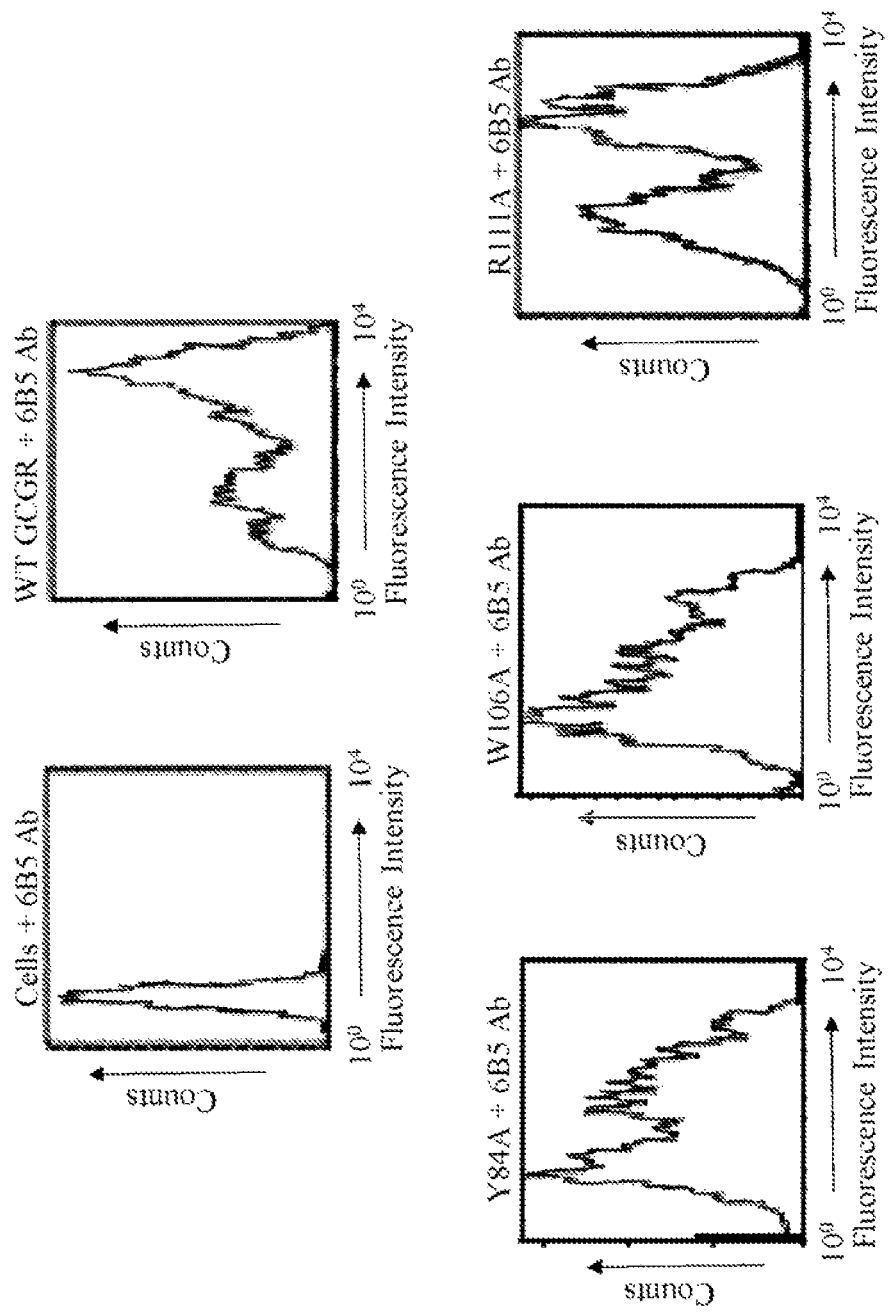

The present disclosure provides proteins that bind glucagon receptors (GCGR). The GCGR-binding proteins may include antibodies and may bind a full-length GCGR, a GCGR fragment (e.g., the extracellular domain), and/or a GCGR epitope. The binding proteins (e.g., antibodies) may be antagonists that have the capability to (i) inhibit binding of glucagon to GCGR, (ii) inhibit glucagon-induced signaling of GCGR, (iii) inhibit a glucagon/GCGR complex, or (iv) inhibit GCGR signaling. The binding proteins (e.g., antibodies) may be useful in methods for the treatment or prevention of hyperglycemia, diabetes, obesity, and/or beta cell defective diseases, disorders, or conditions, or symptoms thereof.

The binding proteins (e.g., antibodies) disclosed herein share a common feature of competing with each other for binding to GCGR. This competition suggests that each protein binds to the same region of GCGR (e.g., the same epitope or overlapping epitopes). The results described herein suggest that the effects observed for an anti-GCGR antibody derived from or based on antibody 6B5 or an antibody in the 6B5 epitope bin can be extrapolated to other anti-GCGR antibodies having the same or similar epitope specificity. For example, the in vitro activities of several exemplary antibodies in Examples 2-4, as well as the in vivo effects of exemplary antibodies in Example 6 are representative of various activities and effects of the anti-GCGR antibodies described herein.

I. Definitions

Unless otherwise defined herein, technical and scientific terms used in the present disclosure have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "binding agent" as used herein refers to a molecule that binds a specific antigen or target (e.g., GCGR). A binding agent may comprise a protein, peptide, nucleic acid, carbohydrate, lipid, or small molecular weight compound. In some embodiments, a binding agent comprises a binding protein. In some embodiments, a binding agent is a binding protein. In some embodiments, a binding agent comprises an antibody or an antigen-binding fragment thereof. In some embodiments, a binding agent is an antibody or an antigen-binding fragment thereof. In some embodiments, a binding agent comprises an alternative protein scaffold or artificial scaffold and an antigen-binding site comprising CDRs or CDR derivatives. In some embodiments, a binding agent is a fusion protein comprising an antigen-binding site. In some embodiments, a binding agent is a bispecific or multispecific molecule comprising at least one antigen-binding site.

The term "antibody" as used herein refers to an immunoglobulin molecule that recognizes and binds a target through at least one antigen-binding site. "Antibody" is used herein in the broadest sense and encompasses various antibody structures, including but not limited to, polyclonal antibodies, recombinant antibodies, monoclonal antibodies, chimeric antibodies, humanized antibodies, human antibodies, bispecific antibodies, multispecific antibodies, diabodies, tribodies, tetrabodies, single chain Fv (scFv) antibodies, single domain antibodies (e.g., camelid/llama antibodies), and antibody fragments.

The term "intact antibody" or "full-length antibody" refers to an antibody having a structure substantially similar to a native antibody structure. This includes an antibody comprising two light chains each comprising a variable region and a light chain constant region (CL) and two heavy chains each comprising a variable region and at least heavy chain constant regions CHL CH2, and CH3.

The term "antibody fragment" as used herein refers to a molecule other than an intact antibody that comprises a portion of an antibody and generally an antigen-binding site. Examples of antibody fragments include, but are not limited to, Fab, Fab', F(ab')2, Fv, disulfide-linked Fv (sdFv), Fd, linear antibodies, single chain antibody molecules (e.g., scFv), diabodies, tribodies, tetrabodies, minibodies, dual variable domain antibodies (DVD), single variable domain antibodies, and multispecific antibodies formed from antibody fragments.

The term "variable region" as used herein refers to the region of an antibody light chain or the region of an antibody heavy chain that is involved in binding the antibody to antigen. The variable region of an antibody heavy chain and an antibody light chain have similar structures, and generally comprise four framework regions and three complementarity determining regions (CDRs) (also known as hypervariable regions).

The term "framework regions" refers to amino acid residues other than the CDR residues within a variable region. The variable region generally comprises four framework regions, FR1, FR2, FR3, and FR4.

The term "monoclonal antibody" as used herein refers to a substantially homogenous antibody population involved in the highly specific recognition and binding of a single antigenic determinant or epitope. The individual antibodies comprising the population are identical, except for possible naturally occurring mutations that may be present in minor amounts. The term "monoclonal antibody" encompasses intact and full-length monoclonal antibodies as well as antibody fragments (e.g., Fab, Fab', F(ab')2, Fv), single chain (scFv) antibodies, fusion proteins comprising an antibody fragment, and any other modified immunoglobulin molecule comprising an antigen-binding site. Furthermore, "monoclonal antibody" refers to such antibodies made by any number of techniques, including but not limited to, hybridoma production, phage library display, recombinant expression, and transgenic animals.

The term "chimeric antibody" as used herein refers to an antibody in which a portion of the heavy and/or light chain is derived from a particular source or species, while the remainder of the heavy and/or light chain is derived from a different source or species.

The term "humanized antibody" as used herein refers to a chimeric antibody that generally comprises human immunoglobulins (e.g., recipient antibody) in which the native CDR residues are replaced by residues from corresponding CDRs from a nonhuman species (e.g., donor antibody) such as mouse, rat, rabbit, or nonhuman primate, wherein the donor antibody has the desired specificity, affinity, and/or activity. In some instances, one or more residues within one or more framework regions of the human immunoglobulin are replaced by corresponding nonhuman residues. Furthermore, humanized antibodies can comprise residues that are not found in the recipient antibody or in the donor antibody. These modifications may be made to further refine and/or optimize antibody characteristics. A humanized antibody may comprise variable regions containing all or substantially all of the CDRs that correspond to those of a nonhuman immunoglobulin and all or substantially all of the framework regions that correspond to those of a human immunoglobulin. In some embodiments, the humanized antibody will comprise at least a portion of an immunoglobulin Fc region (e.g., hinge region, CH1, CH2, and/or CH3), typically that of a human immunoglobulin.

The term "human antibody" as used herein refers to an antibody that possesses an amino acid sequence that corresponds to an antibody produced by a human and/or an antibody that has been made using any of the techniques that are known to those of skill in the art for making human antibodies. These techniques include, but not limited to, phage display libraries, yeast display libraries, transgenic animals, and B-cell hybridoma technology. A human antibody as defined herein excludes a humanized antibody comprising residues from a non-human source.

The terms "epitope" and "antigenic determinant" are used interchangeably herein and refer to that portion of an antigen or target capable of being recognized and bound by a particular binding agent or binding protein (e.g., an antibody). When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. Epitopes can be predicted using any one of a large number of software bioinformatic tools available on the internet. X-ray crystallography may be used to characterize an epitope on a target protein by analyzing the amino acid residue interactions of an antigen/antibody complex.

The term "specifically binds" as used herein refers to a binding protein (e.g., an antibody) that interacts more frequently, more rapidly, with greater duration, with greater affinity, or with some combination of the above to a particular antigen, epitope, protein, or target molecule than with alternative substances. In some embodiments, a protein (e.g., an antibody) that specifically binds an antigen (e.g., human GCGR) may bind related antigens (e.g., cyno GCGR). An antibody that specifically binds an antigen can be identified, for example, by immunoassays, ELISAs, Biacore assays, FACS, or other techniques known to those of ordinary skill in the art.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies, the term "polypeptide" encompasses polypeptides as a single chain and polypeptides of two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two polynucleotides or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 nucleotides or amino acid residues, at least about 60-80 nucleotides or amino acid residues in length, or any integral value there between. In some embodiments, identity exists over a longer region than 60-80 nucleotides or amino acid residues, such as at least about 80-100 nucleotides or amino acid residues, and in some embodiments the sequences are substantially identical over the full length of the sequences being compared, for example, (i) the coding region of a nucleotide sequence or (ii) an amino acid sequence.

The phrase "conservative amino acid substitution" as used herein refers to a substitution in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered to be a conservative substitution. Generally, conservative substitutions in the sequences of polypeptides and/or antibodies do not abrogate the binding of the polypeptide or antibody to the target binding site. Methods of identifying nucleotide and amino acid conservative substitutions that do not eliminate binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

The term "isolated" as used herein refers to a polypeptide, soluble protein, antibody, polynucleotide, vector, cell, or composition that is in a form not found in nature. An "isolated" antibody is substantially free of material from the cellular source from which it is derived. In some embodiments, isolated polypeptides, soluble proteins, antibodies, polynucleotides, vectors, cells, or compositions are those which have been purified to a degree that they are no longer in a form in which they are found in nature. In some embodiments, a polypeptide, soluble protein, antibody, polynucleotide, vector, cell, or composition that is isolated is substantially pure. A polypeptide, soluble protein, antibody, polynucleotide, vector, cell, or composition may be isolated from a natural source or from a source such as an engineered cell line.

The term "substantially pure" as used herein refers to material which is at least 50% pure (i.e., free from contaminants), at least 90% pure, at least 95% pure, at least 98% pure, or at least 99% pure.

The term "subject" refers to any animal (e.g., a mammal), including, but not limited to, humans, non-human primates, canines, felines, rabbits, rodents, and the like, which is to be the recipient of a treatment or therapy. Generally, the terms "subject" and "patient" are used interchangeably herein in reference to a human subject.

The term "pharmaceutically acceptable" as used herein refers to a substance approved or approvable by a regulatory agency or listed in the U.S. Pharmacopeia, European Pharmacopeia, or other generally recognized pharmacopeia for use in animals, including humans.

The terms "pharmaceutically acceptable excipient, carrier, or adjuvant" or "acceptable pharmaceutical carrier" as used herein refer to an excipient, carrier, or adjuvant that can be administered to a subject, together with at least one therapeutic agent (e.g., an antibody), and which does not have an effect on the pharmacological activity of the therapeutic agent. In general, those of skill in the art and the U.S. FDA consider a pharmaceutically acceptable excipient, carrier, or adjuvant to be an inactive ingredient of any formulation.

The term "pharmaceutical formulation" or "pharmaceutical composition" as used herein refers to a preparation that is in such form as to permit the biological activity of the agent (e.g., an antibody) to be effective. A pharmaceutical formulation or composition generally comprises additional components, such as a pharmaceutically acceptable excipient, carrier, adjuvant, buffers, etc.

The term "effective amount" or "therapeutically effective amount" as used herein refers to the amount of a binding protein (e.g., an antibody) which is sufficient to reduce and/or ameliorate the severity and/or duration of a disease, disorder or condition and/or a symptom in a subject. The term also encompasses an amount of a binding protein necessary for the (i) reduction or amelioration of the advancement or progression of a given disease, disorder, or condition, (ii) reduction or amelioration of the recurrence, development, or onset of a given disease, disorder, or condition, and/or (iii) the improvement or enhancement of the prophylactic or therapeutic effect(s) of another agent or therapy (e.g., an agent other than the binding proteins provided herein).

The term "therapeutic effect" as used herein refers to the effect and/or ability of a binding protein (e.g., an antibody) to reduce and/or ameliorate the severity and/or duration of a disease, disorder, or condition and/or a symptom in a subject. The term also encompasses the ability of a binding protein to (i) reduce or ameliorate the advancement or progression of a given disease, disorder, or condition, (ii) reduce or ameliorate the recurrence, development, or onset of a given disease, disorder, or condition, and/or (iii) to improve or enhance the prophylactic or therapeutic effect(s) of another agent or therapy (e.g., an agent other than the binding proteins provided herein).

The term "treat" or "treatment" or "treating" or "to treat" or "alleviate" or "alleviation" or "alleviating" or "to alleviate" as used herein refers to both (1) therapeutic measures that aim to cure, slow down, lessen symptoms of, and/or halt progression of a pathologic condition or disorder and (2) prophylactic or preventative measures that aim to prevent or slow down the development of a targeted pathologic condition or disorder. Thus, those in need of treatment include those already with the disorder, those at risk of having/developing the disorder, and those in whom the disorder is to be prevented.

The term "prevent" or "prevention" or "preventing" as used herein refers to the partial or total inhibition of the development, recurrence, onset, or spread of a disease, disorder, or condition, or a symptom thereof in a subject.

The term "prophylactic agent" as used herein refers to an agent that partially or totally inhibits the development, recurrence, onset, or spread of a disease, disorder or condition, or a symptom thereof in a subject.

As used herein, reference to "about" or "approximately" a value or parameter includes (and describes) embodiments that are directed to that value or parameter. For example, a description referring to "about X" includes description of "X".

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. GCGR-Binding Proteins

Amino acid (aa) sequences for human GCGR (e.g., UniProtKB No. P47871), cynomolgus ("cyno") monkey GCGR (e.g., NCBI Ref. No. XP_005585314.1), mouse GCGR (e.g., UniProtKB No. Q61606), and rat GCGR (e.g., UniProtKB No. P30082) are known to those of skill in the art and representative sequences are provided herein as SEQ ID NO:222, SEQ ID NO:227, SEQ ID NO:228, and SEQ ID NO:229, respectively. As used herein, reference to amino acid positions of GCGR refer to the numbering of amino acid sequences including the signal sequence.

The present disclosure provides agents that specifically bind GCGR. In some embodiments, the agents that bind GCGR are proteins. Generally, these proteins are referred to herein as "GCGR-binding proteins". In some embodiments, a GCGR-binding protein specifically binds a fragment of GCGR. In some embodiments, a GCGR-binding protein specifically binds the extracellular domain of GCGR. In some embodiments, a GCGR-binding protein specifically binds a portion or fragment of the extracellular domain of GCGR. In some embodiments, a GCGR-binding protein specifically binds an epitope on GCGR. In some embodiments, a GCGR-binding protein specifically binds human GCGR. In some embodiments, a GCGR-binding protein specifically binds cyno GCGR. In some embodiments, a GCGR-binding protein specifically binds human GCGR and cyno GCGR. In some embodiments, a GCGR-binding protein specifically binds mouse GCGR. Non-limiting examples of GCGR-binding proteins can be found in U.S. Patent Publication Nos. 2009/0041784, 2009/0252727, 2012/0128679; 2014/0335091, and International Publication No. WO 2011/030935.

In some embodiments, the GCGR-binding protein binds within amino acids 26-136 of human GCGR. In some embodiments, the GCGR-binding protein binds within amino acids 28-123 of human GCGR. In some embodiments, the GCGR-binding protein binds within amino acids 80-119 of human GCGR.

In some embodiments, the GCGR-binding protein binds within amino acids 26-136 of SEQ ID NO:222. In some embodiments, the GCGR-binding protein binds within amino acids 28-123 of SEQ ID NO:222. In some embodiments, the GCGR-binding protein binds within amino acids 80-119 of SEQ ID NO:222. In some embodiments, the GCGR-binding protein binds within SEQ ID NO:224. In some embodiments, the GCGR-binding protein binds within SEQ ID NO:225. In some embodiments, the GCGR-binding protein binds within SEQ ID NO:226.

In some embodiments, the GCGR-binding protein (e.g., an antibody) binds an epitope comprising at least one of L38, L85, R94, and W106 of SEQ ID NO:222. In some embodiments, the GCGR-binding protein (e.g., an antibody) binds an epitope that does not comprise Y84, W106, and/or R111 of SEQ ID NO:222.

In some embodiments, the GCGR-binding protein is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In some embodiments, the antibody is an IgG1 antibody. In some embodiments, the antibody is an IgG2 antibody. In some embodiments, the antibody is an IgG4 antibody. In some embodiments, the antibody is an antibody fragment comprising an antigen-binding site. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody.

In some embodiments, the antibody is isolated. In some embodiments, the antibody is substantially pure.

In some embodiments, the GCGR-binding proteins are polyclonal antibodies. Polyclonal antibodies can be prepared by any known method. In some embodiments, polyclonal antibodies are produced by immunizing an animal (e.g., a rabbit, rat, mouse, goat, donkey) with an antigen of interest (e.g., a purified peptide fragment, a recombinant protein, or a fusion protein) using multiple subcutaneous or intraperitoneal injections. In some embodiments, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from the immunized animal, usually from blood or ascites. The polyclonal antibodies can be purified from serum or ascites according to standard methods in the art including, but not limited to, affinity chromatography, ion-exchange chromatography, gel electrophoresis, and dialysis.

In some embodiments, a GCGR-binding protein is a monoclonal antibody. In some embodiments, monoclonal antibodies are prepared using hybridoma methods known to one of skill in the art. For example, using the hybridoma method, a mouse, rat, rabbit, hamster, or other appropriate host animal, is immunized as described above to elicit the production of antibodies. In some embodiments, lymphocytes are immunized in vitro. In some embodiments, the immunizing antigen is a human protein or a fragment thereof. In some embodiments, the immunizing antigen is a mouse protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen can be identified by a variety of screening methods including, but not limited to, immunoprecipitation, immunoblotting, and in vitro binding assays (e.g., flow cytometry, FACS, ELISA, Biacore, and radioimmunoassay). Once hybridoma cells that produce antibodies of the desired specificity, affinity, and/or activity are identified, the clones may be subcloned by limiting dilution techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin proteins.

In some embodiments, recombinant monoclonal antibodies, or fragments thereof, are isolated from phage display libraries expressing variable domains or CDRs of a desired species. Screening of phage libraries can be accomplished by various techniques known in the art.

In some embodiments, a monoclonal antibody is modified, for example, by using recombinant DNA technology to generate alternative antibodies. In some embodiments, the constant domains of the light chain and heavy chain of a mouse monoclonal antibody are substituted for constant regions of a human antibody to generate a chimeric antibody, or for a non-immunoglobulin polypeptide to generate a fusion antibody. In some embodiments, the constant regions are truncated or removed to generate a desired antibody fragment of a monoclonal antibody. Site-directed or high-density mutagenesis of the variable region(s) can be used to optimize, for example, specificity and affinity of a monoclonal antibody.

In some embodiments, a GCGR-binding protein is a humanized antibody. Various methods for generating humanized antibodies are known in the art. In some embodiments, a human antibody comprises one or more amino acid residues that have been introduced into it from a source that is non-human. These non-human amino acid residues are often referred to as "donor" residues, which are typically taken from a "donor" variable domain. In some embodiments, humanization is performed by substituting one or more non-human CDR sequences for the corresponding CDR sequences of a human antibody. In some embodiments, the humanized antibodies are constructed by CDR grafting, in which the amino acid sequences of all six CDRs of the parent non-human antibody (e.g., rodent) are grafted into a human antibody heavy and light chain variable region sequences.

The decision of which human heavy chain variable region and/or light chain variable region is chosen for generating a humanized antibody can be made based on a variety of factors and by a variety of methods. In some embodiments, the "best-fit" method is used where the sequence of the variable region of a non-human (e.g., rodent) antibody is screened against the entire library of known human variable region sequences. The human sequence that is most similar to that of the rodent sequence is selected as the human variable region sequence for the humanized antibody. In some embodiments, a method is used wherein a particular variable region sequence derived from a consensus sequence of all human antibodies of a particular subgroup of light or heavy chains is selected. In some embodiments, the variable region sequence is derived from the consensus sequences of the most abundant human subclasses. In some embodiments, human germline genes are used as the source of the variable region sequences.

Other methods for humanization include, but are not limited to, a method called "superhumanization" which is described as the direct transfer of CDRs to a human germline framework, a method termed Human String Content (HSC) which is based on a metric of "antibody humanness", methods based on generation of large libraries of humanized variants (including phage, ribosomal, and yeast display libraries), and methods based on framework region shuffling.

In some embodiments, a GCGR-binding protein is a human antibody. Human antibodies can be directly prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, for example, from immunoglobulin variable region gene repertoires from unimmunized donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

In some embodiments, a GCGR-binding protein is a bispecific antibody. Bispecific antibodies are capable of recognizing and binding at least two different antigens or epitopes. The different epitopes can either be within the same molecule (e.g., two epitopes on GCGR) or on different molecules (e.g., one epitope on GCGR and one epitope on a different target). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., tissue) in a subject. In some embodiments, a bispecific antibody has the ability to concentrate the actions of two agents to a common target (e.g., a specific cell type). In some embodiments, a bispecific antibody has the ability to target the actions of two agents to more than one biological pathway or function. In some embodiments, a bispecific antibody has the ability to target two different cells and bring them closer together.

In some embodiments, a bispecific antibody has decreased toxicity and/or side effects. In some embodiments, a bispecific antibody has decreased toxicity and/or side effects as compared to a mixture of the two individual antibodies or the antibodies as single agents. In some embodiments, a bispecific antibody has an increased therapeutic index. In some embodiments, a bispecific antibody has an increased therapeutic index as compared to a mixture of the two individual antibodies or the antibodies as single agents.

Several techniques for making bispecific antibodies are known by those skilled in the art. In some embodiments, the bispecific antibodies comprise heavy chain constant regions with modifications in the amino acids which are part of the interface between the two heavy chains. In some embodiments, the bispecific antibodies are generated using a knobs-into-holes (KIH) strategy. In some embodiments, the bispecific antibodies comprise variant hinge regions incapable of forming disulfide linkages between the heavy chains. In some embodiments, the bispecific antibodies comprise heavy chains with changes in amino acids that result in altered electrostatic interactions. In some embodiments, the bispecific antibodies comprise heavy chains with changes in amino acids that result in altered hydrophobic/hydrophilic interactions. Bispecific antibodies can be intact antibodies or antibody fragments comprising antigen-binding sites.

Antibodies with more than two valencies are also contemplated. For example, trispecific or tetraspecific antibodies can be prepared. Thus, in some embodiments the antibodies to GCGR are multispecific.

In some embodiments, a GCGR-binding protein is an antibody that binds GCGR. In some embodiments, the GCGR-binding protein is an antibody that binds human GCGR. In some embodiments, the GCGR-binding protein is an antibody that binds cyno GCGR. In some embodiments, the GCGR-binding protein is an antibody that binds human and cyno GCGR. In some embodiments, the GCGR-binding protein is an antibody that binds mouse GCGR. In some embodiments, the GCGR-binding protein is an antibody that binds a portion or fragment of GCGR. In some embodiments, the GCGR-binding protein is an antibody that binds the extracellular domain of GCGR. In some embodiments, the GCGR-binding protein is an antibody that binds a fragment or portion of the extracellular domain of GCGR. In some embodiments, the GCGR-binding protein is an antibody that binds a GCGR epitope. In some embodiments, the GCGR epitope is a linear epitope. In some embodiments, the GCGR epitope is a conformational epitope.

In some embodiments, the GCGR-binding protein is an antibody that comprises one, two, three, four, five, and/or six CDRs of any one of the antibodies described herein. In some embodiments, an anti-GCGR antibody comprises (i) one, two, and/or three heavy chain CDRs from Tables 1-10, and/or (ii) one, two, and/or three light chain CDRs from Tables 1-10. CDRs are defined by a variety of methods/ systems by those skilled in the art. These systems and/or definitions have been developed and refined over a number of years and include Kabat, Chothia, IMGT, AbM, and "Contact". The Kabat definition is based on sequence variability and generally is the most commonly used. The Chothia definition is based on the location of the structural loop regions. The IMGT system is based on sequence variability and location within the structure of the variable domain. The AbM definition is a compromise between Kabat and Chothia. The "Contact" definition is based on analyses of the available antibody crystal structures. An Exemplary system, as included in Tables 1-10, is a combination of Kabat and Chothia.

In some embodiments, a GCGR-binding protein (e.g., an antibody) comprises the Exemplary heavy chain CDR1, CDR2, and CDR3 and the Exemplary light chain CDR1, CDR2, and CDR3 from Table 1. In some embodiments, a GCGR-binding protein (e.g., an antibody) comprises the Kabat heavy chain CDR1, CDR2, and CDR3 and the Kabat light chain CDR1, CDR2, and CDR3 from Table 1. In some embodiments, a GCGR-binding protein (e.g., an antibody) comprises the Chothia heavy chain CDR1, CDR2, and CDR3 and the Chothia light chain CDR1, CDR2, and CDR3 from Table 1. In some embodiments, a GCGR-binding protein (e.g., an antibody) comprises the IMGT heavy chain CDR1, CDR2, and CDR3 and the IMGT light chain CDR1, CDR2, and CDR3 from Table 1. In some embodiments, a GCGR-binding protein (e.g., an antibody) comprises the Contact heavy chain CDR1, CDR2, and CDR3 and the Contact light chain CDR1, CDR2, and CDR3 from Table 1. In some embodiments, a GCGR-binding protein (e.g., an antibody) comprises the AbM heavy chain CDR1, CDR2, and CDR3 and the AbM light chain CDR1, CDR2, and CDR3 from Table 1.

In some embodiments, a GCGR-binding protein (e.g., an antibody) comprises the Exemplary heavy chain CDR1, CDR2, and CDR3 and the Exemplary light chain CDR1, CDR2, and CDR3 from Table 2. In some embodiments, a GCGR-binding protein (e.g., an antibody) comprises the Kabat heavy chain CDR1, CDR2, and CDR3 and the Kabat light chain CDR1, CDR2, and CDR3 from Table 2. In some embodiments, a GCGR-binding protein (e.g., an antibody) comprises the Chothia heavy chain CDR1, CDR2, and CDR3 and the Chothia light chain CDR1, CDR2, and CDR3 from Table 2. In some embodiments, a GCGR-binding protein (e.g., an antibody) comprises the IMGT heavy chain CDR1, CDR2, and CDR3 and the IMGT light chain CDR1, CDR2, and CDR3 from Table 2. In some embodiments, a GCGR-binding protein (e.g., an antibody) comprises the Contact heavy chain CDR1, CDR2, and CDR3 and the Contact light chain CDR1, CDR2, and CDR3 from Table 2. In some embodiments, a GCGR-binding protein (e.g., an antibody) comprises the AbM heavy chain CDR1, CDR2, and CDR3 and the AbM light chain CDR1, CDR2, and CDR3 from Table 2.

In some embodiments, a GCGR-binding protein (e.g., an antibody) comprises the Exemplary heavy chain CDR1, CDR2, and CDR3 and the Exemplary light chain CDR1, CDR2, and CDR3 from Table 3. In some embodiments, a GCGR-binding protein (e.g., an antibody) comprises the Kabat heavy chain CDR1, CDR2, and CDR3 and the Kabat light chain CDR1, CDR2, and CDR3 from Table 3. In some embodiments, a GCGR-binding protein (e.g., an antibody) comprises the Chothia heavy chain CDR1, CDR2, and CDR3 and the Chothia light chain CDR1, CDR2, and CDR3 from Table 3. In some embodiments, a GCGR-binding protein (e.g., an antibody) comprises the IMGT heavy chain CDR1, CDR2, and CDR3 and the IMGT light chain CDR1, CDR2, and CDR3 from Table 3. In some embodiments, a GCGR-binding protein (e.g., an antibody) comprises the IMGT heavy chain CDR1, CDR2, and CDR3 and the IMGT light chain CDR1, CDR2, and CDR3 from Table 3. In some embodiments, a GCGR-binding protein (e.g., an antibody) comprises the Contact heavy chain CDR1, CDR2, and CDR3 and the Contact light chain CDR1, CDR2, and CDR3 from Table 3. In some embodiments, a GCGR-binding protein (e.g., an antibody) comprises the AbM heavy chain CDR1, CDR2, and CDR3 and the AbM light chain CDR1, CDR2, and CDR3 from Table 3.

In some embodiments, a GCGR-binding protein (e.g., an antibody) comprises the Exemplary heavy chain CDR1, CDR2, and CDR3 and the Exemplary light chain CDR1, CDR2, and CDR3 from Table 4. In some embodiments, a GCGR-binding protein (e.g., an antibody) comprises the Kabat heavy chain CDR1, CDR2, and CDR3 and the Kabat light chain CDR1, CDR2, and CDR3 from Table 4. In some embodiments, a GCGR-binding protein (e.g., an antibody) comprises the Chothia heavy chain CDR1, CDR2, and CDR3 and the Chothia light chain CDR1, CDR2, and CDR3 from Table 4. In some embodiments, a GCGR-binding protein (e.g., an antibody) comprises the IMGT heavy chain CDR1, CDR2, and CDR3 and the IMGT light chain CDR1, CDR2, and CDR3 from Table 4. In some embodiments, a GCGR-binding protein (e.g., an antibody) comprises the Contact heavy chain CDR1, CDR2, and CDR3 and the Contact light chain CDR1, CDR2, and CDR3 from Table 4. In some embodiments, a GCGR-binding protein (e.g., an antibody) comprises the AbM heavy chain CDR1, CDR2, and CDR3 and the AbM light chain CDR1, CDR2, and CDR3 from Table 4.

In some embodiments, a GCGR-binding protein (e.g., an antibody) comprises the Exemplary heavy chain CDR1, CDR2, and CDR3 and the Exemplary light chain CDR1, CDR2, and CDR3 from Table 5. In some embodiments, a GCGR-binding protein (e.g., an antibody) comprises the Kabat heavy chain CDR1, CDR2, and CDR3 and the Kabat light chain CDR1, CDR2, and CDR3 from Table 5. In some embodiments, a GCGR-binding protein (e.g., an antibody) comprises the Chothia heavy chain CDR1, CDR2, and CDR3 and the Chothia light chain CDR1, CDR2, and CDR3 from Table 5. In some embodiments, a GCGR-binding protein (e.g., an antibody) comprises the IMGT heavy chain CDR1, CDR2, and CDR3 and the IMGT light chain CDR1, CDR2, and CDR3 from Table 5. In some embodiments, a GCGR-binding protein (e.g., an antibody) comprises the Contact heavy chain CDR1, CDR2, and CDR3 and the Contact light chain CDR1, CDR2, and CDR3 from Table 5. In some embodiments, a GCGR-binding protein (e.g., an antibody) comprises the AbM heavy chain CDR1, CDR2, and CDR3 and the AbM light chain CDR1, CDR2, and CDR3 from Table 5.

In some embodiments, a GCGR-binding protein (e.g., an antibody) comprises the Exemplary heavy chain CDR1, CDR2, and CDR3 and the Exemplary light chain CDR1, CDR2, and CDR3 from Table 6. In some embodiments, a GCGR-binding protein (e.g., an antibody) comprises the Kabat heavy chain CDR1, CDR2, and CDR3 and the Kabat light chain CDR1, CDR2, and CDR3 from Table 6. In some embodiments, a GCGR-binding protein (e.g., an antibody) comprises the Chothia heavy chain CDR1, CDR2, and CDR3 and the Chothia light chain CDR1, CDR2, and CDR3 from Table 6. In some embodiments, a GCGR-binding protein (e.g., an antibody) comprises the IMGT heavy chain CDR1, CDR2, and CDR3 and the IMGT light chain CDR1, CDR2, and CDR3 from Table 6. In some embodiments, a GCGR-binding protein (e.g., an antibody) comprises the Contact heavy chain CDR1, CDR2, and CDR3 and the Contact light chain CDR1, CDR2, and CDR3 from Table 6. In some embodiments, a GCGR-binding protein (e.g., an antibody) comprises the AbM heavy chain CDR1, CDR2, and CDR3 and the AbM light chain CDR1, CDR2, and CDR3 from Table 6.

In some embodiments, a GCGR-binding protein (e.g., an antibody) comprises the Exemplary heavy chain CDR1, CDR2, and CDR3 and the Exemplary light chain CDR1, CDR2, and CDR3 from Table 7. In some embodiments, a GCGR-binding protein (e.g., an antibody) comprises the Kabat heavy chain CDR1, CDR2, and CDR3 and the Kabat light chain CDR1, CDR2, and CDR3 from Table 7. In some embodiments, a GCGR-binding protein (e.g., an antibody) comprises the Chothia heavy chain CDR1, CDR2, and CDR3 and the Chothia light chain CDR1, CDR2, and CDR3 from Table 7. In some embodiments, a GCGR-binding protein (e.g., an antibody) comprises the IMGT heavy chain CDR1, CDR2, and CDR3 and the IMGT light chain CDR1, CDR2, and CDR3 from Table 7. In some embodiments, a GCGR-binding protein (e.g., an antibody) comprises the Contact heavy chain CDR1, CDR2, and CDR3 and the Contact light chain CDR1, CDR2, and CDR3 from Table 7. In some embodiments, a GCGR-binding protein (e.g., an antibody) comprises the AbM heavy chain CDR1, CDR2, and CDR3 and the AbM light chain CDR1, CDR2, and CDR3 from Table 7.

In some embodiments, a GCGR-binding protein (e.g., an antibody) comprises the Exemplary heavy chain CDR1, CDR2, and CDR3 and the Exemplary light chain CDR1, CDR2, and CDR3 from Table 8. In some embodiments, a GCGR-binding protein (e.g., an antibody) comprises the Kabat heavy chain CDR1, CDR2, and CDR3 and the Kabat light chain CDR1, CDR2, and CDR3 from Table 8. In some embodiments, a GCGR-binding protein (e.g., an antibody) comprises the Chothia heavy chain CDR1, CDR2, and CDR3 and the Chothia light chain CDR1, CDR2, and CDR3 from Table 8. In some embodiments, a GCGR-binding protein (e.g., an antibody) comprises the IMGT heavy chain CDR1, CDR2, and CDR3 and the IMGT light chain CDR1, CDR2, and CDR3 from Table 8. In some embodiments, a GCGR-binding protein (e.g., an antibody) comprises the Contact heavy chain CDR1, CDR2, and CDR3 and the Contact light chain CDR1, CDR2, and CDR3 from Table 8. In some embodiments, a GCGR-binding protein (e.g., an antibody) comprises the AbM heavy chain CDR1, CDR2, and CDR3 and the AbM light chain CDR1, CDR2, and CDR3 from Table 8.

In some embodiments, a GCGR-binding protein (e.g., an antibody) comprises the Exemplary heavy chain CDR1, CDR2, and CDR3 and the Exemplary light chain CDR1, CDR2, and CDR3 from Table 9. In some embodiments, a GCGR-binding protein (e.g., an antibody) comprises the Kabat heavy chain CDR1, CDR2, and CDR3 and the Kabat light chain CDR1, CDR2, and CDR3 from Table 9. In some embodiments, a GCGR-binding protein (e.g., an antibody) comprises the Chothia heavy chain CDR1, CDR2, and CDR3 and the Chothia light chain CDR1, CDR2, and CDR3 from Table 9. In some embodiments, a GCGR-binding protein (e.g., an antibody) comprises the IMGT heavy chain CDR1, CDR2, and CDR3 and the IMGT light chain CDR1, CDR2, and CDR3 from Table 9. In some embodiments, a GCGR-binding protein (e.g., an antibody) comprises the Contact heavy chain CDR1, CDR2, and CDR3 and the Contact light chain CDR1, CDR2, and CDR3 from Table 9. In some embodiments, a GCGR-binding protein (e.g., an antibody) comprises the AbM heavy chain CDR1, CDR2, and CDR3 and the AbM light chain CDR1, CDR2, and CDR3 from Table 9.

In some embodiments, a GCGR-binding protein (e.g., an antibody) comprises the Exemplary heavy chain CDR1, CDR2, and CDR3 and the Exemplary light chain CDR1, CDR2, and CDR3 from Table 10. In some embodiments, a GCGR-binding protein (e.g., an antibody) comprises the Kabat heavy chain CDR1, CDR2, and CDR3 and the Kabat light chain CDR1, CDR2, and CDR3 from Table 10. In some embodiments, a GCGR-binding protein (e.g., an antibody) comprises the Chothia heavy chain CDR1, CDR2, and CDR3 and the Chothia light chain CDR1, CDR2, and CDR3 from Table 10. In some embodiments, a GCGR-binding protein (e.g., an antibody) comprises the IMGT heavy chain CDR1, CDR2, and CDR3 and the IMGT light chain CDR1, CDR2, and CDR3 from Table 10. In some embodiments, a GCGR-binding protein (e.g., an antibody) comprises the Contact heavy chain CDR1, CDR2, and CDR3 and the Contact light chain CDR1, CDR2, and CDR3 from Table 10. In some embodiments, a GCGR-binding protein (e.g., an antibody) comprises the AbM heavy chain CDR1, CDR2, and CDR3 and the AbM light chain CDR1, CDR2, and CDR3 from Table 10.

In some embodiments, a GCGR-binding protein (e.g., an antibody) comprises a CDR1, CDR2, and CDR3 and a light chain CDR1, CDR2, CDR3 from the antibody designated 6B5. In some embodiments, a GCGR-binding protein (e.g., an antibody) comprises a CDR1, CDR2, and CDR3 and a light chain CDR1, CDR2, CDR3 from the antibody designated 3H5. In some embodiments, a GCGR-binding protein (e.g., an antibody) comprises a CDR1, CDR2, and CDR3 and a light chain CDR1, CDR2, CDR3 from the antibody designated 5B11. In some embodiments, a GCGR-binding protein (e.g., an antibody) comprises a CDR1, CDR2, and CDR3 and a light chain CDR1, CDR2, CDR3 from the antibody designated 1C1. In some embodiments, a GCGR-binding protein (e.g., an antibody) comprises a CDR1, CDR2, and CDR3 and a light chain CDR1, CDR2, CDR3 from the antibody designated 1C3. In some embodiments, a GCGR-binding protein (e.g., an antibody) comprises a CDR1, CDR2, and CDR3 and a light chain CDR1, CDR2, CDR3 from the antibody designated 1H2. In some embodiments, a GCGR-binding protein (e.g., an antibody) comprises a CDR1, CDR2, and CDR3 and a light chain CDR1, CDR2, CDR3 from the antibody designated 4F8. In some embodiments, a GCGR-binding protein (e.g., an antibody) comprises a CDR1, CDR2, and CDR3 and a light chain CDR1, CDR2, CDR3 from the antibody designated 13G9. In some embodiments, a GCGR-binding protein (e.g., an antibody) comprises a CDR1, CDR2, and CDR3 and a light chain CDR1, CDR2, CDR3 from the antibody designated 14F4. In some embodiments, a GCGR-binding protein (e.g., an antibody) comprises a CDR1, CDR2, and CDR3 and a light chain CDR1, CDR2, CDR3 from the antibody designated 14E9.

TABLE 1

Antibody 6B5 Sequences

| | Exemplary | IMGT | Kabat | Chothia | Contact | AbM |
|---|---|---|---|---|---|---|
| Heavy Chain CDR1 | GFTFTNHWLG (SEQ ID NO: 1) | GFTFTNHW (SEQ ID NO: 7) | NHWLG (SEQ ID NO: 12) | GFTFTNH (SEQ ID NO: 13) | TNHWLG (SEQ ID NO: 18) | GFTFTNHWLG (SEQ ID NO: 1) |
| Heavy Chain CDR2 | DIYPGGYYINYNE KFKG (SEQ ID NO: 2) | IYPGGYYI (SEQ ID NO: 8) | DIYPGGYYINYNE KFKG (SEQ ID NO: 2) | PGGY (SEQ ID NO: 14) | WIGDIYPGGYYIN (SEQ ID NO: 19) | DIYPGGYYIN (SEQ ID NO: 24) |
| Heavy Chain CDR3 | HTNYGSDY (SEQ ID NO: 3) | ARHTNYGSDY (SEQ ID NO: 9) | HTNYGSDY (SEQ ID NO: 3) | TNYGSD (SEQ ID NO: 15) | ARHTNYGSD (SEQ ID NO: 20) | HTNYGSDY (SEQ ID NO: 3) |
| Light Chain CDR1 | RSSQSIVDSYGNT FLE (SEQ ID NO: 4) | QSIVDSYGNTF (SEQ ID NO: 10) | RSSQSIVDSYGNT FLE (SEQ ID NO: 4) | SQSIVDSYGNTF (SEQ ID NO: 16) | VDSYGNTFL EWY (SEQ ID NO: 21) | RSSQSIVDSYGNT FLE (SEQ ID NO: 4) |
| Light Chain CDR2 | KVSNRLS (SEQ ID NO: 5) | KVS (SEQ ID NO: 11) | KVSNRLS (SEQ ID NO: 5) | KVS (SEQ ID NO: 11) | LLIYKVSNRL (SEQ ID NO: 22) | KVSNRLS (SEQ ID NO: 5) |
| Light Chain CDR3 | FQGSHVPWT (SEQ ID NO: 6) | FQGSHVPWT (SEQ ID NO: 6) | FQGSHVPWT (SEQ ID NO: 6) | GSHVPW (SEQ ID NO: 17) | FQGSHVPW (SEQ ID NO: 23) | FQGSHVPWT (SEQ ID NO: 6) |

6B5 Heavy chain variable region (SEQ ID NO: 25)
QVQLQQSGTELVRPGTSVKISCKASGFTFTNHWLGWVKQRPGHGLEWIGDIYPGGYYINYNEKFKG
KATLTADTSSSTAYMQLSSLTSEDSAVYFCARHTNYGSDYWGQGTTLTVSS 6B5 Light chain variable region (SEQ ID NO: 26)
DVLMTQIPLSLPVSLGDQASISCRSSQSIVDSYGNTFLEWYLQKPGQSPKWYKVSNRLSGVPDRFSG
TGAGTDFTLKISRVEAEDLGIYYCFQGSHVPWTFGGGTKLEIK

TABLE 2

Antibody 3H5 Sequences

| | Exemplary | IMGT | Kabat | Chothia | Contact | AbM |
|---|---|---|---|---|---|---|
| Heavy Chain CDR1 | GNTFTNYWMH (SEQ ID NO: 27) | GNTFTNYW (SEQ ID NO: 33) | NYWMH (SEQ ID NO: 38) | GNTFTNY (SEQ ID NO: 39) | TNYWMH (SEQ ID NO: 44) | GNTFTNYWMH (SEQ ID NO: 27) |
| Heavy Chain CDR2 | MIHPNSGSTHYNE KFKN (SEQ ID NO: 28) | IHPNSGST (SEQ ID NO: 34) | MIHPNSGSTHYNE KFKN (SEQ ID NO: 28) | PNSG (SEQ ID NO: 40) | WIGMIHPNSG STH (SEQ ID NO: 45) | MIHPNSGSTH (SEQ ID NO: 50) |
| Heavy Chain CDR3 | TADYVMDY (SEQ ID NO: 29) | GATADYVMDY (SEQ ID NO: 35) | TADYVMDY (SEQ ID NO: 29) | ADYVMD (SEQ ID NO: 41) | GATADYVMD (SEQ ID NO: 46) | TADYVMDY (SEQ ID NO: 29) |
| Light Chain CDR1 | KSTKSLLNSDGF TYLD (SEQ ID NO: 30) | KSLLNSDGFTY (SEQ ID NO: 36) | KSTKSLLNSDGF TYLD (SEQ ID NO: 30) | TKSLNSDGFTY (SEQ ID NO: 42) | LNSDGFTYL DWY (SEQ ID NO: 47) | KSTKSLLNSDGF TYLD (SEQ ID NO: 30) |
| Light Chain CDR2 | LVSNRFS (SEQ ID NO: 31) | LVS (SEQ ID NO: 37) | LVSNRFS (SEQ ID NO: 31) | LVS (SEQ ID NO: 37) | LLINLVSNRF (SEQ ID NO: 48) | LVSNRFS (SEQ ID NO: 31) |
| Light Chain CDR3 | FQSNFLPLT (SEQ ID NO: 32) | FQSNFLPLT (SEQ ID NO: 32) | FQSNFLPLT (SEQ ID NO: 32) | SNFLPL (SEQ ID NO: 43) | FQSNFLPL (SEQ ID NO: 49) | FQSNFLPLT (SEQ ID NO: 32) |

3H5 Heavy chain variable region (SEQ ID NO: 51)
QVQLQQSGAELVKPGASVRLSCKASGNTFTNYWMHWVKQRPGQGLEWIGMIHPNSGSTHY
NEKFKNKATLTVDKSSNTAYMQLSGLTSEDSAVYYCGATADYVMDYWGQGTSVTVSS 3H5 Light chain variable region (SEQ ID NO: 52)
DIVLTQTPLSLPVNIGDQASISCKSTKSLLNSDGFTYLDWYLQKPGQSPQLLINLVSNRFSGVP
DRFSGSGSGTEFILKISRVEAEDLGVYYCFQSNFLPLTFGAGTKLELK

TABLE 3

Antibody 5B11 Sequences

| | Exemplary | IMGT | Kabat | Chothia | Contact | AbM |
|---|---|---|---|---|---|---|
| Heavy Chain CDR1 | GNTFTSHWMH (SEQ ID NO: 53) | GNTFTSHW (SEQ ID NO: 57) | SHWMH (SEQ ID NO: 61) | GNTFTSH (SEQ ID NO: 62) | TSHWMH (SEQ ID NO: 65) | GNTFTSHWMH (SEQ ID NO: 53) |
| Heavy Chain CDR2 | MSHPNSGSSNYSGKFKS (SEQ ID NO: 54) | SHPNSGSSN (SEQ ID NO: 58) | MSHPNSGSSNYSGKFKS (SEQ ID NO: 54) | PNSG (SEQ ID NO: 40) | WIGMSHPNSGSSN (SEQ ID NO: 66) | MSHPNSGSSN (SEQ ID NO: 70) |
| Heavy Chain CDR3 | TDYDYDGDY (SEQ ID NO: 55) | ARTDYDYDGDY (SEQ ID NO: 59) | TDYDYDGDY (SEQ ID NO: 55) | DYDYDGD (SEQ ID NO: 63) | ARTDYDYDGD (SEQ ID NO: 67) | TDYDYDGDY (SEQ ID NO: 55) |
| Light Chain CDR1 | KSSKSLLNSDGLTYLD (SEQ ID NO: 56) | KSLLNSDGLTY (SEQ ID NO: 60) | KSSKSLLNSDGLTYLD (SEQ ID NO: 56) | SKSLLNSDGLTY (SEQ ID NO: 64) | LNSDGLTYLDWY (SEQ ID NO: 68) | KSSKSLLNSDGLTYLD (SEQ ID NO: 56) |
| Light Chain CDR2 | LVSNRFS (SEQ ID NO: 31) | LVS (SEQ ID NO: 37) | LVSNRFS (SEQ ID NO: 31) | LVS (SEQ ID NO: 37) | LLIYLVSNRF (SEQ ID NO: 69) | LVSNRFS (SEQ ID NO: 31) |
| Light Chain CDR3 | FQSNFLPLT (SEQ ID NO: 32) | FQSNFLPLT (SEQ ID NO: 32) | FQSNFLPLT (SEQ ID NO: 32) | SNFLPL (SEQ ID NO: 43) | FQSNFLPL (SEQ ID NO: 49) | FQSNFLPLT (SEQ ID NO: 32) |

5B11 Heavy Chain variable region (SEQ ID NO: 71)
QVQLQQSGAELVKPGASVKLSCKASGNTFTSHWMHWVKQRPGQGLEWIGMSHPNSGSSNYSG
KFKSKATLTVDRSSSTAYMQLNSLTSEDSAVYYCARTDYDYDGDYWGQGTTLTVSS 5B11 Light Chain variable region (SEQ ID NO: 72)
DVVLTQTPLSLPVNIGDQASISCKSSKSLLNSDGLTYLDWYLQKPGQSPQLLIYLVSNRFSGVPDR
FSGSGSGTDFTLKISRVEADDLGVYYCFQSNFLPLTFGAGTKLELK

TABLE 4

Antibody 1C1 Sequences

| | Exemplary | IMGT | Kabat | Chothia | Contact | AbM |
|---|---|---|---|---|---|---|
| Heavy Chain CDR1 | GYTFTRNVIH (SEQ ID NO: 73) | GYTFTRNV (SEQ ID NO: 79) | RNVIH (SEQ ID NO: 84) | GYTFTRN (SEQ ID NO: 85) | TRNVIH (SEQ ID NO: 90) | GYTFTRNVIH (SEQ ID NO: 73) |
| Heavy Chain CDR2 | YINPYNDGAKYNAKFKG (SEQ ID NO: 74) | INPYNDGA (SEQ ID NO: 80) | YINPYNDGAKYNAKFKG (SEQ ID NO: 74) | PYND (SEQ ID NO: 86) | WIGYINPYNDGAK (SEQ ID NO: 91) | YINPYNDGAK (SEQ ID NO: 96) |
| Heavy Chain CDR3 | WGNYEDFAMDY (SEQ ID NO: 75) | ARWGNYEDFAM (SEQ ID NO: 81) | WGNYEDFAMDY (SEQ ID NO: 75) | GNYEDFAMD (SEQ ID NO: 87) | ARWGNYEDFAMD (SEQ ID NO: 92) | WGNYEDFAMDY (SEQ ID NO: 75) |
| Light Chain CDR1 | RASESVDIYGNSYMH (SEQ ID NO: 76) | ESVDIYGNSY (SEQ ID NO: 82) | RASESVDIYGNSYMH (SEQ ID NO: 76) | SESVDIYGNSY (SEQ ID NO: 88) | DIYGNSYMHWY (SEQ ID NO: 93) | RASESVDIYGNSYMH (SEQ ID NO: 76) |
| Light Chain CDR2 | LASNLES (SEQ ID NO: 77) | LAS (SEQ ID NO: 83) | LASNLES (SEQ ID NO: 77) | LAS (SEQ ID NO: 83) | LLIYLASNLE (SEQ ID NO: 94) | LASNLES (SEQ ID NO: 77) |
| Light Chain CDR3 | QQNNEDPFT (SEQ ID NO: 78) | QQNNEDPFT (SEQ ID NO: 78) | QQNNEDPFT (SEQ ID NO: 78) | NNEDPF (SEQ ID NO: 89) | QQNNEDPF (SEQ ID NO: 95) | QQNNEDPFT (SEQ ID NO: 78) |

1C1 Heavy chain variable region (SEQ ID NO: 97)
EVQLQQSGPELVKPGATVKMSCKASGYTFTRNVIHWVKQKPGQGLEWIGYINPYNDGAKYNA
KFKGKATVTSDKSSSTAYMELSSLTSEDSAVYYCARWGNYEDFAMDYWGQGTSVTVSS 1C1 Light chain variable region (SEQ ID NO: 98)
NIVLTQSPPSLAVSLGQRATISCRASESVDIYGNSYMHWYQQKPGQPPKWYLASNLESGVPAR
FSGSGSRTEFSLTIDPVEAGDAATYYCQQNNEDPFTFGGGTKLEIK

TABLE 5

Antibody 1C3 Sequences

| | Exemplary | IMGT | Kabat | Chothia | Contact | AbM |
|---|---|---|---|---|---|---|
| Heavy Chain CDR1 | GYTFTSSVMH (SEQ ID NO: 99) | GYTFTSSV (SEQ ID NO: 105) | SSVMH (SEQ ID NO: 110) | GYTFTSS (SEQ ID NO: 111) | TSSVMH (SEQ ID NO: 115) | GYTFTSSVMH (SEQ ID NO: 99) |
| Heavy Chain CDR2 | YINPYNDGTKYNENFKG (SEQ ID NO: 100) | INPYNDGT (SEQ ID NO: 106) | YINPYNDGTKYNENFKG (SEQ ID NO: 100) | PYND (SEQ ID NO: 86) | WIGYINPYNDGTK (SEQ ID NO: 116) | YINPYNDGTK (SEQ ID NO: 121) |
| Heavy Chain CDR3 | GAGYDRGPMAMDY (SEQ ID NO: 101) | ARGAGYDRGPMAMDY (SEQ ID NO: 107) | GAGYDRGPMAMDY (SEQ ID NO: 101) | AGYDRGPMAMD (SEQ ID NO: 112) | ARGAGYDRGPMAMD (SEQ ID NO: 117) | GAGYDRGPMAMDY (SEQ ID NO: 101) |
| Light Chain CDR1 | RASESVDSYGDSFVH (SEQ ID NO: 102) | ESVDSYGDSF (SEQ ID NO: 108) | RASESVDSYGDSFVH (SEQ ID NO: 102) | SESVDSYGDSF (SEQ ID NO: 113) | DSYGDSFVHWY (SEQ ID NO: 118) | RASESVDSYGDSFVH (SEQ ID NO: 102) |
| Light Chain CDR2 | FASNLES (SEQ ID NO: 103) | FAS (SEQ ID NO: 109) | FASNLES (SEQ ID NO: 103) | FAS (SEQ ID NO: 109) | LLIYFASNLE (SEQ ID NO: 119) | FASNLES (SEQ ID NO: 103) |
| Light Chain CDR3 | QQNNEVPFT (SEQ ID NO: 104) | QQNNEVPFT (SEQ ID NO: 104) | QQNNEVPFT (SEQ ID NO: 104) | NNEVPF (SEQ ID NO: 114) | QQNNEVPF (SEQ ID NO: 120) | QQNNEVPFT (SEQ ID NO: 104) |

1C3 Heavy chain variable region (SEQ ID NO: 122)
EVQLQQSGPELVKPGASVKMSCKASGYTFTSSVMHWVKQKPGQALEWIGYINPYNDGTKYN
ENFKGKATLTSDRSSTTAYMELSSLTSEDSAVYYCVTGAGYDRGPMAMDYWGQGTSVTVSS 1C3 Light chain variable region (SEQ ID NO: 123)
NIVLTQSPASLAVSLGQRATISCRASESVDSYGDSFVHWYQQKPGQPPKWYFASNLESGVPA
RFSGSGSRTDFTLTIDPVEADDTATYYCQQNNEVPFTFGSGTKLELK

TABLE 6

Antibody 1H2 Sequences

| | Exemplary | IMGT | Kabat | Chothia | Contact | AbM |
|---|---|---|---|---|---|---|
| Heavy Chain CDR1 | GYTFTSYWIT (SEQ ID NO: 124) | GYTFTSYW (SEQ ID NO: 129) | SYWIT (SEQ ID NO: 133) | GYTFTSY (SEQ ID NO: 134) | TSYWIT (SEQ ID NO: 138) | GYTFTSYWIT (SEQ ID NO: 124) |
| Heavy Chain CDR2 | DIHPGGGDTNYNKKFKS (SEQ ID NO: 125) | IHPGGGDT (SEQ ID NO: 130) | DIHPGGGDTNYNKKFKS (SEQ ID NO: 125) | PGGG (SEQ ID NO: 135) | WIGDIHPGGGDTN (SEQ ID NO: 139) | DIHPGGGDTN (SEQ ID NO: 143) |
| Heavy Chain CDR3 | DDNYVGFTY (SEQ ID NO: 126) | ARDDNYVGFTY (SEQ ID NO: 131) | DDNYVGFTY (SEQ ID NO: 126) | DNYVGFT (SEQ ID NO: 136) | ARDDNYVGFT (SEQ ID NO: 140) | DDNYVGFTY (SEQ ID NO: 126) |
| Light Chain CDR1 | RSSQTIIHSDGNTYLE (SEQ ID NO: 127) | QTIIHSDGNTY (SEQ ID NO: 132) | RSSQTIIHSDGNTYLE (SEQ ID NO: 127) | SQTIIHSDGNTY (SEQ ID NO: 137) | IHSDGNTYLEWY (SEQ ID NO: 141) | RSSQTIIHSDGNTYLE (SEQ ID NO: 127) |
| Light Chain CDR2 | KVSNRFS (SEQ ID NO: 128) | KVS (SEQ ID NO: 11) | KVSNRFS (SEQ ID NO: 128) | KVS (SEQ ID NO: 11) | LLIYKVSNRF (SEQ ID NO: 142) | KVSNRFS (SEQ ID NO: 128) |
| Light Chain CDR3 | FQGSHVPWT (SEQ ID NO: 6) | FQGSHVPWT (SEQ ID NO: 6) | FQGSHVPWT (SEQ ID NO: 6) | GSHVPW (SEQ ID NO: 17) | FQGSHVPW (SEQ ID NO: 23) | FQGSHVPWT (SEQ ID NO: 6) |

Heavy chain variable region (SEQ ID NO: 144)
QVQLQQPGAELVKPGASVKMSCKVSGYTFTSYWITWVKQRPGQGLEWIGDIHPGGGDTNYNK
KFKSKATLTVDTSSSTAYMQLSSLTSEDSAVYHCTSDDNYVGFTYWGQGTLVTVSA Light chain variable region (SEQ ID NO: 145)
DVLMTQTPLSLPVSLGDQASISCRSSQTIIHSDGNTYLEWYLQKPGQSPILLIYKVSNRFSGVPDR
FSGSGSGTDFTLKISRVEAEDLGVYYCFQGSHVPWTFGGGTKLEIK

TABLE 7

Antibody 4F8 Sequences

| | Exemplary | IMGT | Kabat | Chothia | Contact | AbM |
|---|---|---|---|---|---|---|
| Heavy Chain CDR1 | GYTFSNYWIG (SEQ ID NO: 146) | GYTFSNYW (SEQ ID NO: 150) | NYWIG (SEQ ID NO: 154) | GYTFSNY (SEQ ID NO: 155) | SNYWIG (SEQ ID NO: 159) | GYTFSNYWIG (SEQ ID NO: 146) |
| Heavy Chain CDR2 | DIYPGGFYDN YNDKFKG (SEQ ID NO: 147) | IYPGGFYDN (SEQ ID NO: 151) | DIYPGGFYDN YNDKFKG (SEQ ID NO: 147) | PGGF (SEQ ID NO: 156) | WIGDIYPGGF YDN (SEQ ID NO: 160) | DIYPGGFYDN (SEQ ID NO: 163) |
| Heavy Chain CDR3 | SGGLPGAGFTY (SEQ ID NO: 148) | ARSGGLPGAG FTY (SEQ ID NO: 152) | SGGLPGAGFTY (SEQ ID NO: 148) | GGLPGAGFT (SEQ ID NO: 157) | ARSGGLPGAG FT (SEQ ID NO: 161) | SGGLPGAGFTY (SEQ ID NO: 148) |
| Light Chain CDR1 | RSSQHIVYSD GNTYLE (SEQ ID NO: 149) | QHIVYSDGNTY (SEQ ID NO: 153) | RSSQHIVYSD GNTYLE (SEQ ID NO: 149) | SQHIVYSDGNTY (SEQ ID NO: 158) | VYSDGNTYLE WY (SEQ ID NO: 162) | RSSQHIVYSD GNTYLE (SEQ ID NO: 149) |
| Light Chain CDR2 | KVSNRFS (SEQ ID NO: 128) | KVS (SEQ ID NO: 11) | KVSNRFS (SEQ ID NO: 128) | KVS (SEQ ID NO: 11) | LLIYKVSNRF (SEQ ID NO: 142) | KVSNRFS (SEQ ID NO: 128) |
| Light Chain CDR3 | FQGSHVPWT (SEQ ID NO: 6) | FQGSHVPWT (SEQ ID NO: 6) | FQGSHVPWT (SEQ ID NO: 6) | GSHVPW (SEQ ID NO: 17) | FQGSHVPW (SEQ ID NO: 23) | FQGSHVPWT (SEQ ID NO: 6) |

4F8 Heavy chain variable region (SEQ ID NO: 164)
QVQLQQSGAELVRPGTSVTMSCKAAGYTFSNYWIGWVKQRPGHGLEWIGDIYPGGFYDNYND
KFKGKATLTTDTSSSTAYMQLSSLTSEDSAIYYCTRSGGLPGAGFTYWGQGTLVTVSA 4F8 Light chain variable region (SEQ ID NO: 165)
DVLMTQTPLSLPVSLGDQASISCRSSQHIVYSDGNTYLEWYLQKPGQSPKLLIYKVSNRFSGVPD
RFSGSGSGTDFTLEISRVEAEDLGVYYCFQGSHVPWTFGGGTKLEIK

TABLE 8

Antibody 13G9 Sequences

| | Exemplary | IMGT | Kabat | Chothia | Contact | AbM |
|---|---|---|---|---|---|---|
| Heavy Chain CDR1 | GYTFTNYWLG (SEQ ID NO: 166) | GYTFTNYW (SEQ ID NO: 172) | NYWLG (SEQ ID NO: 176) | GYTFTNY (SEQ ID NO: 177) | TNYWLG (SEQ ID NO: 182) | GYTFTNYWLG (SEQ ID NO: 166) |
| Heavy Chain CDR2 | DIYPGGDYNN YNGKFKG (SEQ ID NO: 167) | IYPGGDYN (SEQ ID NO: 173) | DIYPGGDYNN YNGKFKG (SEQ ID NO: 167) | PGGD (SEQ ID NO: 178) | WIGDIYPGGDYNN (SEQ ID NO: 183) | DIYPGGDYNN (SEQ ID NO: 187) |
| Heavy Chain CDR3 | SDDGYS (SEQ ID NO: 168) | ARSDDGYS (SEQ ID NO: 174) | SDDGYS (SEQ ID NO: 168) | DDGY (SEQ ID NO: 179) | ARSDDGY (SEQ ID NO: 184) | SDDGYS (SEQ ID NO: 168) |
| Light Chain CDR1 | RSSQSIVDSY GNTYLE (SEQ ID NO: 169) | QSIVDSYGNTY (SEQ ID NO: 175) | RSSQSIVDSY GNTYLE (SEQ ID NO: 169) | SQSIVDSYGN TY (SEQ ID NO: 180) | VDSYGNTYLE WY (SEQ ID NO: 185) | RSSQSIVDSY GNTYLE (SEQ ID NO: 169) |
| Light Chain CDR2 | KVSNRFA (SEQ ID NO: 170) | KVS (SEQ ID NO: 11) | KVSNRFA (SEQ ID NO: 170) | KVS (SEQ ID NO: 11) | LLIYKVSNRF (SEQ ID NO: 142) | KVSNRFA (SEQ ID NO: 170) |
| Light Chain CDR3 | FQGSHIPWT (SEQ ID NO: 171) | FQGSHIPWT (SEQ ID NO: 171) | FQGSHIPWT (SEQ ID NO: 171) | GSHIPW (SEQ ID NO: 181) | FQGSHIPW (SEQ ID NO: 186) | FQGSHIPWT (SEQ ID NO: 171) |

13G9 Heavy chain variable region (SEQ ID NO: 188)
QVQLQQSGAELVRPGTSVKISCKASGYTFTNYWLGWVKQRPGHGLEWIGDIYPGGDYNNYNG
KFKGKATLTADTSSSTAYIQLSSLTSEDSAVYFCVRSDDGYSWGQGTTLTVSS 13G9 Light chain variable region (SEQ ID NO: 189)
DVLMTQTPLSLPVSLGDQASISCRSSQSIVDSYGNTYLEWYQQKPGQSPTLLIYKVSNRFAGVPD
RFSGSGSGTDFTLKISRVEAEDLGVYYCFQGSHIPWTFGGGTKVEIK

TABLE 9

Antibody 14F4 Sequences

| | Exemplary | IMGT | Kabat | Chothia | Contact | AbM |
|---|---|---|---|---|---|---|
| Heavy Chain CDR1 | GYTFMYWIG (SEQ ID NO: 190) | GYTFMYW (SEQ ID NO: 172) | NYWIG (SEQ ID NO: 154) | GYTFTNY (SEQ ID NO: 177) | MYWIG (SEQ ID NO: 198) | GYTFMYWIG (SEQ ID NO: 190) |
| Heavy Chain CDR2 | DIFPGGFYSNYNEKFKG (SEQ ID NO: 191) | IFPGGFYS (SEQ ID NO: 194) | DIFPGGFYSNYNEKFKG (SEQ ID NO: 191) | PGGF (SEQ ID NO: 156) | WIGDIFPGGFYSN (SEQ ID NO: 199) | DIFPGGFYSN (SEQ ID NO: 202) |
| Heavy Chain CDR3 | IWDRGFDY (SEQ ID NO: 192) | ARMDRGFDY (SEQ ID NO: 195) | IWDRGFDY (SEQ ID NO: 192) | WDRGFD (SEQ ID NO: 196) | ARMDRGFD (SEQ ID NO: 200) | IWDRGFDY (SEQ ID NO: 192) |
| Light Chain CDR1 | RSSQSIVDSYGNTYLE (SEQ ID NO: 169) | QSIVDSYGNTY (SEQ ID NO: 175) | RSSQSIVDSYGNTYLE (SEQ ID NO: 169) | SQSIVDSYGNTY (SEQ ID NO: 180) | VDSYGNTYLEWY (SEQ ID NO: 185) | RSSQSIVDSYGNTYLE (SEQ ID NO: 169) |
| Light Chain CDR2 | KVSNRFS (SEQ ID NO: 128) | KVS (SEQ ID NO: 11) | KVSNRFS (SEQ ID NO: 128) | KVS (SEQ ID NO: 11) | LLIYKVSNRF (SEQ ID NO: 142) | KVSNRFS (SEQ ID NO: 128) |
| Light Chain CDR3 | FQGSHVPYT (SEQ ID NO: 193) | FQGSHVPYT (SEQ ID NO: 193) | FQGSHVPYT (SEQ ID NO: 193) | GSHVPY (SEQ ID NO: 197) | FQGSHVPY (SEQ ID NO: 201) | FQGSHVPYT (SEQ ID NO: 193) |

14F4 Heavy chain variable region (SEQ ID NO: 203)
QVQLQQSGAELVRPGTSVNMSCKATGYTFMYWIGWVKQRPGHGLEWIGDIFPGGFYSNYNE
KFKGKATLTTDTSSSTGYMQLSSLTSEDSAIYYCARIWDRGFDYWGQGTTLTVSS 14F4 Light chain variable region (SEQ ID NO: 204)
DVLMTQSPLSLPVSLGDQASISCRSSQSIVDSYGNTYLEWYLQKPGQSPKWYKVSNRFSGVPD
RFSGSGSGTDFTLKISRVEAEDRGLYYCFQGSHVPYTFGGGTKLEIK

TABLE 10

Antibody 14E9 Sequences

| | Exemplary | IMGT | Kabat | Chothia | Contact | AbM |
|---|---|---|---|---|---|---|
| Heavy Chain CDR1 | GYTFMYWIG (SEQ ID NO: 190) | GYTFMYW (SEQ ID NO: 172) | NYWIG (SEQ ID NO: 154) | GYTFTNY (SEQ ID NO: 177) | MYWIG (SEQ ID NO: 198) | GYTFMYWIG (SEQ ID NO: 190) |
| Heavy Chain CDR2 | DISPGNYYTNYNAKFKD (SEQ ID NO: 205) | ISPGNYYT (SEQ ID NO: 208) | DISPGNYYTNYNAKFKD (SEQ ID NO: 205) | PGNY (SEQ ID NO: 211) | WIGDISPGNYYTN (SEQ ID NO: 214) | DISPGNYYTN (SEQ ID NO: 217) |
| Heavy Chain CDR3 | YDEFAY (SEQ ID NO: 206) | ARYDEFAY (SEQ ID NO: 209) | YDEFAY (SEQ ID NO: 206) | DEFA (SEQ ID NO: 212) | ARYDEFA (SEQ ID NO: 215) | YDEFAY (SEQ ID NO: 206) |
| Light Chain CDR1 | RSSQSIVHSDGNTYLE (SEQ ID NO: 207) | QSIVHSDGNTY (SEQ ID NO: 210) | RSSQSIVHSDGNTYLE (SEQ ID NO: 207) | SQSIVHSDGNTY (SEQ ID NO: 213) | VHSDGNTYLEWY (SEQ ID NO: 216) | RSSQSIVHSDGNTYLE (SEQ ID NO: 207) |
| Light Chain CDR2 | KVSNRFS (SEQ ID NO: 128) | KVS (SEQ ID NO: 11) | KVSNRFS (SEQ ID NO: 128) | KVS (SEQ ID NO: 11) | LLIYKVSNRF (SEQ ID NO: 142) | KVSNRFS (SEQ ID NO: 128) |
| Light Chain CDR3 | FQGSHVPWT (SEQ ID NO: 6) | FQGSHVPWT (SEQ ID NO: 6) | FQGSHVPWT (SEQ ID NO: 6) | GSHVPW (SEQ ID NO: 17) | FQGSHVPW (SEQ ID NO: 23) | FQGSHVPWT (SEQ ID NO: 6) |

14E9 Heavy chain variable region (SEQ ID NO: 218)
QVQLQQSGAELVRPGTSVKMSCKAAGYTFMYWIGWVKQRPGHGLEWIGDISPGNYYTNYNA
KFKDKVSLTADTSSSTAYMQLSSLTSEDSAIYYCARYDEFAYWGQGTLVTVSA 14E9 Light chain variable region (SEQ ID NO: 219)
DVLMTQTPLSLSVSLGDQASISCRSSQSIVHSDGNTYLEWYLQKPGQSPKLLIYKVSNRFSGVPD
RFSGSGSGTDFTLKISRVEAEDLGVYYCFQGSHVPWTFGGGTKLEIK In some embodiments, a GCGR-binding protein (e.g., an antibody) comprises (a) a heavy chain CDR1 comprising SEQ ID NOs: 1, 7, 12, 13, or 18; a heavy chain CDR2 comprising SEQ ID NOs: 2, 8, 14, 19, or 24; and a heavy chain CDR3 comprising SEQ ID NOs: 3, 9, 15, or 20; and/or (b) a light chain CDR1 comprising SEQ ID NOs: 4, 10, 16, or 21; a light chain CDR2 comprising SEQ ID NOs: 5, 11, or 22; and a light chain CDR3 comprising SEQ ID NOs: 6, 17, or 23. In some embodiments, a GCGR-binding protein (e.g., an antibody) comprises a heavy chain CDR1 comprising GFTFTNHWLG (SEQ ID NO:1); a heavy chain CDR2 comprising DIYPGGYYINYNEKFKG (SEQ ID NO:2); and a heavy chain CDR3 comprising HTNYGSDY (SEQ ID NO:3). In some embodiments, the GCGR-binding protein further comprises a light chain CDR1 comprising RSSQSIVDSYGNTFLE (SEQ ID NO:4); a light chain CDR2 comprising KVSNRLS (SEQ ID NO:5); and a light chain CDR3 comprising FQGSHVPWT (SEQ ID NO:6). In some embodiments, a GCGR-binding protein (e.g., an antibody) comprises a light chain CDR1 comprising RSSQSIVDSYGNTFLE (SEQ ID NO:4); a light chain CDR2 comprising KVSNRLS (SEQ ID NO:5); and a light chain CDR3 comprising FQGSHVPWT (SEQ ID NO:6). In some embodiments, a GCGR-binding protein (e.g., an antibody) comprises a heavy chain CDR1 comprising GFTFTNHWLG (SEQ ID NO:1); a heavy chain CDR2 comprising DIYPGGYYINYNEKFKG (SEQ ID NO:2); a heavy chain CDR3 comprising HTNYGSDY (SEQ ID NO:3); a light chain CDR1 comprising RSSQSIVDSYGNTFLE (SEQ ID NO:4); a light chain CDR2 comprising KVSNRLS (SEQ ID NO:5); and a light chain CDR3 comprising FQGSHVPWT (SEQ ID NO:6).

In some embodiments, a GCGR-binding protein (e.g., an antibody) comprises: (a) a heavy chain CDR1 comprising GFTFTNHWLG (SEQ ID NO:1) or a variant thereof comprising 1, 2, 3, or 4 amino acid substitutions; a heavy chain CDR2 comprising DIYPGGYYINYNEKFKG (SEQ ID NO:2) or a variant thereof comprising 1, 2, 3, or 4 amino acid substitutions; a heavy chain CDR3 comprising HTNYGSDY (SEQ ID NO:3) or a variant thereof comprising 1, 2, 3, or 4 amino acid substitutions; a light chain CDR1 comprising RSSQSIVDSYGNTFLE (SEQ ID NO:4) or a variant thereof comprising 1, 2, 3, or 4 amino acid substitutions; a light chain CDR2 comprising KVSNRLS (SEQ ID NO:5) or a variant thereof comprising 1, 2, 3, or 4 amino acid substitutions; and a light chain CDR3 comprising FQGSHVPWT (SEQ ID NO:6) or a variant thereof comprising 1, 2, 3, or 4 amino acid substitutions. In some embodiments, the amino acid substitutions are conservative substitutions. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, a GCGR-binding protein (e.g., an antibody) comprises (a) a heavy chain CDR1 comprising SEQ ID NO:7: a heavy chain CDR2 comprising SEQ ID NO:8; and a heavy chain CDR3 comprising SEQ ID NO:9; and/or (b) a light chain CDR1 comprising SEQ ID NO:10; a light chain CDR2 comprising SEQ ID NO:11; and a light chain CDR3 comprising SEQ ID NO:6. In some embodiments, a GCGR-binding protein (e.g., an antibody) comprises (a) a heavy chain CDR1 comprising SEQ ID NO:12: a heavy chain CDR2 comprising SEQ ID NO:2; and a heavy chain CDR3 comprising SEQ ID NO:3; and/or (b) a light chain CDR1 comprising SEQ ID NO:4; a light chain CDR2 comprising SEQ ID NO:5; and a light chain CDR3 comprising SEQ ID NO:6. In some embodiments, a GCGR-binding protein (e.g., an antibody) comprises (a) a heavy chain CDR1 comprising SEQ ID NO:13: a heavy chain CDR2 comprising SEQ ID NO:14; and a heavy chain CDR3 comprising SEQ ID NO:15; and/or (b) a light chain CDR1 comprising SEQ ID NO:16; a light chain CDR2 comprising SEQ ID NO:11; and a light chain CDR3 comprising SEQ ID NO:17. In some embodiments, a GCGR-binding protein (e.g., an antibody) comprises (a) a heavy chain CDR1 comprising SEQ ID NO:18: a heavy chain CDR2 comprising SEQ ID NO:19; and a heavy chain CDR3 comprising SEQ ID NO:20; and/or (b) a light chain CDR1 comprising SEQ ID NO:21; a light chain CDR2 comprising SEQ ID NO:22; and a light chain CDR3 comprising SEQ ID NO:23. In some embodiments, a GCGR-binding protein (e.g., an antibody) comprises (a) a heavy chain CDR1 comprising SEQ ID NO:1: a heavy chain CDR2 comprising SEQ ID NO:24; and a heavy chain CDR3 comprising SEQ ID NO:3; and/or (b) a light chain CDR1 comprising SEQ ID NO:4; a light chain CDR2 comprising SEQ ID NO:5; and a light chain CDR3 comprising SEQ ID NO:6.

In some embodiments, a GCGR-binding protein comprises a heavy chain CDR1 comprising SEQ ID NO:1, a heavy chain CDR2 comprising SEQ ID NO:2, and a heavy chain CDR3 comprising SEQ ID NO:3. In some embodiments, a GCGR-binding protein comprises a heavy chain CDR1 comprising SEQ ID NO:7, a heavy chain CDR2 comprising SEQ ID NO:8, and a heavy chain CDR3 comprising SEQ ID NO:9. In some embodiments, a GCGR-binding protein comprises a heavy chain CDR1 comprising SEQ ID NO:12, a heavy chain CDR2 comprising SEQ ID NO:2, and a heavy chain CDR3 comprising SEQ ID NO:3. In another embodiment, a GCGR-binding protein comprises a heavy chain CDR1 comprising SEQ ID NO:13, a heavy chain CDR2 comprising SEQ ID NO:14, and a heavy chain CDR3 comprising SEQ ID NO:15. In some embodiments, a GCGR-binding protein comprises a heavy chain CDR1 comprising SEQ ID NO:18, a heavy chain CDR2 comprising SEQ ID NO:19, and a heavy chain CDR3 comprising SEQ ID NO:20. In another embodiment, a GCGR-binding protein comprises a heavy chain CDR1 comprising SEQ ID NO:1, a heavy chain CDR2 comprising SEQ ID NO:24, and a heavy chain CDR3 comprising SEQ ID NO:3. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a light chain CDR1 comprising SEQ ID NO:4, a light chain CDR2 comprising SEQ ID NO:5, and a light chain CDR3 comprising SEQ ID NO:6. In another embodiment, a GCGR-binding protein comprises a light chain CDR1 comprising SEQ ID NO:10, a light chain CDR2 comprising SEQ ID NO:11, and a light chain CDR3 comprising SEQ ID NO:6. In some embodiments, a GCGR-binding protein comprises a light chain CDR1 comprising SEQ ID NO:4, a light chain CDR2 comprising SEQ ID NO:5, and a light chain CDR3 comprising SEQ ID NO:6. In another embodiment, a GCGR-binding protein comprises a light chain CDR1 comprising SEQ ID NO:16, a light chain CDR2 comprising SEQ ID NO:11, and a light chain CDR3 comprising SEQ ID NO:17. In some embodiments, a GCGR-binding protein comprises a light chain CDR1 comprising SEQ ID NO:21, a light chain CDR2 comprising SEQ ID NO:22, and a light chain CDR3 comprising SEQ ID NO:23.

In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In another embodiment, a GCGR-binding protein comprises a heavy chain CDR1 comprising SEQ ID NO:7, a heavy chain CDR2 comprising SEQ ID NO:8, a heavy chain CDR3 comprising SEQ ID NO:9, a light chain CDR1 comprising SEQ ID NO:10, a light chain CDR2 comprising SEQ ID NO:11, and a light chain CDR3 comprising SEQ ID NO:6. In some embodiments, a GCGR-binding protein comprises a heavy chain CDR1 comprising SEQ ID NO:12, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In another embodiment, a GCGR-binding protein comprises a heavy chain CDR1 comprising SEQ ID NO:13, a heavy chain CDR2 comprising SEQ ID NO:14, a heavy chain CDR3 comprising SEQ ID NO:15, a light chain CDR1 comprising SEQ ID NO:16, a light chain CDR2 comprising SEQ ID NO:11, and a light chain CDR3 comprising SEQ ID NO:17. In some embodiments, a GCGR-binding protein comprises a heavy chain CDR1 comprising SEQ ID NO:18, a heavy chain CDR2 comprising SEQ ID NO:19, a heavy chain CDR3 comprising SEQ ID NO:20, a light chain CDR1 comprising SEQ ID NO:21, a light chain CDR2 comprising SEQ ID NO:22, and a light chain CDR3 comprising SEQ ID NO:23. In another embodiment, a GCGR-binding protein comprises a heavy chain CDR1 comprising SEQ ID NO:1, a heavy chain CDR2 comprising SEQ ID NO:24, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a heavy chain CDR1 comprising SEQ ID NO:1, a heavy chain CDR2 comprising SEQ ID NO:2, a heavy chain CDR3 comprising SEQ ID NO:3, and a light chain variable region comprising SEQ ID NO:26. In another embodiment, a GCGR-binding protein comprises a heavy chain CDR1 comprising SEQ ID NO:7, a heavy chain CDR2 comprising SEQ ID NO:8, a heavy chain CDR3 comprising SEQ ID NO:9, and a light chain variable region comprising SEQ ID NO:26. In some embodiments, a GCGR-binding protein comprising a heavy chain CDR1 comprising SEQ ID NO:12, a heavy chain CDR2 comprising SEQ ID NO:2, a heavy chain CDR3 comprising SEQ ID NO:3, and a light chain variable region comprising SEQ ID NO:26. In another embodiment, a GCGR-binding protein comprises a heavy chain CDR1 comprising SEQ ID NO:13, a heavy chain CDR2 comprising SEQ ID NO:14, and a light chain variable region comprising SEQ ID NO:26. In some embodiments, a GCGR-binding protein comprises a heavy chain CDR1 comprising SEQ ID NO:18, a heavy chain CDR2 comprising SEQ ID NO:19, a heavy chain CDR3 comprising SEQ ID NO:20, and a light chain variable region comprising SEQ ID NO:26. In another embodiment, a GCGR-binding protein comprises a heavy chain CDR1 comprising SEQ ID NO:1, a heavy chain CDR2 comprising SEQ ID NO:24, a heavy chain CDR3 comprising SEQ ID NO:3, and a light chain variable region comprising SEQ ID NO:26. In another embodiment, a GCGR-binding protein comprises a heavy chain CDR1 comprising SEQ ID NO:1, a heavy chain CDR2 comprising SEQ ID NO:24, a heavy chain CDR3 comprising SEQ ID NO:3, and a light chain variable region comprising SEQ ID NO:26. In another embodiment, a GCGR-binding protein comprises a heavy chain CDR1 comprising SEQ ID NO:1, a heavy chain CDR2 comprising SEQ ID NO:2, a heavy chain CDR3 comprising SEQ ID NO:3, and a light chain variable region comprising SEQ ID NO:221. In another embodiment, a GCGR-binding protein comprises a heavy chain CDR1 comprising SEQ ID NO:7, a heavy chain CDR2 comprising SEQ ID NO:8, a heavy chain CDR3 comprising SEQ ID NO:9, and a light chain variable region comprising SEQ ID NO:221. In some embodiments, a GCGR-binding protein comprises a heavy chain CDR1 comprising SEQ ID NO:12, a heavy chain CDR2 comprising SEQ ID NO:2, a heavy chain CDR3 comprising SEQ ID NO:3, and a light chain variable region comprising SEQ ID NO:221. In another embodiment, a GCGR-binding protein comprises a heavy chain CDR1 comprising SEQ ID NO:13, a heavy chain CDR2 comprising SEQ ID NO:14, a heavy chain CDR3 comprising SEQ ID NO:15, and a light chain variable region comprising SEQ ID NO:221. In some embodiments, a GCGR-binding protein comprises a heavy chain CDR1 comprising SEQ ID NO:18, a heavy chain CDR2 comprising SEQ ID NO:19, a heavy chain CDR3 comprising SEQ ID NO:20, and a light chain variable region comprising SEQ ID NO:221. In another embodiment, a GCGR-binding protein comprises a heavy chain CDR1 comprising SEQ ID NO:1, a heavy chain CDR2 comprising SEQ ID NO:24, a heavy chain CDR3 comprising SEQ ID NO:3, and a light chain variable region comprising SEQ ID NO:221. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a heavy chain variable region comprising SEQ ID NO:25, a light chain CDR1 comprising SEQ ID NO:4, a light chain CDR2 comprising SEQ ID NO:5, and a light chain CDR3 comprising SEQ ID NO:6. In another embodiment, a GCGR-binding protein comprises a heavy chain variable region comprising SEQ ID NO:25, a light chain CDR1 comprising SEQ ID NO:10, a light chain CDR2 comprising SEQ ID NO:11, and a light chain CDR3 comprising SEQ ID NO:6. In another embodiment, a GCGR-binding protein comprises a heavy chain variable region comprising SEQ ID NO:25, a light chain CDR1 comprising SEQ ID NO:16, a light chain CDR2 comprising SEQ ID NO:11, and a light chain CDR3 comprising SEQ ID NO:17. In some embodiments, a GCGR-binding protein comprises a heavy chain variable region comprising SEQ ID NO:25, a light chain CDR1 comprising SEQ ID NO:21, a light chain CDR2 comprising SEQ ID NO:22, and a light chain CDR3 comprising SEQ ID NO:23. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a heavy chain variable region comprising SEQ ID NO:220, a light chain CDR1 comprising SEQ ID NO:4, a light chain CDR2 comprising SEQ ID NO:5, and a light chain CDR3 comprising SEQ ID NO:6. In another embodiment, a GCGR-binding protein comprises a heavy chain variable region comprising SEQ ID NO:220, a light chain CDR1 comprising SEQ ID NO:10, a light chain CDR2 comprising SEQ ID NO:11, and a light chain CDR3 comprising SEQ ID NO:6. In another embodiment, a GCGR-binding protein comprises a heavy chain variable region comprising SEQ ID NO:220, a light chain CDR1 comprising SEQ ID NO:16, a light chain CDR2 comprising SEQ ID NO:11, and a light chain CDR3 comprising SEQ ID NO:17. In some embodiments, a GCGR-binding protein comprises a heavy chain variable region comprising SEQ ID NO:220, a light chain CDR1 comprising SEQ ID NO:21, a light chain CDR2 comprising SEQ ID NO:22, and a light chain CDR3 comprising SEQ ID NO:23. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a heavy chain CDR1 comprising SEQ ID NO:1, a heavy chain CDR2 comprising $DIX_1PGGX_2YX_3NYNX_4KHKX_5$ (SEQ ID NO:237), and a heavy chain CDR3 comprising SEQ ID NO:3. In another embodiment, a GCGR-binding protein comprises a heavy chain CDR1 comprising SEQ ID NO:7, a heavy chain CDR2 comprising $DIX_1PGGX_2YX_3NYNX_4KHKX_5$ (SEQ ID NO:237), and a heavy chain CDR3 comprising SEQ ID NO:9. In some embodiments, a GCGR-binding protein comprises a heavy chain CDR1 comprising SEQ ID NO:12, a heavy chain CDR2 comprising $DIX_1PGGX_2YX_3NYNX_4KHKX_5$ (SEQ ID NO:237), and a heavy chain CDR3 comprising SEQ ID NO:3. In another embodiment, a GCGR-binding protein comprises a heavy chain CDR1 comprising SEQ ID NO:13, a heavy chain CDR2 comprising $DIX_1GGX_2YX_3NYNX_4KHKX_5$ (SEQ ID NO:237), and a heavy chain CDR3 comprising SEQ ID NO:15. In some embodiments, a GCGR-binding protein comprises a heavy chain CDR1 comprising SEQ ID NO:18, a heavy chain CDR2 comprising $DIX_1PGGX_2YX_3NYNX_4KHKX_5$ (SEQ ID NO:237), and a heavy chain CDR3 comprising SEQ ID NO:20. In another embodiment, a GCGR-binding protein comprises a heavy chain CDR1 comprising SEQ ID NO:11, a heavy chain CDR2 comprising $DIX_1PGGX_2YX_3NYNX_4KHKX_5$ (SEQ ID NO:237), and a heavy chain CDR3 comprising SEQ ID NO:3. In some embodiments, $X_1$ is Y, H, F, or S. In some embodiments, $X_1$ is Y. In another embodiment, $X_1$ is H. In some embodiments, $X_1$ is F. In other embodiments, $X_1$ is S. In some embodiments, $X_2$ is Y, G, F, or D. In some embodiments, $X_2$ is Y. In another embodiment, $X_2$ is G. In some embodiments, $X_2$ is F. In other embodiments, $X_2$ is D. In some embodiments, $X_3$ is I, T, D, N, or S. In some embodiments, $X_3$ is I. In another embodiment, $X_3$ is T. In some embodiments, $X_3$ is D. In other embodiments, $X_3$ is N. In some embodiments, $X_3$ is S. In some embodiments, $X_4$ is E, K, D, G, or A. In some embodiments, $X_4$ is E. In another embodiment, $X_4$ is K. In some embodiments, $X_4$ is D. In other embodiments, $X_4$ is G. In some embodiments, $X_4$ is A. In some embodiments, $X_5$ is G, S, or D. In some embodiments, $X_5$ is G. In another embodiment, $X_5$ is S. In some embodiments, $X_5$ is D. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a heavy chain CDR1 comprising SEQ ID NO:1, a heavy chain CDR2 comprising $DIX_1PGGX_2YX_3NYNX_4KHKX_5$ (SEQ ID NO:237), a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In another embodiment, a GCGR-binding protein comprises a heavy chain CDR1 comprising SEQ ID NO:7, a heavy chain CDR2 comprising $DIX_1PGGX_2YX_3NYNX_4KHKX_5$ (SEQ ID NO:237), a heavy chain CDR3 comprising SEQ ID NO:9, a light chain CDR1 comprising SEQ ID NO:10, a light chain CDR2 comprising SEQ ID NO:11, and a light chain CDR3 comprising SEQ ID NO:6. In some embodiments, a GCGR-binding protein comprises a heavy chain CDR1 comprising SEQ ID NO:12, a heavy chain CDR2 comprising $DIX_1PGGX_2YX_3NYNX_4KHKX_5$ (SEQ ID NO:237), a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In another embodiment, a GCGR-binding protein comprises a heavy chain CDR1 comprising SEQ ID NO:13, a heavy chain CDR2 comprising $DIX_1PGGX_2YX_3NYNX_4KHKX_5$ (SEQ ID NO:237), a heavy chain CDR3 comprising SEQ ID NO:15, a light chain CDR1 comprising SEQ ID NO:16, a light chain CDR2 comprising SEQ ID NO:11, and a light chain CDR3 comprising SEQ ID NO:17. In some embodiments, a GCGR-binding protein comprises a heavy chain CDR1 comprising SEQ ID NO:18, a heavy chain CDR2 comprising $DIX_1PGGX_2YX_3NYNX_4KHKX_5$ (SEQ ID NO:237), a heavy chain CDR3 comprising SEQ ID NO:20, a light chain CDR1 comprising SEQ ID NO:21, a light chain CDR2 comprising SEQ ID NO:22, and a light chain CDR3 comprising SEQ ID NO:23. In some embodiments, $X_1$ is Y, H, F, or S. In some embodiments, $X_1$ is Y. In another embodiment, $X_1$ is H. In some embodiments, $X_1$ is F. In other embodiments, $X_1$ is S. In some embodiments, $X_2$ is Y, G, F, or D. In some embodiments, $X_2$ is Y. In another embodiment, $X_2$ is G. In some embodiments, $X_2$ is F. In other embodiments, $X_2$ is D. In some embodiments, $X_3$ is I, T, D, N, or S. In some embodiments, $X_3$ is I. In another embodiment, $X_3$ is T. In some embodiments, $X_3$ is D. In other embodiments, $X_3$ is N. In some embodiments, $X_3$ is S. In some embodiments, $X_4$ is E, K, D, G, or A. In some embodiments, $X_4$ is E. In another embodiment, $X_4$ is K. In some embodiments, $X_4$ is D. In other embodiments, $X_4$ is G. In some embodiments, $X_4$ is A. In some embodiments, $X_5$ is G, S, or D. In some embodiments, $X_5$ is G. In another embodiment, $X_5$ is S. In some embodiments, $X_5$ is D. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a heavy chain CDR1 comprising SEQ ID NO:1, a heavy chain CDR2 comprising $DIX_1PGGX_2YX_3NYNX_4KHKX_5$ (SEQ ID NO:237), a heavy chain CDR3 comprising SEQ ID NO:3, and a light chain variable region comprising SEQ ID NO:26. In another embodiment, a GCGR-binding protein comprises a heavy chain CDR1 comprising SEQ ID NO:7, a heavy chain CDR2 comprising $DIX_1PGGX_2YX_3NYNX_4KHKX_5$ (SEQ ID NO:237), a heavy chain CDR3 comprising SEQ ID NO:9, and a light chain variable region comprising SEQ ID NO:26. In some embodiments, a GCGR-binding protein comprises a heavy chain CDR1 comprising SEQ ID NO:12, a heavy chain CDR2 comprising DIX$_1$PGGX$_2$YX$_3$NYNX$_4$KHKX$_5$ (SEQ ID NO:237), a heavy chain CDR3 comprising SEQ ID NO:3, and a light chain variable region comprising SEQ ID NO:26. In another embodiment, a GCGR-binding protein comprises a heavy chain CDR1 comprising SEQ ID NO:13, a heavy chain CDR2 comprising DIX$_1$PGGX$_2$YX$_3$NYNX$_4$KHKX$_5$ (SEQ ID NO:237), a heavy chain CDR3 comprising SEQ ID NO:15, and a light chain variable region comprising SEQ ID NO:26. In some embodiments, a GCGR-binding protein comprises a heavy chain CDR1 comprising SEQ ID NO:18, a heavy chain CDR2 comprising DIX$_1$PGGX$_2$YX$_3$NYNX$_4$KHKX$_5$ (SEQ ID NO:237), a heavy chain CDR3 comprising SEQ ID NO:20, and a light chain variable region comprising SEQ ID NO:26. In some embodiments, a GCGR-binding protein comprises a heavy chain CDR1 comprising SEQ ID NO:1, a heavy chain CDR2 comprising DIX$_1$PGGX$_2$YX$_3$NYNX$_4$KHKX$_5$ (SEQ ID NO:237), a heavy chain CDR3 comprising SEQ ID NO:3, and a light chain variable region comprising SEQ ID NO:221. In another embodiment, a GCGR-binding protein comprises a heavy chain CDR1 comprising SEQ ID NO:7, a heavy chain CDR2 comprising DIX$_1$PGGX$_2$YX$_3$NYNX$_4$KHKX$_5$ (SEQ ID NO:237), a heavy chain CDR3 comprising SEQ ID NO:9, and a light chain variable region comprising SEQ ID NO:221. In some embodiments, a GCGR-binding protein comprises a heavy chain CDR1 comprising SEQ ID NO:12, a heavy chain CDR2 comprising DIX$_1$PGGX$_2$YX$_3$NYNX$_4$KHKX$_5$ (SEQ ID NO:237), a heavy chain CDR3 comprising SEQ ID NO:3, and a light chain variable region comprising SEQ ID NO:221. In another embodiment, a GCGR-binding protein comprises a heavy chain CDR1 comprising SEQ ID NO:13, a heavy chain CDR2 comprising DIX$_1$PGGX$_2$YX$_3$NYNX$_4$KHKX$_5$ (SEQ ID NO:237), a heavy chain CDR3 comprising SEQ ID NO:15, and a light chain variable region comprising SEQ ID NO:221. In some embodiments, a GCGR-binding protein comprises a heavy chain CDR1 comprising SEQ ID NO:18, a heavy chain CDR2 comprising DIX$_1$PGGX$_2$YX$_3$NYNX$_4$KHKX$_5$ (SEQ ID NO:237), a heavy chain CDR3 comprising SEQ ID NO:20, and a light chain variable region comprising SEQ ID NO:221. In some embodiments, $X_1$ is Y, H, F, or S. In some embodiments, $X_1$ is Y. In another embodiment, $X_1$ is H. In some embodiments, $X_1$ is F. In other embodiments, $X_1$ is S. In some embodiments, $X_2$ is Y, G, F, or D. In some embodiments, $X_2$ is Y. In another embodiment, $X_2$ is G. In some embodiments, $X_2$ is F. In other embodiments, $X_2$ is D. In some embodiments, $X_3$ is I, T, D, N, or S. In some embodiments, $X_3$ is I. In another embodiment, $X_3$ is T. In some embodiments, $X_3$ is D. In other embodiments, $X_3$ is N. In some embodiments, $X_3$ is S. In some embodiments, $X_4$ is E, K, D, G, or A. In some embodiments, $X_4$ is E. In another embodiment, $X_4$ is K. In some embodiments, $X_4$ is D. In other embodiments, $X_4$ is G. In some embodiments, $X_4$ is A. In some embodiments, $X_5$ is G, S, or D. In some embodiments, $X_5$ is G. In another embodiment, $X_5$ is S. In some embodiments, $X_5$ is D. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a light chain CDR1 comprising RSSQX$_6$IVX$_7$SX$_8$GNTYLE (SEQ ID NO:238), a light chain CDR2 comprising SEQ ID NO:5, and a light chain CDR3 comprising SEQ ID NO:6. In another embodiment, a GCGR-binding protein comprises a light chain CDR1 comprising RSSQX$_6$IVX$_7$SX$_8$GNTYLE (SEQ ID NO:238), a light chain CDR2 comprising SEQ ID NO:11, and a light chain CDR3 comprising SEQ ID NO:6. In some embodiments, a GCGR-binding protein comprises a light chain CDR1 comprising RSSQX$_6$IVX$_7$SX$_8$GNTYLE (SEQ ID NO:238), a light chain CDR2 comprising SEQ ID NO:5, and a light chain CDR3 comprising SEQ ID NO:6. In another embodiment, a GCGR-binding protein comprises a light chain CDR1 comprising RSSQX$_6$IVX$_7$SX$_8$GNTYLE (SEQ ID NO:238), a light chain CDR2 comprising SEQ ID NO:11, and a light chain CDR3 comprising SEQ ID NO:17. In some embodiments, a GCGR-binding protein comprises a light chain CDR1 comprising RSSQX$_6$IVX$_7$SX$_8$GNTYLE (SEQ ID NO:238), a light chain CDR2 comprising SEQ ID NO:22, and a light chain CDR3 comprising SEQ ID NO:23. In some embodiments, $X_6$ is S, T, or H. In some embodiments, $X_6$ is S. In another embodiment, $X_6$ is T. In some embodiments, $X_6$ is H. In some embodiments, $X_7$ is D, H, or Y. In some embodiments, $X_7$ is D. In another embodiment, $X_7$ is H. In some embodiments, $X_7$ is Y. In some embodiments, $X_8$ is Y or D. In some embodiments, $X_8$ is Y. In another embodiment, $X_8$ is D. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a heavy chain CDR1 comprising SEQ ID NO:1, a heavy chain CDR2 comprising SEQ ID NO:2, a heavy chain CDR3 comprising SEQ ID NO:3, a light chain CDR1 comprising RSSQX$_6$IVX$_7$SX$_8$GNTYLE (SEQ ID NO:238), a light chain CDR2 comprising SEQ ID NO:5, and a light chain CDR3 comprising SEQ ID NO:6. In another embodiment, a GCGR-binding protein comprises a heavy chain CDR1 comprising SEQ ID NO:7, a heavy chain CDR2 comprising SEQ ID NO:8, a heavy chain CDR3 comprising SEQ ID NO:9, a light chain CDR1 comprising RSSQX$_6$IVX$_7$SX$_8$GNTYLE (SEQ ID NO:238), a light chain CDR2 comprising SEQ ID NO:11, and a light chain CDR3 comprising SEQ ID NO:6. In some embodiments, a GCGR-binding protein comprises a heavy chain CDR1 comprising SEQ ID NO:12, a heavy chain CDR2 comprising SEQ ID NO:2, a heavy chain CDR3 comprising SEQ ID NO:3, a light chain CDR1 comprising RSSQX$_6$IVX$_7$SX$_8$GNTYLE (SEQ ID NO:238), a light chain CDR2 comprising SEQ ID NO:5, and a light chain CDR3 comprising SEQ ID NO:6. In another embodiment, a GCGR-binding protein comprises a heavy chain CDR1 comprising SEQ ID NO:13, a heavy chain CDR2 comprising SEQ ID NO:14, a heavy chain CDR3 comprising SEQ ID NO:15, a light chain CDR1 comprising RSSQX$_6$IVX$_7$SX$_8$GNTYLE (SEQ ID NO:238), a light chain CDR2 comprising SEQ ID NO:11, and a light chain CDR3 comprising SEQ ID NO:17. In some embodiments, a GCGR-binding protein comprises a heavy chain CDR1 comprising SEQ ID NO:18, a heavy chain CDR2 comprising SEQ ID NO:19, a heavy chain CDR3 comprising SEQ ID NO:20, a light chain CDR1 comprising RSSQX$_6$IVX$_7$SX$_8$GNTYLE (SEQ ID NO:238), a light chain CDR2 comprising SEQ ID NO:22, and a light chain CDR3 comprising SEQ ID NO:23. In another embodiment, a GCGR-binding protein comprises a heavy chain CDR1 comprising SEQ ID NO:1, a heavy chain CDR2 comprising SEQ ID NO:24, a heavy chain CDR3 comprising SEQ ID NO:3, a light chain CDR1 comprising RSSQX$_6$IVX$_7$SX$_8$GNTYLE (SEQ ID NO:238), a light chain CDR2 comprising SEQ ID NO:5, and a light chain CDR3 comprising SEQ ID NO:6. In some embodiments, $X_6$ is S, T, or H. In some embodiments, $X_6$ is S. In another embodiment, $X_6$ is T. In some embodiments, $X_6$ is H. In some embodiments, $X_7$ is D, H, or Y. In some embodiments, $X_7$ is D. In another embodiment, $X_7$ is H. In some embodiments, $X_7$ is Y. In some embodiments, $X_8$ is Y or D. In some embodiments, $X_8$ is Y. In another embodiment, $X_8$ is D. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a heavy chain variable region comprising SEQ ID NO:25, a light chain CDR1 comprising $RSSQX_6IVX_7SX_8GNTYLE$ (SEQ ID NO:238), a light chain CDR2 comprising SEQ ID NO:5, and a light chain CDR3 comprising SEQ ID NO:6. In another embodiment, a GCGR-binding protein comprises a heavy chain variable region comprising SEQ ID NO:25, a light chain CDR1 comprising $RSSQX_6IVX_7SX_8GNTYLE$ (SEQ ID NO:238), a light chain CDR2 comprising SEQ ID NO:11, and a light chain CDR3 comprising SEQ ID NO:6. In another embodiment, a GCGR-binding protein comprises a heavy chain variable region comprising SEQ ID NO:25, a light chain CDR1 comprising $RSSQX_6IVX_7SX_8GNTYLE$ (SEQ ID NO:238), a light chain CDR2 comprising SEQ ID NO:11, and a light chain CDR3 comprising SEQ ID NO:17. In some embodiments, a GCGR-binding protein comprises a heavy chain variable region comprising SEQ ID NO:25, a light chain CDR1 comprising $RSSQX_6IVX_7SX_8GNTYLE$ (SEQ ID NO:238), a light chain CDR2 comprising SEQ ID NO:22, and a light chain CDR3 comprising SEQ ID NO:23. In some embodiments, a GCGR-binding protein comprises a heavy chain variable region comprising SEQ ID NO:220, a light chain CDR1 comprising $RSSQX_6IVX_7SX_8GNTYLE$ (SEQ ID NO:238), a light chain CDR2 comprising SEQ ID NO:5, and a light chain CDR3 comprising SEQ ID NO:6. In another embodiment, a GCGR-binding protein comprises a heavy chain variable region comprising SEQ ID NO:220, a light chain CDR1 comprising $RSSQX_6IVX_7SX_8GNTYLE$ (SEQ ID NO:238), a light chain CDR2 comprising SEQ ID NO:11, and a light chain CDR3 comprising SEQ ID NO:6. In another embodiment, a GCGR-binding protein comprises a heavy chain variable region comprising SEQ ID NO:220, a light chain CDR1 comprising $RSSQX_6IVX_7SX_8GNTYLE$ (SEQ ID NO:238), a light chain CDR2 comprising SEQ ID NO:11, and a light chain CDR3 comprising SEQ ID NO:17. In some embodiments, a GCGR-binding protein comprises a heavy chain variable region comprising SEQ ID NO:220, a light chain CDR1 comprising $RSSQX_6IVX_7SX_8GNTYLE$ (SEQ ID NO:238), a light chain CDR2 comprising SEQ ID NO:22, and a light chain CDR3 comprising SEQ ID NO:23. In some embodiments, $X_6$ is S, T, or H. In some embodiments, $X_6$ is S. In another embodiment, $X_6$ is T. In some embodiments, $X_6$ is H. In some embodiments, $X_7$ is D, H, or Y. In some embodiments, $X_7$ is D. In another embodiment, $X_7$ is H. In some embodiments, $X_7$ is Y. In some embodiments, $X_8$ is Y or D. In some embodiments, $X_8$ is Y. In another embodiment, $X_8$ is D. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein comprises a heavy chain CDR1 comprising SEQ ID NO:1, a heavy chain CDR2 comprising $DIX_1PGGX_2YX_3NYNX_4KHKX_5$ (SEQ ID NO:237), a heavy chain CDR3 comprising SEQ ID NO:3, a light chain CDR1 comprising $RSSQX_6IVX_7SX_8GNTYLE$ (SEQ ID NO:238), a light chain CDR2 comprising SEQ ID NO:5, and a light chain CDR3 comprising SEQ ID NO:6. In another embodiment, a GCGR-binding protein comprises a heavy chain CDR1 comprising SEQ ID NO:7, a heavy chain CDR2 comprising $DIX_1PGGX_2YX_3NYNX_4KHKX_5$ (SEQ ID NO:237), a heavy chain CDR3 comprising SEQ ID NO:9, a light chain CDR1 comprising $RSSQX_6IVX_7SX_8GNTYLE$ (SEQ ID NO:238), a light chain CDR2 comprising SEQ ID NO:11, and a light chain CDR3 comprising SEQ ID NO:6. In some embodiments, a GCGR-binding protein comprises a heavy chain CDR1 comprising SEQ ID NO:12, a heavy chain CDR2 comprising $DIX_1PGGX_2YX_3NYNX_4KHKX_5$ (SEQ ID NO:237), a heavy chain CDR3 comprising SEQ ID NO:3, a light chain CDR1 comprising $RSSQX_6IVX_7SX_8GNTYLE$ (SEQ ID NO:238), a light chain CDR2 comprising SEQ ID NO:5, and a light chain CDR3 comprising SEQ ID NO:6. In another embodiment, a GCGR-binding protein comprises a heavy chain CDR1 comprising SEQ ID NO:13, a heavy chain CDR2 comprising $DIX_1PGGX_2YX_3NYNX_4KHKX_5$ (SEQ ID NO:237), a heavy chain CDR3 comprising SEQ ID NO:15, a light chain CDR1 comprising $RSSQX_6IVX_7SX_8GNTYLE$ (SEQ ID NO:238), a light chain CDR2 comprising SEQ ID NO:11, and a light chain CDR3 comprising SEQ ID NO:17. In some embodiments, a GCGR-binding protein comprises a heavy chain CDR1 comprising SEQ ID NO:18, a heavy chain CDR2 comprising $DIX_1PGGX_2YX_3NYNX_4KHKX_5$ (SEQ ID NO:237), a heavy chain CDR3 comprising SEQ ID NO:20, a light chain CDR1 comprising $RSSQX_6IVX_7SX_8GNTYLE$ (SEQ ID NO:238), a light chain CDR2 comprising SEQ ID NO:22, and a light chain CDR3 comprising SEQ ID NO:23. In some embodiments, $X_1$ is Y, H, F, or S. In some embodiments, $X_1$ is Y. In another embodiment, $X_1$ is H. In some embodiments, $X_1$ is F. In other embodiments, $X_1$ is S. In some embodiments, $X_2$ is Y, G, F, or D. In some embodiments, $X_2$ is Y. In another embodiment, $X_2$ is G. In some embodiments, $X_2$ is F. In other embodiments, $X_2$ is D. In some embodiments, $X_3$ is I, T, D, N, or S. In some embodiments, $X_3$ is I. In another embodiment, $X_3$ is T. In some embodiments, $X_3$ is D. In other embodiments, $X_3$ is N. In some embodiments, $X_3$ is S. In some embodiments, $X_4$ is E, K, D, G, or A. In some embodiments, $X_4$ is E. In another embodiment, $X_4$ is K. In some embodiments, $X_4$ is D. In other embodiments, $X_4$ is G. In some embodiments, $X_4$ is A. In some embodiments, $X_5$ is G, S, or D. In some embodiments, $X_5$ is G. In another embodiment, $X_5$ is S. In some embodiments, $X_5$ is D. In some embodiments, $X_6$ is S, T, or H. In some embodiments, $X_6$ is S. In another embodiment, $X_6$ is T. In some embodiments, $X_6$ is H. In some embodiments, $X_7$ is D, H, or Y. In some embodiments, $X_7$ is D. In another embodiment, $X_7$ is H. In some embodiments, $X_7$ is Y. In some embodiments, $X_8$ is Y or D. In some embodiments, $X_8$ is Y. In another embodiment, $X_8$ is D. In some embodiments, the GCGR-binding protein is an antibody. In some embodiments, the antibody is a humanized antibody. In another embodiment, the GCGR-binding protein is an antigen-binding antibody fragment.

In some embodiments, a GCGR-binding protein (e.g., an antibody) comprises (a) a heavy chain CDR1 comprising SEQ ID NOs: 27, 33, 38, 39, or 44; a heavy chain CDR2 comprising SEQ ID NOs: 28, 34, 40, 45, or 50; and a heavy chain CDR3 comprising SEQ ID NOs: 29, 35, 41, or 46; and/or (b) a light chain CDR1 comprising SEQ ID NOs: 30, 36, 42, or 47; a light chain CDR2 comprising SEQ ID NOs: 31, 37, or 48; and a light chain CDR3 comprising SEQ ID NOs: 32, 43, or 49. In some embodiments, a GCGR-binding protein (e.g., an antibody) comprises (a) a heavy chain CDR1 comprising SEQ ID NO:27; a heavy chain CDR2 comprising SEQ ID NO:28; and a heavy chain CDR3 comprising SEQ ID NO:29; and/or (b) a light chain CDR1 comprising SEQ ID NO:30; a light chain CDR2 comprising SEQ ID NO:31; and a light chain CDR3 comprising SEQ ID NO:32.

In some embodiments, a GCGR-binding protein (e.g., an antibody) comprises (a) a heavy chain CDR1 comprising SEQ ID NOs: 53, 57, 61, 62, or 65; a heavy chain CDR2 comprising SEQ ID NOs: 54, 58, 40, 66, or 70; and a heavy chain CDR3 comprising SEQ ID NOs: 55, 59, 63, or 67; and/or (b) a light chain CDR1 comprising SEQ ID NOs: 56, 60, 64, or 68; a light chain CDR2 comprising SEQ ID NOs: 31, 37, or 69; and a light chain CDR3 comprising SEQ ID NOs: 32, 43, or 49. In some embodiments, a GCGR-binding protein (e.g., an antibody) comprises (a) a heavy chain CDR1 comprising SEQ ID NO:53; a heavy chain CDR2 comprising SEQ ID NO:54; and a heavy chain CDR3 comprising SEQ ID NO:55; and/or (b) a light chain CDR1 comprising SEQ ID NO:56; a light chain CDR2 comprising SEQ ID NO:31; and a light chain CDR3 comprising SEQ ID NO:32.

In some embodiments, a GCGR-binding protein (e.g., an antibody) comprises (a) a heavy chain CDR1 comprising SEQ ID NOs: 73, 79, 84, 85, or 90; a heavy chain CDR2 comprising SEQ ID NOs: 74, 80, 86, 91, or 96; and a heavy chain CDR3 comprising SEQ ID NOs: 75, 81, 87, or 92; and/or (b) a light chain CDR1 comprising SEQ ID NOs: 76, 82, 88, or 93; a light chain CDR2 comprising SEQ ID NOs: 77, 83, or 94; and a light chain CDR3 comprising SEQ ID NOs: 78, 89, or 95. In some embodiments, a GCGR-binding protein (e.g., an antibody) comprises (a) a heavy chain CDR1 comprising SEQ ID NO:73; a heavy chain CDR2 comprising SEQ ID NO:74; and a heavy chain CDR3 comprising SEQ ID NO:75; and/or (b) a light chain CDR1 comprising SEQ ID NO:76; a light chain CDR2 comprising SEQ ID NO:77; and a light chain CDR3 comprising SEQ ID NO:78.

In some embodiments, a GCGR-binding protein (e.g., an antibody) comprises (a) a heavy chain CDR1 comprising SEQ ID NOs: 99, 105, 110, 111, or 115; a heavy chain CDR2 comprising SEQ ID NOs: 100, 106, 86, 116, or 121; and a heavy chain CDR3 comprising SEQ ID NOs: 101, 107, 112, or 117; and/or (b) a light chain CDR1 comprising SEQ ID NOs: 102, 108, 113, or 118; a light chain CDR2 comprising SEQ ID NOs: 103, 109, or 119; and a light chain CDR3 comprising SEQ ID NOs: 104, 114, or 120. In some embodiments, a GCGR-binding protein (e.g., an antibody) comprises (a) a heavy chain CDR1 comprising SEQ ID NO:99; a heavy chain CDR2 comprising SEQ ID NO:100; and a heavy chain CDR3 comprising SEQ ID NO:101; and/or (b) a light chain CDR1 comprising SEQ ID NO:102; a light chain CDR2 comprising SEQ ID NO:103; and a light chain CDR3 comprising SEQ ID NO:104.

In some embodiments, a GCGR-binding protein (e.g., an antibody) comprises (a) a heavy chain CDR1 comprising SEQ ID NOs: 124, 129, 133, 134, or 138; a heavy chain CDR2 comprising SEQ ID NOs: 125, 130, 135, 139, 143; and a heavy chain CDR3 comprising SEQ ID NOs: 126, 131, 136, or 140; and/or (b) a light chain CDR1 comprising SEQ ID NOs: 127, 132, 137, or 141; a light chain CDR2 comprising SEQ ID NOs: 128, 11, or 142; and a light chain CDR3 comprising SEQ ID NOs: 6, 17, or 23. In some embodiments, a GCGR-binding protein (e.g., an antibody) comprises (a) a heavy chain CDR1 comprising SEQ ID NO:124; a heavy chain CDR2 comprising SEQ ID NO:125; and a heavy chain CDR3 comprising SEQ ID NO:126; and/or (b) a light chain CDR1 comprising SEQ ID NO:127; a light chain CDR2 comprising SEQ ID NO:128; and a light chain CDR3 comprising SEQ ID NO:6.

In some embodiments, a GCGR-binding protein (e.g., an antibody) comprises (a) a heavy chain CDR1 comprising SEQ ID NOs: 146, 150, 154, 155, or 159; a heavy chain CDR2 comprising SEQ ID NOs: 147, 151, 156, 160, or 163; and a heavy chain CDR3 comprising SEQ ID NOs: 148, 152, 157, or 161; and/or (b) a light chain CDR1 comprising SEQ ID NOs: 149, 153, 158, or 162; a light chain CDR2 comprising SEQ ID NOs: 128, 11, or 142; and a light chain CDR3 comprising SEQ ID NOs: 6, 17, or 23. In some embodiments, a GCGR-binding protein (e.g., an antibody) comprises (a) a heavy chain CDR1 comprising SEQ ID NO:146; a heavy chain CDR2 comprising SEQ ID NO:147; and a heavy chain CDR3 comprising SEQ ID NO:148; and/or (b) a light chain CDR1 comprising SEQ ID NO:149; a light chain CDR2 comprising SEQ ID NO:128; and a light chain CDR3 comprising SEQ ID NO:6.

In some embodiments, a GCGR-binding protein (e.g., an antibody) comprises (a) a heavy chain CDR1 comprising SEQ ID NOs: 166, 172, 176, 177, or 182; a heavy chain CDR2 comprising SEQ ID NOs: 167, 173, 178, 183, or 187; and a heavy chain CDR3 comprising SEQ ID NOs: 168, 174, 179, or 184; and/or (b) a light chain CDR1 comprising SEQ ID NOs: 169, 175, 180, or 185; a light chain CDR2 comprising SEQ ID NOs: 170, 11, or 142; and a light chain CDR3 comprising SEQ ID NOs: 171, 181, or 186. In some embodiments, a GCGR-binding protein (e.g., an antibody) comprises (a) a heavy chain CDR1 comprising SEQ ID NO:166; a heavy chain CDR2 comprising SEQ ID NO:167; and a heavy chain CDR3 comprising SEQ ID NO:168; and/or (b) a light chain CDR1 comprising SEQ ID NO:169; a light chain CDR2 comprising SEQ ID NO:170; and a light chain CDR3 comprising SEQ ID NO:171.

In some embodiments, a GCGR-binding protein (e.g., an antibody) comprises (a) a heavy chain CDR1 comprising SEQ ID NOs: 190, 172, 154, 177, or 198; a heavy chain CDR2 comprising SEQ ID NOs: 191, 194, 156, 199, or 202; and a heavy chain CDR3 comprising SEQ ID NOs: 192, 195, 196, or 200; and/or (b) a light chain CDR1 comprising SEQ ID NOs: 169, 175, 180, or 185; a light chain CDR2 comprising SEQ ID NOs: 128, 11, or 142; and a light chain CDR3 comprising SEQ ID NOs: 193, 197, or 201. In some embodiments, a GCGR-binding protein (e.g., an antibody) comprises (a) a heavy chain CDR1 comprising SEQ ID NO:190; a heavy chain CDR2 comprising SEQ ID NO:191; and a heavy chain CDR3 comprising SEQ ID NO:192; and/or (b) a light chain CDR1 comprising SEQ ID NO:169; a light chain CDR2 comprising SEQ ID NO:128; and a light chain CDR3 comprising SEQ ID NO:193.

In some embodiments, a GCGR-binding protein (e.g., an antibody) comprises (a) a heavy chain CDR1 comprising SEQ ID NOs: 190, 172, 154, 177, or 198; a heavy chain CDR2 comprising SEQ ID NOs: 205, 208, 211, 214, or 217; and a heavy chain CDR3 comprising SEQ ID NOs: 206, 209, 212, or 215; and/or (b) a light chain CDR1 comprising SEQ ID NOs: 207, 210, 213, or 216; a light chain CDR2 comprising SEQ ID NOs: 128, 11, or 142; and a light chain CDR3 comprising SEQ ID NOs: 6, 17, or 23. In some embodiments, a GCGR-binding protein (e.g., an antibody) comprises (a) a heavy chain CDR1 comprising SEQ ID NO:190; a heavy chain CDR2 comprising SEQ ID NO:205;

and a heavy chain CDR3 comprising SEQ ID NO:206; and/or (b) a light chain CDR1 comprising SEQ ID NO:207; a light chain CDR2 comprising SEQ ID NO:128; and a light chain CDR3 comprising SEQ ID NO:6.

In some embodiments, a GCGR-binding protein (e.g., an antibody) comprises a heavy chain variable region having at least about 80% sequence identity to SEQ ID NO:25 and/or a light chain variable region having at least 80% sequence identity to SEQ ID NO:26. In some embodiments, a GCGR-binding protein comprises a heavy chain variable region having at least about 85%, at least about 90%, at least about 95%, at least about 97%, or at least about 99% sequence identity to SEQ ID NO:25. In some embodiments, a GCGR-binding protein comprises a light chain variable region having at least about 85%, at least about 90%, at least about 95%, at least about 97%, or at least about 99% sequence identity to SEQ ID NO:26. In some embodiments, a GCGR-binding protein comprises a heavy chain variable region having at least about 95% sequence identity to SEQ ID NO:25 and/or a light chain variable region having at least about 95% sequence identity to SEQ ID NO:26. In some embodiments, a GCGR-binding protein comprises a heavy chain variable region comprising SEQ ID NO:25 and/or a light chain variable region comprising SEQ ID NO:26. In some embodiments, a GCGR-binding protein comprises a heavy chain variable region comprising SEQ ID NO:25 and a light chain variable region comprising SEQ ID NO:26. In some embodiments, a GCGR-binding protein comprises a heavy chain variable region consisting essentially of SEQ ID NO:25 and a light chain variable region consisting essentially of SEQ ID NO:26. In some embodiments, a GCGR-binding protein comprises a heavy chain variable region consisting of SEQ ID NO:25 and a light chain variable region consisting of SEQ ID NO:26. In some embodiments, the GCGR-binding protein is an antibody. In some embodiments, the antibody is a humanized antibody. In some embodiments, the GCGR-binding protein is an antigen-binding antibody fragment.

In some embodiments, a GCGR-binding protein (e.g., an antibody) comprises a heavy chain variable region having at least about 80% sequence identity to SEQ ID NO:51 and/or a light chain variable region having at least 80% sequence identity to SEQ ID NO:52. In some embodiments, a GCGR-binding protein comprises a heavy chain variable region having at least about 85%, at least about 90%, at least about 95%, at least about 97%, or at least about 99% sequence identity to SEQ ID NO:51. In some embodiments, a GCGR-binding protein comprises a light chain variable region having at least about 85%, at least about 90%, at least about 95%, at least about 97%, or at least about 99% sequence identity to SEQ ID NO:52. In some embodiments, a GCGR-binding protein comprises a heavy chain variable region having at least about 95% sequence identity to SEQ ID NO:51 and/or a light chain variable region having at least about 95% sequence identity to SEQ ID NO:52. In some embodiments, a GCGR-binding protein comprises a heavy chain variable region comprising SEQ ID NO:51 and/or a light chain variable region comprising SEQ ID NO:52. In some embodiments, a GCGR-binding protein comprises a heavy chain variable region comprising SEQ ID NO:51 and a light chain variable region comprising SEQ ID NO:52. In some embodiments, a GCGR-binding protein comprises a heavy chain variable region consisting essentially of SEQ ID NO:51 and a light chain variable region consisting essentially of SEQ ID NO:52. In some embodiments, a GCGR-binding protein comprises a heavy chain variable region consisting of SEQ ID NO:51 and a light chain variable region consisting of SEQ ID NO:52.

In some embodiments, a GCGR-binding protein (e.g., an antibody) comprises a heavy chain variable region having at least about 80% sequence identity to SEQ ID NO:71 and/or a light chain variable region having at least 80% sequence identity to SEQ ID NO:72. In some embodiments, a GCGR-binding protein comprises a heavy chain variable region having at least about 85%, at least about 90%, at least about 95%, at least about 97%, or at least about 99% sequence identity to SEQ ID NO:71. In some embodiments, a GCGR-binding protein comprises a light chain variable region having at least about 85%, at least about 90%, at least about 95%, at least about 97%, or at least about 99% sequence identity to SEQ ID NO:72. In some embodiments, a GCGR-binding protein comprises a heavy chain variable region having at least about 95% sequence identity to SEQ ID NO:71 and/or a light chain variable region having at least about 95% sequence identity to SEQ ID NO:72. In some embodiments, a GCGR-binding protein comprises a heavy chain variable region comprising SEQ ID NO:71 and/or a light chain variable region comprising SEQ ID NO:72. In some embodiments, a GCGR-binding protein comprises a heavy chain variable region comprising SEQ ID NO:71 and a light chain variable region comprising SEQ ID NO:72. In some embodiments, a GCGR-binding protein comprises a heavy chain variable region consisting essentially of SEQ ID NO:71 and a light chain variable region consisting essentially of SEQ ID NO:72. In some embodiments, a GCGR-binding protein comprises a heavy chain variable region consisting of SEQ ID NO:71 and a light chain variable region consisting of SEQ ID NO:72.

In some embodiments, a GCGR-binding protein (e.g., an antibody) comprises a heavy chain variable region having at least about 80% sequence identity to SEQ ID NO:97 and/or a light chain variable region having at least 80% sequence identity to SEQ ID NO:98. In some embodiments, a GCGR-binding protein comprises a heavy chain variable region having at least about 85%, at least about 90%, at least about 95%, at least about 97%, or at least about 99% sequence identity to SEQ ID NO:97. In some embodiments, a GCGR-binding protein comprises a light chain variable region having at least about 85%, at least about 90%, at least about 95%, at least about 97%, or at least about 99% sequence identity to SEQ ID NO:98. In some embodiments, a GCGR-binding protein comprises a heavy chain variable region having at least about 95% sequence identity to SEQ ID NO:97 and/or a light chain variable region having at least about 95% sequence identity to SEQ ID NO:98. In some embodiments, a GCGR-binding protein comprises a heavy chain variable region comprising SEQ ID NO:97 and/or a light chain variable region comprising SEQ ID NO:98. In some embodiments, a GCGR-binding protein comprises a heavy chain variable region comprising SEQ ID NO:97 and a light chain variable region comprising SEQ ID NO:98. In some embodiments, a GCGR-binding protein comprises a heavy chain variable region consisting essentially of SEQ ID NO:97 and a light chain variable region consisting essentially of SEQ ID NO:98. In some embodiments, a GCGR-binding protein comprises a heavy chain variable region consisting of SEQ ID NO:97 and a light chain variable region consisting of SEQ ID NO:98.

In some embodiments, a GCGR-binding protein (e.g., an antibody) comprises a heavy chain variable region having at least about 80% sequence identity to SEQ ID NO:122 and/or a light chain variable region having at least 80% sequence identity to SEQ ID NO:123. In some embodiments, a GCGR-binding protein comprises a heavy chain variable region having at least about 85%, at least about 90%, at least about 95%, at least about 97%, or at least about 99% sequence identity to SEQ ID NO:122. In some embodiments, a GCGR-binding protein comprises a light chain variable region having at least about 85%, at least about 90%, at least about 95%, at least about 97%, or at least about 99% sequence identity to SEQ ID NO:123. In some embodiments, a GCGR-binding protein comprises a heavy chain variable region having at least about 95% sequence identity to SEQ ID NO:122 and/or a light chain variable region having at least about 95% sequence identity to SEQ ID NO:123. In some embodiments, a GCGR-binding protein comprises a heavy chain variable region comprising SEQ ID NO:122 and/or a light chain variable region comprising SEQ ID NO:123. In some embodiments, a GCGR-binding protein comprises a heavy chain variable region comprising SEQ ID NO:122 and a light chain variable region comprising SEQ ID NO:123. In some embodiments, a GCGR-binding protein comprises a heavy chain variable region consisting essentially of SEQ ID NO:122 and a light chain variable region consisting essentially of SEQ ID NO:123. In some embodiments, a GCGR-binding protein comprises a heavy chain variable region consisting of SEQ ID NO:122 and a light chain variable region consisting of SEQ ID NO:123.

In some embodiments, a GCGR-binding protein (e.g., an antibody) comprises a heavy chain variable region having at least about 80% sequence identity to SEQ ID NO:144 and/or a light chain variable region having at least 80% sequence identity to SEQ ID NO:145. In some embodiments, a GCGR-binding protein comprises a heavy chain variable region having at least about 85%, at least about 90%, at least about 95%, at least about 97%, or at least about 99% sequence identity to SEQ ID NO:144. In some embodiments, a GCGR-binding protein comprises a light chain variable region having at least about 85%, at least about 90%, at least about 95%, at least about 97%, or at least about 99% sequence identity to SEQ ID NO:145. In some embodiments, a GCGR-binding protein comprises a heavy chain variable region having at least about 95% sequence identity to SEQ ID NO:144 and/or a light chain variable region having at least about 95% sequence identity to SEQ ID NO:145. In some embodiments, a GCGR-binding protein comprises a heavy chain variable region comprising SEQ ID NO:144 and/or a light chain variable region comprising SEQ ID NO:145. In some embodiments, a GCGR-binding protein comprises a heavy chain variable region comprising SEQ ID NO:144 and a light chain variable region comprising SEQ ID NO:145. In some embodiments, a GCGR-binding protein comprises a heavy chain variable region consisting essentially of SEQ ID NO:144 and a light chain variable region consisting essentially of SEQ ID NO:145. In some embodiments, a GCGR-binding protein comprises a heavy chain variable region consisting of SEQ ID NO:144 and a light chain variable region consisting of SEQ ID NO:145.

In some embodiments, a GCGR-binding protein (e.g., an antibody) comprises a heavy chain variable region having at least about 80% sequence identity to SEQ ID NO:164 and/or a light chain variable region having at least 80% sequence identity to SEQ ID NO:165. In some embodiments, a GCGR-binding protein comprises a heavy chain variable region having at least about 85%, at least about 90%, at least about 95%, at least about 97%, or at least about 99% sequence identity to SEQ ID NO:164. In some embodiments, a GCGR-binding protein comprises a light chain variable region having at least about 85%, at least about 90%, at least about 95%, at least about 97%, or at least about 99% sequence identity to SEQ ID NO:165. In some embodiments, a GCGR-binding protein comprises a heavy chain variable region having at least about 95% sequence identity to SEQ ID NO:164 and/or a light chain variable region having at least about 95% sequence identity to SEQ ID NO:165. In some embodiments, a GCGR-binding protein comprises a heavy chain variable region comprising SEQ ID NO:164 and/or a light chain variable region comprising SEQ ID NO:165. In some embodiments, a GCGR-binding protein comprises a heavy chain variable region comprising SEQ ID NO:164 and a light chain variable region comprising SEQ ID NO:165. In some embodiments, a GCGR-binding protein comprises a heavy chain variable region consisting essentially of SEQ ID NO:164 and a light chain variable region consisting essentially of SEQ ID NO:165. In some embodiments, a GCGR-binding protein comprises a heavy chain variable region consisting of SEQ ID NO:164 and a light chain variable region consisting of SEQ ID NO:165.

In some embodiments, a GCGR-binding protein (e.g., an antibody) comprises a heavy chain variable region having at least about 80% sequence identity to SEQ ID NO:188 and/or a light chain variable region having at least 80% sequence identity to SEQ ID NO:189. In some embodiments, a GCGR-binding protein comprises a heavy chain variable region having at least about 85%, at least about 90%, at least about 95%, at least about 97%, or at least about 99% sequence identity to SEQ ID NO:188. In some embodiments, a GCGR-binding protein comprises a light chain variable region having at least about 85%, at least about 90%, at least about 95%, at least about 97%, or at least about 99% sequence identity to SEQ ID NO:189. In some embodiments, a GCGR-binding protein comprises a heavy chain variable region having at least about 95% sequence identity to SEQ ID NO:188 and/or a light chain variable region having at least about 95% sequence identity to SEQ ID NO:189. In some embodiments, a GCGR-binding protein comprises a heavy chain variable region comprising SEQ ID NO:188 and/or a light chain variable region comprising SEQ ID NO:189. In some embodiments, a GCGR-binding protein comprises a heavy chain variable region comprising SEQ ID NO:188 and a light chain variable region comprising SEQ ID NO:189. In some embodiments, a GCGR-binding protein comprises a heavy chain variable region consisting essentially of SEQ ID NO:188 and a light chain variable region consisting essentially of SEQ ID NO:189. In some embodiments, a GCGR-binding protein comprises a heavy chain variable region consisting of SEQ ID NO:188 and a light chain variable region consisting of SEQ ID NO:189.

In some embodiments, a GCGR-binding protein (e.g., an antibody) comprises a heavy chain variable region having at least about 80% sequence identity to SEQ ID NO:203 and/or a light chain variable region having at least 80% sequence identity to SEQ ID NO:204. In some embodiments, a GCGR-binding protein comprises a heavy chain variable region having at least about 85%, at least about 90%, at least about 95%, at least about 97%, or at least about 99% sequence identity to SEQ ID NO:203. In some embodiments, a GCGR-binding protein comprises a light chain variable region having at least about 85%, at least about 90%, at least about 95%, at least about 97%, or at least about 99% sequence identity to SEQ ID NO:204. In some embodiments, a GCGR-binding protein comprises a heavy chain variable region having at least about 95% sequence identity to SEQ ID NO:203 and/or a light chain variable region having at least about 95% sequence identity to SEQ ID NO:204. In some embodiments, a GCGR-binding protein comprises a heavy chain variable region comprising SEQ ID NO:203 and/or a light chain variable region comprising SEQ ID NO:204. In some embodiments, a GCGR-binding protein comprises a heavy chain variable region comprising SEQ ID NO:203 and a light chain variable region comprising SEQ ID NO:204. In some embodiments, a GCGR-binding protein comprises a heavy chain variable region consisting essentially of SEQ ID NO:203 and a light chain variable region consisting essentially of SEQ ID NO:204. In some embodiments, a GCGR-binding protein comprises a heavy chain variable region consisting of SEQ ID NO:203 and a light chain variable region consisting of SEQ ID NO:204.

In some embodiments, a GCGR-binding protein (e.g., an antibody) comprises a heavy chain variable region having at least about 80% sequence identity to SEQ ID NO:218 and/or a light chain variable region having at least 80% sequence identity to SEQ ID NO:219. In some embodiments, a GCGR-binding protein comprises a heavy chain variable region having at least about 85%, at least about 90%, at least about 95%, at least about 97%, or at least about 99% sequence identity to SEQ ID NO:218. In some embodiments, a GCGR-binding protein comprises a light chain variable region having at least about 85%, at least about 90%, at least about 95%, at least about 97%, or at least about 99% sequence identity to SEQ ID NO:219. In some embodiments, a GCGR-binding protein comprises a heavy chain variable region having at least about 95% sequence identity to SEQ ID NO:218 and/or a light chain variable region having at least about 95% sequence identity to SEQ ID NO:219. In some embodiments, a GCGR-binding protein comprises a heavy chain variable region comprising SEQ ID NO:218 and/or a light chain variable region comprising SEQ ID NO:219. In some embodiments, a GCGR-binding protein comprises a heavy chain variable region comprising SEQ ID NO:218 and a light chain variable region comprising SEQ ID NO:219. In some embodiments, a GCGR-binding protein comprises a heavy chain variable region consisting essentially of SEQ ID NO:218 and a light chain variable region consisting essentially of SEQ ID NO:219. In some embodiments, a GCGR-binding protein comprises a heavy chain variable region consisting of SEQ ID NO:218 and a light chain variable region consisting of SEQ ID NO:219.

In some embodiments, a GCGR-binding protein is a humanized version of any one of the antibodies disclosed herein. In some embodiments, a GCGR-binding protein is a humanized version of the antibody 6B5, 3H5, 5B11, 1C1, 1C3, 1H2, 4F8, 13G9, 14F4, or 14E9. In some embodiments, a GCGR-binding protein is a humanized version of the antibody 6B5, for example, Hz6B5. In some embodiments, a GCGR-binding protein (e.g., an antibody) comprises a heavy chain variable region having at least about 80% sequence identity to SEQ ID NO:220 and/or a light chain variable region having at least 80% sequence identity to SEQ ID NO:221. In some embodiments, a GCGR-binding protein comprises a heavy chain variable region having at least about 85%, at least about 90%, at least about 95%, at least about 97%, or at least about 99% sequence identity to SEQ ID NO:220. In some embodiments, a GCGR-binding protein comprises a light chain variable region having at least about 85%, at least about 90%, at least about 95%, at least about 97%, or at least about 99% sequence identity to SEQ ID NO:221. In some embodiments, a GCGR-binding protein comprises a heavy chain variable region having at least about 95% sequence identity to SEQ ID NO:220 and/or a light chain variable region having at least about 95% sequence identity to SEQ ID NO:221. In some embodiments, a GCGR-binding protein comprises a heavy chain variable region comprising SEQ ID NO:220 and/or a light chain variable region comprising SEQ ID NO:221. In some embodiments, a GCGR-binding protein comprises a heavy chain variable region comprising SEQ ID NO:220 and a light chain variable region comprising SEQ ID NO:221. In some embodiments, a GCGR-binding protein comprises a heavy chain variable region consisting essentially of SEQ ID NO:220 and a light chain variable region consisting essentially of SEQ ID NO:221. In some embodiments, a GCGR-binding protein comprises a heavy chain variable region consisting of SEQ ID NO:220 and a light chain variable region consisting of SEQ ID NO:221. In some embodiments, a GCGR-binding protein is a humanized antibody comprising a heavy chain variable region comprising SEQ ID NO:220 and a light chain variable region comprising SEQ ID NO:221.

As known to those of skill in the art, antibodies (and other binding agents) may be characterized by epitope binning assays. Epitope binning is based on competitive immunoassays to characterize a set of antibodies against a target protein. Each antibody is screened against all of the other antibodies in the set for binding to the target in a pairwise fashion to determine if a first antibody blocks a second antibody from binding to the target. After screening, each antibody has a profile created based on the competitive assay results. Antibodies with similar profiles (e.g., they block or do not block similar antibodies) are "binned" together and are considered to bind the same epitope, a closely related epitope, or an overlapping epitope. In some embodiments, antibodies that specifically bind GCGR are sorted into an "epitope bin". In some embodiments, an antibody is sorted into the epitope bin of the antibodies described herein. In some embodiments, an antibody is sorted into an epitope bin comprising at least one antibody from the group consisting of: 6B5, 3H5, 5B11, 1C1, 1C3, 1H2, 4F8, 13G9, 14F4, and 14E9.

In some embodiments, alternative GCGR-binding proteins (e.g., antibodies) compete for binding to GCGR with one or more of the antibodies described herein. In some embodiments, a GCGR-binding protein (e.g., an antibody) binds the same epitope as one of the antibodies described herein. In some embodiments, a GCGR-binding protein (e.g., an antibody) binds an epitope overlapping with an epitope bound by one of the antibodies described herein. Binding proteins (e.g., antibodies) that compete with or bind to the same epitope as a first antibody often demonstrate similar functional properties.

In some embodiments, a GCGR-binding protein (e.g., an antibody) competes with an antibody comprising one, two, three, four, five, or all six CDRs from an antibody defined in Tables 1-10. In some embodiments, a GCGR-binding protein (e.g., an antibody) competes with an antibody comprising a heavy chain variable region and a light chain variable region selected from those provided in Tables 1-10.

In some embodiments, a GCGR-binding protein (e.g., an antibody) competes for binding to GCGR with an anti-GCGR antibody described herein. In some embodiments, a GCGR-binding protein (e.g., an antibody) competes for binding to GCGR with a reference antibody, wherein the reference antibody comprises: (a) a heavy chain CDR1 comprising GFTFTNHWLG (SEQ ID NO:1); a heavy chain CDR2 comprising DIYPGGYYINYNEKFKG (SEQ ID NO:2); and a heavy chain CDR3 comprising HTNYGSDY (SEQ ID NO:3); and (b) a light chain CDR1 comprising RSSQSIVDSYGNTFLE (SEQ ID NO:4); a light chain CDR2 comprising KVSNRLS (SEQ ID NO:5); and a light chain CDR3 comprising FQGSHVPWT (SEQ ID NO:6). In some embodiments, a GCGR-binding protein (e.g., an antibody) competes for binding to GCGR with a reference antibody, wherein the reference antibody comprises a heavy chain CDR1 comprising SEQ ID NO:27; a heavy chain CDR2 comprising SEQ ID NO:28; a heavy chain CDR3 comprising SEQ ID NO:29; a light chain CDR1 comprising SEQ ID NO:30; a light chain CDR2 comprising SEQ ID NO:31; and a light chain CDR3 comprising SEQ ID NO:32. In some embodiments, a GCGR-binding protein (e.g., an antibody) competes for binding to GCGR with a reference antibody, wherein the reference antibody comprises a heavy chain CDR1 comprising SEQ ID NO:53; a heavy chain CDR2 comprising SEQ ID NO:54; a heavy chain CDR3 comprising SEQ ID NO:55; a light chain CDR1 comprising SEQ ID NO:56; a light chain CDR2 comprising SEQ ID NO:31; and a light chain CDR3 comprising SEQ ID NO:32. In some embodiments, a GCGR-binding protein (e.g., an antibody) competes for binding to GCGR with a reference antibody, wherein the reference antibody comprises a heavy chain CDR1 comprising SEQ ID NO:73; a heavy chain CDR2 comprising SEQ ID NO:74; a heavy chain CDR3 comprising SEQ ID NO:75; a light chain CDR1 comprising SEQ ID NO:76; a light chain CDR2 comprising SEQ ID NO:77; and a light chain CDR3 comprising SEQ ID NO:78. In some embodiments, a GCGR-binding protein (e.g., an antibody) competes for binding to GCGR with a reference antibody, wherein the reference antibody comprises a heavy chain CDR1 comprising SEQ ID NO:99; a heavy chain CDR2 comprising SEQ ID NO:100; a heavy chain CDR3 comprising SEQ ID NO:101; a light chain CDR1 comprising SEQ ID NO:102; a light chain CDR2 comprising SEQ ID NO:103; and a light chain CDR3 comprising SEQ ID NO:104. In some embodiments, a GCGR-binding protein (e.g., an antibody) competes for binding to GCGR with a reference antibody, wherein the reference antibody comprises a heavy chain CDR1 comprising SEQ ID NO:124; a heavy chain CDR2 comprising SEQ ID NO:125; a heavy chain CDR3 comprising SEQ ID NO:126; a light chain CDR1 comprising SEQ ID NO:127; a light chain CDR2 comprising SEQ ID NO:128; and a light chain CDR3 comprising SEQ ID NO:6. In some embodiments, a GCGR-binding protein (e.g., an antibody) competes for binding to GCGR with a reference antibody, wherein the reference antibody comprises a heavy chain CDR1 comprising SEQ ID NO:146; a heavy chain CDR2 comprising SEQ ID NO:147; a heavy chain CDR3 comprising SEQ ID NO:148; a light chain CDR1 comprising SEQ ID NO:149; a light chain CDR2 comprising SEQ ID NO:128; and a light chain CDR3 comprising SEQ ID NO:6. In some embodiments, a GCGR-binding protein (e.g., an antibody) competes for binding to GCGR with a reference antibody, wherein the reference antibody comprises a heavy chain CDR1 comprising SEQ ID NO:166; a heavy chain CDR2 comprising SEQ ID NO:167; a heavy chain CDR3 comprising SEQ ID NO:168; a light chain CDR1 comprising SEQ ID NO:169; a light chain CDR2 comprising SEQ ID NO:170; and a light chain CDR3 comprising SEQ ID NO:171. In some embodiments, a GCGR-binding protein (e.g., an antibody) competes for binding to GCGR with a reference antibody, wherein the reference antibody comprises a heavy chain CDR1 comprising SEQ ID NO:190; a heavy chain CDR2 comprising SEQ ID NO:191; a heavy chain CDR3 comprising SEQ ID NO:192; a light chain CDR1 comprising SEQ ID NO:169; a light chain CDR2 comprising SEQ ID NO:128; and a light chain CDR3 comprising SEQ ID NO:193. In some embodiments, a GCGR-binding protein (e.g., an antibody) competes for binding to GCGR with a reference antibody, wherein the reference antibody comprises a heavy chain CDR1 comprising SEQ ID NO:190; a heavy chain CDR2 comprising SEQ ID NO:205; a heavy chain CDR3 comprising SEQ ID NO:206; a light chain CDR1 comprising SEQ ID NO:207; a light chain CDR2 comprising SEQ ID NO:128; and a light chain CDR3 comprising SEQ ID NO:6.

In some embodiments, a GCGR-binding protein (e.g., antibody) competes for binding to GCGR with a reference antibody, wherein the reference antibody comprises (a) a heavy chain variable region comprising SEQ ID NO:25 and a light chain variable region comprising SEQ ID NO:26; (b) a heavy chain variable region comprising SEQ ID NO:220 and a light chain variable region comprising SEQ ID NO:221; (c) a heavy chain variable region comprising SEQ ID NO:51 and a light chain variable region comprising SEQ ID NO:52; (d) a heavy chain variable region comprising SEQ ID NO:71 and a light chain variable region comprising SEQ ID NO:72; (e) a heavy chain variable region comprising SEQ ID NO:97 and a light chain variable region comprising SEQ ID NO:98; (f) a heavy chain variable region comprising SEQ ID NO:122 and a light chain variable region comprising SEQ ID NO:123; (g) a heavy chain variable region comprising SEQ ID NO:144 and a light chain variable region comprising SEQ ID NO:145; (h) a heavy chain variable region comprising SEQ ID NO:164 and a light chain variable region comprising SEQ ID NO:165; (i) a heavy chain variable region comprising SEQ ID NO:188 and a light chain variable region comprising SEQ ID NO:189; (j) a heavy chain variable region comprising SEQ ID NO:203 and a light chain variable region comprising SEQ ID NO:204; and/or (k) a heavy chain variable region comprising SEQ ID NO:218 and a light chain variable region comprising SEQ ID NO:219.

In some embodiments, the GCGR-binding proteins described herein comprise antibodies (e.g., full-length antibodies) in which at least one or more of the constant regions has been modified or deleted. In some embodiments, the antibodies may comprise modifications to one or more of the three heavy chain constant regions (CHL CH2 or CH3) and/or to the light chain constant region (CL). In some embodiments, the heavy chain constant region of the modified antibodies comprises at least one human constant region. In some embodiments, the heavy chain constant region of the modified antibodies comprises more than one human constant region. In some embodiments, modifications to the constant region comprise additions, deletions, or substitutions of one or more amino acids in one or more regions. In some embodiments, one or more regions are partially or entirely deleted from the constant regions of the modified antibodies. In some embodiments, the entire CH2 domain has been removed from an antibody (ΔCH2 constructs). In some embodiments, a deleted constant region is replaced by a short amino acid spacer that provides some of the molecular flexibility typically imparted by the absent constant region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

It is known in the art that the constant region(s) of an antibody mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a cell expressing a Fc receptor (FcR). There are a number of Fc receptors that are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In some embodiments, an antibody comprises a variant Fc region. The amino acid sequences of the Fc region of human IgG1, IgG2, IgG3, and IgG4 are known to those of ordinary skill in the art (e.g., human IgG1—SEQ ID NO:230). Fc regions with amino acid variations have been identified in native antibodies. In some embodiments, a variant Fc region is engineered with substitutions at specific amino acid positions as compared to a native Fc region (e.g., SEQ ID NO:231 and SEQ ID NO:232).

In some embodiments, the modified antibodies provide for altered effector functions that, in turn, affect the biological profile of the administered antibody. For example, in some embodiments, the deletion or inactivation (through point mutations or other means) of a constant region may reduce Fc receptor binding of the circulating modified antibody. In some embodiments, the constant region modifications increase the serum half-life of the antibody. In some embodiments, the constant region modifications reduce the serum half-life of the antibody. In some embodiments, the constant region modifications enhance or increase ADCC and/or complement-dependent cytotoxicity (CDC) of the antibody. In some embodiments, the constant region modifications decrease or remove ADCC and/or CDC of the antibody. For example, specific amino acid substitutions in a human IgG1 Fc region with corresponding IgG2 or IgG4 residues may reduce effector functions (e.g., ADCC and CDC) in the modified antibody. Thus, in some embodiments, an antibody does not have one or more effector functions. In some embodiments, the antibody has no ADCC activity and/or no CDC activity. In some embodiments, the antibody does not bind an Fc receptor and/or complement factors. In some embodiments, the antibody has no effector function(s). In some embodiments, the constant region is modified to eliminate disulfide linkages or oligosaccharide moieties. In some embodiments, the constant region is modified to add/substitute one or more amino acids to provide, for example, one or more cytotoxin or carbohydrate attachment sites. In this respect, it may be possible to disrupt the activity or effector function provided by a specific sequence or region while substantially maintaining the structure, binding activity, and other desired characteristics of the modified antibody.

Modifications to the constant region of antibodies described herein may be made using well known biochemical or molecular engineering techniques. In some embodiments, antibody variants can be prepared by introducing appropriate nucleotide changes into the encoding DNA, and/or by synthesis of the desired antibody or polypeptide.

The present disclosure further embraces additional variants and equivalents that are substantially homologous to the recombinant, monoclonal, chimeric, humanized, and human antibodies, or antibody fragments thereof, described herein. In some embodiments, it may be desirable to improve the binding affinity of the antibody. In some embodiments, it may be desirable to modulate other biological properties of the antibody, including but not limited to, specificity, thermostability, expression level, effector function(s), glycosylation, immunogenicity, and/or solubility. Those skilled in the art will appreciate that some amino acid changes may alter post-translational modifications of an antibody, such as changing the number or position of glycosylation sites or altering membrane anchoring characteristics.

Variations may be a substitution, deletion, or insertion of one or more nucleotides encoding the antibody or polypeptide that results in a change in the amino acid sequence as compared with the native antibody or polypeptide sequence. Amino acid substitutions can be the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In some embodiments, the substitution, deletion, or insertion comprises less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. Variations in the amino acid sequence that are biologically useful and/or relevant may be determined by systematically making insertions, deletions, or substitutions in the sequence and testing the resulting variant proteins for activity as compared to the parental protein.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein, i.e., a fusion protein. In some embodiments, a variant comprises a detectable label and/or protein (e.g., an enzyme).

In some embodiments, a cysteine residue not involved in maintaining the proper conformation of an antibody may be substituted or deleted to modulate the antibody's characteristics, for example, to improve oxidative stability and/or prevent aberrant disulfide crosslinking. Conversely, in some embodiments, one or more cysteine residues may be added to create disulfide bond(s) to improve stability.

In some embodiments, an antibody of the present disclosure is "deimmunized". The deimmunization of antibodies generally consists of introducing specific amino acid mutations (e.g., substitutions, deletions, additions) to remove T-cell epitopes without significantly reducing the binding affinity or other desired activities of the antibody.

The variant antibodies or polypeptides described herein may be generated using methods known in the art, including but not limited to, site-directed mutagenesis, alanine scanning mutagenesis, and PCR mutagenesis.

In some embodiments, a GCGR-binding protein described herein is chemically modified. In some embodiments, a binding protein is an antibody that has been chemically modified by glycosylation, acetylation, pegylation, phosphorylation, amidation, derivatization by known protecting/blocking groups, proteolytic cleavage, and/or linkage to another protein. Any of numerous chemical modifications may be carried out by known techniques.

The present disclosure encompasses binding proteins built upon non-immunoglobulin backbones, wherein the proteins bind to the same epitope or essentially the same epitope as an anti-GCGR antibody disclosed herein. In some embodiments, a non-immunoglobulin-based binding protein is a protein that competes with an anti-GCGR antibody described herein in a competitive binding assay. In some embodiments, an alternative binding protein comprises a scaffold protein. Generally, scaffold proteins can be assigned to one of three groups based on the architecture of their backbone: (1) scaffolds consisting of α-helices; (2) small scaffolds with few secondary structures or an irregular architecture of α-helices and β-sheets; and (3) scaffolds consisting of predominantly β-sheets. Scaffold proteins include, but are not limited to, anticalins, which are based upon the lipocalin scaffold; adnectins, which are based on the $10^{th}$ domain of human fibronectin type 3; affibodies, which are based on the B-domain in the Ig-binding region of Staphylococcus aureus protein A; darpins, which are based on ankyrin repeat domain proteins; fynomers, which are based on the SH3 domain of the human Fyn protein kinase; affitins, which are based on Sac7d from Sulfolobus acidocaldarius; affilins, which are based on human γ-B-crystallin or human ubiquitin; avimers, which are based on the A-domains of membrane receptor proteins; knottins (cysteine knot miniproteins), which are based upon a stable 30-amino acid anti-parallel β-strand protein fold; and Kunitz domain inhibitor scaffolds, which are based upon a structure that contains three disulfide bonds and three loops. In some embodiments, a GCGR-binding protein comprises an engineered scaffold protein comprising one or more CDRs from an antibody defined in Tables 1-10. In some embodiments, a GCGR-binding protein comprises an engineered scaffold protein comprising the Exemplary heavy CDR1, CDR2, and CD3 and the Exemplary light chain CDR1, CDR2, and CDR3 from Table 1. In some embodiments, a GCGR-binding protein comprises an engineered scaffold protein comprising the Kabat heavy CDR1, CDR2, and CD3 and the Kabat light chain CDR1, CDR2, and CDR3 from Table 1. In some embodiments, a GCGR-binding protein comprises an engineered scaffold protein comprising the Chothia heavy CDR1, CDR2, and CD3 and the Chothia light chain CDR1, CDR2, and CDR3 from Table 1. In some embodiments, a GCGR-binding protein comprises an engineered scaffold protein comprising the Exemplary heavy CDR1, CDR2, and CD3 and the Exemplary light chain CDR1, CDR2, and CDR3 from Table 2. In some embodiments, a GCGR-binding protein comprises an engineered scaffold protein comprising the Kabat heavy CDR1, CDR2, and CD3 and the Kabat light chain CDR1, CDR2, and CDR3 from Table 2. In some embodiments, a GCGR-binding protein comprises an engineered scaffold protein comprising the Chothia heavy CDR1, CDR2, and CD3 and the Chothia light chain CDR1, CDR2, and CDR3 from Table 2. In some embodiments, a GCGR-binding protein comprises an engineered scaffold protein comprising the Exemplary heavy CDR1, CDR2, and CD3 and the Exemplary light chain CDR1, CDR2, and CDR3 from Table 3. In some embodiments, a GCGR-binding protein comprises an engineered scaffold protein comprising the Kabat heavy CDR1, CDR2, and CD3 and the Kabat light chain CDR1, CDR2, and CDR3 from Table 3. In some embodiments, a GCGR-binding protein comprises an engineered scaffold protein comprising the Chothia heavy CDR1, CDR2, and CD3 and the Chothia light chain CDR1, CDR2, and CDR3 from Table 3. In some embodiments, a GCGR-binding protein comprises an engineered scaffold protein comprising the Exemplary heavy CDR1, CDR2, and CD3 and the Exemplary light chain CDR1, CDR2, and CDR3 from Table 4. In some embodiments, a GCGR-binding protein comprises an engineered scaffold protein comprising the Kabat heavy CDR1, CDR2, and CD3 and the Kabat light chain CDR1, CDR2, and CDR3 from Table 4. In some embodiments, a GCGR-binding protein comprises an engineered scaffold protein comprising the Chothia heavy CDR1, CDR2, and CD3 and the Chothia light chain CDR1, CDR2, and CDR3 from Table 4. In some embodiments, a GCGR-binding protein comprises an engineered scaffold protein comprising the Exemplary heavy CDR1, CDR2, and CD3 and the Exemplary light chain CDR1, CDR2, and CDR3 from Table 5. In some embodiments, a GCGR-binding protein comprises an engineered scaffold protein comprising the Kabat heavy CDR1, CDR2, and CD3 and the Kabat light chain CDR1, CDR2, and CDR3 from Table 5. In some embodiments, a GCGR-binding protein comprises an engineered scaffold protein comprising the Chothia heavy CDR1, CDR2, and CD3 and the Chothia light chain CDR1, CDR2, and CDR3 from Table 5. In some embodiments, a GCGR-binding protein comprises an engineered scaffold protein comprising the Exemplary heavy CDR1, CDR2, and CD3 and the Exemplary light chain CDR1, CDR2, and CDR3 from Table 6. In some embodiments, a GCGR-binding protein comprises an engineered scaffold protein comprising the Kabat heavy CDR1, CDR2, and CD3 and the Kabat light chain CDR1, CDR2, and CDR3 from Table 6. In some embodiments, a GCGR-binding protein comprises an engineered scaffold protein comprising the Chothia heavy CDR1, CDR2, and CD3 and the Chothia light chain CDR1, CDR2, and CDR3 from Table 6. In some embodiments, a GCGR-binding protein comprises an engineered scaffold protein comprising the Exemplary heavy CDR1, CDR2, and CD3 and the Exemplary light chain CDR1, CDR2, and CDR3 from Table 7. In some embodiments, a GCGR-binding protein comprises an engineered scaffold protein comprising the Kabat heavy CDR1, CDR2, and CD3 and the Kabat light chain CDR1, CDR2, and CDR3 from Table 7. In some embodiments, a GCGR-binding protein comprises an engineered scaffold protein comprising the Chothia heavy CDR1, CDR2, and CD3 and the Chothia light chain CDR1, CDR2, and CDR3 from Table 7. In some embodiments, a GCGR-binding protein comprises an engineered scaffold protein comprising the Exemplary heavy CDR1, CDR2, and CD3 and the Exemplary light chain CDR1, CDR2, and CDR3 from Table 8. In some embodiments, a GCGR-binding protein comprises an engineered scaffold protein comprising the Kabat heavy CDR1, CDR2, and CD3 and the Kabat light chain CDR1, CDR2, and CDR3 from Table 8. In some embodiments, a GCGR-binding protein comprises an engineered scaffold protein comprising the Chothia heavy CDR1, CDR2, and CD3 and the Chothia light chain CDR1, CDR2, and CDR3 from Table 8. In some embodiments, a GCGR-binding protein comprises an engineered scaffold protein comprising the Exemplary heavy CDR1, CDR2, and CD3 and the Exemplary light chain CDR1, CDR2, and CDR3 from Table 9. In some embodiments, a GCGR-binding protein comprises an engineered scaffold protein comprising the Kabat heavy CDR1, CDR2, and CD3 and the Kabat light chain CDR1, CDR2, and CDR3 from Table 9. In some embodiments, a GCGR-binding protein comprises an engineered scaffold protein comprising the Chothia heavy CDR1, CDR2, and CD3 and the Chothia light chain CDR1, CDR2, and CDR3 from Table 9. In some embodiments, a GCGR-binding protein comprises an engineered scaffold protein comprising the Exemplary heavy CDR1, CDR2, and CD3 and the Exemplary light chain CDR1, CDR2, and CDR3 from Table 10. In some embodiments, a GCGR-binding protein comprises an engineered scaffold protein comprising the Kabat heavy CDR1, CDR2, and CD3 and the Kabat light chain CDR1, CDR2, and CDR3 from Table 10. In some embodiments, a GCGR-binding protein comprises an engineered scaffold protein comprising the Chothia heavy CDR1, CDR2, and CD3 and the Chothia light chain CDR1, CDR2, and CDR3 from Table 10. In some embodiments, a GCGR-binding protein comprises an engineered scaffold protein comprising the six CDRs of antibody 6B5, 3H5, 5B11, 1C1, 1C3, 1H2, 4F8, 13G9, 14F4, or 14E9, Generally speaking, antigen-antibody interactions are non-covalent and reversible, formed by a combination of hydrogen bonds, hydrophobic interactions, electrostatic and van der Waals forces. When describing the strength of an antigen-antibody complex, affinity and/or avidity are usually mentioned. The binding of an antibody to its antigen is a reversible process, and the affinity of the binding is typically reported as an equilibrium dissociation constant ($K_D$) $K_D$ is the ratio of an antibody dissociation rate ($k_{off}$) (how quickly it dissociates from its antigen) to the antibody association rate ($k_{on}$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. $K_D$ values may be used to evaluate and rank order the strength of individual antibody/antigen interactions. The lower the $K_D$ of an antibody, the higher the affinity of the antibody for its target. Avidity gives a measure of the overall strength of an antibody-antigen complex. It is dependent on three major parameters: (i) affinity of the antibody for the epitope, (ii) valency of both the antibody and antigen, and (iii) structural arrangement of the parts that interact.

In some embodiments, a GCGR-binding protein (e.g., an antibody) binds GCGR with a dissociation constant ($K_D$) of about 1 μM or less, about 100 nM or less, about 40 nM or less, about 20 nM or less, about 10 nM or less, about 1 nM or less, about 0.1 nM or less, 50 pM or less, 10 pM or less, or 1 pM or less. In some embodiments, a GCGR-binding protein binds GCGR with a $K_D$ of about 20 nM or less. In some embodiments, a GCGR-binding protein binds GCGR with a $K_D$ of about 10 nM or less. In some embodiments, a GCGR-binding protein binds GCGR with a $K_D$ of about 1 nM or less. In some embodiments, a GCGR-binding protein binds GCGR with a $K_D$ of about 0.5 nM or less. In some embodiments, a GCGR-binding protein binds GCGR with a $K_D$ of about 0.1 nM or less. In some embodiments, a GCGR-binding protein binds GCGR with a $K_D$ of about 50 pM or less. In some embodiments, a GCGR-binding protein binds GCGR with a $K_D$ of about 25 pM or less. In some embodiments, a GCGR-binding protein binds GCGR with a $K_D$ of about 10 pM or less. In some embodiments, a GCGR-binding protein binds GCGR with a $K_D$ of about 1 pM or less. In some embodiments, the dissociation constant of the binding protein (e.g., an antibody) to GCGR is the dissociation constant determined using a GCGR fusion protein comprising at least a portion or fragment of GCGR immobilized on a Biacore chip. In some embodiments, the dissociation constant of the binding protein (e.g., an antibody) to GCGR is the dissociation constant determined using the extracellular domain of GCGR (or a portion/fragment of the extracellular domain) immobilized on a Biacore chip. In some embodiments, the dissociation constant of the binding protein (e.g., an antibody) to GCGR is the dissociation constant determined using the binding protein captured by an anti-human IgG antibody on a Biacore chip and soluble GCGR or a fragment thereof.

In some embodiments, a GCGR-binding protein (e.g., an antibody) binds GCGR with a half maximal effective concentration (EC50) of about 1 μM or less, about 100 nM or less, about 40 nM or less, about 20 nM or less, about 10 nM or less, about 1 nM or less, or about 0.1 nM or less. In some embodiments, a GCGR-binding protein binds to human GCGR with an EC50 of about 1 μM or less, about 100 nM or less, about 40 nM or less, about 20 nM or less, about 10 nM or less, about 1 nM or less, or about 0.1 nM or less. In some embodiments, a GCGR-binding protein binds mouse GCGR and/or human GCGR with an EC50 of about 40 nM or less, about 20 nM or less, about 10 nM or less, about 1 nM or less or about 0.1 nM or less.

The binding proteins (e.g., antibodies) described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known to those of skill in the art, in order to obtain high expression levels of a transfected gene in a host, the gene must be operatively linked to transcriptional and translational expression control sequences that are functional in the chosen expression host.

In some embodiments, recombinant expression vectors are used to amplify and express DNA encoding antibodies, or fragments thereof, against human GCGR. For example, recombinant expression vectors can be replicable DNA constructs which have synthetic or cDNA-derived DNA fragments encoding a polypeptide chain of a GCGR-binding protein, such as an anti-GCGR antibody, or an antigen-binding fragment thereof, operatively linked to suitable transcriptional and/or translational regulatory elements derived from mammalian, microbial, viral, or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from E. coli, including pCR1, pBR322, pMB9 and their derivatives, and wider host range plasmids, such as M13 and other filamentous single-stranded DNA phages.

The GCGR-binding proteins (e.g., antibodies) of the present disclosure can be expressed from one or more vectors. For example, in some embodiments, a heavy chain polypeptide is expressed by one vector and a light chain polypeptide is expressed by a second vector. In some embodiments, a heavy chain polypeptide and a light chain polypeptide are expressed by one vector.

Suitable host cells for expression of a GCGR-binding protein (e.g., an antibody) or a GCGR protein or fragment thereof to use as an antigen or immunogen include prokaryotes, yeast cells, insect cells, or higher eukaryotic cells under the control of appropriate promoters. Prokaryotes include gram-negative or gram-positive organisms, for example, E. coli or Bacillus. Higher eukaryotic cells include established cell lines of mammalian origin as described herein. Cell-free translation systems may also be employed. Appropriate cloning and expression vectors for use with bacterial, fungal, yeast, and mammalian cellular hosts, as well as methods of protein production, including antibody production are well known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well known to those of skill in the art.

Thus, the present disclosure provides cells comprising the GCGR-binding proteins described herein. In some embodiments, the cells produce the GCGR-binding proteins described herein. In some embodiments, the cells produce an antibody. In some embodiments, the cells produce an antibody that binds human GCGR. In some embodiments, the cells produce an antibody that binds cyno GCGR. In some embodiments, the cells produce an antibody that binds human GCGR and cyno GCGR. In some embodiments, the cells produce an antibody designated 6B5, 3H5, 5B11, 1C1, 1C3, 1H2, 4F8, 13G9, 14F4, or 14E9. In some embodiments, the cells produce an antibody designated 6B5. In some embodiments, the cells produce a humanized version of antibody 6B5, referred to as Hz6B5. In some embodiments, the cell is a hybridoma cell. In some embodiments, the cell is a mammalian cell. In some embodiments, the cell is a prokaryotic cell. In some embodiments, the cell is an eukaryotic cell.

Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column Affinity chromatography used for purifying immunoglobulins can include Protein A, Protein G, and Protein L chromatography. Isolated proteins can be physically characterized using such techniques as proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems that secrete recombinant protein into culture media are first concentrated using a commercially available protein concentration filter, for example, an Amicon® or Millipore Pellicon® ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reverse-phase HPLC steps employing hydrophobic RP-HPLC media, e.g., silica gel having pendant methyl or other aliphatic groups, are employed to further purify a recombinant protein. In some embodiments, hydrophobic interaction chromatography (HIC) is used to separate recombinant proteins based on their hydrophobicity. HIC is a useful separation technique for purifying proteins while maintaining biological activity due to the use of conditions and matrices that operate under less denaturing conditions than some other techniques. Some or all of the foregoing purification steps, in various combinations, can be employed to provide a homogeneous recombinant protein.

GCGR-binding proteins of the present disclosure may be analyzed for their physical/chemical properties and/or biological activities by various assays known in the art. In some embodiments, a GCGR-binding protein (e.g., an anti-GCGR antibody) is evaluated for its ability to bind GCGR. Binding assays include, but are not limited to, Biacore, ELISA, and FACS.

In some embodiments, antibodies generated against GCGR are characterized based upon their binding properties. In some embodiments, antibodies are grouped together based upon the epitope each individual antibody recognizes and/or binds to, a process known as "epitope binning" Generally, in epitope binning antibodies are tested in a pairwise combinatorial manner and antibodies that compete with each other (i.e., bind the same or similar epitopes) are grouped together into bins. For example, in a binning assay, a first antibody is immobilized on a surface and a premixed solution of a second antibody and antigen/target protein is flowed over the immobilized first antibody. In tandem, the antigen/target protein is immobilized on a surface and the two antibodies are flowed over the immobilized antigen and compete to bind to the immobilized antigen/target protein. In each of these techniques, antibodies that block one another can be identified. A competitive blocking profile is created for each antibody relative to the other antibodies. The results determine which bin each antibody is placed in. High-throughput methods of epitope binning are known in the art and allow for screening and characterization of large numbers of antibodies within a short period of time. Antibodies that bind similar epitopes often share similar functions. Conversely, antibodies that bind different epitopes may have different functional activities.

Epitope mapping is the process of identifying the binding site (e.g., epitope) on a target protein where an antibody (or other binding agent) binds. A variety of methods are known in the art for mapping binding sites and/or epitopes on target proteins. These methods include mutagenesis, including but not limited to, shotgun mutagenesis, site-directed mutagenesis, and alanine scanning mutagenesis; domain or fragment scanning; peptide scanning (e.g., Pepscan technology); display methods (e.g., phage display, microbial display, and ribosome/mRNA display); methods involving proteolysis and mass spectroscopy; and structural determination (e.g., X-ray crystallography and NMR).

In some embodiments, anti-GCGR antibodies are characterized by assays including, but not limited to, N-terminal sequencing, amino acid analysis, high pressure liquid chromatography (HPLC), mass spectrometry, ion exchange chromatography, and papain digestion.

In some embodiments, a GCGR-binding protein (e.g., an anti-GCGR antibody) is tested for its ability to modulate GCGR activity. In some embodiments, assays are provided for identifying anti-GCGR antibodies that enhance GCGR activity. In some embodiments, assays are provided for identifying anti-GCGR antibodies that inhibit GCGR activity. Cyclic AMP (cAMP) is one of the most important GPCR intracellular mediators. In many cell types, cAMP production results from the regulation of adenylate cyclase by the Gα subunit of a G-protein. For example, activation of GCGR by glucagon results in production of cAMP. In some embodiments, GCGR activation can be assessed by assaying for production of cAMP and in turn, GCGR antagonists can be screened for their ability to inhibit cAMP production. For example, in some embodiments, cells are prepared and dispensed into plates and then incubated with a GCGR-binding protein (e.g., an anti-GCGR antibody). After an appropriate period of time, the cell/GCGR-binding protein mixture is incubated with glucagon. Finally, cAMP levels are determined in the cells treated with the GCGR-binding proteins and compared to the cAMP levels in appropriate control cells. In some embodiments, the IC50 of a GCGR antagonist (e.g., an anti-GCGR antibody) is determined. "IC50" refers to the half maximal inhibitory concentration of an agent and is a measure of the effectiveness of the agent in inhibiting a specific biological or biochemical function.

The present disclosure also provides conjugates comprising any one of the GCGR-binding proteins described herein. In some embodiments, an anti-GCGR antibody is attached to a second molecule. In some embodiments, an anti-GCGR antibody is conjugated to a cytotoxic agent or moiety. In some embodiments, an anti-GCGR antibody is conjugated to a cytotoxic agent to form an ADC (antibody-drug conjugate). In some embodiments, the cytotoxic agent is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic agent is a microtubule inhibitor including, but not limited to, auristatins, maytansinoids (e.g., DMI and DM4), and tubulysins. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, a GCGR-binding protein (e.g., an antibody) is conjugated to one or more small molecule toxins, such as calicheamicins, maytansinoids, trichothenes, and CC1065. A derivative of any of these toxins can also be used, as long as the derivative retains cytotoxic activity.

Conjugates comprising a protein (e.g., an antibody) may be made using any suitable method known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, a GCGR-binding protein (e.g., an anti-GCGR antibody) is conjugated to a detectable substance or molecule that allows the protein to be used for diagnosis and/or detection. The detectable substance may be selected from a group including but not limited to, enzymes, such as horseradish peroxidase, alkaline phosphatase, betagalactosidase, and acetylcholinesterase; prosthetic groups, such as streptavidin/biotin and avidin/biotin; fluorescent materials, such as, umbelliferone, fluorescein, fluorescein isothiocynate, rhodamine, dichlorotriazinylamine fluorescein, dansyl chloride, and phycoerythrin; bioluminescent materials, such as luciferase, luciferin, and aequorin; chemiluminescent materials, such as luminol and acridinium; radioactive materials, such as $^{131}$I, $^{125}$I, $^{123}$I, $^{121}$I, $^{14}$C, $^{35}$S, $^{3}$H, $^{115}$In, $^{113}$In, $^{112}$In, $^{111}$In, $^{99m}$Tc, $^{201}$Ti, $^{68}$Ga, $^{67}$Ga, $^{103}$Pd, $^{99}$Mo, $^{133}$Xe, $^{18}$F, $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{67}$Cu, $^{212}$Bi, and $^{117}$Sn; positron emitting metals; and non-radioactive paramagnetic metal ions.

In some embodiments, a GCGR-binding protein (e.g., an anti-GCGR antibody) described herein can be conjugated to a second antibody to form an antibody heteroconjugate.

In some embodiments, a GCGR-binding protein (e.g., an anti-GCGR antibody) described herein may be attached to a solid support and used in immunoassays or for purification of the target antigen. Such solid supports include, but are not limited to, glass, cellulose, polyacrylamide, nylon, polystyrene, polyvinyl chloride, or polypropylene.

III. Polynucleotides

In some embodiments, the disclosure encompasses polynucleotides comprising polynucleotides encoding a GCGR-binding protein described herein. The term "polynucleotides encoding a polypeptide" encompasses a polynucleotide that includes only coding sequences for the polypeptide as well as a polynucleotide which includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, a polynucleotide comprises a polynucleotide (e.g., a nucleotide sequence) encoding a polypeptide comprising an amino acid sequence selected from the group consisting of: SEQ ID NOs: 220, 221, 25, 26, 51, 52, 71, 72, 97, 98, 122, 123, 144, 145, 164, 165, 188, 189, 203, 204, 218, and 219. In some embodiments, a polynucleotide comprises a polynucleotide (e.g., a nucleotide sequence) encoding a polypeptide comprising an amino acid sequence selected from the group consisting of: SEQ ID NOs: 233, 234, 235, and 236. In some embodiments, a polynucleotide comprises a polynucleotide (e.g., a nucleotide sequence) encoding a polypeptide comprising more than one amino acid sequence selected from the group consisting of: SEQ ID NOs: 220, 221, 25, 26, 51, 52, 71, 72, 97, 98, 122, 123, 144, 145, 164, 165, 188, 189, 203, 204, 218, and 219. In some embodiments, a polynucleotide comprises a polynucleotide (e.g., a nucleotide sequence) encoding a polypeptide comprising more than one amino acid sequence selected from the group consisting of: SEQ ID NOs: 233, 234, 235, and 236. In some embodiments, a polynucleotide comprises a polynucleotide (e.g., a nucleotide sequence) encoding a polypeptide comprising SEQ ID NO:233 and SEQ ID NO:235. In some embodiments, a polynucleotide comprises a polynucleotide (e.g., a nucleotide sequence) encoding a polypeptide comprising SEQ ID NO:234 and SEQ ID NO:236.

In some embodiments, a polynucleotide comprises a polynucleotide having a nucleotide sequence at least about 80% identical, at least about 85% identical, at least about 90% identical, at least about 95% identical, and in some embodiments, at least about 96%, 97%, 98%, or 99% identical to a polynucleotide encoding an amino acid sequence selected from the group consisting of: SEQ ID NOs: 220, 221, 25, 26, 51, 52, 71, 72, 97, 98, 122, 123, 144, 145, 164, 165, 188, 189, 203, 204, 218, and 219. In some embodiments, a polynucleotide comprises a polynucleotide having a nucleotide sequence at least about 80% identical, at least about 85% identical, at least about 90% identical, at least about 95% identical, and in some embodiments, at least about 96%, 97%, 98%, or 99% identical to a polynucleotide encoding an amino acid sequence selected from the group consisting of: SEQ ID NOs: 233, 234, 235, and 236. Also provided is a polynucleotide that comprises a polynucleotide that hybridizes to a polynucleotide encoding an amino acid sequence selected from the group consisting of: SEQ ID NOs: 220, 221, 25, 26, 51, 52, 71, 72, 97, 98, 122, 123, 144, 145, 164, 165, 188, 189, 203, 204, 218, 219, 233, 234, 235, and 236. In some embodiments, the hybridization is under conditions of high stringency as is known to those skilled in the art.

In some embodiments, a polynucleotide comprises the coding sequence for a polypeptide (e.g., an antibody) fused in the same reading frame to a polynucleotide which aids, for example, in expression and secretion of a polypeptide from a host cell (e.g., a leader sequence which functions as a secretory sequence for controlling transport of a polypeptide). The polypeptide can have the leader sequence cleaved by the host cell to form a "mature" form of the polypeptide.

In some embodiments, a polynucleotide comprises the coding sequence for a polypeptide (e.g., an antibody) fused in the same reading frame to a marker or tag sequence. For example, in some embodiments, a marker sequence is a hexa-histidine tag supplied by a vector that allows efficient purification of the polypeptide fused to the marker in the case of a bacterial host. In some embodiments, a marker sequence is a hemagglutinin (HA) tag derived from the influenza hemagglutinin protein when a mammalian host (e.g., COS-7 cells) is used. In some embodiments, the marker sequence is a FLAG-tag. In some embodiments, a marker may be used in conjunction with other affinity tags.

The present disclosure further relates to variants of the polynucleotides described herein, wherein the variant encodes, for example, fragments, analogs, and/or derivatives of a polypeptide. In some embodiments, the present disclosure provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a GCGR-binding protein described herein.

As used herein, the phrase "a polynucleotide having a nucleotide sequence at least, for example, 95% identical to a reference nucleotide sequence" is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations that produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, the polynucleotides are isolated. In some embodiments, the polynucleotides are substantially pure.

Vectors and cells comprising the polynucleotides described herein are also provided. In some embodiments, an expression vector comprises a polynucleotide molecule. In some embodiments, a host cell comprises an expression vector. In some embodiments, a host cell comprises an expression vector comprising a polynucleotide molecule. In some embodiments, a host cell comprises a polynucleotide molecule.

IV. Methods of Use and Pharmaceutical Compositions

A GCGR-binding protein of the present disclosure may be used in, for example, in vitro, ex vivo, and in vivo therapeutic methods. In some embodiments, the present disclosure provides methods, either in vivo or in vitro, comprising exposing a cell to a GCGR-binding protein (e.g., an anti-GCGR antibody).

The GCGR-binding proteins (e.g., antibodies) described herein are useful in a variety of applications including, but not limited to, therapeutic treatment of a variety of syndromes, disorders, and/or diseases. In some embodiments, a method is provided for treating a disease, disorder or condition in a subject, wherein the method comprises administering to the subject an effective amount of an anti-GCGR antibody described herein. In certain embodiments, a method for treating a disease, disorder, or condition in a subject comprises administering to a subject an effective amount of a pharmaceutical formulation comprising an anti-GCGR antibody described herein and, optionally, at least one additional therapeutic agent.

In some embodiments, a GCGR-binding protein described herein is administered to a human for therapeutic purposes. In some embodiments, a GCGR-binding protein described herein is administered to a non-human mammal (e.g., a primate, dog, cat, pig, rat, or mouse). In some embodiments, a GCGR-binding protein is administered to a non-human mammal for veterinary purposes or for testing in an animal model of human disease. In some embodiments, animal models are useful for evaluating the therapeutic efficacy of a GCGR-binding protein described herein (e.g., testing of dosages and/or time courses of administration).

In some embodiments, a GCGR-binding protein (e.g., an antibody) described herein is useful in methods for inhibiting GCGR activity. In some embodiments, a GCGR-binding protein (e.g., an antibody) described herein is useful in methods for inhibiting glucagon activity. In some embodiments, a GCGR-binding protein (e.g., an antibody) described herein is useful in methods for reducing or lowering blood glucose levels. In some embodiments, a GCGR-binding protein (e.g., an antibody) described herein is useful in methods for increasing blood C-peptide levels. In some embodiments, a GCGR-binding protein (e.g., an antibody) described herein is useful in methods for increasing blood insulin levels. In some embodiments, a GCGR-binding protein (e.g., an antibody) described herein is useful in methods for increasing pancreatic levels of insulin. In some embodiments of the methods described herein, the GCGR-binding protein is an anti-GCGR antibody selected from the group consisting of 6B5, 3H5, 5B11, 1C1, 1C3, 1H2, 4F8, 13G9, 14F4, and 14E9. In some embodiments of the methods described herein, the GCGR-binding protein is an antibody that comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments of the methods described herein, the GCGR-binding protein is an antibody that comprises a heavy chain variable region comprising SEQ ID NO:25 and a light chain variable region comprising SEQ ID NO:26. In some embodiments of the methods described herein, the GCGR-binding protein is an antibody that comprises a heavy chain variable region comprising SEQ ID NO:220 and a light chain variable region comprising SEQ ID NO:221. In some embodiments of the methods described herein, the GCGR-binding protein is anti-GCGR antibody Hz6B5.

In some embodiments, a GCGR-binding protein (e.g., an antibody) described herein is useful in methods for treating hyperglycemia. In some embodiments, a GCGR-binding protein (e.g., an antibody) described herein is useful in methods for treating diabetes. In some embodiments, a GCGR-binding protein (e.g., an antibody) described herein is useful in methods for treating Type 1 diabetes. In some embodiments, a GCGR-binding protein (e.g., an antibody) described herein is useful in methods for treating Type 2 diabetes. In some embodiments of the methods described herein, the GCGR-binding protein is an anti-GCGR antibody selected from the group consisting of 6B5, 3H5, 5B11, 1C1, 1C3, 1H2, 4F8, 13G9, 14F4, and 14E9. In some embodiments of the methods described herein, the GCGR-binding protein is an antibody that comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments of the methods described herein, the GCGR-binding protein is an antibody that comprises a heavy chain variable region comprising SEQ ID NO:25 and a light chain variable region comprising SEQ ID NO:26. In some embodiments of the methods described herein, the GCGR-binding protein is an antibody that comprises a heavy chain variable region comprising SEQ ID NO:220 and a light chain variable region comprising SEQ ID NO:221. In some embodiments of the methods described herein, the GCGR-binding protein is anti-GCGR antibody Hz6B5.

In some embodiments, a GCGR-binding protein (e.g., an antibody) described herein is useful for treatment of a disease, disorder, or condition associated with beta cell dysfunction. In some embodiments, a GCGR-binding protein (e.g., an antibody) described herein is useful for treatment of a beta cell defective disease, disorder, or condition. The phrase "a disease, disorder, or condition associated with beta cell dysfunction" is used interchangeably with the phrase "a beta cell defective disease, disorder, or condition". As used herein, "a disease, disorder, or condition associated with beta cell dysfunction" refers to any disease that is completely or partially caused by or is the result of a defect or deficiency in beta cells. In some embodiments, the disease, disorder, or condition associated with beta cell dysfunction is diabetes mellitus. In certain embodiments, the disease, disorder, or condition associated with beta cell dysfunction is insulin-dependent or Type 1 diabetes (e.g., juvenile diabetes, brittle diabetes, insulin-dependent diabetes mellitus (IDDM)). In some embodiments, the disease, disorder, or condition associated with beta cell dysfunction is non-insulin-dependent diabetes mellitus (NIDDM)/Type 2 diabetes. In some embodiments, the disease, disorder, or condition associated with beta cell dysfunction is latent autoimmune diabetes of adults (LADA). In certain embodiments, the disease, disorder, or condition associated with beta cell dysfunction is a dyslipidemia and one of its sequelae (e.g., atherosclerosis, coronary artery disease, and cerebrovascular disorders), hyperlipidemia, hyperglycemia, a hyperglycemic-related disorder (e.g., kidney damage (e.g., tubule damage or nephropathy), liver degeneration, eye damage (e.g., diabetic retinopathy or cataracts), and diabetic foot disorders), hypercholesterolemia, hypertriglyceridemia, hypertension, cardiovascular disease, stroke, heart failure, hyperinsulinemia, a diabetic complication, glucose intolerance, insulin resistance, abnormal glucose metabolism, "pre-diabetes" (impaired fasting glucose or impaired glucose tolerance), obesity (including co-morbid conditions of obesity, such as, but not limited to, obstructive sleep apnea, nonalcoholic fatty liver disease (NAFLD), nonalcoholic steatohepatitis (NASH), and polycystic ovarian syndrome), or an undesirable body weight or mass (e.g., a greater than normal body mass index, or "BMI" relative to an appropriate matched subject of comparable age, gender, race, etc.), or any combination of two or more thereof. In some embodiments, the disease, disorder, or condition associated with beta cell dysfunction is NAFLD. In some embodiments, the disease, disorder, or condition associated with beta cell dysfunction is NASH. In some embodiments of the methods described herein, the GCGR-binding protein is an anti-GCGR antibody selected from the group consisting of 6B5, 3H5, 5B11, 1C1, 1C3, 1H2, 4F8, 13G9, 14F4, and 14E9. In some embodiments of the methods described herein, the GCGR-binding protein is an antibody that comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments of the methods described herein, the GCGR-binding protein is an antibody that comprises a heavy chain variable region comprising SEQ ID NO:25 and a light chain variable region comprising SEQ ID NO:26. In some embodiments of the methods described herein, the GCGR-binding protein is an antibody that comprises a heavy chain variable region comprising SEQ ID NO:220 and a light chain variable region comprising SEQ ID NO:221. In some embodiments of the methods described herein, the GCGR-binding protein is anti-GCGR antibody Hz6B5.

In some embodiments, a method described herein includes treating, preventing, or alleviating a disease, disorder, or condition, including treating, preventing, or alleviating one or more symptoms of a disease, disorder, or condition in a subject. In some embodiments, a disease, disorder, or condition to be treated or prevented includes a glucose utilization disorder and the sequelae associated therewith, including diabetes mellitus (Type 1 and Type 2), gestational diabetes, hyperglycemia, insulin resistance, abnormal glucose metabolism, "pre-diabetes", or other physiological disorders associated with, or that result from, a hyperglycemic condition, including, for example, histopathological changes such as pancreatic beta cell destruction. In some embodiments, a subject with a disease, disorder, or condition in need of treatment has a fasting blood glucose level greater than about 100 mg/dL. Other hyperglycemic-related disorders, include but are not limited to, kidney damage (e.g., tubule damage or nephropathy), liver degeneration, eye damage (e.g., diabetic retinopathy or cataracts), and diabetic foot disorders. In some embodiments, a disease, disorder, or condition to be treated or prevented includes a dyslipidemia and the sequelae associated therewith, such as atherosclerosis, coronary artery disease, cerebrovascular disorders and the like. In some embodiments, a disease, disorder, or condition to be treated or prevented is associated with metabolic syndrome, including, but not limited to, obesity and elevated body mass, NAFLD, NASH, PCOS, thromboses, hypercoagulable and prothrombotic states (arterial and venous), hypertension, cardiovascular disease, stroke, and heart failure. In some embodiments, a disease, disorder, or condition to be treated or prevented is obesity. In some embodiments, a disease, disorder, or condition to be treated or prevented is NAFLD. In some embodiments, a disease, disorder, or condition to be treated or prevented is NASH. In some embodiments, a disease, disorder, or condition to be treated or prevented includes atherosclerosis, chronic inflammatory bowel diseases (e.g., Crohn's disease and ulcerative colitis), asthma, lupus erythematosus, arthritis, or other inflammatory rheumatic disorders. In some embodiments, a disease, disorder, or condition to be treated or prevented includes adipose cell tumors, lipomatous carcinomas including, for example, liposarcomas, solid tumors, and neoplasms. In some embodiments, a disease, disorder, or condition to be treated or prevented includes neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy, and Guillain-Barre syndrome. In some embodiments, a disease, disorder, or condition to be treated or prevented includes skin and dermatological disorders and/or disorders of wound healing processes, including erythemato-squamous dermatoses. In some embodiments, a disease, disorder, or condition to be treated or prevented includes syndrome X, osteoarthritis, and acute respiratory distress syndrome. In some embodiments of the methods described herein, the GCGR-binding protein is an anti-GCGR antibody selected from the group consisting of 6B5, 3H5, 5B11, 1C1, 1C3, 1H2, 4F8, 13G9, 14F4, and 14E9. In some embodiments of the methods described herein, the GCGR-binding protein is an antibody that comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments of the methods described herein, the GCGR-binding protein is an antibody that comprises a heavy chain variable region comprising SEQ ID NO:25 and a light chain variable region comprising SEQ ID NO:26. In some embodiments of the methods described herein, the GCGR-binding protein is an antibody that comprises a heavy chain variable region comprising SEQ ID NO:220 and a light chain variable region comprising SEQ ID NO:221. In some embodiments of the methods described herein, the GCGR-binding protein is anti-GCGR antibody Hz6B5.

In some embodiments, a GCGR-binding protein (e.g., an antibody) described herein is used to treat or prevent a disease, disorder, or condition, including, for example, hyperglycemia, Type 1 diabetes, Type 2 diabetes, obesity, dyslipidemia, NASH, cardiovascular disease, metabolic syndrome or broadly any disease, disorder, or condition in which it is desirable to inhibit the in vivo effects of glucagon. In some embodiments of the methods described herein, the GCGR-binding protein is an anti-GCGR antibody selected from the group consisting of 6B5, 3H5, 5B11, 1C1, 1C3, 1H2, 4F8, 13G9, 14F4, and 14E9. In some embodiments of the methods described herein, the GCGR-binding protein is an antibody that comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments of the methods described herein, the GCGR-binding protein is an antibody that comprises a heavy chain variable region comprising SEQ ID NO:25 and a light chain variable region comprising SEQ ID NO:26. In some embodiments of the methods described herein, the GCGR-binding protein is an antibody that comprises a heavy chain variable region comprising SEQ ID NO:220 and a light chain variable region comprising SEQ ID NO:221. In some embodiments of the methods described herein, the GCGR-binding protein is anti-GCGR antibody Hz6B5.

In some embodiments, a method of treating Type 1 diabetes in a subject comprises administering to the subject a therapeutically effective amount of an anti-GCGR antibody described herein. Type 1 diabetes is an autoimmune disease condition characterized by high blood glucose levels resulting from a loss of pancreatic beta cell mass and/or function and a loss of insulin production. Type 1 diabetes symptoms are generally the result of hyperglycemia and a breakdown of body fat. Symptoms include, but are not limited to, excessive thirst (polydipsia), frequent urination (polyuria), extreme hunger (polyphagia), extreme fatigue, weight loss, and ketones present in their urine. In some embodiments, the Type 1 diabetes is latent autoimmune diabetes of adults (LADA). In some embodiments, the anti-GCGR antibody is selected from the group consisting of 6B5, 3H5, 5B11, 1C1, 1C3, 1H2, 4F8, 13G9, 14F4, and 14E9. In some embodiments, the anti-GCGR antibody comprises a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the anti-GCGR antibody comprises a heavy chain variable region comprising SEQ ID NO:25 and a light chain variable region comprising SEQ ID NO:26. In some embodiments, the anti-GCGR antibody comprises a heavy chain variable region comprising SEQ ID NO:220 and a light chain variable region comprising SEQ ID NO:221. In some embodiments, the anti-GCGR antibody is Hz6B5.

In some embodiments, a method of treating Type 2 diabetes in a subject comprises administering to the subject a therapeutically effective amount of an anti-GCGR antibody described herein. Generally, Type 2 diabetes results from insulin resistance and/or reduced insulin secretion. However, many subjects with Type 2 diabetes also have significantly reduced pancreatic beta cell mass and function, which ultimately results in an insulin deficiency. Symptoms of Type 2 diabetes include, but are not limited to, hyperglycemia, fatigue, dry or itchy skin, blurred vision, increased thirst, frequent urination, slow healing cuts or sores, high rate of infections, and numbness or tingling in the feet. If left untreated, more serious symptoms can result, including severe hyperglycemia (e.g., glucose levels over 600 mg/dL), lethargy, confusion, shock, and/or a hyperosmolar hyperglycemic nonketotic coma. In some embodiments, the anti-GCGR antibody is selected from the group consisting of 6B5, 3H5, 5B11, 1C1, 1C3, 1H2, 4F8, 13G9, 14F4, and 14E9. In some embodiments, the anti-GCGR antibody comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the anti-GCGR antibody comprises a heavy chain variable region comprising SEQ ID NO:25 and a light chain variable region comprising SEQ ID NO:26. In some embodiments, the anti-GCGR antibody comprises a heavy chain variable region comprising SEQ ID NO:220 and a light chain variable region comprising SEQ ID NO:221. In some embodiments, the anti-GCGR antibody is Hz6B5.

In some embodiments, a method of treating hyperglycemia in a subject comprises administering to the subject a therapeutically effective amount of an anti-GCGR antibody described herein. As used herein, the term "hyperglycemia" or "hyperglycemic" when used in reference to a disease, disorder, or condition of a subject refers to a transient or chronic abnormally high level of glucose present in the blood of a subject. The disease, disorder, or condition may be caused by a delay in glucose metabolism or absorption such that the subject exhibits glucose intolerance or a state of elevated glucose not typically found in normal subjects. Fasting blood glucose levels are considered to be in a "normal" range at less than about 100 mg/dL, for impaired glucose metabolism, between about 100 and 126 mg/dL, and for diabetics greater than about 126 mg/dL. In some embodiments, the anti-GCGR antibody is selected from the group consisting of 6B5, 3H5, 5B11, 1C1, 1C3, 1H2, 4F8, 13G9, 14F4, and 14E9. In some embodiments, the anti-GCGR antibody comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the anti-GCGR antibody comprises a heavy chain variable region comprising SEQ ID NO:25 and a light chain variable region comprising SEQ ID NO:26. In some embodiments, the anti-GCGR antibody comprises a heavy chain variable region comprising SEQ ID NO:220 and a light chain variable region comprising SEQ ID NO:221. In some embodiments, the anti-GCGR antibody is Hz6B5.

In some embodiments, a method of treating obesity or an undesirable body mass in a subject (including the co-morbid conditions of obesity, for example, obstructive sleep apnea, arthritis, cancer (e.g., breast, endometrial, and colon), gallstones, or hyperglycemia) comprises administering to the subject a therapeutically effective amount of an anti-GCGR antibody described herein. In some embodiments, a subject has a body mass index greater than 25, for example, 25-30, 30-35, 35-40, or greater than 40. In some embodiments, the anti-GCGR antibody is selected from the group consisting of 6B5, 3H5, 5B11, 1C1, 1C3, 1H2, 4F8, 13G9, 14F4, and 14E9. In some embodiments, the anti-GCGR antibody comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the anti-GCGR antibody comprises a heavy chain variable region comprising SEQ ID NO:25 and a light chain variable region comprising SEQ ID NO:26. In some embodiments, the anti-GCGR antibody comprises a heavy chain variable region comprising SEQ ID NO:220 and a light chain variable region comprising SEQ ID NO:221. In some embodiments, the anti-GCGR antibody is Hz6B5.

In some embodiments, a method of treating a disease, disorder, or condition associated with beta cell dysfunction in a subject comprises administering to the subject a therapeutically effective amount of an anti-GCGR antibody described herein. In some embodiments, a method of treating a beta cell defective disease, disorder, or condition, or a symptom thereof, in a subject comprises administering to the subject a therapeutically effective amount of an anti-GCGR antibody described herein. In some embodiments, the disease, disorder, or condition is Type 1 diabetes. In some embodiments, the disease, disorder, or condition is Type 2 diabetes. In some embodiments, the anti-GCGR antibody is selected from the group consisting of 6B5, 3H5, 5B11, 1C1, 1C3, 1H2, 4F8, 13G9, 14F4, and 14E9. In some embodiments, the anti-GCGR antibody comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the anti-GCGR antibody comprises a heavy chain variable region comprising SEQ ID NO:25 and a light chain variable region comprising SEQ ID NO:26. In some embodiments, the anti-GCGR antibody comprises a heavy chain variable region comprising SEQ ID NO:220 and a light chain variable region comprising SEQ ID NO:221. In some embodiments, the anti-GCGR antibody is Hz6B5.

In some embodiments of the methods described herein, the treatment (i) reduces blood glucose levels, (ii) increases C-peptide level in the blood, (iii) increases C-peptide levels in the pancreas, (iv) reduces blood glucose levels and increases C-peptide in the blood, and/or (v) reduces blood glucose levels and increases C-peptide in the pancreas. In some embodiments of the methods described herein, the treatment reduces blood glucose levels. In some embodiments of the methods described herein, the treatment increases C-peptide level in the blood. In some embodiments of the methods described herein, the treatment increases C-peptide levels in the pancreas. In some embodiments of the methods described herein, the treatment reduces blood glucose levels and increases C-peptide in the blood. In some embodiments of the methods described herein, the treatment reduces blood glucose levels and increases C-peptide in the pancreas. In some embodiments, the treatment increases insulin level in the blood. In some embodiments, the treatment increases insulin level/content in the pancreas.

In some embodiments, a method of improving beta cell function in a subject comprises administering to the subject a therapeutically effective amount of an anti-GCGR antibody described herein. In some embodiments, the improvement in beta cell function is indicated by a decrease in blood glucose, an increase in C-peptide, and/or an increase in insulin. In some embodiments, insulin production is assessed using any direct or indirect method known to those skilled in the art. In some embodiments, the anti-GCGR antibody is selected from the group consisting of 6B5, 3H5, 5B11, 1C1, 1C3, 1H2, 4F8, 13G9, 14F4, and 14E9. In some embodiments, the anti-GCGR antibody comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the anti-GCGR antibody comprises a heavy chain variable region comprising SEQ ID NO:25 and a light chain variable region comprising SEQ ID NO:26. In some embodiments, the anti-GCGR antibody comprises a heavy chain variable region comprising SEQ ID NO:220 and a light chain variable region comprising SEQ ID NO:221. In some embodiments, the anti-GCGR antibody is Hz6B5.

In some embodiments, a method of reducing or lowering blood glucose levels in a subject comprises administering to the subject a therapeutically effective amount of an anti-GCGR antibody described herein. In some embodiments, a method of increasing the level of insulin in the blood of a subject comprises administering to the subject a therapeutically effective amount of an anti-GCGR antibody described herein. In some embodiments, a method of increasing the level of insulin in the pancreas of a subject comprises administering to the subject a therapeutically effective amount of an anti-GCGR antibody described herein. In some embodiments, a method of increasing the level of C-peptide in the blood of a subject comprises administering to the subject a therapeutically effective amount of an anti-GCGR antibody described herein. In some embodiments, a method of increasing the level of insulin in the blood of a subject comprises administering to the subject a therapeutically effective amount of an anti-GCGR antibody described herein. In some embodiments, a method of reducing or lowering blood glucose levels and increasing the level of C-peptide in the blood of a subject comprises administering to the subject a therapeutically effective amount of an anti-GCGR antibody described herein. In some embodiments of the methods described herein, the level of C-peptide is measured in a blood sample, a serum sample, a plasma sample, or a pancreatic sample. In some embodiments of the methods described herein, the level of insulin is measured in a blood sample, a serum sample, a plasma sample, or a pancreatic sample. In some embodiments, the anti-GCGR antibody is selected from the group consisting of 6B5, 3H5, 5B11, 1C1, 1C3, 1H2, 4F8, 13G9, 14F4, and 14E9. In some embodiments, the anti-GCGR antibody comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the anti-GCGR antibody comprises a heavy chain variable region comprising SEQ ID NO:25 and a light chain variable region comprising SEQ ID NO:26. In some embodiments, the anti-GCGR antibody comprises a heavy chain variable region comprising SEQ ID NO:220 and a light chain variable region comprising SEQ ID NO:221. In some embodiments, the anti-GCGR antibody is Hz6B5.

In certain embodiments, a method comprises assessing the efficacy of an anti-GCGR antibody described herein in preventing or treating a beta cell defective disease, disorder, or condition, or a symptom thereof, in a subject, wherein the method comprises comparing the beta cell function in the subject before and after administration of the antibody. In some embodiments, an increase in beta cell function after administration of the antibody as compared to before administration of the antibody is indicative of the efficacy of the antibody in preventing or treating the beta cell defective disease, disorder, or condition, or symptom thereof. In some embodiments, a method comprises assessing the efficacy of an anti-GCGR antibody described herein in preventing or treating a beta cell defective disease, disorder, or condition, or a symptom thereof, in a subject, wherein the method comprises comparing serum or plasma C-peptide in the subject before and after administration of the antibody. In some embodiments, an increase in serum or plasma C-peptide after administration of the antibody as compared to before administration of the antibody is indicative of the efficacy of the antibody in preventing or treating the beta cell defective disease, disorder, or condition, or symptom thereof. In some embodiments, a method comprises assessing the efficacy of an anti-GCGR antibody described herein in preventing or treating a beta cell defective disease, disorder, or condition, or a symptom thereof, in a subject, wherein the method comprises comparing pancreatic gene expression of Ins1, Ins2, and/or Ngn3 in the subject before and after administration of the antibody. In some embodiments, an increase in pancreatic expression of Insl, Ins2, and/or Ngn3 after administration of the antibody as compared to before administration of the antibody is indicative of the efficacy of the antibody in preventing or treating the beta cell defective disease, disorder, or condition, or symptom thereof. In some embodiments, a decrease in blood glucose after administration of the antibody as compared to before administration of the antibody is indicative of the efficacy of the antibody in preventing or treating the beta cell defective disease, disorder or condition, or symptom thereof. In some embodiments, the method further comprises one or more subsequent administrations of the antibody to the subject following the assessment of efficacy. In some embodiments, the anti-GCGR antibody is selected from the group consisting of 6B5, 3H5, 5B11, 1C1, 1C3, 1H2, 4F8, 13G9, 14F4, and 14E9. In some embodiments, the anti-GCGR antibody comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the anti-GCGR antibody comprises a heavy chain variable region comprising SEQ ID NO:25 and a light chain variable region comprising SEQ ID NO:26. In some embodiments, the anti-GCGR antibody comprises a heavy chain variable region comprising SEQ ID NO:220 and a light chain variable region comprising SEQ ID NO:221. In some embodiments, the anti-GCGR antibody is Hz6B5.

In some embodiments, a method comprises selecting a group of subjects having beta cell defective disease, disorder, or condition, or a symptom thereof, based on beta cell function for the purposes of predicting clinical response, monitoring clinical response, or monitoring subject compliance to dosing with an anti-GCGR antibody described herein. In some embodiments of the various methods provided herein, the subject has increased beta cell function after treatment. In certain embodiments, a method comprises selecting a group of subjects having beta cell defective disease, disorder, or condition, or a symptom thereof, based on serum C-peptide, blood insulin, pancreatic insulin, and/or blood glucose for the purposes of predicting clinical response, monitoring clinical response, or monitoring subject compliance to dosing with an anti-GCGR antibody described herein. In some embodiments of the various methods provided herein, the subject has increased serum C-peptide, increased serum insulin, increased pancreatic insulin, and/or decreased blood glucose after treatment. In certain embodiments, a method comprises selecting a group of subjects having beta cell defective disease, disorder, or condition, or a symptom thereof, based on the pancreatic gene expression of Ins1, Ins2, and/or Ngn3 for the purposes of predicting clinical response, monitoring clinical response, or monitoring subject compliance to dosing with an anti-GCGR antibody described herein. In some embodiments of the various methods provided herein, the subject has increased pancreatic expression ofInsl, Ins2, and/or Ngn3 after treatment. In certain embodiments, the levels are compared to the normal population. In some embodiments, of the various methods provided herein, the subject is a subject in need thereof. In some embodiments, the anti-GCGR antibody is selected from the group consisting of 6B5, 3H5, 5B11, 1C1, 1C3, 1H2, 4F8, 13G9, 14F4, and 14E9. In some embodiments, the anti-GCGR antibody comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the anti-GCGR antibody comprises a heavy chain variable region comprising SEQ ID NO:25 and a light chain variable region comprising SEQ ID NO:26. In some embodiments, the anti-GCGR antibody comprises a heavy chain variable region comprising SEQ ID NO:220 and a light chain variable region comprising SEQ ID NO:221. In some embodiments, the anti-GCGR antibody is Hz6B5.

In some embodiments of the methods described herein, a method comprises administering a GCGR-binding protein (e.g., an antibody) described herein in combination with at least one additional therapeutic agent or therapeutic therapy. Treatment with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistance to an agent will develop.

In some embodiments, the combination of a GCGR-binding protein (e.g., an antibody) described herein and at least one additional therapeutic agent results in additive or synergistic results. In some embodiments, the combination therapy results in an increase in the therapeutic index of the GCGR-binding protein. In some embodiments, the combination therapy results in an increase in the therapeutic index of the additional therapeutic agent(s). In some embodiments, the combination therapy results in a decrease in the toxicity and/or side effects of the GCGR-binding protein. In some embodiments, the combination therapy results in a decrease in the toxicity and/or side effects of the additional therapeutic agent(s).

In some embodiments, an additional therapeutic agent can be administered prior to, concurrently with, and/or subsequently to, administration of the GCGR-binding protein. In some embodiments, the at least one additional therapeutic agent comprises 1, 2, 3, or more additional therapeutic agents.

Combined administration can include co-administration, either in a single pharmaceutical formulation or using separate formulations, or consecutive administration in either order but generally within a time period such that all active agents can exert their biological activities. Preparation and dosing schedules for additional therapeutic agents can be used according to manufacturers' instructions or as determined empirically by the skilled practitioner.

Additional therapeutic agents may be administered in combination with the GCGR-binding proteins described herein. In some embodiments, the GCGR-binding protein is an anti-GCGR antibody selected from the group consisting of 6B5, 3H5, 5B11, 1C1, 1C3, 1H2, 4F8, 13G9, 14F4, and 14E9. In some embodiments, the anti-GCGR antibody comprises: a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, the anti-GCGR antibody comprises a heavy chain variable region comprising SEQ ID NO:25 and a light chain variable region comprising SEQ ID NO:26. In some embodiments, the anti-GCGR antibody comprises a heavy chain variable region comprising SEQ ID NO:220 and a light chain variable region comprising SEQ ID NO:221. In some embodiments, the GCGR-binding protein is anti-GCGR antibody Hz6B5. In some embodiments, an additional therapeutic agent is a hyperglycemia or diabetes drug. Hyperglycemia or diabetes drugs include, but are not limited to, insulin and insulin mimetics; PPAR (peroxisome proliferator-activated receptor) γ-agonists, such as pioglitazone, troglitazone, ciglitazone, rivoglitazone, rosiglitazone, and other 2,4-thiazolidinedione derivatives; DPP-4 inhibitors, such as sitagliptin (JANUVIA), vildagliptin, saxagliptin, linagliptin (TRADJENTA), dutogliptin, gemigliptin, and alogliptin (NESINA); GLP-1 analogs, such as exenatide, liraglutide, taspoglutide, albiglutide, and lixisenatide; biguanidine derivatives, such as metformin (GLUMETZA, GLUCOPHAGE), buformin, and phenformin; ATP-sensitive potassium channel modulators, such as mitiglinide, repaglinide, and nateglinide; sulfonylurea derivatives, such as tolbutamide, chlorpropamide, tolazamide, acetohexamide, glipizide, gliclazide, glimepiride, gliquidone, glibornuride, glisoxepid, glibenclamide, glisentide, glisolamide, glybuzole, and glyclopyramide; α-glucosidase inhibitors, such as miglitol (GLYSET), acarbose (PRECOSE), and voglibose; and SGLT2 inhibitors, such as canagliflozin (INVOKANA), dapagliflozin (FARXIGA), and empagliflozin (JARDIANCE).

In some embodiments, an additional therapeutic agent is an obesity drug. Obesity drugs include, but are not limited to, orlistat (XENICAL), phentermine/topiramate (QSYMIA), lorcaserin (BELVIQ), naltrexone/bupropion (CONTRAVE) and liraglutide (SAXENDA).

In some embodiments, an additional therapeutic agent is a lipid-lowering drug or a cholesterol-lowering drug. Lipid-lowering drugs include, but are not limited to, fibrates, statins, omega-3 fatty acids, and niacin. In some embodiments, an additional therapeutic agent is a fibrate. Fibrates are a class of amphipathic carboxylic acids and include, but are not limited to, aluminum clofibrate, bezafibrate, ciprofibrate, choline fenofibrae, clinofibrate, clofibrate (e.g., ATROMID-S), clofibride, fenofibrate (e.g., FIBRICOR, LOFIBRA, TRICOR), gemfibrozil (e.g., LOPID), ronifibrate, simfibrate, and fenofibric acid. In some embodiments, an additional therapeutic agent is a statin. Statins are HMG-CoA reductase inhibitors and include, but are not limited to, atorvastatin (LIPITOR), fluvastatin (LESCOL), lovastatin (MEVACOR), pravastatin (PRAVACHOL), rosuvastatin (ZOCOR), and pitavastatin (LIVALO). In some embodiments, the additional therapeutic agent is niacin (vitamin B3). In some embodiments, the additional therapeutic agent is an omega-3 fatty acid.

In some embodiments, an additional therapeutic agent is selected from the group including, but to limited to, glucagon receptor antagonists; GLP-1, GLP-1 mimetics, and GLP-1 receptor agonists; GIP, GIP mimetics, and GIP receptor agonists; PACAP, PACAP mimetics, and PACAP receptor 3 agonists; cholesterol-lowering agents such as HMG-CoA reductase inhibitors, sequestrants, nicotinyl alcohol, nicotinic acid and salts thereof, PPAR alpha agonists, PPAR alpha/gamma dual agonists, inhibitors of cholesterol absorption, acyl CoA: cholesterol acyltransferase inhibitors, anti-oxidants, and LXR modulators; PPAR delta agonists; anti-obesity compounds; ileal bile acid transporter inhibitors; anti-inflammatory agents excluding glucocorticoids; protein tyrosine phosphatase-1B (PTP-IB) inhibitors, and CB1 antagonists/inverse agonists.

In some embodiments, an additional therapeutic agent is selected from the group including, but not limited to, analgesic agents, antibiotics, or immunomodulatory agents, or any other agent listed in the U.S. Pharmacopoeia and/or Physician's Desk Reference. In some embodiments, an additional therapeutic agent is a non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and pyrazolones (apazone, bezpiperylon, feprazone, mofebutazone, oxyphenbutazone, phenylbutazone). In some embodiments, an additional therapeutic agent is a cyclooxygenase-2 (COX-2) inhibitor. In some embodiments, an additional therapeutic agent is a steroid such as prednisolone, prednisone, methylprednisolone, betamethasone, dexamethasone, or hydrocortisone. In some embodiments, an additional therapeutic agent is a cytokine suppressive anti-inflammatory drug (CSAID) or an antibody to or antagonist of other human cytokines or growth factors such as TNF, LT, IL-1β, IL-2, IL-6, IL-7, IL-8, IL-15, IL-16, IL-18, EMAP-II, GM-CSF, FGF, and PDGF. In some embodiments, an additional therapeutic agent is a TNF antagonist such as an TNF antibody (e.g., REMICADE), an anti-TNF antibody fragment (e.g., CDP870), a soluble p55 or p75 TNF receptor or derivatives thereof, ENBREL, LENERCEPT, a soluble IL-13 receptor, a TNF-alpha converting enzyme (TACE) inhibitor, an IL-1 inhibitor, interleukin 11, an anti-P7s, p-selectin glycoprotein ligand (PSGL), interferon-beta-la (AVONEX), interferon-beta-lb (BETASERON), copaxone, hyperbaric oxygen, intravenous immunoglobulin, or clabribin. In some embodiments, an additional therapeutic agent is betatrophin. In some embodiments, an additional therapeutic agent is ciliary neurotrophic factor (CNTF).

For the treatment of a disease, the appropriate dosage of a GCGR-binding protein (e.g., an antibody) of the present disclosure depends on the disorder or disease to be treated, the severity and course of the disorder or disease, the responsiveness of the disorder or disease, whether the agent is administered for therapeutic or preventative purposes, previous therapy, the patient's clinical history, and so on. The GCGR-binding protein can be administered one time or over a series of treatments lasting from several days to several months, or until a cure is effected or a diminution of the disease state is achieved.

It will be appreciated that the combination of a GCGR-binding protein (e.g., an antibody) described herein and at least one additional therapeutic agent may be administered in any order or concurrently. In some embodiments, the GCGR-binding protein is administered to subjects that have previously undergone treatment with a therapeutic agent. In some embodiments, the GCGR-binding protein and a second therapeutic agent is administered substantially simultaneously or concurrently. For example, a subject may be given a GCGR-binding protein while undergoing a course of treatment with a second therapeutic agent (e.g., anti-diabetic agent). In some embodiments, a GCGR-binding protein is administered within 1 year of the treatment with a second therapeutic agent. In some embodiments, a GCGR-binding protein is administered within 10, 8, 6, 4, or 2 months of any treatment with a second therapeutic agent. In some embodiments, a GCGR-binding protein is administered within 4, 3, 2, or 1 weeks of any treatment with a second therapeutic agent. In some embodiments, a GCGR-binding protein is administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

The dose of a GCGR-binding protein (e.g., an antibody) described herein may vary depending on the nature and/or severity of the disease or disorder, as well as the condition of the subject. In some embodiments, dosage of the protein is from 0.01 μg to 100 mg/kg of body weight, from 0.1 μg to 100 mg/kg of body weight, from 1 μg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In some embodiments, dosage of the protein is from about 0.1 mg to about 20 mg/kg of body weight. In some embodiments, dosage of the protein is about 0.5 mg/kg of body weight. In some embodiments, dosage of the protein is about 1 mg/kg of body weight. In some embodiments, dosage of the protein is about 1.5 mg/kg of body weight. In some embodiments, dosage of the protein is about 2 mg/kg of body weight. In some embodiments, dosage of the protein is about 2.5 mg/kg of body weight. In some embodiments, dosage of the protein is about 5 mg/kg of body weight. In some embodiments, dosage of the protein is about 7.5 mg/kg of body weight. In some embodiments, dosage of the protein is about 10 mg/kg of body weight. In some embodiments, dosage of the protein is about 12.5 mg/kg of body weight. In some embodiments, dosage of the protein is about 15 mg/kg of body weight. In some embodiments, the protein is dosed once or more daily, weekly, monthly, or yearly. In some embodiments, the protein is dosed once every week, once every two weeks, once every three weeks, or once every four weeks.

The present disclosure provides compositions comprising a GCGR-binding protein (e.g., an antibody) described herein. In some embodiments, a composition comprises an anti-GCGR antibody selected from the group consisting of 6B5, 3H5, 5B11, 1C1, 1C3, 1H2, 4F8, 13G9, 14F4, and 14E9. In some embodiments, to composition comprises an anti-GCGR antibody that comprises a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, a composition comprises an anti-GCGR antibody that comprises a heavy chain variable region comprising SEQ ID NO:25 and a light chain variable region comprising SEQ ID NO:26. In some embodiments, a composition comprises an anti-GCGR antibody that comprises a heavy chain variable region comprising SEQ ID NO:220 and a light chain variable region comprising SEQ ID NO:221. In some embodiments, a composition comprises the anti-GCGR antibody Hz6B5. The present disclosure also provides pharmaceutical compositions comprising a GCGR-binding protein (e.g., an antibody) described herein and a pharmaceutically acceptable vehicle. In some embodiments, a pharmaceutical composition comprises an anti-GCGR antibody selected from the group consisting of 6B5, 3H5, 5B11, 1C1, 1C3, 1H2, 4F8, 13G9, 14F4, and 14E9. In some embodiments, a pharmaceutical composition comprises an anti-GCGR antibody that comprises a heavy chain CDR1 comprising SEQ ID NO:1, a heavy chain CDR2 comprising SEQ ID NO:2, a heavy chain CDR3 comprising SEQ ID NO:3, a light chain CDR1 comprising SEQ ID NO:4, a light chain CDR2 comprising SEQ ID NO:5, and a light chain CDR3 comprising SEQ ID NO:6. In some embodiments, a pharmaceutical composition comprises an anti-GCGR antibody that comprises a heavy chain variable region comprising SEQ ID NO:25 and a light chain variable region comprising SEQ ID NO:26. In some embodiments, a pharmaceutical composition comprises an anti-GCGR antibody that comprises a heavy chain variable region comprising SEQ ID NO:220 and a light chain variable region comprising SEQ ID NO:221. In some embodiments, a pharmaceutical composition comprises the anti-GCGR antibody Hz6B5.

Formulations are prepared for storage and/or use by combining a purified protein or antibody of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition. A formulation prepared for storage of a binding protein may be different or distinct from a formulation or composition prepared for use in a subject, for example, a preparation for intravenous injection.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy, 22$^{nd}$ Edition,* 2012, Pharmaceutical Press, London.). In some embodiments, the formulation is in the form of an aqueous solution. In some embodiments, the formulation is lyophilized or in an alternative dried form.

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present disclosure, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol, and cellulose acetate.

The binding proteins of the present disclosure may be formulated in any suitable form for delivery to a target cell/tissue. In some embodiments, a GCGR-binding protein (e.g., an antibody) is formulated as a liposome, microparticle, microcapsule, albumin microsphere, microemulsion, nano-particle, nanocapsule, or macroemulsion. In some embodiments, the pharmaceutical formulation includes a protein of the present disclosure complexed with liposomes. Methods to produce liposomes are known to those of skill in the art. For example, some liposomes are generated by reverse phase evaporation with a lipid composition comprising phosphatidylcholine, cholesterol, and PEG-derivatized phosphatidylethanolamine (PEG-PE).

In some embodiments, a GCGR-binding protein (e.g., an antibody) is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions or formulations of the present disclosure can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

Various delivery systems are known and can be used to administer a GCGR-binding protein (e.g., an antibody) described herein. In some embodiments, a GCGR-binding protein (e.g., an antibody) or a composition described herein is delivered in a controlled release or sustained release system. In some embodiments, a pump is used to achieve a controlled or sustained release. In some embodiments, polymeric materials are used to achieve a controlled or sustained release of a GCGR-binding protein (e.g., an antibody) described herein. Examples of polymers used in sustained release formulations include, but are not limited to, poly 2-hydroxy ethyl methacrylate, polymethyl methacrylate, polyacrylic acid, polyethylene-co-vinyl acetate, polymethacrylic acid, polyglycolides (PLG), polyanhydrides, poly N-vinyl pyrrolidone, polyvinyl alcohol (PVA), polyacrylamide, polyethylene glycol (PEG), polylactides (PLA), polylactide-co-glycolides (PLGA), and polyorthoesters. Any polymer used in a sustained release formulation should be inert, free of leachable impurities, stable on storage, sterile, and biodegradable.

In some embodiments, additional delivery systems are used to administer a GCGR-binding protein (e.g., an antibody) described herein including, but not limited to, injectable drug delivery devices and osmotic pumps. Injectable drug delivery devices include, for example, hand-held devices (e.g., autoinjectors) or wearable devices. Different types of osmotic pump systems may include single compartment systems, dual compartment systems, and multiple compartment systems.

V. Assays and/or Kits Comprising GCGR-Binding Proteins

In some embodiments, the anti-GCGR antibodies and fragments thereof described herein are useful for detecting GCGR in a biological sample. Such anti-GCGR antibodies can include those that bind to human and/or cyno GCGR, but do not inhibit GCGR activity. The term "detecting" as used herein encompasses quantitative or qualitative detection. In some embodiments, a biological sample comprises a cell, tissue, blood, or other bodily fluid.

In some embodiments, a method of detecting GCGR in a biological sample comprises contacting the biological sample with an anti-GCGR antibody under conditions permissive for binding of the anti-GCGR antibody to GCGR, and detecting whether a complex is formed between the anti-GCGR antibody and GCGR. The methods may include assays known by those of skill in the art, such as Western blot analyses, radioimmunoassays, ELISAs (enzyme linked immunosorbent assays), "sandwich" immunoassays, immunoprecipitation assays, fluorescent immunoassays, protein A immunoassays, and immunohistochemistry (IHC).

In some embodiments, an anti-GCGR antibody is tagged with a detectable label. The detectable label may be a fluorescent molecule, a chemiluminescent molecule, a bioluminescent molecule, an enzyme, or a radioisotope.

The present disclosure provides kits that comprise a GCGR-binding protein (e.g., an antibody) described herein and that can be used to perform the methods described herein. In some embodiments, a kit comprises at least one purified GCGR-binding protein in one or more containers. In some embodiments, a GCGR-protein protein is an anti-GCGR antibody selected from the group consisting of 6B5, 3H5, 5B11, 1C1, 1C3, 1H2, 4F8, 13G9, 14F4, and 14E9. In some embodiments, a GCGR-binding protein is the anti-GCGR antibody Hz6B5. In some embodiments, the kits contain all of the components necessary and/or sufficient to perform a detection assay, including all controls, directions for performing assays, and any necessary software for analysis and presentation of results. One skilled in the art will readily recognize that the disclosed GCGR-binding proteins of the present disclosure can be readily incorporated into one of the established kit formats that are well known in the art. Further provided are kits that comprise a GCGR-binding protein (e.g., an antibody) as well as at least one additional therapeutic agent.

EXAMPLES

Example 1

Generation of Antibodies

Antibodies to glucagon receptor (GCGR) were generated by injecting mice (i) with cells expressing human GCGR or (ii) with a His-tagged soluble protein comprising an extracellular domain of human GCGR.

GCGR-expressing cells were prepared as follows. CHO 3E7 cells were transfected with a nucleic acid sequence encoding human GCGR. Cells were analyzed for expression of GCGR by FACS and positive cells were isolated. The soluble protein comprising an extracellular domain of human GCGR was generated by standard recombinant techniques and purified using the His tag. Mice were immunized with a membrane preparation of the GCGR-expressing cells or the soluble GCGR protein. Mice were boosted to induce high titers. Antibody titers in serum were determined by ELISA and FACS. Single cell suspensions of lymphocytes were obtained from the spleen and draining lymph nodes of mice with suitable titers. Lymphocytes were fused with SP2/0 myeloma cells at a ratio of 1:1 by electrofusion. Fused cells were plated into 384-well plates in the presence of HAT selection media. After 10-14 days of culture, supernatants were collected and initially screened by (i) FACS using GCGR-expressing cells or (ii) Biacore using soluble GCGR (e.g., the extracellular domain of GCGR) to identify binders.

Example 2

Screening for GCGR Binding

Supernatants produced from the hybridoma fusions described in Example 1 were screened for binding to human GCGR using CHO cells that stably expressed full length GCGR in a FACS-based binding assay or a CellInsight™ HCS platform (ThermoFischer Scientific). Briefly, hybridoma supernatants were incubated with human GCGR-expressing cells for 30 minutes at 4° C. After washing with PBS/1% BSA/0.1% azide, the cells were incubated with a labeled anti-mouse Fc antibody (Jackson Immunoresearch) for 30 minutes at 4° C. After washing with PBS/1% BSA/0.1% azide, the cells were analyzed using a flow cytometer (BD FACSCalibur instrument) and cytometric analytical software (FLOWJO™) or the CELLINSIGHT™ Platform.

In some experiments, supernatants were screened for binding to human GCGR using a Biacore SPR system. Briefly, anti-mouse Fc antibody (Sigma-Aldrich) was immobilized on all four flow cells of a CM5 chip using amine coupling reagents (GE Healthcare Life Sciences). Hybridoma supernatants were diluted three-fold with PBS-P buffer (PBS containing 0.005% P20) and injected for 30 seconds over flow cells 2, 3 and 4 to capture the test antibodies and using flow cell 1 as a reference. The next step was a injection of soluble human GCGR extracellular domain (100 nM in PBS-P buffer) at a flow rate of 50 µL/min and monitoring of the binding kinetics at 25° C. Kinetic data were collected over time and fit using the simultaneous global fit equation to yield affinity constants ($K_D$ values) for each antibody.

More than 1500 antibodies were identified as binding to human GCGR. A subset of the positive binders were purified and subsequently re-tested for their binding affinities to human GCGR and cyno GCGR. Antibodies were rank-ordered based on their binding affinities to human GCGR as determined by Biacore.

Representative results are reported as $K_D$ (nM) values as shown in Table 11.

TABLE 11

| Anti-GCGR Antibody | $K_D$ (nM) |
| --- | --- |
| 6B5 | 0.22 |
| 5B11 | 1.2 |
| 3H5 | 2.2 |
| 1H7 | 2.4 |
| 1A2 | 0.98 |
| 1B4 | 7.7 |
| 1C1 | 1.9 |
| 1H2 | 3.7 |
| 1C3 | 1.4 |
| 1D2 | 4.1 |
| 13G9 | 0.25 |
| 14E9 | 0.8 |
| 14F4 | 0.57 |
| 4F8 | 0.5 |

Example 3

Additional Binding and Competition Binding Assays

Antibodies identified as binding to GCGR as described in Example 2 were evaluated in competition binding assays and/or epitope binning experiments.

To evaluate the binding sites of the antibodies on human GCGR extracellular domain, epitope binning experiments were set up on an Octet® QK 384 System (ForteBio). $K_D$ values for exemplary antibodies were derived using ForteBio software. Exemplary antibodies 6B5, 13G9, 14E9, 14F4, 4F8, 1G7, 1A8, 1H7, 1A2, 1B4, 1C1, 1H2, 1C3, and 1D2 were immobilized on biosensor tips. Soluble human GCGR extracellular domain (500 nM) was incubated with the antibodies for 3 minutes. This resulted in formation of an antibody-GCGR complex on the biosensor tip. The biosensor tips with bound antibody-GCGR complex were then dipped in 6B5, 5B11, or 3H5 antibody solution and the change in signal measured as a nm shift. Results of a representative experiment are shown in Table 12. If the antibody in solution recognized the same epitope as the antibody immobilized on the chip surface, then <0.1 nm shift in signal (noise level of Octet®) would be observed. If the antibody in solution recognized a distinct epitope relative to the immobilized antibody, an increase in signal of >0.15 nm shift would be observed. In the latter scenario, the antibody in solution could bind to the immobilized antibody-GCGR complex (presumably to a different epitope) resulting in the observed increase in signal.

In competition binding experiments using the Octet system, antibody 6B5 competed with itself for binding to GCGR and also competed with antibodies 13G9, 14E9, 14F4, 4F8, 1G7, 1A8, 1H7, 1A2, 1B4, 1C1, 1H2, 1C3 and 1D2. As shown in Table 12, antibodies 5B11 and 3H5 also competed with antibodies 6B5, 13G9, 14E9, 14F4, 4F8, 1G7, 1A8, 1H7, 1A2, 1B4, 1C1, 1H2, 1C3 and 1D2. These results suggested that all of these antibodies bind to the same epitope, a similar epitope, and/or an overlapping epitope. Therefore, these antibodies were grouped as members of the 6B5 epitope bin.

TABLE 12

| Antibody Immobilized on Biosensor | Shift on Octet by Antibody in Solution (nm) | | |
|---|---|---|---|
| | 6B5 | 5B11 | 3H5 |
| 6B5 | <0.05 | <0.05 | <0.05 |
| 13G9 | <0.05 | <0.05 | <0.05 |
| 14E9 | <0.05 | <0.05 | <0.05 |
| 14F4 | <0.05 | <0.05 | <0.05 |
| 4F8 | <0.05 | <0.05 | <0.05 |
| 1G7 | <0.05 | <0.05 | <0.05 |
| 1A8 | <0.05 | <0.05 | <0.05 |
| 1H7 | <0.05 | <0.05 | <0.05 |
| 1A2 | <0.05 | <0.05 | <0.05 |
| 1B4 | <0.05 | <0.05 | <0.05 |
| 1C1 | <0.05 | <0.05 | <0.05 |
| 1H2 | <0.05 | <0.05 | <0.05 |
| 1C3 | <0.05 | <0.05 | <0.05 |
| 1D2 | <0.05 | <0.05 | <0.05 |

Example 4

Functional Assays

Exemplary antibodies that bind to GCGR as described in Examples 1-3 were tested for their functional activity in cell-based assays. Since glucagon stimulates cAMP via activation of GCGR, anti-GCGR antibodies were tested for their ability to inhibit glucagon-induced cAMP production. For these experiments, the level of intracellular cAMP was measured using a cAMP cell-based assay kit following the manufacturer's instructions (Cisbio). Briefly, CHO cells transfected with full-length human GCGR cDNA were seeded at 1,000 cells/well in a 384 well plate. Anti-GCGR antibodies were serially diluted using culture medium containing 5 nM glucagon (Sigma) and 5 µL were added to each well. Cells were incubated for one hour in the dark. Each assay plate was read using a fluorescent plate reader at 615 nm/665 nm.

Results of several representative cAMP assays with anti-GCGR antibodies 6B5, 5B11, 3H5, 1H7, 1A2, 1B4, 1C1, 1H2, 1C3, 13G9, 13E9, 14F4, and 4F8 are shown in Table 13. Results are shown as IC50 determinations for each antibody.

TABLE 13

| Antibody | cAMP assay-1 $IC_{50}$ (nM) | cAMP assay-2 $IC_{50}$ (nM) | cAMP assay-3 $IC_{50}$ (nM) |
|---|---|---|---|
| 6B5 | 6.42 | 12.35 | 2.07 |
| 5B11 | 7.22 | | |
| 3H5 | 24.64 | | |
| 1H7 | 16.02 | | |
| 1A2 | | 28 | |
| 1B4 | | 6.68 | |
| 1C1 | | 14.35 | |
| 1H2 | 3.78 | | |
| 1C3 | 6.42 | 13.58 | |
| 13G9 | 7.22 | | 0.99 |
| 14E9 | 24.64 | | 1.32 |
| 14F4 | 16.02 | | 6.48 |
| 4F8 | | | 3.84 |

Example 5

Humanized Antibody

A number of the anti-GCGR antibodies described in Examples 1-4 were selected for sequence analyses. CDRs and heavy chain and light chain variable region amino acid sequences are shown in Tables 1-10 and the heavy chain and light chain variable sequences are aligned in FIGS. 1A-1 and 1A-2. An exemplary anti-GCGR antibody, 6B5, was selected for humanization. Human germline sequences which had significant similarity to the murine 6B5 heavy chain variable region and light chain variable region sequences were identified. Suitable human framework acceptors for heavy chain variable region included IGHV1-46, IGHV1-2, IGHV1-69 and IGHV5-51. Suitable acceptor sequences for light chain variable region included IGKV2-30, IGKV3-20, IGKV3-11 or IGKV1-39. Consideration of a multiplicity of factors, including sequence similarities, biophysical properties, and potential immunogenicity, led to the selection of IGHV1-69 and IGKV2-30 human framework sequences. Subsequently framework 4 sequences were selected using a similar approach. Sequences for mouse 6B5 heavy chain variable region and light chain variable region were searched against human immunoglobulin sequences in the Immunogenetics database (IMGT). IGHJ6-1 as well as IGKJ2-1 were selected as human donor sequences. The CDR sequences of murine 6B5 were then transferred (e.g., grafted) into the corresponding positions of IGHV1-69 and IGKV2-30 and J-region residues corresponding to framework 4 were added. The resulting protein sequence was back-translated into a DNA sequence, codon optimized for expression in mammalian cells, and synthesized (GeneArt/LifeTechnologies). Subsequently, the synthesized DNA fragment was cloned using In-Fusion (Clontech) into a pTT5 vector (NRC Biotechnology Research Institute) to create a hIgGK signal peptide-humanized 6B5vH-hIgG1 constant region and a hIgGK signal peptide-humanized 6B5VK-hIgGK constant region expression constructs (HC-199-69a and LC-199-30a respectively). Next, individual residues in the framework regions were empirically selected and back-mutated to mouse residues using QuikChange site-directed mutagenesis (Agilent). To determine whether the selected back mutations were beneficial for binding affinities of humanized antibodies to GCGR-derived from murine 6B5 sequences, various mutated heavy chain sequences were expressed with a chimeric 6B5 light chain and vice versa (mutated light chain sequences were expressed with chimeric 6B5 heavy chain). Surprisingly, the fully humanized sequences with zero back mutations showed similar binding affinities compared to the fully mouse antibody, as well as several additional humanized sequences. In contrast, most humanized light chain variants showed reduced binding. Surprisingly, one of the light chain variants (LC-199-30e with F42Y back mutation) showed comparable binding affinities and a second variant (LC-199-30g with R52L mutation) showed beneficial mutations. In additional assays, LC-199-30e plus an additional light chain variant with these two back mutations (LC-199-30i) were tested in combination with humanized heavy chain variants. After testing in additional assays such as described in Examples 2-4 (e.g., binding, affinity and cAMP assays), HC-199-69f and LC-199-30i were selected as humanized heavy chain variable region and light chain variable region sequences.

Example 6

Alanine Scanning Analysis

To assist in gathering information on the GCGR epitope that the 6B5 binning group bound to, "alanine scanning mutagenesis" was undertaken. Thse alanine scanning mutagenesis platform is a technique used for mapping both linear and conformational antigen epitopes by evaluating the effects of point mutations across a target protein. Single residues in a target protein are replaced by alanine one at a time to construct a mutant library. Each variant is assayed for its ability to bind to an antibody of interest. A failure of binding suggests that that amino acid is a part of or important to the binding site or epitope. Amino acids across the extracellular domain of GCGR were mutated to alanine and the anti-GCGR antibody Hz6B5 was tested for binding to the alanine mutants. The Hz6B5 antibody comprises a heavy variable region comprising SEQ ID NO:220 (also referred to as HC-199-69f) and a light chain variable region comprising SEQ ID NO:221 (also referred to as LC-199-30i).

The wild-type GCGR extracellular domain and the alanine mutants were each transfected into 293XP cells and incubated for 24 hours. Antibody Hz6B5 was incubated with the transfected cells for 30 minutes at 4° C. After washing with PBS/1% BSA/0.1% azide, the cells were incubated with a labeled anti-mouse Fc antibody (Jackson Immunoresearch) for 30 minutes at 4° C. After washing with PBS/1% BSA/0.1% azide, the cells were analyzed using a flow cytometer BD (FACSCalibur instrument) and cytometric analytical software (FLOWJO™). A serum sample from a mouse immunized with human GCGR was used as positive control to confirm expression of the alanine mutants.

A representative set of results are shown in Table 14 and FIG. 2.

TABLE 14

| GCGR - Ala Mutant | Hz6B5 (% positive cells) | Control mouse bleed |
| --- | --- | --- |
| 293 Control | 0.6 | 0.183 |
| WT GCGR | 87.8 | 89.5 |

TABLE 14-continued

| GCGR - Ala Mutant | Hz6B5 (% positive cells) | Control mouse bleed |
| --- | --- | --- |
| F31A | 85.1 | |
| L32A | 76.9 | |
| F33A | 71.8 | |
| W36A | 70.9 | |
| L38A | 3.3 | 24.2 |
| Y39A | 65.8 | |
| D41A | 84.3 | |
| H44A | 82.2 | |
| H45A | 81.3 | |
| L50A | 86.6 | |
| F62A | 62.8 | |
| K64A | 87.6 | |
| Y65A | 64.8 | |
| T75A | 84.9 | |
| W83A | 72.6 | |
| Y84A | 63.4 | |
| L85A | 11.7 | 34.6 |
| W87A | 74.7 | |
| K90A | 83.0 | |
| R94A | 0 | 66.8 |
| K98A | 82.5 | |
| W106A | 60.8 | |
| R111A | 84.5 | |
| R108A | 87.0 | |
| P110A | 84.7 | |
| Q113A | 83.4 | |
| R116A | 85.9 | |

Example 7

Animal Studies

Exemplary anti-GCGR antibodies 5B11, 3H5, and 6B5 were evaluated in animal studies. Anti-GCGR antibodies were tested for their effects on blood glucose in a TET-DTA mouse model.

TET-DTA transgenic mice were generated by crossing two transgenic lines: 1) B6.Cg-Tg(tetO-DTA), which expresses diphtheria toxin A (DTA) under the control of a tetracycline operator (tetO; also called tetracycline-responsive element (TRE) or tet-operator) and a cytomegalovirus minimal promoter; and 2) Ins2-rtTA, which expresses the reverse tetracycline-controlled transactivator (rtTA) protein under the control of the rat insulin 2 (Ins2) promoter. In the resultant double-transgenic TET-DTA mice, pancreatic beta cell expression of diphtheria toxin A is regulated by the tetracycline analog, doxycycline (dox). When induced by doxycycline, the production of diphtheria toxin A results in destruction of pancreatic beta cells.

TET-DTA transgenic mice were administered doxycycline through chow diet (2000 mg/kg). Five to six-week-old male mice were treated with doxycycline for 4 days and blood glucose levels were monitored. Within approximately 1 week, blood glucoses levels increased to approximately 500 mg/dL.

One week after doxycycline treatment, the mice were treated with anti-GCGR antibodies 3H5, 6B5, or 5B11 or control anti-KLH antibody. The antibodies were injected intraperitoneally at a dose of 10 mg/kg once a week for four weeks. Once a week, fed blood glucose levels were measured in tail blood using ACCU-CHEK Active test strips and an ACCU-CHEK Active meter (Roche Diagnostics) following the manufacturer's instructions.

Figure 3:
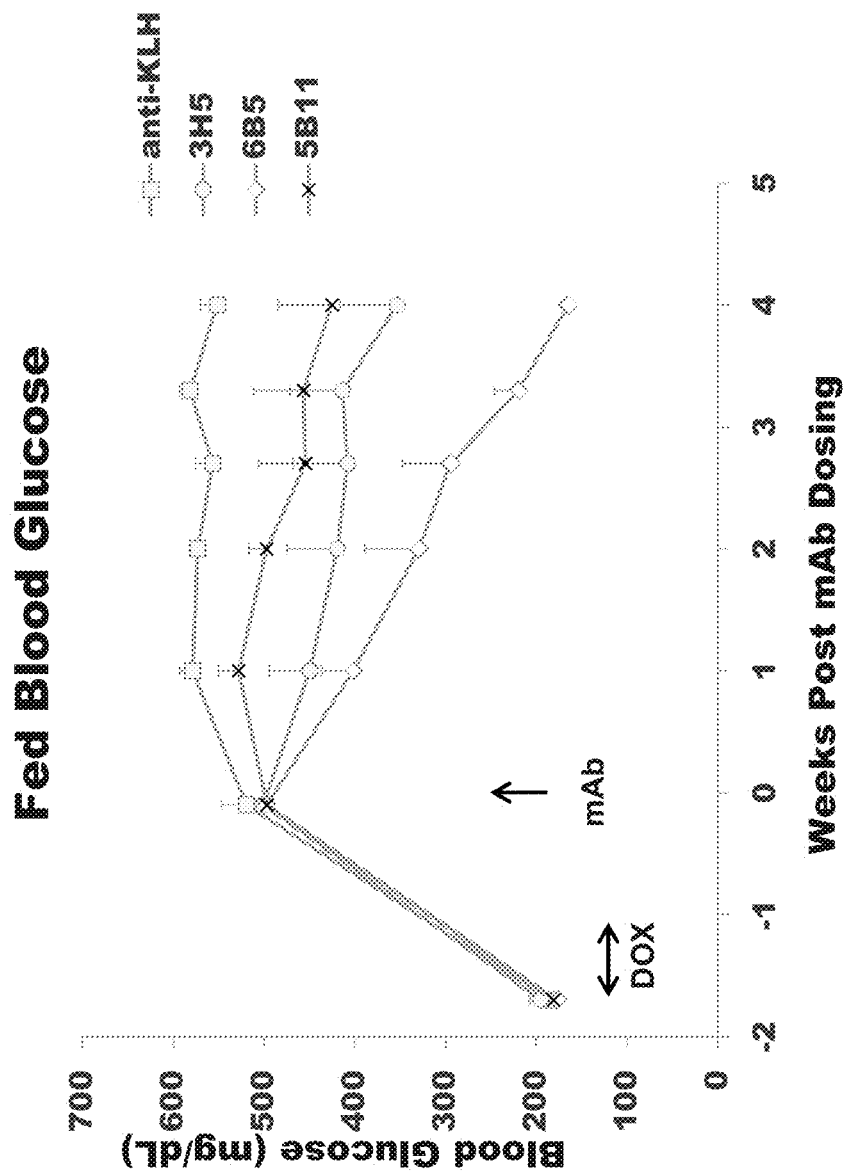
FIG. 3 depicts the results of an experiment comprising the administration of anti-GCGR antibodies 3H5, 6B5, and 5B11 in a TET-DTA mouse model.

As shown in FIG. 3, treatment with anti-GCGR antibodies 5B11, 3H5, or 6B5 significantly reduced blood glucose levels in the treated mice. Particularly, by week 4, blood glucose in the blood from mice treated with anti-GCGR antibody 6B5 was reduced to approximately 200 mg/dL, i.e., a level equivalent to the glucose level in the mice prior to destruction of beta cells.

Plasma insulin levels, plasma C-peptide levels, and pancreatic insulin content were determined at the end of 4 weeks of treatment to assess beta cell function. For blood insulin and C-peptide determinations, after a four hour fasting period tail blood was collected from mice in the four treatment groups. Whole blood (about 50 µl/mouse) from mouse tail snips was collected into plain capillary tubes. Serum and blood cells were separated by spinning the tubes in an Autocrit Ultra™ 3 centrifuge (Becton Dickinson). Commercially available ELISA kits (ALPCO) were used for analysis of blood insulin and C-peptide following the manufacturer's instructions. For pancreatic insulin content determination, after the mice were euthanized, approximately 50 mg of pancreatic tissue was homogenized in acid alcohol using TissueLyser™ (QIAGEN). Samples were incubated on a rotator in a cold room overnight. After spinning down the samples for 15 minutes at 12,000 rpm, supernatants were used for analysis of insulin content by ELISA. Samples were serially diluted from 1:20-1:200 and analyzed by ELISA.

Figures 4A, 4B, 4C:
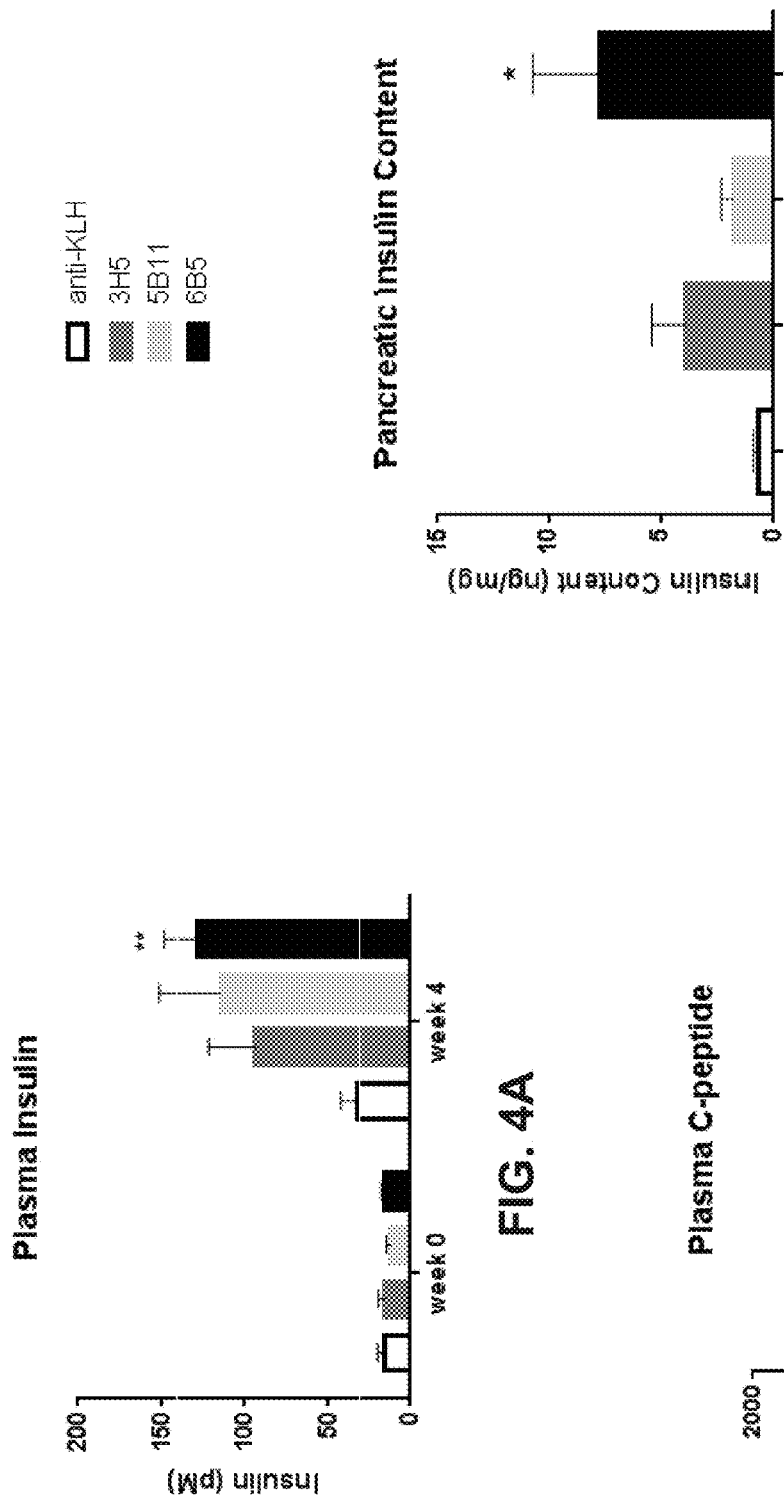
FIGS. 4A-4C depict the results of an experiment comprising the administration of anti-GCGR antibodies 3H5, 6B5, and 5B11 in a TET-DTA mouse model. (A) plasma levels of insulin; (B) plasma C-peptide; and (C) pancreatic insulin content.

As shown in FIGS. 4A and 4B, treatment with anti-GCGR antibodies 3H5, 5B11, and 6B5 increased plasma levels of both insulin and C-peptide. For example, after treatment with antibody 6B5, plasma insulin levels increased approximately 4-fold as compared to treatment with a control antibody. Similarly, after treatment with antibody 6B5 plasma C-peptide increased about 2-fold as compared to the treatment with the control antibody. In addition, as shown in FIG. 4C treatment with anti-GCGR antibodies 3H5, 5B11, or 6B5 increased pancreatic insulin content. In this experiment, treatment with anti-GCGR antibody 6B5 increased pancreatic insulin content by over 10-fold as compared to treatment with a control antibody.

These results suggest that treatment with anti-GCGR antibodies improved beta cell function in TET-DTA mice after destruction of beta cells.

A similar experiment as described above was undertaken in the TET-DTA mouse model to assess a humanized version of anti-GCGR antibody 6B5, Hz6B5.07mc. Antibody Hz6B5.07mc is a chimeric antibody that comprises a humanized heavy chain variable region, a humanized light chain variable region, and mouse heavy chain and light chain constant regions.

Figure 5B:
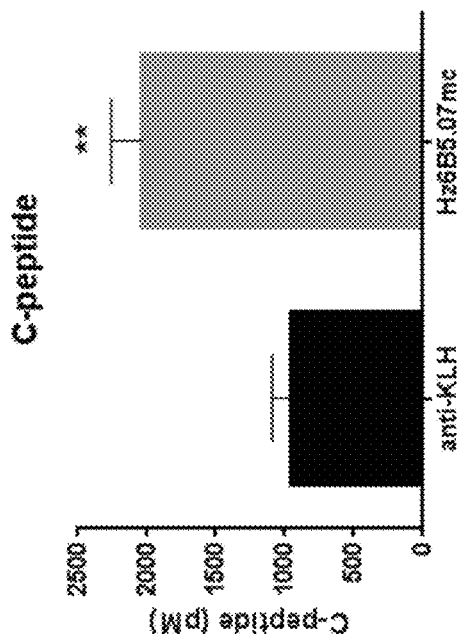
FIGS. 5A-5C depict the results of an experiment comprising the administration of humanized chimeric anti-GCGR antibody Hz6B5.07mc in a TET-DTA mouse model. (A) blood glucose; (B) C-peptide; and (C) pancreatic insulin content.
Figure 5C:
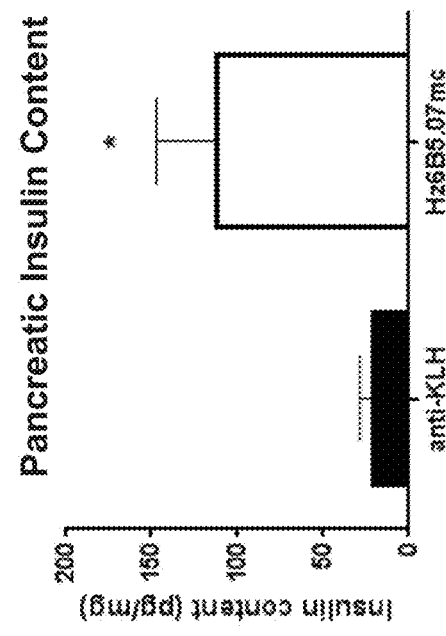
Figure 5A:
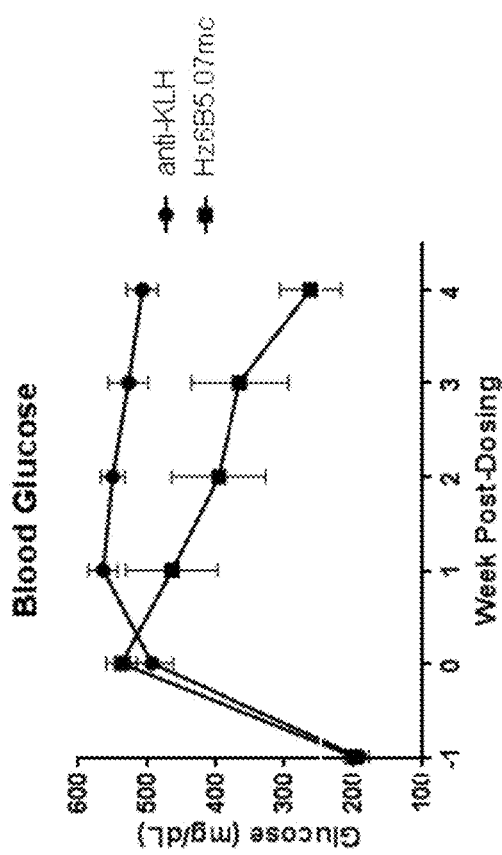

As shown in FIGS. 5A and 5B, treatment with anti-GCGR antibody Hz6B5.07mc significantly reduced blood glucose and increased blood C-peptide. In addition, as shown in FIG. 5C, treatment with anti-GCGR antibody Hz6B5.07mc significantly increased pancreatic insulin content.

These results demonstrated that a humanized version of an anti-GCGR antibody had similar functional capabilities as the parental anti-GCGR antibody.

Although the foregoing present disclosure has been described in some detail by way of illustration and example for purposes of clarity of understanding, the descriptions and examples should not be construed as limiting the scope of the present disclosure. The embodiments of the present disclosure described herein are intended to be merely exemplary, and those skilled in the art will recognize numerous equivalents to the specific procedures described herein. All such equivalents are considered to be within the scope of the present disclosure and are covered by the embodiments.

All publications, patents, patent applications, internet sites, and accession numbers/database sequences including both polynucleotide and polypeptide sequences cited herein are hereby incorporated by reference in their entirety for all purposes to the same extent as if each individual publication, patent, patent application, internet site, or accession number/database sequence were specifically and individually indicated to be so incorporated by reference.

Following are the sequences disclosed in the application with the exception of the sequences defined in Tables 1-10.

---

SEQUENCE LISTING

Hz6B5 Heavy chain variable region (SEQ ID NO: 220)
QVQLVQSGAEVKKPGSSVKVSCKASGFTFTNHWLGWVRQAPGQGLEWIGDIYPGGYYINY
NEKFKGRVTITADESTSTAYMELSSLRSEDTAVYYCARHTNYGSDYWGQGTIVIVSS Hz6B5 Light chain variable region (SEQ ID NO: 221)
DVVMTQSPLSLPVTLGQPASISCRSSQSIVDSYGNTFLEWYQQRPGQSPRLLIYKVSNRLS
GVPDRFSGSGSGTDFTLKISRVEAEDVGVYYCFQGSHVPWTFGQGTKLEIK Human CGCR amino acid sequence with predicted signal sequence
underlined (SEQ ID NO: 222)
MPPCQPQRPLLLLLLLACQPQVPSAQVMDFLFEKWKLYGDQCHHNLSLLPPPTELVCNR
TFDKYSCWPDTPANTTANISCPWYLPWHHKVQHRFVFKRCGPDGQWVRGPRGQPWRDASQ
CQMDGEEIEVQKEVAKMYSSFQVMYTVGYSLSLGALLLALAILGGLSKLHCTRNAIHANL
FASFVLKASSVLVIDGLLRTRYSQKIGDDLSVSTWLSDGAVAGCRVAAVFMQYGIVANYC
WLLVEGLYLHNLLGLATLPERSFFSLYLGIGWGAPMLFVVPWAVVKCLFENVQCWTSNDN
MGFWWILRFPVFLAILINFFIFVRIVQLLVAKLRARQMHHTDYKFRLAKSTLTLIPLLGV
HEVVFAFVTDEHAQGTLRSAKLFFDLFLSSFQGLLVAVLYCFLNKEVQSELRRRWHRWRL
GKVLWEERNTSNHRASSSPGHGPPSKELQFGRGGGSQDSSAETPLAGGLPRLAESPF Human CGCR amino acid sequence without predicted signal
sequence (SEQ ID NO: 223)
AQVMDFLFEKWKLYGDQCHHNLSLLPPPTELVCNRTFDKYSCWPDTPANTTANISCPWYL
PWHHKVQHRFVFKRCGPDGQWVRGPRGQPWRDASQCQMDGEEIEVQKEVAKMYSSFQVMY
TVGYSLSLGALLLALAILGGLSKLHCTRNAIHANLFASFVLKASSVLVIDGLLRTRYSQK
IGDDLSVSTWLSDGAVAGCRVAAVFMQYGIVANYCWLLVEGLYLHNLLGLATLPERSFFS
LYLGIGWGAPMLFVVPWAVVKCLFENVQCWTSNDNMGFWWILRFPVFLAILINFFIFVRI
VQLLVAKLRARQMHHTDYKFRLAKSTLTLIPLLGVHEVVFAFVTDEHAQGTLRSAKLFFD
LFLSSFQGLLVAVLYCFLNKEVQSELRRRWHRWRLGKVLWEERNTSNHRASSSPGHGPPS
KELQFGRGGGSQDSSAETPLAGGLPRLAESPF

SEQUENCE LISTING

Human CGCR extracellular domain (amino acids 26-136) (SEQ ID NO: 224)
AQVMDFLFEKWKLYGDQCHHNLSLLPPPTELVCNRTFDKYSCWPDTPANTTANISCPWYL
PWHHKVQHRFVFKRCGPDGQWVRGPRGQPWRDASQCQMDGEEIEVQKEVAK Human CGCR extracellular domain (amino acids 28-123) (SEQ ID NO: 225)
VMDFLFEKWKLYGDQCHHNLSLLPPPTELVCNRTFDKYSCWPDTPANTTANISCPWYLPW
HHKVQHRFVFKRCGPDGQWVRGPRGQPWRDASQCQM Human CGCR extracellular domain (amino acids 80-119) (SEQ ID NO: 226)
SCPWYLPWHHKVQHRFVFKRCGPDGQWVRGPRGQPWRDAS Cynomolgus monkey GCGR (SEQ ID NO: 227)
MPPCQPRRPLLLLLLLLACQPQAPSAQVMDFLFEKWKLYGDQCHHNLSLLPPPTELVCNR
TFDKYSCWPDTPANTTANISCPWYLPWHHKVQHRFVFKRCGPDGQWVRGPRGQPWRDASQ
CQMDGEELEVQKEVAKMYSSFQVMYTVGYSLSLGALLLALAVLGGISKLHCTRNAIHANL
FVSFVLKASSVLVIDGLLRTRYSQKIGDDLSVSIWLSDGAVAGCRVAAVFMQYGVVANYC
WLLVEGLYLHNLLGLATLPERSFFSLYLGIGWGAPMLFIIPWVVVRCLFENIQCWTSNDN
MGFWWILRFPVFLAILINFFIFIRIVHLLVAKLRAREMHHTDYKFRSFQGLLVAVLYCFL
NKEVQSELRRHWHRWRLGKVLQEERGTSNHKAPSAPGQGLPGKKLQSGRDGGSQDSSAEI
PLAGGLPRLAESPFSTLLGPQLGLDSGT Mouse GCGR (SEQ ID NO: 228)
MPLTQLHCPHLLLLLLVLSCLPEAPSAQVMDFLFEKWKLYSDQCHHNLSLLPPPTELVCN
RTFDNYSCWPDTPNNTANISCPWYLPWCHKVQHRLVFKRCGPDGQWVRGPRGQPWRNAS
QCQLDDEEIEVQKGVAKMYSSQQVMYTVGYSLSLGALLLALVILLGLRKLHCTRNYIHGN
LFASFVLKAGSVLVIDWLLKTRYSQKIGDDLSVSVWLSDGAMAGCRVATVIMQYGIIPNY
CWLLVEGVYLYSLLSLATFSERSFFSLYLGIGWGAPLLFVIPWVVVKCLFENVQCWTSND
NMGFWWILRIPVFLALLINFFIFVHIIQLLVAKLRAHQMYADYKFRLARSTLTLIPLLG
VHEVVVFAFVTDEHAQGTLRSTKLFFDLFLSSFQGLLVAVLYCFLNKEVQAELMRRWRQWQ
EGKALQEERLASSHGSHMAPAGPCHGDPCEKLQLMSAGSSSGTGCVPSMETSLASSLPRL
ADSPT Rat GCGR (SEQ ID NO: 229)
MLLTQLHCPYLLLLLVVLSCLPKAPSAQVMDFLFEKWKLYSDQCHHNLSLLPPPTELVCN
RTFDKYSCWPDTPPNTTANISCPWYLPWYHKVQHRLVFKRCGPDGQWVRGPRGQSWRDAS
QCQMDDDEIEVQKGVAKMYSSYQVMYTVGYSLSLGALLLALVILLGLRKLHCTRNYIHGN
LFASFVLKAGSVLVIDWLLKTRYSQKIGDDLSVSVWLSDGAVAGCRVATVIMQYGIIANY
CWLLVEGVYLYSLLSITTFSEKSFFSLYLCIGWGSPLLFVIPWVVVKCLFENVQCWTSND
NMGFWWILRIPVLLAILINFFIFVRIIHLLVAKLRAHQMHYADYKFRLARSTLTLIPLLG
VHEVVVFAFVTDEHAQGTLRSTKLFFDLFFSSFQGLLVAVLYCFLNKEVQAELLRRWRRWQ
EGKALQEERMASSHGSHMAPAGTCHGDPCEKLQLMSAGSSSGTGCEPSAKTSLASSLPRL
ADSPT Human IgG1 (SEQ ID NO: 230)
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK Human IgG1 E233A/L235A (SEQ ID NO: 231)
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPALAGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK Human IgG1 L234A/L235A (SEQ ID NO: 232)
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPEAAGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK Hz6B5 Heavy Chain amino acid sequence signal sequence
underlined (SEQ ID NO: 233)
<u>MDMRVPAQLLGLLLLWLRGARC</u>QVQLVQSGAEVKKPGSSVKVSCKASGFTFTNHWLGWVR
QAPGQGLEWIGDIYPGGYYINYNEKFKGRVTITADESTSTAYMELSSLRSEDTAVYYCAR
HTNYGSDYWGQGTTVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVEPK
SCDKTHTCPPCPAPALAGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK

SEQUENCE LISTING

Hz6B5 Heavy Chain amino acid sequence without signal
sequence (SEQ ID NO: 234)
QVQLVQSGAEVKKPGSSVKVSCKASGFTFTNHWLGWVRQAPGQGLEWIGDIYPGGYYINY
NEKFKGRVTITADESTSTAYMELSSLRSEDTAVYYCARHTNYGSDYWGQGTIVIVSSAST
KGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPALAGGPSV
FLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK Hz6B5 Light chain signal sequence underlined (SEQ ID NO: 235)
<u>MDMRVPAQLLGLLLLWLRGARC</u>DVVMTQSPLSLPVTLGQPASISCRSSQSIVDSYGNTFL
EWYQQRPGQSPRLLIYKVSNRLSGVPDRFSGSGSGTDFTLKISRVEAEDVGVYYCFQGSH
VPWTFGQGTKLEIKRTVAAPSVFIFPPSDEQLKSGTASVVCLLNNEYPREAKVQWKVDNA
LQSGNSQESVTEQDSKDSTYSLSSTLTLSKADYEKHKVYACEVTHQGLSSPVTKSENRGE
C Hz6B5 Light chain without signal sequence (SEQ ID NO: 236)
DVVMTQSPLSLPVTLGQPASISCRSSQSIVDSYGNTFLEWYQQRPGQSPRLLIYKVSNRL
SGVPDRFSGSGSGTDFTLKISRVEAEDVGVYYCFQGSHVPWTFGQGTKLEIKRTVAAPSV
FIFPPSDEQLKSGTASVVCLLNNEYPREAKVQWKVDNALQSGNSQESVTEQDSKDSTYSL
SSTLTLSKADYEKHKVYACEVTHQGLSSPVIKSENRGEC Heavy chain CDR2 consensus sequence (SEQ ID NO: 237)
DIX$_1$PGGX$_2$YX$_3$NYNX$_4$KHKX$_5$ wherein X$_1$ is Y, H, F, or S; X$_2$ is Y, G, F, or D;
X$_3$ is I, T, D, N, or S; X$_4$ is E, K, D, G, or A; X$_5$ is G, S, or D Light chain CDR1 consensus sequence (SEQ ID NO: 238)
RSSQX$_6$IVX$_7$SX$_8$GNTYLE wherein X$_6$ is S, T, or H; X$_7$ is D, H, or Y; X$_8$ is Y
or D The present specification is being filed with a computer readable form (CRF) copy of the Sequence Listing. The CRF entitled 13370-070-999_SEQ_LISTING.txt, which was created on Jan. 25, 2018 and is 108,270 bytes in size, is incorporated herein by reference in its entirety.

What is claimed:

1. An antibody that specifically binds human glucagon receptor (GCGR; SEQ ID NO:223), wherein the antibody comprises a heavy chain comprising the amino acid sequence set forth in SEQ ID NO:234 and a light chain comprising the amino acid sequence set forth in SEQ ID NO:236.

2. A pharmaceutical composition comprising the antibody of claim 1, and a pharmaceutically acceptable carrier.

3. An antibody that binds human glucagon receptor (GCGR; SEQ ID NO:223), wherein the antibody comprises a heavy chain variable region comprising the amino acid sequence set forth in SEQ ID NO:220 and a light chain variable region comprising the amino acid sequence set forth in SEQ ID NO:221.

4. The antibody of claim 3, which comprises a human IgG1 heavy chain constant region.

5. The antibody of claim 3, which comprises a human kappa light chain constant region.

6. The antibody of claim 3, which comprises a human IgG1 heavy chain constant region and a human kappa light chain constant region.

7. A pharmaceutical composition comprising the antibody of claim 3, and a pharmaceutically acceptable carrier.

8. A pharmaceutical composition comprising the antibody of claim 6, and a pharmaceutically acceptable carrier.

9. An antibody that specifically binds human glucagon receptor (GCGR; SEQ ID NO:223), wherein the antibody comprises:
(a) a heavy chain variable region comprising a heavy chain variable region CDR1 comprising GFTFTNHWLG (SEQ ID NO:1), a heavy chain variable region CDR2 comprising DIYPGGYYINYNEKFKG (SEQ ID NO:2), and a heavy chain variable region CDR3 comprising HTNYGSDY (SEQ ID NO:3); and
(b) a light chain variable region comprising a light chain variable region CDR1 comprising RSSQSIVDSYGNTFLE (SEQ ID NO:4), a light chain variable region CDR2 comprising KVSNRLS (SEQ ID NO:5), and a light chain variable region CDR3 comprising FQGSHVPWT (SEQ ID NO:6).

10. A pharmaceutical composition comprising the antibody of claim 9, and a pharmaceutically acceptable carrier.

11. The antibody of claim 9, wherein:
(a) the heavy chain variable region comprises an amino acid sequence having at least 90% sequence identity to SEQ ID NO:25 and the light chain variable region comprises an amino acid sequence having at least 90% sequence identity to SEQ ID NO:26; or
(b) the heavy chain variable region comprises an amino acid sequence having at least 90% sequence identity to SEQ ID NO:220 and the light chain variable region comprises an amino acid sequence having at least 90% sequence identity to SEQ ID NO:221.

12. The antibody of claim 9, wherein the heavy chain variable region comprises the amino acid sequence set forth in SEQ ID NO:25 and the light chain variable region comprises the amino acid sequence set forth in SEQ ID NO:26.

13. The antibody of claim 9, which is a monoclonal antibody, a humanized antibody, a chimeric antibody, a bispecific antibody, a multispecific antibody, an IgG antibody, or an antibody fragment comprising at least one antigen-binding site.

14. An antibody that competes with the antibody of claim 9 for specific binding to GCGR, wherein the antibody that competes with the antibody of claim 9 comprises:
(a) a heavy chain variable region comprising a heavy chain variable region CDR1 comprising the amino acid sequence set forth in SEQ ID NO:27, a heavy chain variable region CDR2 comprising the amino acid sequence set forth in SEQ ID NO:28, and a heavy chain variable region CDR3 comprising the amino acid sequence set forth in SEQ ID NO:29, and a light chain variable region comprising a light chain variable region CDR1 comprising the amino acid sequence set forth in SEQ ID NO:30, a light chain variable region CDR2 comprising the amino acid sequence set forth in SEQ ID NO:31, and a light chain variable region CDR3 comprising the amino acid sequence set forth in SEQ ID NO:32;

(b) a heavy chain variable region comprising a heavy chain variable region CDR1 comprising the amino acid sequence set forth in SEQ ID NO:53, a heavy chain variable region CDR2 comprising the amino acid sequence set forth in SEQ ID NO:54, and a heavy chain variable region CDR3 comprising the amino acid sequence set forth in SEQ ID NO:55, and a light chain variable region comprising a light chain variable region CDR1 comprising the amino acid sequence set forth in SEQ ID NO:56, a light chain variable region CDR2 comprising the amino acid sequence set forth in SEQ ID NO:31, and a light chain variable region CDR3 comprising the amino acid sequence set forth in SEQ ID NO:32;

(c) a heavy chain variable region comprising a heavy chain variable region CDR1 comprising the amino acid sequence set forth in SEQ ID NO:73, a heavy chain variable region CDR2 comprising the amino acid sequence set forth in SEQ ID NO:74, and a heavy chain variable region CDR3 comprising the amino acid sequence set forth in SEQ ID NO:75, and a light chain variable region comprising a light chain variable region CDR1 comprising the amino acid sequence set forth in SEQ ID NO:76, a light chain variable region CDR2 comprising the amino acid sequence set forth in SEQ ID NO:77, and a light chain variable region CDR3 comprising the amino acid sequence set forth in SEQ ID NO:78;

(d) a heavy chain variable region comprising a heavy chain variable region CDR1 comprising the amino acid sequence set forth in SEQ ID NO:99, a heavy chain variable region CDR2 comprising the amino acid sequence set forth in SEQ ID NO:100, and a heavy chain variable region CDR3 comprising the amino acid sequence set forth in SEQ ID NO:101, and a light chain variable region comprising a light chain variable region CDR1 comprising the amino acid sequence set forth in SEQ ID NO:102, a light chain variable region CDR2 comprising the amino acid sequence set forth in SEQ ID NO:103, and a light chain variable region CDR3 comprising the amino acid sequence set forth in SEQ ID NO:104;

(e) a heavy chain variable region comprising a heavy chain variable region CDR1 comprising the amino acid sequence set forth in SEQ ID NO:124, a heavy chain variable region CDR2 comprising the amino acid sequence set forth in SEQ ID NO:125, and a heavy chain variable region CDR3 comprising the amino acid sequence set forth in SEQ ID NO:126, and a light chain variable region comprising a light chain variable region CDR1 comprising the amino acid sequence set forth in SEQ ID NO:127, a light chain variable region CDR2 comprising the amino acid sequence set forth in SEQ ID NO:128, and a light chain variable region CDR3 comprising the amino acid sequence set forth in SEQ ID NO:6;

a heavy chain variable region comprising a heavy chain variable region CDR1 comprising the amino acid sequence set forth in SEQ ID NO:146, a heavy chain variable region CDR2 comprising the amino acid sequence set forth in SEQ ID NO:147, and a heavy chain variable region CDR3 comprising the amino acid sequence set forth in SEQ ID NO:148, and a light chain variable region comprising a light chain variable region CDR1 comprising the amino acid sequence set forth in SEQ ID NO:149, a light chain variable region CDR2 comprising the amino acid sequence set forth in SEQ ID NO:128, and a light chain variable region CDR3 comprising the amino acid sequence set forth in SEQ ID NO:6;

(g) a heavy chain variable region comprising a heavy chain variable region CDR1 comprising the amino acid sequence set forth in SEQ ID NO:166, a heavy chain variable region CDR2 comprising the amino acid sequence set forth in SEQ ID NO:167, and a heavy chain variable region CDR3 comprising the amino acid sequence set forth in SEQ ID NO:168, and a light chain variable region comprising a light chain variable region CDR1 comprising the amino acid sequence set forth in SEQ ID NO:169, a light chain variable region CDR2 comprising the amino acid sequence set forth in SEQ ID NO:170, and a light chain variable region CDR3 comprising the amino acid sequence set forth in SEQ ID NO:171;

(h) a heavy chain variable region comprising a heavy chain variable region CDR1 comprising the amino acid sequence set forth in SEQ ID NO:190, a heavy chain variable region CDR2 comprising the amino acid sequence set forth in SEQ ID NO:191, and a heavy chain variable region CDR3 comprising the amino acid sequence set forth in SEQ ID NO:192, and a light chain variable region comprising a light chain variable region CDR1 comprising the amino acid sequence set forth in SEQ ID NO:169, a light chain variable region CDR2 comprising the amino acid sequence set forth in SEQ ID NO:128, and a light chain variable region CDR3 comprising the amino acid sequence set forth in SEQ ID NO:193; or (i) a heavy chain variable region comprising a heavy chain variable region CDR1 comprising the amino acid sequence set forth in SEQ ID NO:190, a heavy chain variable region CDR2 comprising the amino acid sequence set forth in SEQ ID NO:205, and a heavy chain variable region CDR3 comprising the amino acid sequence set forth in SEQ ID NO:206, and a light chain variable region comprising a light chain variable region CDR1 comprising the amino acid sequence set forth in SEQ ID NO:207, a light chain variable region CDR2 comprising the amino acid sequence set forth in SEQ ID NO:128, and a light chain variable region CDR3 comprising the amino acid sequence set forth in SEQ ID NO:6.

15. The antibody of claim 14, wherein:

(a) the heavy chain variable region of the antibody that competes with the antibody of claim 9 comprises the amino acid sequence set forth in SEQ ID NO:51 and the light chain variable region of the antibody that competes with the antibody of claim 9 comprises the amino acid sequence set forth in SEQ ID NO:52;

(b) the heavy chain variable region of the antibody that competes with the antibody of claim 9 comprises the amino acid sequence set forth in SEQ ID NO:71 and the light chain variable region of the antibody that competes with the antibody of claim 9 comprises the amino acid sequence set forth in SEQ ID NO:72;

(c) the heavy chain variable region of the antibody that competes with the antibody of claim 9 comprises the amino acid sequence set forth in SEQ ID NO:97 and the light chain variable region of the antibody that competes with the antibody of claim 9 comprises the amino acid sequence set forth in SEQ ID NO:98;

(d) the heavy chain variable region of the antibody that competes with the antibody of claim 9 comprises the amino acid sequence set forth in SEQ ID NO:122 and the light chain variable region of the antibody that competes with the antibody of claim 9 comprises the amino acid sequence set forth in SEQ ID NO:123;

(e) the heavy chain variable region of the antibody that competes with the antibody of claim 9 comprises the amino acid sequence set forth in SEQ ID NO:144 and the light chain variable region of the antibody that competes with the antibody of claim 9 comprises the amino acid sequence set forth in SEQ ID NO:145;

(f) the heavy chain variable region of the antibody that competes with the antibody of claim 9 comprises the amino acid sequence set forth in SEQ ID NO:164 and the light chain variable region of the antibody that competes with the antibody of claim 9 comprises the amino acid sequence set forth in SEQ ID NO:165;

(g) the heavy chain variable region of the antibody that competes with the antibody of claim 9 comprises the amino acid sequence set forth in SEQ ID NO:188 and the light chain variable region of the antibody that competes with the antibody of claim 9 comprises the amino acid sequence set forth in SEQ ID NO:189;

(h) the heavy chain variable region of the antibody that competes with the antibody of claim 9 comprises the amino acid sequence set forth in SEQ ID NO:203 and the light chain variable region of the antibody that competes with the antibody of claim 9 comprises the amino acid sequence set forth in SEQ ID NO:204; or (i) the heavy chain variable region of the antibody that competes with the antibody of claim 9 comprises the amino acid sequence set forth in SEQ ID NO:218 and the light chain variable region of the antibody that competes with the antibody of claim 9 comprises the amino acid sequence set forth in SEQ ID NO:219.

16. The antibody of claim 9, which:
(a) inhibits GCGR signaling in cells expressing GCGR;
(b) inhibits GCGR activity in a cell expressing GCGR; or
(c) inhibits cAMP activity.

17. The antibody of claim 9, which inhibits GCGR activity in a cell expressing GCGR, wherein the GCGR activity is induced by glucagon.

18. The antibody of claim 9, which:
(i) reduces blood glucose levels;
(ii) increases the level of C-peptide; and/or
(iii) increases the level of insulin.

19. The antibody of claim 9, wherein the heavy chain variable region comprises the amino acid sequence set forth in SEQ ID NO:220.

20. The antibody of claim 9, wherein the light chain variable region comprises the amino acid sequence set forth in SEQ ID NO:221.

21. The antibody of claim 9, wherein the heavy chain variable region comprises the amino acid sequence set forth in SEQ ID NO:220 and the light chain variable region comprises the amino acid sequence set forth in SEQ ID NO:221.

22. The antibody of claim 9, which comprises: (i) a heavy chain that is at least 90% identical to the amino acid sequence set forth in SEQ ID NO:234; and (ii) a light chain that is at least 90% identical to the amino acid sequence set forth in SEQ ID NO:236.

23. The antibody of claim 9, which comprises a heavy chain comprising the amino acid sequence set forth in SEQ ID NO:234.

24. The antibody of claim 9, which comprises a light chain comprising the amino acid sequence set forth in SEQ ID NO:236.

25. The antibody of claim 9, which comprises an IgG1 heavy chain constant region.

26. The antibody of claim 9, which comprises a kappa light chain constant region.

27. The antibody of claim 9, which comprises an IgG1 heavy chain constant region and a kappa light chain constant region.

28. The antibody of claim 9, which is a humanized antibody.

29. A pharmaceutical composition comprising the antibody of claim 27, and a pharmaceutically acceptable carrier.

* * * * *

UNITED STATES PATENT AND TRADEMARK OFFICE
CERTIFICATE OF CORRECTION

PATENT NO. : 10,995,145 B2
APPLICATION NO. : 15/881493
DATED : May 4, 2021
INVENTOR(S) : Wenyan Shen et al.

Page 1 of 1

It is certified that error appears in the above-identified patent and that said Letters Patent is hereby corrected as shown below:

In the Claims

Column 209, Line 57, In Claim 14:
Before "a heavy chain variable" insert -- (f) --.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*